US007074397B1

(12) United States Patent
Matthews

(10) Patent No.: US 7,074,397 B1
(45) Date of Patent: *Jul. 11, 2006

(54) METHOD FOR ENHANCING PROLIFERATION OR DIFFERENTIATION OF A CELL USING OB PROTEIN

(75) Inventor: William Matthews, Woodside, CA (US)

(73) Assignee: Genentech, Inc., South San Francisco, CA (US)

( * ) Notice: This patent issued on a continued prosecution application filed under 37 CFR 1.53(d), and is subject to the twenty year patent term provisions of 35 U.S.C. 154 (a)(2).

Subject to any disclaimer, the term of this patent is extended or adjusted under 35 U.S.C. 154(b) by 268 days.

(21) Appl. No.: 08/667,197

(22) Filed: Jun. 20, 1996

Related U.S. Application Data

(60) Provisional application No. 60/064,855, filed on Jan. 8, 1996, now abandoned.

(51) Int. Cl.
*A61K 45/00* (2006.01)
*A61K 38/00* (2006.01)
*C07K 1/00* (2006.01)
*C07K 14/00* (2006.01)
*C07K 17/00* (2006.01)

(52) U.S. Cl. .................. 424/85.1; 530/351; 424/85.2; 514/12

(58) Field of Classification Search ............... 424/85.1, 424/85.2, 178.1, 193.1, 198.1, 195.11; 514/2, 514/8, 12; 530/351
See application file for complete search history.

(56) References Cited

U.S. PATENT DOCUMENTS

| 5,116,951 A | 5/1992 | Druez et al. |
| 5,264,416 A | 11/1993 | Park et al. |
| 5,349,053 A * | 9/1994 | Landolfi ..................... 530/351 |
| 5,378,808 A | 1/1995 | D'Andrea et al. .......... 530/350 |
| 5,453,491 A | 9/1995 | Takatsu et al. |
| 5,455,165 A | 10/1995 | Capon et al. |
| 5,521,283 A | 5/1996 | DiMarchi et al. |
| 5,532,336 A | 7/1996 | DiMarchi et al. |
| 5,543,320 A | 8/1996 | Park et al. |
| 5,569,744 A | 10/1996 | Basinski et al. |
| 5,571,513 A | 11/1996 | Burstein |
| 5,580,954 A | 12/1996 | DiMarchi et al. |
| 5,599,905 A | 2/1997 | Mosley et al. |
| 5,605,886 A | 2/1997 | Basinski et al. |
| 5,635,177 A | 6/1997 | Bennett et al. |
| 5,635,388 A | 6/1997 | Bennett et al. |
| 5,639,605 A | 6/1997 | Kitamura et al. |
| 5,643,748 A * | 7/1997 | Snodgrass et al. ......... 435/69.1 |
| 5,670,373 A | 9/1997 | Kishimoto et al. |
| 5,698,389 A | 12/1997 | de la Brousse et al. |
| 5,763,211 A | 6/1998 | Snodgrass et al. |
| 5,827,734 A | 10/1998 | Weigle et al. ............. 435/325 |
| 5,856,098 A | 1/1999 | Snodgrass et al. ............. 435/6 |
| 5,858,967 A | 1/1999 | Weigle et al. .................. 514/2 |
| 5,869,610 A | 2/1999 | Snodgrass et al. .......... 530/350 |
| 5,882,860 A | 3/1999 | Snodgrass et al. ............. 435/6 |
| 5,912,123 A | 6/1999 | Snodgrass et al. ............. 435/6 |
| 5,935,810 A | 8/1999 | Friedman et al. .......... 435/69.1 |
| 5,968,779 A | 10/1999 | Campfield et al. ......... 435/69.4 |
| 5,972,621 A | 10/1999 | Tartaglia et al. ............. 435/7.1 |
| 6,001,968 A | 12/1999 | Friedman et al. ........... 530/350 |
| 6,005,080 A | 12/1999 | Snodgrass et al. ....... 530/387.9 |
| 6,025,325 A * | 2/2000 | Campfiled et al. |
| 6,124,439 A | 9/2000 | Friedman et al. ...... 530/388.24 |
| 6,355,237 B1 * | 3/2002 | Snodgrass et al. |
| 6,506,877 B1 | 1/2003 | Tartaglia et al. |
| 2002/0037553 A1 | 3/2002 | Al-Barazanji et al. ..... 435/69.1 |
| 2003/0203837 A1 | 10/2003 | Pelleymounter |

FOREIGN PATENT DOCUMENTS

| EP | 372752 | 6/1990 |
| EP | 0 396 387 A2 | 11/1990 |
| EP | 0 396 387 A3 | 11/1990 |
| EP | 0 741 187 A2 | 11/1996 |
| EP | 0 956 862 A1 | 11/1999 |
| WO | WO 91/01004 | 1/1991 |
| WO | WO 91/01743 | 2/1991 |
| WO | WO 94/05332 | 3/1994 |
| WO | WO 94/11404 | 5/1994 |
| WO | GB96/01388 | 6/1995 |
| WO | WO 95/14930 | 6/1995 |
| WO | WO 95/21864 | 8/1995 |
| WO | WO 96/03438 | 2/1996 |
| WO | WO 96/05309 | 2/1996 |
| WO | WO 96/08510 | 3/1996 |
| WO | WO 96/23517 | 8/1996 |
| WO | WO 96/24670 | 8/1996 |
| WO | WO 96/31526 | 10/1996 |
| WO | WO 96/34885 A2 | 11/1996 |
| WO | WO 96/34885 A3 | 11/1996 |
| WO | WO 96/35787 | 11/1996 |
| WO | WO 97/00319 | 1/1997 |

(Continued)

OTHER PUBLICATIONS

Migliarcia et al., Blood 72(4) 1988, p. 1388.*

(Continued)

*Primary Examiner*—Robert S. Landsman
(74) *Attorney, Agent, or Firm*—Knobbe Martens Olson & Bear LLP

(57) ABSTRACT

Uses for WSX ligands in hematopoiesis are disclosed. In particular, in vitro and in vivo methods for stimulating hematopoiesis (e.g., myelopoiesis, erythropoiesis and especially, lymphopoiesis) using a WSX ligand (e.g., anti-WSX receptor agonist antibodies or OB protein), and optionally another cytokine, are described.

37 Claims, 74 Drawing Sheets

FOREIGN PATENT DOCUMENTS

| WO | WO 97/12037 | 4/1997 |
|---|---|---|
| WO | WO 97/19952 | 6/1997 |
| WO | WO 97/25424 | 7/1997 |
| WO | WO 97/26272 | 7/1997 |
| WO | WO 97/26335 | 7/1997 |
| WO | WO 97/26370 | 7/1997 |
| WO | WO 97/26523 | 7/1997 |
| WO | WO 97/27286 | 7/1997 |
| WO | WO 97/41217 | 11/1997 |
| WO | WO 97/41263 | 11/1997 |
| WO | WO 97/48419 | 12/1997 |
| WO | WO 97/48806 | 12/1997 |
| WO | 98/18486 | 5/1998 |
| WO | WO 98/28427 | 7/1998 |

OTHER PUBLICATIONS

Gainsford et al. *PNAS* 93, 1996, p. 14564-68.*
Cosman et al, *TIBS* 15, 1990, p. 265.*
Schuld et al., *Cykine* vol. 7, 1995, p. 679-80.*
Shin et al. *Inter. Rev. Immunol.* 10, 1993, p. 177-86.*
Francis, Forms of Growth Factors, vol. 3, 1992 p. 4-10.*
Koike et al. *J Exp Med* 168, 1988, p. 879-90.*
Ishigaka et al *Int. Arch Allergy Appl Immunol* 1989, p. 46-49, vol. 84.*
Bruno et al. *Exp Dematol* 16, 1988, p. 371-77.*
Arai et al., BioAssy 5(4) 1986, p. 166-71.*
Gainsford et al., *PWAS* 93, 1996, p. 4564-68.*
De Vas et al, *JBC* 270(7) 1995 p. 15958.*
Grunfill et al, Eur Cytokine Netw. vol. 7, 1996 p. 258.*
Rousenoff et al., Arthritis & Pheumation, vol. 39(9) 1996, p. 577.*
Ma et al, Surg Forum 1996, p. 47, p. 17-20.*
Batra JK, et al. Mol. Immunol. 30(4):379-386, 1993.*
Allen TM TiPS 15(7):215-220, 1994.*
Zaghouni H, et al. Intern. Rev. Immunol. 10:265-278, 1993.*
Ashkenazi et al., "Protection Against Endotoxic Shock by a Tumor Necrosis Factor Receptor Immunoadhesion" *Proc. Natl. Acad. Sci.* 88:10535-10539 (1991).
Barinaga, M., "Obesity: Leptin Receptor Weighs In" *Science* 271:29 (Jan. 5, 1996).
Bennet et al., "A role for Leptin and its cognate receptor in hematopoiesis" *Current Biology* 6(9) :1170-1180 (Sep. 1, 1996).
Genbank, "Release 100" *Homo sapiens cDNA clone 84708 5'*(Mar. 2, 1995).
*Antibodies. A Laboratory Manual*, Harlow and Lane, Cold Spring Harbor Laboratory pp. 341 (1988).
"Polyethylene glycol and derivatives" *Catalog Shearwater Polymers, Inc., Functionalized Biocompatible Polymers for Research* (Jan. 1994).
Ashkenazi and Chamow, "Immunoadhesins: An Alternative to Human Monoclonal Antibodies" *Methods: A Companion to Methods in Enzymology* 8:104-115 (1995).
Barin, Marcia, ""Obese" protein slims mice" *Science* 269:475-476 (1995).
Baumann et al., "Multiple regions within the cytoplasmic domains of the leukemia inhibitory factor receptor and gp130 cooperate in signal transduction in hepatic and neuronal cells" *Molecular & Cellular Biology* 14(1) :138-146 (1994).
Beck et al., "Generation of soluble interleukin-1 receptor from an immunoadhesin by specific cleavage" *Molecular Immunology* 31(17):1335-1344 (1994).

Bennett et al., "Extracellular Domain-IgG Fusion Proteins for Three Human Natriuretic Peptide Receptors. Hormone Pharmacology and Application to Solid Phase Screening of Synthetic Peptide Antisera" *The Journal of Biological Chemistry* 266(34):23060-23067 (Dec. 5, 1991).
Campfield et al., "Recombinant mouse ob protein: evidence for peripheral signal linking adiposity and central neural networks" *Science* 269:546-549 (1995).
Carter et al. *Mutagenesis. A Practical Approach*, Mcpherson,ed., Oxford, UK:IRL Press vol. Chapter 1:1-25 (1991).
Carter et al., "Engineering Subtilisin BPN' for Site-Specific Proteolysis" *Proteins: Struct. Funct. . Genet.* 6:240-248 (1989).
Carter et al., "Humanization of an anti-p1185$^{HER2}$ antibody for human cancer therapy" *Proc. Natl. Acad. Sci.* 89:4285-4289 (1992).
Chen et al., "Evidence that the diabetes gene encodes the leptin receptor: identification of a mutation in the leptin receptor gene in db/db mice" *Cell* 84:491-495 (1996).
Cioffi et al., "Novel B219/OB receptor isoforms: possible role leptin in hematopoiesis and reproduction" *Nature* 2(5):585-589 (1996).
Colditz, G.A., "Economic costs of obesity" *Am. J. Clin. Nutr.* 55:503S-507S (1992).
Coleman and Hummal, "Effects of parabiosis of normal with genetically diabetic mice" *Am. J. Physiol.* 217:1299-1304 (1969).
Coleman et al., "Obese and Diabetes: Two Mutant Genes Causing Diabetes-Obesity Syndromes in Mice" *Diebetologia* 14:141-148 (1978).
Coleman, D. L., "Effects of parabiosis of obese with diabetes and normal mice" *Diabetol* 9:294-298 (1973).
Considine, R. et al., "Serum immunoreactive-leptin concentrations in normal-weight and obese humans" *The New England Journal of Medicine* pp. 292-295 (Feb. 1, 1996).
D'Andrea, A. D., "Cytokine receptors in congenital hematopoietic disease" *New England J. of Medicine* 330(12) :839-846 (1994).
Dexter et al., "Growth and Differentiation in the Hemopoietic System" *Ann. Rev. Cell Biol.* 3:423-441 (1987).
Eisenberg, R., "Structure and Function in Gene Patenting" *Nature Genetics* 15:125-129 (1997).
Friedman et al., "Molecular mapping of the mouse ob mutation"*Genomics* 11:1054-1062 (1991).
Fukunaga R. et al., "Functional domains of the granulocyte colony-stimulating factor receptor" *EMBO Journal* 10(10):2855-2865 (1991).
Griffiths et al., "Isolation of High Affinity Human Antibodies Directly From Large Synthetic Repertoires" *EMBO Journal* 13:3245-3260 (1994).
Grupe et al., "Transgenic Knockouts Reveal a Critical Requirement for Pancreatic β Cell Glucokinase in Maintaining Glucose Homeostasis" *Cell* 83:69-78 (1995).
Halaas et al., "Weight-reducing effects of the plasma protein encoded by the obese gene" *Science* 269:543-546 (1995).
Hardy et al., "Resolution and characterization of pro-B and pre-pro-B cell stages in normal mouse bone marrow" *Journal of Experimental Medicine* 173:1213-1225 (1991).
Hillier et al., "WashU-Merck EST Project" *GenBank* (1995).
Holmes et al., "Structure and Functional Expression of a Human Interleukin-8 Receptor" *Science* 253(5025):1278-1280 (Sep. 13, 1991).
Humphries et al., "Self-Renewal of Hemopoietic Stem Cells During Mixed Colony Formation in Vitro" *Proc. Natl. Acad. Sci.* 78:3629-3633 (1981).

Kim et al., "Detection of Human Leukemia Inhibitory Factor by Monoclonal Antibody Based ELISA" *Journal of Immunological Methods* 156:9-17 (1992).

Kishimoto, "Cytokine Signal Transduction" *Cell* 76:253-262 (Jan. 28, 1994).

Kuczmarski et al., "Increasing prevalence of overweight among US adults" *J. Am. Med. Assoc.* 272(3):205-211 (1994).

Laskov et al., "Extinction of B-cell surface differentiation markers in hybrids between murine B-lymphoma and myeloma cells" *Cellular Immunology* 55(2):251-264 (1980).

Lee, G. et al., "Abnormal splicing of the leptin in diabetic mice" *Nature* 379:632-635 (Feb. 1996).

Levin et al., "Decreased Food Intake Does Not Completely Account For Adiposity Reduction After ob Protein Infusion" *Proc. Natl. Acad. Sci.* 93:1726-1730 (1996).

Maffei et al., "Increased expression in adipocytes of ob RNA in mice with lesions of the hypothalamus and with mutations at the db locus" *Proc. Natl. Acad. Sci.* 92:6957-6960 (1995).

Mark et al., "rse, a Novel Receptor-type Tyrosine Kinase with Homology to Ax1/Ufo, Is Expressed at High Levels in the Brain" *Journal of Biological Chemistry* 269(14):10720-10728 (Apr. 8, 1994).

McNiece et al., "The Role of recombinant stem cell factor in early B cell development. Synergistic interaction with IL-7" *J. Immunol.* 146:3785-3790 (1991).

Miyajima et al., "Receptors for Granulocyte-Macrophage Colony-Stimulating Factor, Interleukin-3, and Interleukin-5" *Blood* 82(7):1960-1974 (Oct. 1, 1993).

Murakami et al., "Critical cytoplasmic region of the interleukin 6 signal transducer gp130 is conserved in the cytokine receptor family" *Proc. Natl. Acad. Sci. USA* 88:11349-11353 (Dec. 1991).

Nicola, N., "Cytokine Pleiotrophy and Redundancy: A View From the Receptor" *Stem Cells* 12(Suppl.1):3-12 (1994).

Pelleymounter et al., "Effects of the obese gene product on body weight regulation in ob/ob mice" *Science* 269:540-543 (1995).

Pi-Sunyer, F. X., "Medical Hazards of Obesity" *Anns. Int. Med.* 119:655-660 (1993).

Rink, Timothy J., "In search of a satiety factor" *Nature* 372:406-407 (1994).

Stewart et al., "Introduction of Type 1 Diabetes by Interferon-A in Transgenic Mice" *Science* 260:1942-1946 (1993).

Suva et al., "A parathyroid hormone-related protein implicated in malignant hypercalcemia: cloning and expression" *Science* 237(4817):893-896 (Aug. 1987).

Tartaglia et al., "Identification and expression cloning of a leptin receptor, ob-r" *Cell* 83:1263-1271 (1995).

Tavassoli, M., "Lodegment of haemopoietic cells in the course of haemopoiesis on cellulose ester membrane: an experimental model for haemopoietic cell trapping" *Brit. J. Haematology* 57:71-80 (1984).

Vaisse et al., "Leptin Activation of Stat3 in the Hypothalamus of Wild-Type and ob/ob Mice But Not db/db Mice" *Nature Genetics* 14:95-97 (1996).

Vaughan et al., "Human Antibodies With Sub-nanomolar Affinities Isolated From a Large Non-immunized Phage Display Library" *Nature Biotechnology* 14:309-314 (1996).

Wells, J., "Structural and functional basis for hormone binding and receptor oligomerization" *Cell Biology* 6:163-173 (1994).

Zeigler et al., "Cellular and Molecular Characterization of the Role of the FLK-2/FLT-3 Receptor Tyrosine Kinase in Hematopoietic Stem Cells" *Blood* (8):2422-2430 (1994).

Zhang et al., "Positional cloning of the mouse obese gene and its human homologue" *Nature* 372:425-431 (1994).

Hollenbaugh et al., *Current Protocols in Immunology*, vol. 2, pp. 10.19.1-10.19.11 (1492).

Shin et al., *Hybrid Antibodies*, Intern. Rev. Immunol. vol. 10, pp. 177-186 (1993).

H. Baumann et al., "The full-length leptin receptor has signaling capabilities of interleukin 6-type cytokine receptors," *Proc. Natl. Acad. Sci. USA*, vol. 93, pp. 8374-8378 (Aug. 1996).

B. D. Bennett et al., "A role for leptin and its cognate receptor in hematopoiesis," *Current Biology*, vol. 6, No. 9, pp. 1170-1180 (1996).

B. Burguera et al., "The Long Form of the Leptin Receptor (OB-Rb) is Widely Expressed in the Human Brain," *Neuroendocrinology*, vol. 61, pp. 187-195 (2000).

S. C. Chua Jr. et al., "Phenotypes of Mouse *diabetes* and Rat *fatty* Due to Mutations in the OB (Leptin) Receptor", *Science*, vol. 271, pp. 994-996 (Feb. 16, 1996).

N. Hoggard et al., "Ontogeny of the expression of leptin and its receptor in the murine fetus and placenta," *British Journal of Nutrtion*, vol. 83, pp. 317-326 (2000).

S-M Luoh et al., "Cloning and characterization of a human leptin receptor using a biologically ctive leptin immunoadhesin", *Journal of Molecular Endocrinology*, vol. 18, pp. 77-85 (1997).

Harlow et al. Antibodies: A Laboratory Manual, 1988, Cold Spring Harbor.

Bell-Anderson et al. Leptin as a Potential Treatment for Obesity. Treaty Endocrinol. 3(1) 11-18. 2003.

Calandra et al. The role of leptin in the etiopathogenesis of anorexia nervosa and bulimia. Eat Weight Discord. 8(2): 130-7 Jun. 2003 (abstract).

Campfield et al. Strategies and Potential Molecular Targets for Obesity Treatment. Science 280: 1383-1387. May 29, 1998.

Gale et al. Energy Homeostasis, Obesity and Eating Disorders: Recent Advances in Endocrinology. J. Nutr. 134:295-298, 2004.

Ganong. Endocrine Functions of the Pancreas and the Regulation of Carbohydrate Metabolism. 299-300, 1989.

Herpertz et al. Plasma concentrations of leptons in a bulimic patient. Int J Eat Disord. 23 (4): 459-463, May 1998.

Hirsch, J. The search for new ways to treat obesity. PNAS, 99(14): 9096-9097. Jul. 9, 2002.

Rudikoff et al. Single amino acid substitution altering antigen-binding specificity. Proc Natl Acad Sci USA, 79: 1979-1983, Mar. 1992.

Woods et al. Signals That Regulate Food Intake and Energy Homeostasis. Science 280: 1378-1383. May 29, 1998.

* cited by examiner sites: std
length: 4102 (circular)

```
                  pleI
                  hinfI
           xhoI   salI
           paeR7I taqI                           aluI                                    eco57I
     ecoRI taqI hincII/hindII tru9I                                                      bslI              fokI         mnlI
     apoI aval aciI         mseI                                                                                         ddeI
  1  GAATTCTCGA GTCGACGGCG GGCGTTAAAG CTCTCCTGTGGC ATTATCCTTC AGTGGGGCTA TTGGACTGAC TTTTCTTATG CTGGGATGTG CCTTAGAGGA
     CTTAAGAGCT CAGCTGCCGC CCGCAATTTC GAGAGGACACCG TAATAGGAAG TCACCCCGAT AACCTGACTG AAAAGAATAC GACCCTACAC GGAATCTCCT rsaI                                                                                                              tru9I
     csp6I  eco57I                                        apoI              maeIII      apoI                           mseI
101  TTATGGGTGT ACTTCTCTGA AGTAAGATGA TTTGTCAAAA ATTCTGTGTG GTTTTGTTAC ATTGGGAATT TATTTATGTG ATAACTGCGT TTAACTTGTC
     AATACCCACA TGAAGAGACT TCATTCTACT AAACAGTTTT TAAGACACAC CAAAACAATG TAACCCTTAA ATAAATACAC TATTGACGCA AATTGAACAG
  1       M   I   C   Q   K   F   C   V   L   L   H   W   E   F   I   Y   V   I   T   A   F   N   L   S nlaIII
                                                 sphI
                       styI                      nspI                                         pleI
              tru9I    bsaJI                     nspHI       apoI                             hinfI            apoI
201  ATATCCAATT ACTCCTTGGA GATTAAGTT GTCTTGCATG CCACCAAATT CAACCTATGA CTACTTCCTT TTGCCTGCTG GACTCTCAAA GAATACTTCA
     TATAGGTTAA TGAGGAACCT CTAATTCAA CAGAACGTAC GGTGGTTTAA GTTGGATACT GATGAAGGAA AACGGACGAC CTGAGAGTTT CTTATGAAGT
 26   Y   P   I   T   P   W   R   F   K   L   S   C   M   P   P   N   S   T   Y   D   Y   F   L   L   P   A   G   L   S   K   N   T   S taqI
       sfuI
       bstBI               pvuII
       bsiCI               nspBII                tru9I        rsaI
       asuII         bsmAI aluI                  mseI         csp6I                                          apoI      sfaNI
301  AATTCGAATG GACATTATGA GACAGCTGTT GAACCTAAGT TTAATTCAAG TGGTACTCAC TTTTCTAACT TATCCAAAAC AACTTTCCAC TGTTGCTTC
     TTAAGCTTAC CTGTAATACT CTGTCGACAA CTTGGATTCA AATTAAGTTC ACCATGAGTG AAAAGATTGA ATAGGTTTG TTGAAAGGTG ACAACGAAAG
 59   N   S   N   G   H   Y   E   T   A   V   E   P   K   F   N   S   S   G   T   H   F   S   N   L   S   K   T   F   H   C   C   F   R apoI
401  GGAGTGAGCA AGATAGAAAC TGCTCCCTTAT GTGCAGACAA CATTGAAGGA AAGACATTTG TTTCAACAGT GTTTTTCAAC AAATAGATGC
     CCTCACTCGT TCTATCTTTG ACGAGGGAATA CACGTCTGTT GTAACTTCCT TTCTGTAAAC AAAGTTGTCA CAAAAAGTTG TTTATCTACG
 93   S   E   Q   D   R   N   C   S   L   C   A   D   N   I   E   G   K   T   F   V   S   T   V   N   S   L   V   F   Q   Q   I   D   A
```

FIG. 1A

```
                                                                         xmnI
                                                                         tfiI                             sau96I
                                                                         hinfI                            avaII
                                              tru9I          pleI        mseI asp700                      asuI
                              bsmAI mseI      hinfI                                           nlaIII
         bsrI                                                                                 rcaI
501 AAACTGGAAC ATACAGTGCT GGCTAAAAGG AGACTTAAAA TTATTCATCT GTTATGTGAA GTCATTATTT AAGAATCAT TCAGGAATTA TAACTATAAG
    TTTGACCTTG TATGTCACGA CCGATTTTCC TCTGAATTTT AATAAGTAGA CAATACACTT CAGTATAAA TTCTTAGATA AGTCCTTAAT ATTGATATTC
126  N  W  N   I  Q  C  W   L  K  G   D  L  K   L  F  I  C   Y  V  E   S  L  F   K  N  L  F  R  N  Y   N  Y  K
                                tfiI                                              bspHI
                                hinfI mnlI bslI                      muII     bsrI mnII
                     eco57I     mboII hphI  nlaIV
601 GTCCATCTTT TATATGTTCT GCCTGAAGTG TTAGAAGATT CACCTCTGGT TCCCCAAAAA GGCAGTTTTC AGATGGTTCA CTGCAATTGC AGTGTTCATG
    CAGGTAGAAA ATATACAAGA CGGACTTCAC AATCTTCTAA GTGGAGACCA AGGGGTTTTT CCGTCAAAAG TCTACCAAGT GACGTTAACG TCACAAGTAC
159  V  H  L   L  Y  V  L   P  E  V   L  E  D   S  P  L  V   P  Q  K   G  S  F   Q  M  V  H  C  N  C   S  V  H  E
                                                                                                   hphI
                                                                                                   maeIII
                                                                                              bsrI  mnlI
701 AATGTTGTGA ATGCTTGTG CCTGTGCCAA CAGCCAAACT CAACGACACT CTCCTTATGT GTTTGAAAAT CACATCTGGT GGAGTAATTT TCCAGTCACC
    TTACAACACT TACGAACAC GGACACGGTT GTCGGTTTGA GTTGCTGTGA GAGGAATACA CAAACTTTTA GTGTAGACCA CCTCATTAAA AGGTCAGTGG
193  C  C  E   C  L  V   P  V  P  T   A  K  L   N  D  T   L  L  M  C   L  K  I   T  S  G   G  V  I  F   Q  S  P
                          bslI
                          sau3AI
                          mboI/ndeII[dam-]
                          dpnI[dam+]
                          dpnII[dam-]                                                                      xcmI
                          alwI[dam-]              ndeI                                        tru9I    sau96I
            bstXI  hphI                                                                       mseI     avaII
                                                                                            ahaIII/draI  asuI
801 TCTAATGTCA GTTCAGCCCA TAAATATGGT GAAGCCTGAT CCACCATTAG GTTTGCATAT GGAAATCACA GATGATGGTA ATTTAAAGAT TTCTTGGTCC
    AGATTACAGT CAAGTCGGGT ATTTATACCA CTTCGGACTA CCAAACGTATA CCTTTAGTGT CTACTACCAT TAAATTCTA AAGAACCAGG
226  L  M  S   V  Q  P  I   N  M  V   K  P  D   P  P  L  G   L  H  M   E  I  T   D  D  G  N  L  K  I   S  W  S
```

```
                                      rsaI
                                      csp6I
                                      nlaIV
                                      kpnI
                                      hgiCI
                                      banI                                                           ecoRI                         drdI            ddeI
                                      asp718                        sspI          apoI              aluI           bsmAI aluI fokI
       bslI                           acc65I                        AATATTCAGA GAATTCTACA ACAGTTATCA GAGAAGCTGA CAAGATTGTC TCAGCTACAT
 901 AGCCCACCAT TGGTACCATT TCCACTTTCAA TATCAAGTGA
     TCGGGTGGTA ACCATGGTAA AGGTGAAGTT ATAGTTCACT TTATAAGTCT CTTAAGATGT TGTCAATAGT CTCTTCGACT GTTCTAACAG AGTCGATGTA
 259  S  P  P  L  V  P  F  P  L  Q  Y  Q  V  K  Y  S  E  N  S  T  V  I  R  E  A  D  K  I  V  S  A  T  S
                                                                          ^begin12u
                                                                    tfiI
                                                                    scrFI
                                                                    mvaI
                                         bpuAI                      ecoRII
                                         scrFI                      dsaV
                                         mvaI  bbsI                 bstNI
                              acc          ecoRII                  bstXI          apyI[dcm+]
                    accI      bst1107I     dsaV                    sau96I         haeIII/palI                          rsaI
                    rmaI      bsaJI mboII  bstNI                mnlI              asuI  hinfI     maeIII    scaI
          maeI      acc       apyI[dcm+]   mnlI       hphI      bsmAI fokI bsaJI    bsrI          gsuI/bpmI  gsuI/bpmI  mnlI
1001 CCCTGCTAGT AGACAGTATA CTTCCTGGGT CTTCGTATGA GGTTCAGGTG AGGGCAAGA GACTGGATGG CCCAGGAATC TGGAGTGACT GGAGTACTCC
     GGGACGATCA TCTGTCATAT GAAGGACCCA GAAGCATACT CCAAGTCCAC TCCCCGTTCT CTGACCTACC GGGTCCTTAG ACCTCACTGA CCTCATGAGG
 293  L  L  V  D  S  I  L  P  G  S  S  Y  E  V  Q  V  R  G  K  R  L  D  G  P  G  I  W  S  D  W  S  T  P
                                                apoI                                                       sfaNI
1101 TCGTGTCTTT ACCACACAAG ATGTCATATA CTTTCCACCT AAAATTCTGA CAAGTGTTGG GTCTAATGTT TCTTTTCACT GCATCTATAA GAAGGAAAAC
     AGCACAGAAA TGGTGTGTTC TACAGTATAT GAAAGGTGGA TTTTAAGACT GTTCACAACC CAGATTACAA AGAAAAGTGA CGTAGATATT CTTCCTTTTG
 326  R  V  F  T  T  Q  D  V  I  Y  F  P  P  K  I  L  T  S  V  G  S  N  V  S  F  H  C  I  Y  K  E  N
```

```
                                                                                                                                              nlaIII
                                                                                                                                              sau3AI
                                                                                                                                              mboI/ndeII[dam-]
                                                                                                                                              dpnI[dam+]
                                                                                                                                              dpnII[dam-]
                           mnlI            fokI         apoI    aluI  apoI   ddeI         apoI mnlI              bsrI              bcII[dam-]                          maeIII
1201 AAGATTGTTC CCTCAAAAGA GATTGTTGG TGGATGAATT TAGCTGAGAA AATTCCTCAA ATCGACTCTT TTAAGGAGTT AGCCAGTATG TCGGTCATAC TACAACACTC ATGTTGTGAG TGATCATGTT ACTAGTACAA AGCAAAGTTA TCGTTTCAAT
     TTCTAACAAG GGAGTTTTCT CTAACAAACC ACCTACTTAA ATCGACTCTT TTAAGGAGTT TAGCTGAGAA AATTCCTCAA TCGGTCATAC AGCCAGTATG ATGTTGTGAG TACAACACTC ACTAGTACAA TGATCATGTT TCGTTTCAAT AGCAAAGTTA
 359 K  I  V  P  S  K  E    I  V  W   M  N  L    A  E  K    I  P  Q   S  Q  Y   D  V  V    V  S  D    H  V      S  K  V  T taqI
                                xhoI
                                paeR7I
                                avaI
                                mnlI mnlI                     sfaNI               rsaI fnu4HI              bsmI
                                                                                  csp6I bbvI              nlaIII
1301 CTTTTTTCAA TCTGAATGAA ACCAAACCTC GAGGAAAAGTT TACCTATGAT GCAGTGTACT GCTGCAATGA ACATGAATGC CATCATCGCT ATGCTGAATT
     GAAAAAAGTT AGACTTACTT TGGTTTGGAG CTCCTTTTCAA ATGGATACTA CGTCACATGA CGACGTTACT TGTACTTACG GTAGTAGCGA TACGACTTAA
 393 F  F  N    L  N  E    T  K  P  R  G  K  F    T  Y  D    A  V  V  Y  C        C  N  E    H  H  R  Y   A  E  L tru9I                                                         rsaI
                                   mseI                                                          csp6I
                                   rsaI                                        bsrI       maeIII
                                   csp6I                                       hincII/hindII bsrI aciI
1401 ATATGTGATT GATGTCAATA TCAATATCTC ATGTGAAACT GATGGGTACT TAACTAAAAT GACTTGCAGA TGGTCAACCA GTACAATCCA GTCACTTGCG
     TATACACTAA CTACAGTTAT AGTTATAGAG TACACTTTGA CTACCCATGA ATTGATTTTA CTGAACGTCT ACCAGTTGGT CATGTTAGGT CAGTGAACGC
 426 Y  V  I    D  V  N  I  N  I  S   C  E  T    D  G  Y  L  T  K  M   T  C  R    W  S  T  S   T  I  Q   S  L  A hgiJII
                                                                                               bsp1286
                                                                                               bmyI
                                                                                               banII
                                fnu4HI                                               fokI      ddeI
                                bbvI
1501 GAAAGCACTT TGCAATTGAG GTATCATAGG AGCAGCCTTT ACTGTTCTGA TATTCCATCT ATTCATCCCA TATTCTGAGCC CAAAGATTGC TATTTGCAGA
     CTTTCGTGAA ACGTTAACTC CATAGTATCC TCGTCGGAAA TGACAAGACT ATAAGGTAGA TAAGTAGGGT ATAAGACTCGG GTTTCTAACG ATAAACGTCT
 459 E  S  T  L  Q  L  R   Y  H  R     S  S  L  Y  C  S  D    I  P  S    I  H  P   I  S  E  P  K  D  C   Y  L  Q  S
```

FIG. 1D

```
                                                    sau3AI
                                                    mboI/ndeII[dam-]
                                                     dpnI[dam+]
                                                     dpnII[dam-]
                                                      alwI[dam-]
                                     mamI[dam-]                                           rmaI    pleI
                         draIII      bsaBI[dam-]                                          maeI    hinfI
      ppu10I
      nsiI/avaIII
       bsmI                mboII
1601 GTATGAATGC ATTTCCAGC CAATCTTCCT ATTATCTGGC TACACAATGT GGATTAGGAT CAATCACTCT CTAGGTTCAC TTGACTCTCC
     CACTACCAAA AATACTTACG GTTAGAAGGA TAATAGACCG ATGTGTTACA CCTAATCCTA GTTAGTGAGA GATCCAAGTG AACTGAGAGG
493   D  G  F   Y  E  C   I  F  Q  P  I  F  L   L  S  G   Y  T  M  W  I  R  I   N  H  S   L  G  S  L   D  S  P
           ^begin13-2 nlaIII
       nspI
       nspHI              tfiI
        aflIII            hinfI     hphI                    foKI
                                                             mnlI    bsrI
1701 ACCAACATGT GTCCTTCCTG ATTCTGTGGT GAAGCCACTG CCTCCATCCA GTGTGAAAGC AGAAATTACT ATAAACATTG GATTATTGAA AATATCTTGG
     TGGTTGTACA CAGGAAGGAC TAAGACACCA CTTCGGTGAC GGAGGTAGGT CACACTTTCG TCTTTAATGA TATTTGTAAC CTAATAACTT TTATAGAACC
526   P  T  C   V  L  P  D  S  V  V   K  P  L   P  P  S  S  V  K  A  E  I  T   I  N  I  G   L  L  K   I  S  W tfiI
                                            hinfI         tru9I         rsaI
        bsrI                                xcmI          mseI          csp6I    mboII            mnlI    sfaNI
1801 GAAAGCCAG TCTTTCCAGA GAATAACCTT CAATTCCAGA TTTAAGTGGA AAAGAAGTAC AATGGAAGAT GTATGAGGTT TATGATGCAA
     CTTTCGGTC AGAAAGGTCT CTTATTGGAA GTTAAGGTCT AAGGATACC TTTCCATG TTACCTTCTA CATACTCCAA ATACTACGTT
                                                                   hinPI
                                                                   hhaI/cfoI mnlI maeI    bsrI
1801 GAAAGCCAG TCTTTCCAGA GAATAACCTT CAATTCCAGA TTCGCTATGG AAAGAAGTAC AATGGAAGAT GTATGAGGTT TATGATGCAA ATACTACGTT
     CTTTCGGTC AGAAAGGTCT CTTATTGGAA GTTAAGGTCT AAGGATACC TTTCCACCT TTACCTTCTA CATACTCCAA ATACTACGTT
559   E  K  P   V  F  P  E  N  N  L   Q  F  Q  I  R  Y  G   L  S  G  K  E  V  Q   W  K  M   Y  E  V   Y  D  A  K hinPI
                                                              hhaI/cfoI mnlI maeI    bsrI
       bsmAI bsrI
1901 AATCAAAATC TGTCAGTCTC CCAGTTCCAG ACTTGTGTGC AGTCTATGCT GTTCAGGTGC GCTGTAAGAG GCTAGATGGA CTGGGATATT GGAGTAATTG
     TTAGTTTTAG ACAGTCAGAG GGTCAAGGTC TGAACACACG TCAGATACGA CAAGCCACG CGACATTCTC CGATCTACCT GACCCTATAA CCTCATTAAC
593   S  K  S   V  S  L  P  V  P  D   L  C  A   V  Y  A   V  Q  V  R  C  K  R   L  D  G   L  G  Y  W   S  N  W sau96I
                   avaII
                   asuI
                   ppuMI                                                    tru9I
        nlaIII      ecoO109I/draII           apoI                           mseI
        econI       bslI     mnlI                                           aseI/asnI/vspI
2001 GAGCAATCCA GCCTACACAG TTGTCATGGA TATAAAAGTT CCTATGAGAG GACCTGAATT TGGAGAATA ATTAATGGAG ATACTATGAA AAAGGAGAAA
     CTCGTTAGGT CGGATGTGTC AACAGTACCT ATATTTTCAA GGATACTCTC CTGGACTTAA ACCTCTTAT TAATTACCTC TATGATACTT TTTCCTCTTT
626   S  N  P   A  Y  T  V  V  M  D   I  K  V   P  M  R  G  P  E  F  W  R  I   I  N  G  D   T  M  K   K  E  K
```

```
                                                                                    sau3AI
                                                                                    mboI/ndeII[dam-]
                                                                                    dpnI[dam+]
                                                                                    dpnII[dam-]
                                                                          bstYI/xhoII                                    bsrI
                     nlaIII           sfaNI                bsmAI         bglII                                          maeIII
2901 TACATCATGG AAAAATAAAG ATGAGAGAAC TACTTCAAC TACTTTCAAC AACAGATCTT GAAAAGGGTT CTGTTTGTAT TAGTGACCAG
     ATGTAGTACC TTTTTATTTC TACTCTACTA CGGTTGTTGA CACCAGAGAG ATGAAAGTTG TTGTCTAGAA CTTTCCCCAA GACAAACATA ATCACTGGTC
 926  T  S  W  K  N  K  D  E  M  M  P  T  T  V  V  S  L  S  T  T  D  L  E  K  G  S  V  C  I  S  D  Q tru9I
           mseI                         ddeI maeIII                                                sau3AI
          hpaI      ddeI ddeI          rsaI mnlI                             tru9I                 mboI/ndeII[dam+]
          hincII/hindII mnlI mnlI csp6I bstEII           mnlI   bsmAI         mseI                 dpnI[dam+]
                                                                                                   dpnII[dam-]
                                                                                                   bclI[dam-]
3001 TTCAACAGTG TTAACTTCTC TGAGGCTGAG GGTACTGAGG TAACCTATGA GGACGAAAGC CAGAGACAAC CCTTTGTTAA ATACGCCACG CTGATCAGCA
     AAGTTGTCAC AATTGAAGAG ACTCCGACTC CCATGACTCC ATTGGATACT CCTGCTTTCG GTCTCTGTTG GGAAACAATT TATGCGGTGC GACTAGTCGT
 959  F  N  S  V  N  F  S  E  A  E  G  T  E  V  T  Y  E  D  E  S  Q  R  Q  P  F  V  K  Y  A  T  L  I  S  N draIII
                hphI                                hphI                                        tfiI
                bsrI mboII                          maeIII       rmaI                           hinfI
3101 ACTCTAAACC AAGTGAAACT GGTGAAGAAC AAGGGCTTAT AAATAGTTCA GTCACCAAGT GCTTCTCTAG CAAAAATTCT CCGTTGAAGG ATTCTTTCTC
     TGAGATTTGG TTCACTTTGA CCACTTCTTG TTCCCGAATA TTTATCAAGT CAGTGGTTCA CGAAGAGATC GTTTTTAAGA GGCAACTCC TAAGAAAGAG
 993  S  K  P  S  E  T  G  E  E  Q  G  L  I  N  S  S  V  T  K  C  F  S  S  K  N  S  P  L  K  D  S  F  S scrFI
                              mvaI
                              ecoRII
                              dsaV
                              bstNI                sfaNI
                              apyI[dcm+]           sau3AI foKI
                              sau96I               mboI/ndeII[dam-]
                              haeIII/palI    mamI[dam-]
                              asuI            dpnI[dam+]
                nlaIII                        dpnII[dam-]
     aluI       mnlI bsaJI                    bsaBI[dam-]                 hphI              mnlI  ddeI          foKI
3201 TAATAGCTCA TGGGAGATAG AGGCCCAGGC ATTTTTTATA TTATCAGATC AGCATCCCAA CATAATTTCA CCACACCTCA CATTCTCAGA AGGATTGGAT
     ATTATCGAGT ACCCTCTATC TCCGGGTCCG TAAAAAATAT AATAGTCTAG TCGTAGGGTT GTATTAAAGT GGTGTGGAGT GTAAGAGTCT TCCTAACCTA
1026  N  S  S  W  E  I  E  A  Q  A  F  F  I  L  S  D  Q  H  P  N  I  I  S  P  H  L  T  F  S  E  G  L  D
```

FIG. 1H

```
                                                             mnlI
                                                             hphI
                              mboII                          maeIII
                  mnlI  apoI  eco57I                         bstEII
3301 GAACTTTGA AATTGGAGGG AAATTTCCCT GAAGAAAATA ATGATAAAAA GTCTATCTAT TATTTAGGGG TCACCTCAAT CAAAAAGAGA GAGAGTGGTG
     CTTGAAACT TTAACCTCCC TTTAAAGGGA CTTCTTTTAT TACTATTTT CAGATAGATA ATAAATCCCC AGTGGAGTTA GTTTTCTCT CTCTCACCAC
1059 E  L  L  K  L  E  G  N  F  P  E  E  N  N  D  K  K  S  I  Y  Y  L  G  V  T  S  I  K  K  R  E  S  G  V scrFI
                                                                              mvaI
                                                                              ecoRII
                                                                              dsaV
                                                                              bstNI
                                                                              apyI[dcm+]
             drdI                                                             gsuI/bpmI
3401 TGCTTTTGAC TGACAAGTCA AGGGTATCGT GCCCATTCCC AGCCCCCTGT TTATTCACGG ACATCAGAGT TCTCCAGGAC AGTTGCTCAC ACTTTGTAGA
     ACGAAAACTG ACTGTTCAGT TCCCATAGCA CGGGTAAGGG TCGGGGGACA AATAAGTGCC TGTAGTCTCA AGAGGTCCTG TCAACGAGTG TGAAACATCT
1093 L  L  T  D  K  S  R  V  S  C  P  F  P  A  P  C  L  F  T  D  I  R  V  L  Q  D  S  C  S  H  F  V  E nlaIII
                                                                                                    sau3AI
                                 mboII          nlaIII                                     pleI     mboI/ndeII[dam-]
                                 bpuAI          nspI                                       hinfI    dpnI[dam+]
                           rmaI  bbsI     sfaNI nspHI mnlI                           ddeI           dpnII[dam-]
                     ddeI  maeI           ccaa ccaaaactgt tgcctccaatt ccaaacttgt tctactcaga ctcataagat catggaaaac
3501 AAATAATATC AACTTAGGAA CTTCTAGTAA GAAGACTTTT GCATCTTACA TGCCTCAATT CCAAACTTGT TCTACTCAGA CTCATAAGAT CATGGAAAAC
     TTTATTATAG TTGAATCCTT GAAGATCATT CTTCTGAAAA CGTAGAATGT ACGGAGTTAA GGTTTGAACA AGATGAGTCT GAGTATTCTA GTACCTTTTG
1126 N  N  I  N  L  G  T  S  S  K  K  T  F  A  S  Y  M  P  Q  F  Q  T  C  S  T  Q  T  H  K  I  M  E  N mboII
           maeIII   eco57I
3601 AAGATGTGTG ACCTAACTGT GTAATTCAC TGAAGAAACC TTCAGATTTG TGTTATAATG GGTAATATAA AGTGTAATAG ATTATAGTTG TGGGTGGGAG
     TTCTACACAC TGGATTGACA CATTAAAGTG ACTTCTTTGG AAGTCTAAAC ACAATATTATT CCATTATATT TCACATTATC TAATATCAAC ACCCACCCTC
1159 K  M  C  D  L  T  V pleI                                                                                    xmnI
            hinfI                                                              ddeI maeIII          apoI   asp700
3701 AGAGAAAAGA AACCAGAGTC AAATTTGAAA ATAATTGTTC CAAATGAATG TTGTCTGTTT GTTCTCTCTT AGTAACATAG ACAAAAAATT TGAGAAAGCC
     TCTCTTTTCT TTGGTCTCAG TTTAAACTTT TATTAACAAG GTTTACTTAC AACAGACAAA CAAGAGAGAA TCATTGTATC TGTTTTTAA ACTCTTTCGG
```

FIG. 1I

```
                                                sau96I
                                                nlaIv
                                                avaII                                        sfuI
                                rmaI            asuI               rmaI                      bstBI
                                maeI            ppuMI              maeI                      bsiCI
                                aluI            ecoO109I/draII     aluI                      asuII
            mboII                                                                nspI        ecoRI
            earI/ksp632I                                                         nspHI       apoI
            sapI                                                rsaI             tru9I nlaIII
     accI                                              mnlI     csp6I            mseI aflIII tru9I
                                                                                             mseI 3801 TTCATAAGCC TACCAATGTA GACACGCTCT TCTATTTTAT TCCCAAGCTC TAGTGGGAAG GTCCCTTGTT TCCAGCTAGA AATAAGCCCA ACAGACACCA
     AAGTATTCGG ATGGTTACAT CTGTGCGAGA AGATAAAATA AGGGTTCGAG ATCACCCTTC CAGGGAACAA AGGTCGATCT TTATTCGGGT TGTCTGTGGT 3901 TCTTTTGTGA GATGTAATTG TTTTTTCAGA GGGCGTGTTG TTTACCTTCA AGTTTTTGTT TTGTACCAAC ACACACACAC ACACACATTC TTAACACATG
     AGAAAACACT CTACATTAAC AAAAAAGTCT CCCGCACAAC AAATGGAAGT TCAAAAACAA AACATGGTTG TGTGTGTGTG TGTGTGTAAG AATTGTGTAC scfI
4001 TCCTTGTGTG TTTTGAGAGT ATATTATGTA TTTATATTTT GTGCTATCAG ACTGTAGGAT TTGAAGTAGG ACTTTCCTAA ATGTTTAAGA TAAACAGAAT
     AGGAACACAC AAAACTCTCA TATAATACAT AAATATAAAA CACGATAGTC TGACATCCTA AACTTCATCC TGAAAGGATT TACAAATTCT ATTTGTCTTA
taqI
4101 TC
     AG length: 4102
```

FIG. 1J

| | | |
|---|---|---|
| wsxfull.6.4.variant | 1 | MICQKFCVVLLHWEFIYVITAFNLSYPITPWRFKLSCMPPPNSTYDYFLLP |
| wsxfull.12.1.variant | 1 | MICQKFCVVLLHWEFIYVITAFNLSYPITPWRFKLSCMPPPNSTYDYFLLP |
| wsxfull.13.2.variant | 1 | MICQKFCVVLLHWEFIYVITAFNLSYPITPWRFKLSCMPPPNSTYDYFLLP |
| wsxfull.6.4.variant | 51 | AGLSKNTSNSNGHYETAVEPKFNSSGTHFSNLSKTTFHCCFRSEQDRNCS |
| wsxfull.12.1.variant | 51 | AGLSKNTSNSNGHYETAVEPKFNSSGTHFSNLSKTTFHCCFRSEQDRNCS |
| wsxfull.13.2.variant | 51 | AGLSKNTSNSNGHYETAVEPKFNSSGTHFSNLSKTTFHCCFRSEQDRNCS |
| wsxfull.6.4.variant | 101 | LCADNIEGKTFVSTVNSLVFQQIDANWNIQCWLKGDLKLFICYVESLFKN |
| wsxfull.12.1.variant | 101 | LCADNIEGKTFVSTVNSLVFQQIDANWNIQCWLKGDLKLFICYVESLFKN |
| wsxfull.13.2.variant | 101 | LCADNIEGKTFVSTVNSLVFQQIDANWNIQCWLKGDLKLFICYVESLFKN |
| wsxfull.6.4.variant | 151 | LFRNYNYKVHLLYVLPEVLEDSPLVPQKGSFQMVHCNCSVHECCECLVPV |
| wsxfull.12.1.variant | 151 | LFRNYNYKVHLLYVLPEVLEDSPLVPQKGSFQMVHCNCSVHECCECLVPV |
| wsxfull.13.2.variant | 151 | LFRNYNYKVHLLYVLPEVLEDSPLVPQKGSFQMVHCNCSVHECCECLVPV |
| wsxfull.6.4.variant | 201 | PTAKLNDTLLMCLKITSGGVIFQSPLMSVQPINMVKPDPPLGLHMEITDD |
| wsxfull.12.1.variant | 201 | PTAKLNDTLLMCLKITSGGVIFQSPLMSVQPINMVKPDPPLGLHMEITDD |
| wsxfull.13.2.variant | 201 | PTAKLNDTLLMCLKITSGGVIFQSPLMSVQPINMVKPDPPLGLHMEITDD |
| wsxfull.6.4.variant | 251 | GNLKISWSSPPLVPFPLQYQVKYSENSTTVIREADKIVSATSLLVDSILP |
| wsxfull.12.1.variant | 251 | GNLKISWSSPPLVPFPLQYQVKYSENSTTVIREADKIVSATSLLVDSILP |
| wsxfull.13.2.variant | 251 | GNLKISWSSPPLVPFPLQYQVKYSENSTTVIREADKIVSATSLLVDSILP |

FIG. 2A

| | | |
|---|---|---|
| wsxfull.6.4.variant | 301 | G S S Y E V Q V R G K R L D G P G I W S D W S T P R V F T T Q D V I Y F P P K I L T S V G S N V S F |
| wsxfull.12.1.variant | 301 | G S S Y E V Q V R G K R L D G P G I W S D W S T P R V F T T Q D V I Y F P P K I L T S V G S N V S F |
| wsxfull.13.2.variant | 301 | G S S Y E V Q V R G K R L D G P G I W S D W S T P R V F T T Q D V I Y F P P K I L T S V G S N V S F |
| wsxfull.6.4.variant | 351 | H C I Y K K E N K I V P S K E I V W W M N L A E K I P Q S Q Y D V V S D H V S K V T F F N L N E T K |
| wsxfull.12.1.variant | 351 | H C I Y K K E N K I V P S K E I V W W M N L A E K I P Q S Q Y D V V S D H V S K V T F F N L N E T K |
| wsxfull.13.2.variant | 351 | H C I Y K K E N K I V P S K E I V W W M N L A E K I P Q S Q Y D V V S D H V S K V T F F N L N E T K |
| wsxfull.6.4.variant | 401 | P R G K F T Y D A V Y C C N E H E C H H R Y A E L Y V I D V N I N I S C E T D G Y L T K M T C R W S |
| wsxfull.12.1.variant | 401 | P R G K F T Y D A V Y C C N E H E C H H R Y A E L Y V I D V N I N I S C E T D G Y L T K M T C R W S |
| wsxfull.13.2.variant | 401 | P R G K F T Y D A V Y C C N E H E C H H R Y A E L Y V I D V N I N I S C E T D G Y L T K M T C R W S |
| wsxfull.6.4.variant | 451 | T S T I Q S L A E S T L Q L R Y H R S S L Y C S D I P S I H P I S E P K D C Y L Q S D G F Y E C I F |
| wsxfull.12.1.variant | 451 | T S T I Q S L A E S T L Q L R Y H R S S L Y C S D I P S I H P I S E P K D C Y L Q S D G F Y E C I F |
| wsxfull.13.2.variant | 451 | T S T I Q S L A E S T L Q L R Y H R S S L Y C S D I P S I H P I S E P K D C Y L Q S D G F Y E C I F |
| wsxfull.6.4.variant | 501 | Q P I F L L S G Y T M W I R I N H S L G S L D S P P T C V L P D S V V K P L P P S S V K A E I T I N |
| wsxfull.12.1.variant | 501 | Q P I F L L S G Y T M W I R I N H S L G S L D S P P T C V L P D S V V K P L P P S S V K A E I T I N |
| wsxfull.13.2.variant | 501 | Q P I F L L S G Y T M W I R I N H S L G S L D S P P T C V L P D S V V K P L P P S S V K A E I T I N |
| wsxfull.6.4.variant | 551 | I G L L K I S W E K P V F P E N N L Q F Q I R Y G L S G K E V Q W K M Y E V V Y D A K S K S V S L P V |
| wsxfull.12.1.variant | 551 | I G L L K I S W E K P V F P E N N L Q F Q I R Y G L S G K E V Q W K M Y E V V Y D A K S K S V S L P V |
| wsxfull.13.2.variant | 551 | I G L L K I S W E K P V F P E N N L Q F Q I R Y G L S G K E V Q W K M Y E V V Y D A K S K S V S L P V |

FIG. 2B

```
wsxfull.6.4.variant   601  PDLCAVYYAVQVRCKRLDGLGYWSNWSNPAYTVVMDIKVPMRGPEFWRIIN
wsxfull.12.1.variant  601  PDLCAVYYAVQVRCKRLDGLGYWSNWSNPAYTVVMDIKVPMRGPEFWRIIN
wsxfull.13.2.variant  601  PDLCAVYYAVQVRCKRLDGLGYWSNWSNPAYTVVMDIKVPMRGPEFWRIIN wsxfull.6.4.variant   651  GDTMKKEKNVTLLWKPLMKNDSLCSVQRYVINHHTSCNGTWSEDVGNHTK
wsxfull.12.1.variant  651  GDTMKKEKNVTLLWKPLMKNDSLCSVQRYVINHHTSCNGTWSEDVGNHTK
wsxfull.13.2.variant  651  GDTMKKEKNVTLLWKPLMKNDSLCSVQRYVINHHTSCNGTWSEDVGNHTK wsxfull.6.4.variant   701  FTFLWTEQAHTVTVLAINSIGASVANFNLTFSWPMSKVNIVQSLSAYPLN
wsxfull.12.1.variant  701  FTFLWTEQAHTVTVLAINSIGASVANFNLTFSWPMSKVNIVQSLSAYPLN
wsxfull.13.2.variant  701  FTFLWTEQAHTVTVLAINSIGASVANFNLTFSWPMSKVNIVQSLSAYPLN wsxfull.6.4.variant   751  SSCVIVSWILSPSDYKLMYFIIEWKNLNEDGEIKWLRISSSVKKYYIHDH
wsxfull.12.1.variant  751  SSCVIVSWILSPSDYKLMYFIIEWKNLNEDGEIKWLRISSSVKKYYIHDH
wsxfull.13.2.variant  751  SSCVIVSWILSPSDYKLMYFIIEWKNLNEDGEIKWLRISSSVKKYYIHDH wsxfull.6.4.variant   801  FIPIEKYQFSLYPIFMEGVGKPKIINSFTQDDIEKHQSDAGLYVIVPVII
wsxfull.12.1.variant  801  FIPIEKYQFSLYPIFMEGVGKPKIINSFTQDDIEKHQSDAGLYVIVPVII
wsxfull.13.2.variant  801  FIPIEKYQFSLYPIFMEGVGKPKIINSFTQDDIEKHQSDAGLYVIVPVII wsxfull.6.4.variant   851  SSILLGTLLISHQRMKKLFWEDVPNPKNCSWAQGLNFQK........MF.
wsxfull.12.1.variant  851  SSILLGTLLISHQRMKKLFWEDVPNPKNCSWAQGLNFQK........MF.
wsxfull.13.2.variant  851  SSILLGTLLISHQRMKKLFWEDVPNPKNCSWAQGLNFQKPETFEHLFI
```

FIG. 2C

```
                                                              Box 2
wsxfull.13.2.variant   901  KHTASVTC GPLLLEPETISEDI SVDTSWKNKDEMMPTTVVSLLSTTDLEK
                                     Box 3
wsxfull.13.2.variant   951  GSVCIS DQFNSVNFSEAEGTEVTYEDESQRQ PFVKYATLISNSKPSETGE wsxfull.6.4.variant    892  . . . . . . . . . . . . . . . . . . . . . . . . . . . . . . . . . . . . . . . . . . . . . . . . R
wsxfull.12.1.variant   894  . . . . . . . . . . . . . . . . . . . . . . . . . . . . . . . . . . . . . . . . . RT PR I VPGH
wsxfull.13.2.variant   1001 EQGLINSSVTKCFSSKNSPLKDSFSNSSWEIEAQAFFILSDQHPN I SPH wsxfull.6.4.variant    893  . . . . . . . . . . . . . . . . . . . . . . . . . . . . . . . . . . . . . . . TD I L . . .
wsxfull.12.1.variant   903  . . . . . . . . . . . . . . . . . . . . . . . . . . . . . . . . . . . . . . . KD L I F . .
wsxfull.13.2.variant   1051 LTFSEGLDELLKLEGNFPEENNDKKSIYYLGVTSIKKRESGV LTDKSRV wsxfull.12.1.variant   908  . . . . . . . RRC L KAA CSL R V I TTP . . . . . . . . . . . . . . . . . .
wsxfull.13.2.variant   1101 SCPFPAPCLFTDI RV QDSCSHF V ENNINLGTSSKKTFASYMPQFQTCST wsxfull.13.2.variant   1151 QTHKIMENKMCDLTV
```

```
                    1   GAATTCCGGGTTAAAAGCTCTCGTGGCATTATCCTTCAGTGGGGCTATTGG
wsxfull.6.4.variant 51   ACTGACTTTTCTTATGCTGGGATGTGCCTTAGAGGATTA.....TTTGCCA
wsxfull.6.4.variant
                    1   .................................GAATTCTCGAGTC
wsxfull.12.1.variant
                    1   .................................GAATTCTCGAGTC
wsxfull.13.2.variant 101   GTTCACCCTGACCATCTTGAAAAATAAGTTATCTCTGATCTCTGTAT
wsxfull.6.4.variant
                   14   GACGGCGGGCGTTAAAGCTCTCGTGGCATTATCCTTCAGTGGGCTATTG
wsxfull.12.1.variant
                   14   GACGGCGGGCGTTAAAGCTCTCGTGGCATTATCCTTCAGTGGGCTATTG
wsxfull.13.2.variant 151   GTTACTTCTCCCCTCACCAATGGGATGTGCCTTAGAGGATTATGGGTACT
wsxfull.6.4.variant
                   64   GACTGACTTTTCTTATGCTGGGATGTGCCTTAGAGGATTATGGGTGTACT
wsxfull.12.1.variant
                   64   GACTGACTTTTCTTATGCTGGGATGTGCCTTAGAGGATTATGGGTGTACT
wsxfull.13.2.variant 201   TCTCTGAAGTAAGATGATTTGTCAAAAATTCTGTGGTTTTGTTACATT
wsxfull.6.4.variant
                  114   TCTCTGAAGTAAGATGATTTGTCAAAAATTCTGTGGTTTTGTTACATT
wsxfull.12.1.variant
                  114   TCTCTGAAGTAAGATGATTTGTCAAAAATTCTGTGGTTTTGTTACATT
wsxfull.13.2.variant 251   GGGAATTTATTTATGTGATAACTGCGTTTAACTTGTCATATCCAATTACT
wsxfull.6.4.variant
                  164   GGGAATTTATTTATGTGATAACTGCGTTTAACTTGTCATATCCAATTACT
wsxfull.12.1.variant
                  164   GGGAATTTATTTATGTGATAACTGCGTTTAACTTGTCATATCCAATTACT
wsxfull.13.2.variant 301   CCTTGGAGATTTAAGTTGTCTTGCATGCCACCAAATTCAACCTATGACTA
wsxfull.6.4.variant
                  214   CCTTGGAGATTTAAGTTGTCTTGCATGCCACCAAATTCAACCTATGACTA
wsxfull.12.1.variant
                  214   CCTTGGAGATTTAAGTTGTCTTGCATGCCACCAAATTCAACCTATGACTA
wsxfull.13.2.variant
```

```
wsxfull.6.4.variant    351  CTTCCTTTTGCCTGGACTCTCAAAGAATACTTCAAATTCGAATGGAC
wsxfull.12.1.variant   264  CTTCCTTTTGCCTGGACTCTCAAAGAATACTTCAAATTCGAATGGAC
wsxfull.13.2.variant   264  CTTCCTTTTGCCTGGACTCTCAAAGAATACTTCAAATTCGAATGGAC wsxfull.6.4.variant    401  ATTATGAGACAGCTGTTGAACCTAAGTTTAATTCAAGTGGTACTCACTTT
wsxfull.12.1.variant   314  ATTATGAGACAGCTGTTGAACCTAAGTTTAATTCAAGTGGTACTCACTTT
wsxfull.13.2.variant   314  ATTATGAGACAGCTGTTGAACCTAAGTTTAATTCAAGTGGTACTCACTTT wsxfull.6.4.variant    451  TCTAAACTTTATCCAAAAACAACTTTCCACTGTTGCTTTCGGAGTGAGCAAGA
wsxfull.12.1.variant   364  TCTAAACTTTATCCAAAAACAACTTTCCACTGTTGCTTTCGGAGTGAGCAAGA
wsxfull.13.2.variant   364  TCTAAACTTTATCCAAAAACAACTTTCCACTGTTGCTTTCGGAGTGAGCAAGA wsxfull.6.4.variant    501  TAGAAAACTGCTCCTTATGTGCAGACAACATTGAAAGGAAAGACATTTGTTT
wsxfull.12.1.variant   414  TAGAAAACTGCTCCTTATGTGCAGACAACATTGAAAGGAAAGACATTTGTTT
wsxfull.13.2.variant   414  TAGAAAACTGCTCCTTATGTGCAGACAACATTGAAAGGAAAGACATTTGTTT wsxfull.6.4.variant    551  CNACAGTAAAATTCTTTTAGTTTTTCAACAAAATAGATGCAAACTGGAACATA
wsxfull.12.1.variant   464  CAACAGTAAAATTCTTTTAGTTTTTCAACAAAATAGATGCAAACTGGAACATA
wsxfull.13.2.variant   464  CAACAGTAAAATTCTTTTAGTTTTTCAACAAAATAGATGCAAACTGGAACATA wsxfull.6.4.variant    601  CAGTGCTGGCTAAAAGGAGACTTAAAATTATTCATCTGTTATGTGGAGTC
wsxfull.12.1.variant   514  CAGTGCTGGCTAAAAGGAGACTTAAAATTATTCATCTGTTATGTGGAGTC
wsxfull.13.2.variant   514  CAGTGCTGGCTAAAAGGAGACTTAAAATTATTCATCTGTTATGTGGAGTC
```

FIG. 3B

| | | |
|---|---|---|
| wsxfull.6.4.variant | 651 | ATTATTTAAGAATCTATTCAGGAATTATAAACTATAAGGTCCATCTTTTAT |
| wsxfull.12.1.variant | 564 | ATTATTTAAGAATCTATTCAGGAATTATAAACTATAAGGTCCATCTTTTAT |
| wsxfull.13.2.variant | 564 | ATTATTTAAGAATCTATTCAGGAATTATAAACTATAAGGTCCATCTTTTAT |
| wsxfull.6.4.variant | 701 | ATGTTCTGCCTGAAGTGTTAGAAGATTCACCTCTGGTTCCCCAAAAAGGC |
| wsxfull.12.1.variant | 614 | ATGTTCTGCCTGAAGTGTTAGAAGATTCACCTCTGGTTCCCCAAAAAGGC |
| wsxfull.13.2.variant | 614 | ATGTTCTGCCTGAAGTGTTAGAAGATTCACCTCTGGTTCCCCAAAAAGGC |
| wsxfull.6.4.variant | 751 | AGTTTCAGATGGTTCACTGCAATTGCAGTGTTCATGAATGTTGTGAATG |
| wsxfull.12.1.variant | 664 | AGTTTCAGATGGTTCACTGCAATTGCAGTGTTCATGAATGTTGTGAATG |
| wsxfull.13.2.variant | 664 | AGTTTCAGATGGTTCACTGCAATTGCAGTGTTCATGAATGTTGTGAATG |
| wsxfull.6.4.variant | 801 | TCTTGTGCCTGTGCCAACAGCCAAACTCAACGACACTCTCCTTATGTGTT |
| wsxfull.12.1.variant | 714 | TCTTGTGCCTGTGCCAACAGCCAAACTCAACGACACTCTCCTTATGTGTT |
| wsxfull.13.2.variant | 714 | TCTTGTGCCTGTGCCAACAGCCAAACTCAACGACACTCTCCTTATGTGTT |
| wsxfull.6.4.variant | 851 | TGAAAATCACATCTGGTGGAGTAATTTTCCAGTCACCTCTAATGTCAGTT |
| wsxfull.12.1.variant | 764 | TGAAAATCACATCTGGTGGAGTAATTTTCCAGTCACCTCTAATGTCAGTT |
| wsxfull.13.2.variant | 764 | TGAAAATCACATCTGGTGGAGTAATTTTCCAGTCACCTCTAATGTCAGTT |
| wsxfull.6.4.variant | 901 | CAGCCCATAAAATATGGTGAAGCCTGATCCACCATTAGGTTTGCATATGGA |
| wsxfull.12.1.variant | 814 | CAGCCCATAAAATATGGTGAAGCCTGATCCACCATTAGGTTTGCATATGGA |
| wsxfull.13.2.variant | 814 | CAGCCCATAAAATATGGTGAAGCCTGATCCACCATTAGGTTTGCATATGGA |

FIG. 3C

```
wsxfull.6.4.variant    951   AATCACAGATGATGGTAATTTAAAGATTTCTTGGTCCAGCCCACCATTGG
wsxfull.12.1.variant   864   AATCACAGATGATGGTAATTTAAAGATTTCTTGGTCCAGCCCACCATTGG
wsxfull.13.2.variant   864   AATCACAGATGATGGTAATTTAAAGATTTCTTGGTCCAGCCCACCATTGG wsxfull.6.4.variant   1001   TACCATTTCCACTTCAATATCAAGTGAAATATTCAGAGAATTCTACAACA
wsxfull.12.1.variant   914   TACCATTTCCACTTCAATATCAAGTGAAATATTCAGAGAATTCTACAACA
wsxfull.13.2.variant   914   TACCATTTCCACTTCAATATCAAGTGAAATATTCAGAGAATTCTACAACA wsxfull.6.4.variant   1051   GTTATCAGAGAAGCTGACAAGATTGTCTCAGCTACATCCCTGCTAGTAGA
wsxfull.12.1.variant   964   GTTATCAGAGAAGCTGACAAGATTGTCTCAGCTACATCCCTGCTAGTAGA
wsxfull.13.2.variant   964   GTTATCAGAGAAGCTGACAAGATTGTCTCAGCTACATCCCTGCTAGTAGA wsxfull.6.4.variant   1101   CAGTATACTTTCCTGGGTCTTCGTATGAGGTTCAGGTGAGGGCAAGAGAC
wsxfull.12.1.variant  1014   CAGTATACTTTCCTGGGTCTTCGTATGAGGTTCAGGTGAGGGCAAGAGAC
wsxfull.13.2.variant  1014   CAGTATACTTTCCTGGGTCTTCGTATGAGGTTCAGGTGAGGGCAAGAGAC wsxfull.6.4.variant   1151   TGGATGGCCCAGGAATCTGGAGTGACTGGAGTACTCCTCGTGTCTTTACC
wsxfull.12.1.variant  1064   TGGATGGCCCAGGAATCTGGAGTGACTGGAGTACTCCTCGTGTCTTTACC
wsxfull.13.2.variant  1064   TGGATGGCCCAGGAATCTGGAGTGACTGGAGTACTCCTCGTGTCTTTACC wsxfull.6.4.variant   1201   ACACAAGATGTCATATACTTTCCACCTAAAATTCTGACAAGTGTTGGGTC
wsxfull.12.1.variant  1114   ACACAAGATGTCATATACTTTCCACCTAAAATTCTGACAAGTGTTGGGTC
wsxfull.13.2.variant  1114   ACACAAGATGTCATATACTTTCCACCTAAAATTCTGACAAGTGTTGGGTC
```

FIG. 3D

```
wsxfull.6.4.variant   1251 TAATGTTTCTTTTCACTGCATCTATAAGAAGGAAAACAAGATTGTTCCCT
wsxfull.12.1.variant  1164 TAATGTTTCTTTTCACTGCATCTATAAGAAGGAAAACAAGATTGTTCCCT
wsxfull.13.2.variant  1164 TAATGTTTCTTTTCACTGCATCTATAAGAAGGAAAACAAGATTGTTCCCT wsxfull.6.4.variant   1301 CAAAAGAGATTGTTTGGTGGATGAATTTAGCTGAGAAAATTCCTCAAAGC
wsxfull.12.1.variant  1214 CAAAAGAGATTGTTTGGTGGATGAATTTAGCTGAGAAAATTCCTCAAAGC
wsxfull.13.2.variant  1214 CAAAAGAGATTGTTTGGTGGATGAATTTAGCTGAGAAAATTCCTCAAAGC wsxfull.6.4.variant   1351 CAGTATGATGTTGTGAGTGATCATGTTAGCAAAGTTACTTTTTTTCAATCT
wsxfull.12.1.variant  1264 CAGTATGATGTTGTGAGTGATCATGTTAGCAAAGTTACTTTTTTTCAATCT
wsxfull.13.2.variant  1264 CAGTATGATGTTGTGAGTGATCATGTTAGCAAAGTTACTTTTTTTCAATCT wsxfull.6.4.variant   1401 GAATGAAACCAAACCCTCGAGGAAAAGTTTTACCTATGATGCAGTGTACTGCT
wsxfull.12.1.variant  1314 GAATGAAACCAAACCCTCGAGGAAAAGTTTTACCTATGATGCAGTGTACTGCT
wsxfull.13.2.variant  1314 GAATGAAACCAAACCCTCGAGGAAAAGTTTTACCTATGATGCAGTGTACTGCT wsxfull.6.4.variant   1451 GCAATGAAACATGAATCTCATGTGAAACTGCTATTATATGTGATTGAT
wsxfull.12.1.variant  1364 GCAATGAAACATGAATCTCATGTGAAACTGCTATTATATGTGATTGAT
wsxfull.13.2.variant  1364 GCAATGAAACATGAATCTCATGTGAAACTGCTATTATATGTGATTGAT wsxfull.6.4.variant   1501 GTCAATATCAATATCTCATGTGAAACTGATGGGTACTTAACTAAAATGAC
wsxfull.12.1.variant  1414 GTCAATATCAATATCTCATGTGAAACTGATGGGTACTTAACTAAAATGAC
wsxfull.13.2.variant  1414 GTCAATATCAATATCTCATGTGAAACTGATGGGTACTTAACTAAAATGAC
```

FIG. 3E

| | | |
|---|---|---|
| wsxfull.6.4.variant | 1551 | TTGCAGATGGTCAACCAGTACAATCCAGTCACTTTGCGGAAAGCACTTTGC |
| wsxfull.12.1.variant | 1464 | TTGCAGATGGTCAACCAGTACAATCCAGTCACTTTGCGGAAAGCACTTTGC |
| wsxfull.13.2.variant | 1464 | TTGCAGATGGTCAACCAGTACAATCCAGTCACTTTGCGGAAAGCACTTTGC |
| | | |
| wsxfull.6.4.variant | 1601 | AATTGAGGTATCATAGGAGCAGCCCTTTACTGTTCTGATATTCCATCTATT |
| wsxfull.12.1.variant | 1514 | AATTGAGGTATCATAGGAGCAGCCCTTTACTGTTCTGATATTCCATCTATT |
| wsxfull.13.2.variant | 1514 | AATTGAGGTATCATAGGAGCAGCCCTTTACTGTTCTGATATTCCATCTATT |
| | | |
| wsxfull.6.4.variant | 1651 | CATCCCATATCTGAGCCCAAAGATTGCTATTTGCAGAGTGATGGTTTTTA |
| wsxfull.12.1.variant | 1564 | CATCCCATATCTGAGCCCAAAGATTGCTATTTGCAGAGTGATGGTTTTTA |
| wsxfull.13.2.variant | 1564 | CATCCCATATCTGAGCCCAAAGATTGCTATTTGCAGAGTGATGGTTTTTA |
| | | |
| wsxfull.6.4.variant | 1701 | TGAATGCATTTTCCAGCCAATCTTCCTATTATCTGGCTACACAATGTGGA |
| wsxfull.12.1.variant | 1614 | TGAATGCATTTTCCAGCCAATCTTCCTATTATCTGGCTACACAATGTGGA |
| wsxfull.13.2.variant | 1614 | TGAATGCATTTTCCAGCCAATCTTCCTATTATCTGGCTACACAATGTGGA |
| | | |
| wsxfull.6.4.variant | 1751 | TTAGGATCAATCACTCACTCTCTAGGTTCACTTGACTCTCCACCAACATGTGTC |
| wsxfull.12.1.variant | 1664 | TTAGGATCAATCACTCACTCTCTAGGTTCACTTGACTCTCCACCAACATGTGTC |
| wsxfull.13.2.variant | 1664 | TTAGGATCAATCACTCACTCTCTAGGTTCACTTGACTCTCCACCAACATGTGTC |
| | | |
| wsxfull.6.4.variant | 1801 | CTTCCTGATTCTGTGGTGAAGCCACTGCCTCCATCCAGTGTGAAAGCAGA |
| wsxfull.12.1.variant | 1714 | CTTCCTGATTCTGTGGTGAAGCCACTGCCTCCATCCAGTGTGAAAGCAGA |
| wsxfull.13.2.variant | 1714 | CTTCCTGATTCTGTGGTGAAGCCACTGCCTCCATCCAGTGTGAAAGCAGA |

FIG. 3F

| | | |
|---|---|---|
| wsxfull.6.4.variant | 1851 | AATTACTATAAACATTGGATTATTGAAAATATCTTGGGAAAAGCCAGTCT |
| wsxfull.12.1.variant | 1764 | AATTACTATAAACATTGGATTATTGAAAATATCTTGGGAAAAGCCAGTCT |
| wsxfull.13.2.variant | 1764 | AATTACTATAAACATTGGATTATTGAAAATATCTTGGGAAAAGCCAGTCT |
| | | |
| wsxfull.6.4.variant | 1901 | TTCCAGAGAATAACCTTCAATTCCAGATTCGCTATGGTTTAAGTGGAAAA |
| wsxfull.12.1.variant | 1814 | TTCCAGAGAATAACCTTCAATTCCAGATTCGCTATGGTTTAAGTGGAAAA |
| wsxfull.13.2.variant | 1814 | TTCCAGAGAATAACCTTCAATTCCAGATTCGCTATGGTTTAAGTGGAAAA |
| | | |
| wsxfull.6.4.variant | 1951 | GAAGTACAATGGAAGATGTATGAGGTTTATGATGCAAAATCAAAATCTGT |
| wsxfull.12.1.variant | 1864 | GAAGTACAATGGAAGATGTATGAGGTTTATGATGCAAAATCAAAATCTGT |
| wsxfull.13.2.variant | 1864 | GAAGTACAATGGAAGATGTATGAGGTTTATGATGCAAAATCAAAATCTGT |
| | | |
| wsxfull.6.4.variant | 2001 | CAGTCTCCCAGTTCCAGACTTGTGTGCAGTCTATGCTGTTCAGGTGCGCT |
| wsxfull.12.1.variant | 1914 | CAGTCTCCCAGTTCCAGACTTGTGTGCAGTCTATGCTGTTCAGGTGCGCT |
| wsxfull.13.2.variant | 1914 | CAGTCTCCCAGTTCCAGACTTGTGTGCAGTCTATGCTGTTCAGGTGCGCT |

| | | |
| wsxfull.6.4.variant | 2051 | GTAAGAGGCTAGATGGACTGGGATATTGGAGTAATTGGAGCAATCCAGCC |
| wsxfull.12.1.variant | 1964 | GTAAGAGGCTAGATGGACTGGGATATTGGAGTAATTGGAGCAATCCAGCC |
| wsxfull.13.2.variant | 1964 | GTAAGAGGCTAGATGGACTGGGATATTGGAGTAATTGGAGCAATCCAGCC |
| | | |
| wsxfull.6.4.variant | 2101 | TACACAGTTGTCATGGATATAAAAGTTCCTATGAGAGGACCTGAATTTTG |
| wsxfull.12.1.variant | 2014 | TACACAGTTGTCATGGATATAAAAGTTCCTATGAGAGGACCTGAATTTTG |
| wsxfull.13.2.variant | 2014 | TACACAGTTGTCATGGATATAAAAGTTCCTATGAGAGGACCTGAATTTTG |

FIG. 3G

| | | |
|---|---|---|
| wsxfull.6.4.variant | 2151 | GAGAATAATTAATGGAGAGATACTATGAAAAAAGGAGAAAAATGTCACTTTTAC |
| wsxfull.12.1.variant | 2064 | GAGAATAATTAATGGAGAGATACTATGAAAAAAGGAGAAAAATGTCACTTTTAC |
| wsxfull.13.2.variant | 2064 | GAGAATAATTAATGGAGAGATACTATGAAAAAAGGAGAAAAATGTCACTTTTAC |
| wsxfull.6.4.variant | 2201 | TTTGGAAGCCCCTGATGAAAAATGACTCATTGTGCAGTGTTCAGAGATAT |
| wsxfull.12.1.variant | 2114 | TTTGGAAGCCCCTGATGAAAAATGACTCATTGTGCAGTGTTCAGAGATAT |
| wsxfull.13.2.variant | 2114 | TTTGGAAGCCCCTGATGAAAAATGACTCATTGTGCAGTGTTCAGAGATAT |
| wsxfull.6.4.variant | 2251 | GTGATAAACCATCATACTTCCTGCAATGGAACATGGTCAGAAGATGTGGG |
| wsxfull.12.1.variant | 2164 | GTGATAAACCATCATACTTCCTGCAATGGAACATGGTCAGAAGATGTGGG |
| wsxfull.13.2.variant | 2164 | GTGATAAACCATCATACTTCCTGCAATGGAACATGGTCAGAAGATGTGGG |
| wsxfull.6.4.variant | 2301 | AAATCACACGAAATTCACTTTCCTGTGGACAGAGCAAGCACATACTGTTA |
| wsxfull.12.1.variant | 2214 | AAATCACACGAAATTCACTTTCCTGTGGACAGAGCAAGCACATACTGTTA |
| wsxfull.13.2.variant | 2214 | AAATCACACGAAATTCACTTTCCTGTGGACAGAGCAAGCACATACTGTTA |
| wsxfull.6.4.variant | 2351 | CGGTTCTGGCCATCAATTCAATTGGTGCTTCTGTTGCAAATTTTAATTTA |
| wsxfull.12.1.variant | 2264 | CGGTTCTGGCCATCAATTCAATTGGTGCTTCTGTTGCAAATTTTAATTTA |
| wsxfull.13.2.variant | 2264 | CGGTTCTGGCCATCAATTCAATTGGTGCTTCTGTTGCAAATTTTAATTTA |
| wsxfull.6.4.variant | 2401 | ACCTTTTCATGGCCTATGAGCAAAGTAAATATCGTGCACTCACTCAGTGC |
| wsxfull.12.1.variant | 2314 | ACCTTTTCATGGCCTATGAGCAAAGTAAATATCGTGCACTCACTCAGTGC |
| wsxfull.13.2.variant | 2314 | ACCTTTTCATGGCCTATGAGCAAAGTAAATATCGTGCACTCACTCAGTGC |

FIG. 3H

| | | |
|---|---|---|
| wsxfull.6.4.variant | 2451 | TTATCCTTTTAAAACAGCAGTTGTGTGATTGTTTCCTGGATACTATCACCCA |
| wsxfull.12.1.variant | 2364 | TTATCCTTTTAAAACAGCAGTTGTGTGATTGTTTCCTGGATACTATCACCCA |
| wsxfull.13.2.variant | 2364 | TTATCCTTTTAAAACAGCAGTTGTGTGATTGTTTCCTGGATACTATCACCCA |
| | | |
| wsxfull.6.4.variant | 2501 | GTGATTACAAGCTAATGTATATTTTATTATTGAGTGGAAAAATCTTAATGAA |
| wsxfull.12.1.variant | 2414 | GTGATTACAAGCTAATGTATATTTTATTATTGAGTGGAAAAATCTTAATGAA |
| wsxfull.13.2.variant | 2414 | GTGATTACAAGCTAATGTATATTTTATTATTGAGTGGAAAAATCTTAATGAA |
| | | |
| wsxfull.6.4.variant | 2551 | GATGGTGAAAATAAAAAAATGGCTTAGAATCTCTTCATCTCTGTTAAGAAGTATTA |
| wsxfull.12.1.variant | 2464 | GATGGTGAAAATAAAAAAATGGCTTAGAATCTCTTCATCTCTGTTAAGAAGTATTA |
| wsxfull.13.2.variant | 2464 | GATGGTGAAAATAAAAAAATGGCTTAGAATCTCTTCATCTCTGTTAAGAAGTATTA |
| | | |
| wsxfull.6.4.variant | 2601 | TATCCATGATCATTTTATCCCCATTGAGAAGTACCAGTTCAGTCTTTACC |
| wsxfull.12.1.variant | 2514 | TATCCATGATCATTTTATCCCCATTGAGAAGTACCAGTTCAGTCTTTACC |
| wsxfull.13.2.variant | 2514 | TATCCATGATCATTTTATCCCCATTGAGAAGTACCAGTTCAGTCTTTACC |
| | | |
| wsxfull.6.4.variant | 2651 | CAATATTTATGGAAGGAGTGGGAAAAACCAAAGATAATTAATAGTTTCACT |
| wsxfull.12.1.variant | 2564 | CAATATTTATGGAAGGAGTGGGAAAAACCAAAGATAATTAATAGTTTCACT |
| wsxfull.13.2.variant | 2564 | CAATATTTATGGAAGGAGTGGGAAAAACCAAAGATAATTAATAGTTTCACT |
| | | |
| wsxfull.6.4.variant | 2701 | CAAGATGATATTGAAAACACCAGAGTGATGCAGGTTTATATGTAATTGT |
| wsxfull.12.1.variant | 2614 | CAAGATGATATTGAAAACACCAGAGTGATGCAGGTTTATATGTAATTGT |
| wsxfull.13.2.variant | 2614 | CAAGATGATATTGAAAACACCAGAGTGATGCAGGTTTATATGTAATTGT |

```
wsxfull.12.1.variant  2964  GACCTTTGTTCACTTGTTATCTGCTGACCCTCCCTCCACTATTGTCCTA
wsxfull.13.2.variant  2964  AGATCTTGAAAAGGGTTCGTTGTTGTATTAGTGACCAGTTCACAGTTA wsxfull.12.1.variant  3014  TGACCCTGCCAAATCCCCCCTCTGTGAGAACACCCAGAATCAATA
wsxfull.13.2.variant  3014  ACTTCTCTGAGGCTGAGGGTACTGAGGTAACCTATGAGGACGAAAGCCAG wsxfull.12.1.variant  3064  AAAAAAAAAAAAGTCGACTCGAGAATTC..........
wsxfull.13.2.variant  3064  AGACAAACCCTTTGTTAAATACGCCACGCTGATCAGCAACTCTAAACCAAG wsxfull.13.2.variant  3114  TGAAACTGGTGAAGAACAAGGGCTTATAAATAGTTCAGTCACCAAGTGCT wsxfull.13.2.variant  3164  TCTCTAGCAAAAATTCTCCGTTGAAGGATTCTTTCTCTAATAGCTCATGG wsxfull.13.2.variant  3214  GAGATAGAGGCCCAGGCATTTTTTATATTATCAGATCAGCATCCCAACAT wsxfull.13.2.variant  3264  AATTTCACCACACCTCACACATTCTCAGAAAAATAATGATAAAAAGTCTATCTATTAT wsxfull.13.2.variant  3314  TGGAGGGAAATTTCCCTGAAGAATCAAAAAGAGAGAGTGGTGCTTTTGAAAT wsxfull.13.2.variant  3364  TTAGGGGTCACCTCAAGGGTATCGTGCCCATTCCCAGCCCCCTGTTTATTCACGGACTGA wsxfull.13.2.variant  3414  CAAGTCAAGGGTATCGTGCCCATTCCCAGCCCCCTGTTTATTCACGGACA wsxfull.13.2.variant  3464  TCAGAGTTCTCCAGGACAGTTGCTCACACTTTGTAGAAAATAATATCAAC
```

FIG. 3K wsxfull.13.2.variant 3514 TTAGGAACTTCTAGTAAGAAGACTTTTGCATCTTACATGCCTCAATTCCA wsxfull.13.2.variant 3564 AACTTGTTCTACTCAGACTCATAAGATCATGGAAAACAAGATGTGACC wsxfull.13.2.variant 3614 TAACTGTGTAATTTCACTGAAGAAACCTTCAGATTTGTGTTATAATGGGT wsxfull.13.2.variant 3664 AATATAAAGTGTAATAGATTATAGTTGTGGGTGGGAGAGAGAAAAGAAAC wsxfull.13.2.variant 3714 CAGAGTCAAATTTGAAAATAATTGTTCCAAATGAATGTTGTCTGTTTGTT wsxfull.13.2.variant 3764 CTCTCTTAGTAACATAGACAAAAATTTGAGAAAGCCTTCATAAGCCTAC wsxfull.13.2.variant 3814 CAATGTAGACACGCTCTTCTATTTATTCCCAAGCTCTAGTGGGAAGGTC wsxfull.13.2.variant 3864 CCTTGTTTCCAGCTAGAAATAAGCCCAACAGACACCATCTTTGTGAGAT wsxfull.13.2.variant 3914 GTAAATTGTTTTTTCAGAGGGCGTGTTTTACCTCAAGTTTTTGTTTTG wsxfull.13.2.variant 3964 TACCAACACACACACACACATTCTTAACACATGTCCTTGTGTGTTT wsxfull.13.2.variant 4014 TGAGAGTATATTATGTATTTATTTTGTGCTATCAGACTGTAGGATTTG wsxfull.13.2.variant 4064 AAGTAGGACTTTCCTAAATGTTTAAGATAAACAGAATTC

FIG. 3L

```
wsxfull.13.2.variant    1    MICQKFCVVLLHWEFIYVITAFNLSYPITPWRFKLSCMPPNSTYDYFLLP
mu.wsx.ecd              1    MMCQKFYVVLLHWEFLYVIAALNLAYPISPWKFKLFCGPPNTDDSFLSP wsxfull.13.2.variant   51    AGLSKNTSNSNGHYETAVEPKFNSSGTHFSNLSKTTFHCCFRSEQDRNCS
mu.wsx.ecd             51    AGAPNNASALKGASEAIVEAKFNSSGIYVPELSKTVFHCCFGNEQGQNCS wsxfull.13.2.variant  101    LCADNIEGKTFVSTVNSLVFQQIDANWNIQCWLKGDLKLFICYVESLFKN
mu.wsx.ecd            101    ALTDNTEGKTLASVVKASVFRQLGVNWDIECWMKGDLTLFICHMEPLPKN wsxfull.13.2.variant  151    LFRNYNYKVHLLYVLPEVLEDSPLVPQKGSFQMVHCNCSVHECCECLVPV
mu.wsx.ecd            151    PFKNYDSKVHLLYDLPEVIDDSPLPPLKDSFQTVQCNCSLRG-CECHVPV wsxfull.13.2.variant  201    PTAKLNDTLLMCLKITSGGVIFQSPLMSVQPINMVKPDPPLGLHMEITDD
mu.wsx.ecd            200    PRAKLNYALLMYLEITSAGVSFQSPLMSLQPMLVKPDPPLGLHMEVTDD wsxfull.13.2.variant  251    GNLKISWSSPPLVPFFPLQYQVKYSENSTTVIREADKIVSATSLLVDSILP
mu.wsx.ecd            250    GNLKISWDSQTMAPFPLQYQVKYLENS-TIVREAAEIVSATSLLVDSVLP
```

FIG. 4A

```
wsxfull.13.2.variant  301  GSSYEVQVRGKRLDGPGIWSDWSTPRVFTTQDVIYFPPKILTSVGSNVSF
mu.wsx.ecd            299  GSSYEVQVRSKRLDGSGVWSDWSSPQVFTTQDVVYFPPKILTSVGSNASF wsxfull.13.2.variant  351  HCIYKKENKIVPSKEIVWWMNLAEKIPQSQYDVVSDHVSKVTFFNLNETK
mu.wsx.ecd            349  HCIYKNENQIVSSKQIVWWRNLAEKIPEIQYSIVSDRVSKVTFSNLKATR wsxfull.13.2.variant  401  PRGKFTYDAVYCCNEHECHHRYAELYVIDVNINISCETDGYLTKMTCRWS
mu.wsx.ecd            399  PRGKFTYDAVYCCNEQACHHRYAELYVIDVNINISCETDGYLTKMTCRWS wsxfull.13.2.variant  451  TSTIQSLAESTLQLRYHRSSLYCSDIPSIHPISEPKDCYLQSDGFYECIF
mu.wsx.ecd            449  PSTIQSLVGSTVQLRYHRCSLYCPDSPSIHPTSEPKTASYRETAFMNVFS wsxfull.13.2.variant  501  QPIFLLSGYTMWIRINHSLGSLDSPPTCVLPDSVVKPLPPSSVKAEITIN
mu.wsx.ecd            499  SQSFYYLAIQCGFRINHSLGSLDSPPTCVLPDSVVKPLPPSNVKAEITVN wsxfull.13.2.variant  551  IGLLKISWEKPVFPENNLQFQIRYGLSGKEVQWKMYEVYDAKSKSVSLPV
mu.wsx.ecd            549  TGLLKVSWEKPVFPENNLQFQIRYGLSGKEIQWKTHEVFDAKSKSASLLV
```

FIG. 4B

| | | |
|---|---|---|
| wsxfull.13.2.variant | 601 | P D L C A V Y A V Q V R C K R L D G L G Y W S N W S N P A Y T V V M D I K V P M R G P E F W R I I N |
| mu.wsx.ecd | 599 | S D L C A V Y V V Q V R C R R L D G L G Y W S N W S S P A Y T L V M D V K V P M R G P E F W R K M D |
| wsxfull.13.2.variant | 651 | G D T M K K E K N V T L L W K P L M K N D S L C S V Q R Y V I N H H T S C N G T W S E D V G N H T K |
| mu.wsx.ecd | 649 | G D V T K K E R N V T L L W K P L T K N D S L C S V R R Y V V K H R T A H N G T W S E D V G N R T N |
| wsxfull.13.2.variant | 701 | F T F L W T E Q A H T V T V L A I N S I G A S V A N F N L T F S W P M S K V N I V Q S L S A Y P L N |
| mu.wsx.ecd | 699 | L T F L W T E P A H T V T V L A V N S L G A S L V N F N L T F S W P M S K V S A V E S L S A Y P L S |
| wsxfull.13.2.variant | 751 | S S C V I V S W I L S P S D Y K L M Y F I I E W K N L N E D G E I K W L R I S S S V K K Y Y I H D H |
| mu.wsx.ecd | 749 | S S C V I L S W T L S P D D Y S L L Y L V I E W K I L N E D D G M K W |
| wsxfull.13.2.variant | 801 | F I P I E K Y Q F S L Y P I F M E G V G K P K I I N S F T Q D D I E K H Q S D A G L Y V I V P V I I |
| wsxfull.13.2.variant | 851 | S S S I L L L G T L L I S H Q R M K K L F W E D V P N P K N C S W A Q G L N F Q K P E T F E H L F I |

FIG. 4C

```
wsxfull.13.2.variant   901  KHTASVTCGPLLLEPETISEDISVDTSWKNKDEMMPTTVVSLLSTTDLEK
wsxfull.13.2.variant   951  GSVCISDQFNSVNFSEAEGTEVTYEDESQRQPFVKYATLISNSKPSETGE
wsxfull.13.2.variant  1001  EQGLINSSVTKCFSSKNSPLKDSFSNSSWEIEAQAFFILSDQHPNIISPH
wsxfull.13.2.variant  1051  LTFSEGLDELLKLEGNFPEENNDKKSIYYLGVTSIKKRESGVLLTDKSRV
wsxfull.13.2.variant  1101  SCPFPAPCLFTDIRVLQDSCSHFVENNINLGTSSKKTFASYMPQFQTCST
wsxfull.13.2.variant  1151  QTHKIMENKMCDLTV
```

FIG. 4D

```
mu.wsx.ecd    1 GGGCCCCCCCTCGAAGTCGACGGTATCGATAAGCTTGATATCGAATTCCG
mu.wsx.ecd   51 GCCGGGGACACAGGTGGGACACTCTTTTAGTCCTCAATCCCTGGCGCGAGG
mu.wsx.ecd  101 CCACCCAAGGCAACGCAGGACGCAGGGCGTTTGGGGACCAGGCAGCAGAC
mu.wsx.cd   151 TGGGGCGGTACCTGCGGAGAGCCACGCAACTTCTCCAGGCCTCTGACTAC
mu.wsx.ecd  201 TTTGGAAACTGCCCGGGGCTGCGACATCAACCCCTTAAGTCCCGGAGGCG
mu.wsx.ecd  251 GAAAGAGGGTGGGTTTGGTTTGAAAGACACAAGGAAGAAAAATGTGCTGTG
mu.wsx.ecd  301 GGGCGGGGTTAAGTTTCCCACCCTCTTCCCCCTTCCCGAGCAAATTAGAAA
mu.wsx.ecd  351 CAAAACAAATAGAAAAAGCCAGCCCTCCGGCCAACCAAAGCCAAGCGGA
wsxfull.13.2.variant 1 ......................................GAATTCTGAGTCGAC
```

```
mu.wsx.ecd              2794 A C C T G A T T A T A G T C T G T T T A T A T C T G G T T A T T G A T G G A A G A T C C T T A
wsxfull.13.2.variant    2409 A C C C A G T G A T T A C A A G C T A A T G T A T T T T T A T T G A G T G G A A A A T C T T A mu.wsx.ecd              2844 A T G A A G A T G A T G G A A T G A A G T G G C T
wsxfull.13.2.variant    2459 A T G A A G A T G G T G A A A T A A A A T G G C T T A G A A T C T C T T C A T C T G T T A A G A A G wsxfull.13.2.variant    2509 T A T T

```
wsxfull.13.2.variant  2809  TTTGAGCATCTTTTTATCAAGCATACAGCATCAGTGACATGTGGTCCTCT wsxfull.13.2.variant  2859  TCTTTTGGAGCCTGAAACAATTTCAGAAGATATCAGTGTTGATACATCAT wsxfull.13.2.variant  2909  GGAAAAATAAAGATGAGATGATGCCAACAACTGTGGTCTCTCTACTTTCA wsxfull.13.2.variant  2959  ACAACAGATCTTGAAAAGGGTTCTGTTTGTATTAGTGACCAGTTCAAACAG wsxfull.13.2.variant  3009  TGTTAACTTCTCTCTGAGGCTGAGGGTACTGAGGTAACCTATGAGGACGAAA wsxfull.13.2.variant  3059  GCCAGAGACAACCCTTTGTTAAATACGCCACGCTGATCAGCAACTCTAAA wsxfull.13.2.variant  3109  CCAAGTGAAACTGGTGAAGAACAAGGGCTTATAAATAGTTCAGTCACCAA wsxfull.13.2.variant  3159  GTGCTTCTCTAGCAAAAATTCTCCGTTGAAGGATTCTTTCTCTAATAGCT wsxfull.13.2.variant  3209  CATGGGAGATAGAGGCCCAGGCATTTTTTATATTATCAGATCAGCATCCC
```

FIG. 5K

```
wsxfull.13.2.variant  3259  AACATAATTTTCACCACACCCTCACATTCTCAGAAGGATTGGATGAACTTTT
wsxfull.13.2.variant  3309  GAAATTGGAGGGAAATTTCCCTGAAGAAAATAATGATAAAAAGTCTATCT
wsxfull.13.2.variant  3359  ATTATTTAGGGGTCACCCTCAATCAAAAAGAGAGAGAGTGGTGTGCTTTTG
wsxfull.13.2.variant  3409  ACTGACAAGTCAAGGGTATCGTGCCCATTCCCAGCCCCCTGTTTATTCAC
wsxfull.13.2.variant  3459  GGACATCAGAGAGTTCTCCAGGACAGTTGCTCACACTTTGTAGAAAATAATA
wsxfull.13.2.variant  3509  TCAAACTTAGGAACTTCTAGTAAGAAGACTTTTGCATCTTACATGCCTCAA
wsxfull.13.2.variant  3559  TTCCAAACTTGTTCTACTCAGACTCATAAGATCATGGAAAACAAGATGTG
wsxfull.13.2.variant  3609  TGACCTAACTGTGTAATTTCACTGAAGAAACCTTCAGATTTGTGTTATAA
wsxfull.13.2.variant  3659  TGGGTAATATAAAGTGTAATAGATTATAGTTGTGGGTGGGAGAGAGAAAA
```

FIG. 5L

```
wsxfull.13.2.variant  3709  GAAACCAGAGTCAAATTTGAAAATAATTGTTCCAAATGAATGTTGTCTGT wsxfull.13.2.variant  3759  TTGTTCTCTCTTAGTAACATAGACAAAAATTTGAGAAAGCCTTCATAAG wsxfull.13.2.variant  3809  CCTACCAATGTAGACACGCTCTTCTATTTTATTCCCAAGCTCTAGTGGGA wsxfull.13.2.variant  3859  AGGTCCCTTGTTTCCAGCTAGAAATAAGCCAACAGACAOCATCTTTTGT wsxfull.13.2.variant  3909  GAGATGTAATTGTTTTTCAGAGGGCGTGTTTTACCTCAAGTTTTG wsxfull.13.2.variant  3959  TTTTGTACCAACACACACACACACACATTCTTAACACATGTCCTTGTG wsxfull.13.2.variant  4009  TGTTTTGAGAGTATATTATGTATTTATTTTGTGCTATCAGACTGTAGG wsxfull.13.2.variant  4059  ATTTGAAGTAGGACTTTCCTAAATGTTTAAGATAAACAGAATTC
```

FIG. 5M

Murine

| | | | |
|---|---|---|---|
| -213 | Sense: | GGGTTAAGTTTCCCACCC | (SEQ ID NO:9) |
| | Antisense: | GGGTGGGAAACTTAACCC | (SEQ ID NO:10) |
| | Scrambled: | AGGATACAGTGGGATCCC | (SEQ ID NO:11) |
| -99 | Sense: | GCCCGAGCACTCCTTTAA | (SEQ ID NO:12) |
| | Antisense: | TTAAAGGAGTGCTCCCGC | (SEQ ID NO:13) |
| | Scrambled: | GAGCGGCCCTGTTAGATA | (SEQ ID NO:14) |
| -20 | Sense: | GTATACCTCTGAAGAA | (SEQ ID NO:15) |
| | Antisense: | TTCTTCAGAGGTGTACAC | (SEQ ID NO:16) |
| | Scrambled: | ATGCGAGGCTACTTCTAT | (SEQ ID NO:17) |
| +84 | Sense: | CTCTCCCTGGAAATTTAA | (SEQ ID NO:18) |
| | Antisense: | TTAAATTTCCAGGGAGAG | (SEQ ID NO:19) |
| | Scrambled: | ATTTGAAGGAGTTAAGCC | (SEQ ID NO:20) |
| +211 | Sense: | AATTTAATTCAAGTGGTA | (SEQ ID NO:21) |
| | Antisense: | TACCAGTTGAATTAAATT | (SEQ ID NO:22) |
| | Scrambled: | GTATCACTTCATAATATA | (SEQ ID NO:23) |

Human

| | | | |
|---|---|---|---|
| 5L | Sense: | GATGGTCAGGGTGAACTG | (SEQ ID NO:24) |
| | Antisense: | CAGTTCACCCTGACCATC | (SEQ ID NO:25) |
| | Scrambled: | GAGGCGAATGTGCGGATT | (SEQ ID NO:26) |
| +85 | Sense: | CTTAAATCTCCAAGGAGT | (SEQ ID NO:27) |
| | Antisense: | ACTCCTTGGAGATTTAAG | (SEQ ID NO:28) |
| | Scrambled: | AAGTCTTAAGCCAGACTT | (SEQ ID NO:29) |
| -47 | Sense: | TCTAAGGCACATCCCAGC | (SEQ ID NO:30) |
| | Antisense: | GCTGGGATGTGCCTTAGA | (SEQ ID NO:31) |
| | Scrambled: | CGCAATGAATTGACCCCC | (SEQ ID NO:32) |
| -20 | Sense: | TACTTCAGAGAAGTACAC | (SEQ ID NO:33) |
| | Antisense: | GTGTACTTCTCTGAAGTA | (SEQ ID NO:34) |
| | Scrambled: | GAATCACGGTAACTATCA | (SEQ ID NO:35) |
| +185 | Sense: | CAGCTGTCTCATAATGTC | (SEQ ID NO:36) |
| | Antisense: | GACATTATGAGACAGCTG | (SEQ ID NO:37) |
| | Scrambled: | TTCGTCAAGCCATCTGAT | (SEQ ID NO:38) |

FIG. 7

```
> sites: std
> length: 7127 (circular)

aluI
      sstI
      sacI
      hgiJII
      hgiAI/aspHI
      ecl136II
      bsp1286
      bsiHKAI
      bmyI                                rmaI   tru9I
      banII                               maeI   mseI                                                                                                  thaI
      taqI                          speI  aseI/asnI/vspI                                                                bslI                           fnuDII/mvnI
                                                                                                                                                       bstUI
                                                                                                                                                       bsh1236I
                                                                                                                                                       aclI maeIII
  1 TTCGAGCTCG CCCGACATTG ATTATTGACT AGTAATCAAT AGTATTGACT TACGGGGTCA TTAGTTCATA GCCCATATAT GGAGTTCCGC GTTACATAAC
    AAGCTCGAGC GGGCTGTAAC TAATAACTGA TCATTAGTTA TCATTAGTTA ATGCCCCAGT AATCAAGTAT CGGGTATATA CCTCAAGGCG CAATGTATTG scrFI
                    mvaI
                    ecoRII
                    dsaV
                    aclI
                    bglI bstNI                                    maeII
                    sau96I                                        hinlI/acyI
                    haeIII/palI        aclI                       ahaII/bsaHI
                    asuI apyI[dcm+]                               atlI           maeII
101 TTACGGTAAA TGGCCCGCCT GGCTGACCGC CCAACGACCC CCGCCCATTG ACGTCAATAA ACGTCAATAG GGACTTTCCA
    AATGCCATTT ACCGGGCGGA CCGACTGGCG GGTTGCTGGG GGCGGGTAAC TGCAGTTATT TGCAGTTATC CCTGAAAGGT maeII                                                                                                       maeII
      hinlI/acyI                                                                                                  hinlI/acyI
      ahaII/bsaHI                                  rsaI                ndeI                                       ahaII/bsaHI
      aatII                                        csp6I                                                          aatII
201 TTGACGTCAA TGGGTGGAGT ATTTACGGTA AACTGCCCAC TTGGCAGTAC ATCAAGTGTA TCATATGCCA AGTACGCCCC CTATTGACGT CAATGACGGT
    AACTGCAGTT ACCCACCTCA TAAATGCCAT TTGACGGGTG AACCGTCATG TAGTTCACAT AGTATACGGT TCATGCGGGG GATAACTGCA GTTACTGCCA

FIG. 16A
```

```
              scrFI
              mvaI
              ecoRII
         aclI
         bglI  dsaV
         sau96I bstNI                                                                           nlaIII
         haeIII/palI                                                          styI
         asuI  apyI(dcm+)      rsaI                     rsaI        maeII              ncoI
              bsrI nlaIII      csp6I                    csp6I       snaBI              dsaI hphI acII
301 AAATGGCCCG CCTGGCATTA TGCCCAGTAC ATGACCTTAT GGGACTTTCC TACTTGGCAG TACATCTACG TATTAGTCAT CGCTATTACC ATGGTGATGC                                                                                                        bsaJI sfaNI
    TTTACCGGGC GGACCGTAAT ACGGGTCATG TACTGGAATA CCCTGAAAGG ATGAACCGTC ATGTAGATGC ATAATCAGTA GCGATAATGG TACCACTACG maeII
                                                                    hinII/acyI
              rsaI                          pleI                    ahaII/bsaHI                       nlaIV
              csp6I                  acII   hinfI            bsmAI  aatII                             hglCI
401 GGTTTTGGCA GTACATCAAT CGGCGTGAT AGCGGTTGA CTCACGGGGA TTTCCAAGTC TCCACCCCAT TGACGTCAAT GGGAGTTTGT TTTGGCACCA                                                                                                          banI
    CCAAAACCGT CATGTAGTTA GCCGCACTA TCGCCAACT GAGTGCCCCT AAAGGTTCAG AGGTGGGGTA ACTGCAGTTA CCCTCAAACA AAACCGTGGT aluI
                                                                                                      sstI
                                                                                                      sacI
                                                                                                      hgiJII
                                                                                                      hgiAI/aspHI
                                                rsaI                                                  ecl136II
              maeIII   acII                     csp6I       mnlI                                      bsp1286
501 AAATCAACGG GACTTTCCAA AATGTCGTAA CAACTCGCTAA CAATTGACGC CCATTGACGC AAATGGGGCG TAGGCGTGTA CGGTGGGAGG TCTATATAAG CAGAGCTCGT                                                                                            bslHKAI
    TTTAGTTGCC CTGAAAGGTT TTACAGCATT GTTGAGCGGG GGTAACTGCG TTTACCCGCC ATCCGCACAT GCCACCCTCC AGATATATTC GTCTCGAGCA                                                                                                        bmyI
                                                                                                      banII
```

```
                                                                                    sau96I
                                                                                    avaII
                                                                                    asuI
                                                                                    scrFI
                                                                                    mvaI
                                                                                    ecoRII
                                                                                    dsaV
                                                                                    bstNI
                                                              foKI                  apyI[dcm+]
                                         maeIII          scfI                  bslI bsaJI
                                    hphI      scfI                             
 801 CATAACCTTA TGTATCATAC ACATACGATT TAGGTGACAC CATCCACTTT GCCTTTCTCT CCACAGGTGT CCACTCCCAG GTCCAACTGC
     GTATTGGAAT ACATAGTATG TGTATGCTAA ATCCACTGTG ATATCTTATT GTAGGTGAAA CGGAAAGAGA GGTGTCCACA CAGGTTGACG
                                                          ^sp6 RNA start ppu10I                    tfiI         sau96I
           taqI nsiI/avaIII           hinfI       haeIII/palI         bsp1286
     mnlI  claI/bsp106  nlaIV         aciI       asuI         aluI bmyI fokI
 901 ACCTCGGTTC TATCGATATG CATTGGGGAA CCCTGTGCGG ATTCTTGTGG CTTTGGCCCT ATCTTTTCTA TGTCCAAGCT GTGCCCATCC AAAAAGTCCA
     TGGAGCCAAG ATAGCTATAC GTAACCCCTT GGGACACGCC TAAGAACACC GAAACCGGGA TAGAAAAGAT ACAGGTTCGA CACGGGTAGG TTTTTCAGGT
   1  Met HisTrpGlyT hrLeuCysGl yPheLeuTrp LeuTrpProT yrLeuPheTy rValGlnAla ValProLeuG lnLysValGln
     ^cl ning linker ^human OB start sau3AI
                              mboI/ndeII[dam-]
                              dpnII[dam+]
                         scrFI
                         mvaI                                          mspI
                         ecoRII                                  hpaII
                         dsaV                                    cfr10I        bsaWI
                         bstNI                                                 ageI
                        apyI[dcm+]                                             hphI
          mnlI     hphI  dpnII[dam-]                              bsmAI         maeIII
1001 AGATGACACC AAAACCCTCA TCAAGACAAT TGTCACCAGG ATCAATGACA TTTCACACAC GCAGTCAGTC TCCTCCAAAC AGAAAGTCAC CGGTTTGGAC
     TCTACTGTGG TTTTGGGAGT AGTTCTGTTA ACAGTGGTCC TAGTTACTGT AAAGTGTGTG CGTCAGTCAG AGGAGGTTTG TCTTTCAGTG GCCAAACCTG
  29 AspAspThr LysThrLeuI leLysThrI eValThrArg IleAsnAspI leSerHisTh rGlnSerVal SerSerLysG lnLysValTh rGlyLeuAsp
```

```
                                                        acII
                                                        thaI
                                                        fnuDII/mvnI
                                                        bstUI
                                                        bsh1236I
                                                        sacII/sstII
                                                        nspBII
                                                        kspI                                                                              scrFI
                                                        dsaI                                                                              mvaI
                                                        bsaJI                                                rsaI                         ecoRII
                                                        acII                                                csp6I                         dsaV
                  mnlI                                  fnu4HI mnlI              rsaI            maeII                  hphI      ecoNI bstNI
                                                                                 csp6I           bsaAI                  mnlI      bslI apyI(dcm+)
1601  CCTGGACGGC GTGGAGGTGC ATAATGCCAA GACAAAGCCG CGGGACGAGC AGTACAACAG CACGTACCGT GTGGTCAGCG TCCTCACCGT CCTGCACCAG
      GGACCTGCCG CACCTCCACG TATTACGGTT CTGTTTCGGC GCCCTGCTCG TCATGTTGTC GTGCATGGCA CACCAGTCGC AGGAGTGGCA GGACGTGGTC
229   ValAspGly ValGluValH lsAsnAlaLy sThrLysPro ArgGluGluG lnTyrAsnSe rThrTyrArg ValValSerV alLeuThrVa lLeuHisGln fnu4HI
          bsrI                             rsaI             bsmAI                                           bbvI  avaI
                                           csp6I            bsaI                 mnlI           taqI
1701  GACTGGCTGA ATGGCAAGGA GTACAAGTGC AAGGTCTCCA ACAAAGCCCT CCCAGCCCCC ATCGAGAAAA CCATCTCCAA AGCCAAAGGG CAGCCCGAG
      CTGACCGACT TACCGTTCCT CATGTTCACG TTCCAGAGGT TGTTTCGGGA GGGTCGGGGG TAGCTCTTTT GGTAGAGGTT TCGGTTTCCC GTCGGGCTC
262   AspTrpLeuA sNGlyLysGl uTyrLysCys LysValSerA sNLysAlaLe uProAlaPro IleGluLysT hrIleSerLy sAlaLysGly GlnProArgGlu scrFI
                         ncII
                         mspI
                         hpaII
                         dsaV
                         cauII
                         xmaI/pspAI
                         smaI
                         scrFI                                                  scrFI
                         ncII                                                   mvaI
                         dsaV                                                   ecoRII
                         cauII                                                  dsaV
          rsaI                         fokI                                     bstNI                                 dsaI
          csp6I           bslI bsaJI mboII                                      apyI(dcm+)                            bslI
          bsp1407I        bslI avaI  earI/ksp632I                               sexAI                                 bspMI            bsaJI
1801  AACCACAGT GTACACCCTG CCCCATCCC GGGAAGAGAT GACCAAGAAC CAGGTCAGCC TGACCTGCCT GGTCAAAGGC TTCTATCCCA GCGACATCGC
      TTGGTGTCCA CATGTGGGAC GGGGTAGGG CCCTTCTCTA CTGGTTCTTG GTCCAGTCGG ACTGGACGGA CCAGTTTCCG AAGATAGGGT CGCTGTAGCG
296   ProGlnVa lTyrThrLeu ProProSerA rgGluGluMe tThrLysAsn GlnValSerL euThrCysLe uValLysGly PheTyrPros erAspIleAla
```

```
                                                                                                          rsaI
                                                                                                          csp6I
                                                                        haeIII/palI                       nlaIV
                                                                        haeI                              kpnI
                                                                                                          hgiCI                          scrFI
                                            tru9I               fnu4HI styI                               banI                           mvaI                  bstNI
                    taqI[dam-]                                  bbvI   ncoI                               asp718                         ecoRII               apyI[dcm+]
                    claI/bsp106[dam-]       mseI                hinPI  dsaI                       mnlI    acc65I ddeI aclI               dsaV                 sexAI
              sau3AI                                    asel/asnI/vspI bsaJI                                                scrFI   sfaNI                     scrFI
              mboI/ndeII[dam-]                          hhaI/cfoI nlaIII         mnlI       mnlI                            mvaI    ppuI0I                     nlaIV
       nlaIII alwI[dam-] asp700                     ^sv40 origin                                                            ecoRII   nslII/avaIII             sphI      nspI sfaNI
2301 CTTATCATGT CTGGATCGAT CGGGAATTAA TTCGGGCCAG CACCATGGCC TGAAATAACC TCTGAAAGAG GAACTTGGTT AGGTACCTTC TGAGGCGGAA
     GAATAGTACA GACCTAGCTA GCCCTTAATT AAGCCCGGTC GTGGTACCGG ACTTTATTGG AGACTTTCTC CTTGAACCAA TCCATGGAAG ACTCCGCCTT nlaIV
                                                    scrFI                                                   scrFI
                                                    mvaI                                                    mvaI                    bstNI
                                                    ecoRII                                                  ecoRII                  apyI[dcm+]
                                                    dsaV                                 ppuI0I             dsaV                    sexAI
              aluI                                  bstNI                   sfaNI        nslII/avaIII       bstNI                   scrFI
              pvuII                                 apyI[dcm+]                           nlaIII            sphI     nspI            nlaIV
              nspBII                                bsaJI                                                          nspHI
2401 AGAACCAGCT GTGAATGTG TGTCAGTTAG GGTGTGGAAA GTCCCCAGGC TCCCCACCAG GCAGAAGTAT GCAAAGCATG CATCTCCAATT AGTCAGCAAC
     TCTTGGTCGA CACCTTACAC ACAGTCAATC CCACACCTTT CAGGGGTCCG AGGGGTGGTC CGTCTTCATA CGTTTCGTAC GTAGAGTTAA TCAGTCGTTG aclI   aclI fokI
                                                                                                           aclI          CGCCCCTAAC TCCGCCATC
2501 CAGGTGTGGA AAGTCCCAG GCTCCCCAGC AGGCAGAGAAGT ATGCAAAGCA TGCATCTCCAA TTAGTCAGCA ACCATAGTCC CGCCCCTAAC TCCGCCATC
     GTCCACACCT TTCAGGGGTC CGAGGGGTCG TCCGTCTTCA TACGTTTCGT ACGTAGAGTT AATCAGTCGT TGGTATCAGG GCGGGGATTG AGGCGGTAG
```

FIG. 16I

```
                                                      fnu4HI
                                                      bglI
                                                      sfiI
                                      nlaIII          haeIII/palI
                                      styI            mnlI  mnlI   ddeI
                                      ncoI            haeIII/palI bsaJI mnlI  alul                    scrFI
                        bsrI          bslI dsaI       mnlI bsaJI aclI  haeIII/palI                    mvaI
       aclI  aclI       aclI bsaJI                                                                    sau96I
                                                                                                      nlaIV
                                                                                                      avaII    sau96I
                                                                                                      thaI     ecoRII
                                                                                                      fnuDII/mvnI
                                                                                                      bstUI    dsaV
                                                                                                      bsh1236I avaII
                                                                                                      hinPI    bstNI
                                                                                                      hhaI/cfoI asuI
                                                                                                      fnu4HI asuI apyI[dcm+]
                                                                                                      aclI aclI  bsaJI              sau3AI
                                                                                                                                    mboI/ndeII[dam-]
                                                                                                                                    dpnI[dam+]
2601 CCGCCCCTAA CTCCGGGCCAG TTCCGCCCCAT TCTCCGCCCC ATGGCTGACT AATTTTTTT ATTTATGCAT CGCCTCGGCC TCTGAGCTAT GGGGGGCGGG TCCCAGGTCC
     GGCGGGGATT GAGGGCCGGTC AAGGCGGGTA AGAGGCGGGG TACCGACTGA TTAAAAAAAA TAAATACGTC TCCGGCTCCG GGGAGCCGG AGACTCGATA CCGCCGGCCC AGGGTCCAGG
                                                                                                                                    sau3AI
                                                                                                                                    mboI/ndeII[dam-]
                                                                                                                                    dpnI[dam+]
                                                                             sfuI                                                   bstYI/xhoII
                                                                             bstBI                                                  bglII  dpnII[dam-]
                                  styI                                       bsiCI                                                  fnu4HI   bclI[dam-]
                                  bsaJI                                      asuI
                                  blnI                 tru9I
                             haeIII/palI               alul msel taqI    sfaNI
                             stuI rmaI
                             haeI maeI
                      mnlI   mnlI avrII
2701 TCCAGAAGTA GTGAGGAGGC TTTTTTGGAG GCCTAGGCTT TTGCAAAAAG CTGTTAATTC GAACACGCAG ATGCAGTCGG CTTGTGCGTC TACGTCAGCC CCCCGGCGCC AGGGTCCAGG
     AGGTCTTCAT CACTCCTCCG AAAAAACCTC CGGATCCGAA AACGTTTTTC GACAATTAAG CTTGTGCGTC GAACACGCAG ATGCAGTCGG
                                                                            ^start pUC118
                                                                                      ^TK promoter
                                      fnu4HI
                                      bbvI
                                      scfI
                              haeIII/palI    pstI                    tru9I  hincII/hindII aclI dpnII[dam-] bsmAI
     thaI                     haeI  taqI    bsgI       aclI msel hgaI       fnu4HI bclI[dam-]
     fnuDII/mvnI
     bstUI
     mluI
     aflIII
     hphI bsh1236I mnlI
     tru9I hgaI   haeIII/palI
     msel maeIII   haeI  taqI
2801 ACTTCGCATA TTAAGGTGAC GGCTGTGGCC TCGAACACGG AGCGACCCTG CAGCGACCCG AGGCGACCGT TCAACAGCGT GCCAGCAGATC TGATCAAGAG
     TGAAGCGTAT AATTCCACTG CCGACACCGG AGCTTGTGGC TCGCTGGGAC GTCGCTGGGC GAATTGTCGCA CGGTGTCGCA CGGCGTCTAG ACTAGTTCTC
                                                           tn5 neomycin phosphotransferase gene.  ^
```

```
                                                                                fnu4HI           sau3AI
     scrFI                                                                      fnu4HI           mboI/ndeII[dam-]
     ncII         sau3AI                                                        acII             dpnI[dam+]
     mspI         mboI/ndeII[dam-]                                              fnu4HI           dpnII[dam-]
     hpaII        dpnI[dam+]                                                    acII  bbvI       alwI[dam-]
     dsaV         dpnII[dam-]                           nlaIII    sfaNI         gcgggcgctg   catacgcttg
     cauII        bstYI/xhoII            hphI                                   cgcccgac    gtatgcaac
     bsaJI        alwI[dam-]
3201 TTGGGCGAAG TGCCGGGGCA GGATCTCCTG TCATCTCACC TTGCTCCTGC CGAGAAAGTA TCCATCATGG CTGATGCAAT GCGGGCGCTG CATACGCTTG
     AACCCGCTTC ACGGCCCCGT CCTAGAGGAC AGTAGAGTGG AACGAGGACG GCTCTTTCAT AGGTAGTACC GACTACGTTA CGCCCGCGAC GTATGCGAAC sau3AI
                                                                                                mboI/ndeII[dam-]
                                                rsaI                                            fokI
                                                csp6I                                           sau3AI    dpnI[dam+]
                                                bsaAI                                           mboI/ndeII[dam-]    sapI
                                                hgiAI/aspHI                                     dpnI[dam+]           mboII
                                                bsp1286                            mspI         dpnII[dam-] dpnII[dam-]
                              taqI   bsiHKAI             bmyI maeII     fokI       hpaII        taqI[dam-] dpnII[dam-]  earI/ksp632I
     mspI            sfaNI                                              cfr10I              taqI[dam-] dpnII[dam-]
     hpaII bspMI       taqI
3301 ATCCGGCTAC CTGCCATTC GACCACCAAG CGAAACATCG CATCGAGCGA GCACGTACTC GGATGGAAGC CGGTCTTGTC GATCAGGATG ATCTGGACGA
     TAGGCCGATG GACGGTAAG CTGGTGGTTC GCTTTGTAGC GTAGCTCGCT CGTGCATGAG CCTACCTTCG GCCAGAACAG CTAGTCCTAC TAGACCTGCT sphI
                        nspI
                        nspHI
              hinPI
              thaI                                       sau3AI
              fnuDII/mvnI                                mboI/ndeII[dam-]
              bstUI                                      dpnI[dam+]               styI
              scrFI    fnuDII/mvnI                       dpnI[dam-]
              mval     bstUI                             bstYI/xhoII     ncoI
     hgiJII   ecoRII    bsh1236I                         alwI[dam-]      dsaI
     bsp1286  dsaV   hinPI  nlaIII                       mnlI       maeIII   nlaIII
     bmyI bsh1236I   bstNI  hhaI/cfoI
     sfaNI  banII hhaI/cfoI  apyI[dcm+]  bssHII
3401 AGAGCATCAG GGGCTCGCGC CAGCCGAACT GTTCGCCAGG CTCAAGCGCG CATGCCCGA CGGCGAGGAT CTCGTCGTGA CCATGGCCGA TGCCTGCTTG
     TCTCGTAGTC CCCGAGCGCG GTCGGCTTGA CAAGCGGTCC GAGTTCGCGC GTACGGGCT GCCGCTCCTA GAGCAGCACT GGTACCGGCT ACGGACGAAC

FIG. 16L
```

```
                                                                  bslI
                                              mspI                sau96I
                                              hpaII               avaII
                                              naeI                asuI
                                              cfr10I              rsrII/cspI
                                              haeIII/palI         cpoI
                acII                          eaeI                acII acII
                fnu4HI               tfII     cfrI                hinPI
                haeIII/palI          hinfI    taqI                hhaI/cfoI
           eaeI                                                           bsrBI     tfII  fnu4HI
           cfrI                                                           acII      hinfI bbvI sfaNI
     nlaIII                                                               fnu4HI    hinfI bbvI sfaNI
3501 CCGAATATCA TGGTGGAAAA TGGCCCGCTTT TCTGGATTCA TCGACTGTGG CCCGGCTGGGT GTGGCGGACC CATAGGGTTG GCTACCCGTG
     GGCTTATAGT ACCACCTTTT ACCGGGCGAAA AGACCTAAGT AGCTGACACC GGGCCGACCCA CACCGCCTGG CGATAGTCCT GTATCGCAAC CGATGGGCAC sapI
     mboII     fnu4HI                                                               hinPI
     earI/ksp632I                                                          bsrBI   hhaI/cfoI
     eco57I aluI acII                           acrI mnlI                  acII    tfII fnu4HI              tfII   acII
3601 ATATTGCTGA AGAGCTTGGC GGGGAATGGG CTGACCGCTT CCTCGTGCTT TACGGTATCG TTCGCAGCGC CCCCTCCCGA ATCGCCTTCT ATCGCCTTCT
     TATAACGACT TCTCGAACCG CCCGCTTACCC GACTGGCGAA GGAGCACGAA ATGCCATAGC GGGAGGGCT AAGCGGTCGCG TAGCGGAAGA TAGCGGAAGA taqI
                         sfuI
                         bstBI
                acII     bsiCI          hinII/acyI
          ddeI  pleI     asuII          hgaI    bspMI                                     tfII    acII
          mboII bsrBI hinfI             ahaII/bsaHI                                       hinfI   fnu4HI
3701 TGACGAGTTC TTCTGAGCGG GACTCTGGGG TTCGAAATGA CCGACCAAGC GACGCCCAAC CTGCCATCAC GAGATTTCGA TTCCACCGCC GCCTTCTATG
     ACTGCTCAAG AAGACTCGCC CTGAGACCCC AAGCTTTACT GGCTGGTTCG CTGCGGGTTG GACGGTAGTG CTCTAAAGCT AAGGTGGCGG CGGAAGATAC

FIG. 16M
```

```
                                                                                                      scrFI
                                                                                                      ncII
                                                                                                      mspI
                                                                                                      hpaII
                                                                                                      dsaV
                                                                                                      cauII
                                                                                                      bsII
                                                              thaI   sau3AI                           xmaI/pspAI
                                              hinlI/acyI     bslI  fnuDII/mvnI                        smaI
                                              hgaI           gsuI/bpmI  bstYI/xhoII                   scrFI
                                              ahaII/bsaiII  mnII  hinPI alwII[dam-]                   ncII
                                scrFI         sau3AI        hhaI/cfoI            gsuI/bpmI            dsaV
                                ncII          mboI/ndeII[dam-] mboI/ndeII[dam-]                       cauII
                                mspI   mspI   dpnI[dam+] bstUI  dpnI[dam+]                            bsaJI
                                hpaII  hpaII  dpnII[dam-] acII dpnII[dam-]                            bsaJI
                        tfII    dsaV   naeI   cfr10I fokI alwII[dam-] bshI236I  nlaIII   mboII bslI avaI
                        hinfI   cauII  cfr10I fokI alwII[dam-] ACGCCGGCTG GATGATCCTC CAGCGCGGGG ATCTCATGCT GGAGTTCTTC GCCCACCCCG GGAGATGGGG
3801 AAAGGTTGGG CTTCGGAATC GTTTTCCGGG ACGCCGGCTG GATGATCCTC CAGCGCGGGG ATCTCATGCT GGAGTTCTTC GCCCACCCCG GGAGATGGGG
     TTTCCAACCC GAAGCCTTAG CAAAAGGCCC TGCGGCCGAC CTACTAGGAG GTCGCGCCCC TAGAGTACGA CCTCAAGAAG CGGGTGGGGC CCTCTACCCC
                                                                                              HSV1 tk terminator SmaI-PvuII
                                              hinPI
                                              hhaI/cfoI
                                              thaI
                                              fnuDII/mvnI
                                 mspI         bstUI
                                 hpaII        bshI236I
                         bsaWI   nlaIV acII
                mnII
3901 GAGGCTAACT GAAACACGGA AGGAGACAAT ACCGGAAGGA ACCCGCGCTA TGACGGCAAT AAAAAGACAG AATAAAACGC ACCGGGTGTG GGTCGTTTGT
     CTCCGATTGA CTTTGTGCCT TCCTCTGTTA TGGCCTTCCT TGGGCGCGAT ACTGCCGTTA TTTTTCTGTC TTATTTTGCG TGGCCACAC CCAGCAAACA
              scrFI
              mvaI
              ecoRII
              dsaV
              bstNI
              bsaJI
              bslI
      acII    sau96I
      thaI    nlaIV                                                   haeIII/palI  thaI
      fnuDII/mvnI  bsaJI                                              sau96I      fnuDII/mvnI
      bstUI   avaII                                    bsmAI          asuI        bstUI
      bshI236I  asuI apyI[dcm+]    taqI                bsaI           nlaIV       bshI236I
                                                                                  acII      mboII
4001 TCATAAACGC GGGGTTCGGT CCCAGGGCTG GCACTCTGTC GATACCCCAC CGAGACCCCA TTGGGCCAA TACGCCCGCG TTTCTTCCTT TTCCCACCCC
     AGTATTTGCG CCCCAAGCCA GGGTCCCGAC CGTGAGACAG CTATGGGGTG GCTCTGGGGT AACCCCGGTT ATGCGGGCGC AAGAAGGAA AAGGGGTGGG
```

```
                                                                                      acII
                                                                                      thaI
                                                                                      fnuDII/mvnI
                                                                                      bstUI
                                                                                      sacII/sstII
                                                                        haeIII/palI bshl236I
                                                                                 mcrI   nspBII
                                                                            dsaI        kspI
                                                                            bsaJI       dsaI
                                                                    hphI eagI/xmaIII/eclXI
                                                                    maeIII  eaeI      bsaJI
                                                                    bstEII  cfrI      acII
          mspI                                                                              hinPI  mspI
          hpaII                         mnlI     hinPI                                      hhaI/cfoI
     acII           bslI                rsaI     hhaI/cfoI                          thaI    hpaII
     fnu4HI                   sfaNI     csp6I    haeII                                      fnuDII/mvnI
                                        eco47III                                            bstUI  bsaWI
                                                                                            bshl236I
                                                                                   fnu4HI   aciI  bslI
                                                                      mboII        aciI bcgI     nlaIII
                                                                      bpuAI
                                                             nlaIII   bbsI
```

4401 GCCGCCGGAC GAACTAAACC TGACTACGGC ATCTCTGCCC CTTCTTCGCT GGTACGAGGA GCCCTTTTGT TTTGTATTGG TCACCACGGC CGAGTTTCCG
     CGGCGGCCTG CTTGATTTGG ACTGATGCCG TAGAGACGGG GAAGAAGCGA CCATGCTCCT CGGGAAAACA AAACATAACC AGTGGTGCCG GCTCAAAGGC

```
     scrFI       nlaIV
     ncII        hgiCI
     dsaV   scrFI
     cauII  mvaI
     bslI   ecoRII
     bsaJI  dsaV
     sau96I bstNI
     nlaIV  bsaJI
     avaII  haeIII/palI
     asuI   eaeI
     ppuMI  cfrI  bsp1286
     nlaIV  mspI  apyI(dcm+)
     eco0109I/draII bmyI
                  banI
```

4501 CGGGACCCCG GCCAGGCGAC CTGTCCTACG AGTTGCATGA TAAAGAAGAC AGTCATAAGT GCGGCGACGA TAGTCATGCC CCGCGCCCAC CGGAAGGAGC
     GCCCTGGGGC CGGTCCGCTG GACAGGATGC TCAACGTACT ATTTCTTCTG TCAGTATTCA CGCCGCTGCT ATCAGTACGG GGCGCGGGTG GCCTTCCTCG

^pBR322 sequence

```
                                                                                              thaI
                                                                                              fnuDII/mvnI
                                       tru9I                                  tru9I    apoI  tru9I
                                       mseI                    alul    mseI    mseI   bstUI  mseI    sspI
                    haeIII/palI
5001 GGGCTATTCT TTTGATTTAT AAGGGATTTT GCCGATTTCG GCCTATTGGT TAAAAAATGA GCTGATTTAA CAAAATTTA ACGGGAATTT TAACAAAATA
     CCCGATAAGA AACTAATA TTCCCTAAAA CGGCTAAAGC CGGATAACCA ATTTTTACT CGACTAAATT GTTTTAAAT TGCCCTTAAA ATTGTTTTAT
                        mnlI
      maeII         haeIII/palI                                                                         maeII
      psp1406I      stuI                                       tru9I    rcaI                            hinII/acyI
      tru9I         haeI                                       mseI    bspHI                            ahaII/bsaHI
      mseI                                        nlaIII                                   ddeI   aatII
5101 TTAACGTTTA CAATTTATG GTGCAGGCCT CGTGATACGC CTATTTTTAT AGTTAATGT CATGATAATA ATGGTTTCTT AGACGTCAGG TGGCACTTTT
     AATTGCAAAT GTTAAATAC CACGTCCGGA GCACTATGCG GATAAAAATA TCCAATTACA GTACTATTAT TACCAAAGAA TCTGCAGTCC ACCGTGAAAA
                                                ^delta 2a
              nlaIV
              aciI
              thaI
              fnuDII/mvnI                                                 rcaI
              bstUI                                                       bspHI
              bsh1236I                                                  bsrBI   bsmAI
              hinPI                                                     aciI nlaIII                      sspI
              hhaI/cfoI
5201 CGGGGAAATG TGCGCGGAAC CCCTATTGT TTATTTTCT AAATACATTC CCGCTCATGA GACAATAACC CTGATAAATG CTTCAATAAT
     GCCCCTTTAC ACGCGCCTTG GGGATAAACA AATAAAAGA TTTATGTAAG GGCGAGTACT CGTTATTGG GACTATTTAC GAAGTTATTA
       mboII                                                 fnu4HI                                     hphI
       earI/ksp632I                                          aciI
5301 ATTGAAAAAG GAAGAGTATG AGTATTCAAC ATTTCCGTGT CGCCCTTATT CCCTTTTTTG CGGCATTTTG CCTTCCTGTT TTTGCTCACC CAGAAACGCT
     TAACTTTTTC CTTCTCATAC TCATAAGTTG TAAAGGCACA GCGGGAATAA GGGAAAAAAC GCCGTAAAAC GGAAGGACAA AACGACGTGG GTCTTTGCGA
                                      hgiAI/aspHI
                                      bsp1286                          sau3AI                sau3AI
                                      bsiHKAI                          mboI/ndeII[dam-]      mboI/ndeII[dam-]
                 sau3AI                                                dpnI[dam+]            dpnI[dam+]
                 mboI/ndeII[dam-]  bmyI                                dpnII[dam-]           dpnII[dam-]
                 dpnI[dam+]                                            bstYI/xhoI            alwI[dam-]
                 dpnII[dam-]              apaLI/snoI             bsrI     alwI[dam-]  aciI   bstYI/xhoII
        hphI     eco57I    sfaNI mboII[dam-] alw44I/snoI maeIII taqI  alwI[dam-]  nspBII              mboII
5401 GGTGAAAGTA AAGATGCTG AAGATCAGTT GGTGCACGA GTGGGTTACA TCGAACTGGA TCTCAACAGC GGTAAGATCC TTGAGAGTTT TCGCCCCGAA
     CCACTTTCAT TTCTACGAC TTCTAGTCAA CCACGTGCT CACCCAATGT AGCTTGACCT AGAGTTGTCG CCATTCTAGG AACTCTCAAA AGCGGGGCTT
```

```
                                                                                       mspI
                                                                                       hpaII
                                               hinPI                                   bslI       fnu4HI
                                               hhaI/cfoI                               bsaWI     acII
                        ddeI          scfI     haeII                          acII
6701 CGAACGACCT ACACCGAACT GAGATACCTA CAGGGTGAGC ATTGAGAAAG CGCCACGCTT CCCGAAGGGA GAAAGGCGGA CAGGTATCCG GTAAGCGGCA
     GCTTGCTGGA TGTGGCTTGA GTCTATGGAT GTCCACTCG TAACTCTTTC GCGGTGCGAA GGGCTTCCCT CTTTCCGCCT GTCCATAGGC CATTCGCCGT scrFI                                                                           taqI
                             mvaI                  scrFI                               mnlI drdI             hgaI
                             ecoRII      mvaI                  dsaV
                hinPI mnlI   dsaV        ecoRII                bstNI
                hhaI/cfoI alu nlaIV  bstNI        bsaJI apyI[dcm+]
6801 GGGTCGGAAC AGGAGGAGC ACGAGGGAGC TTCCAGGGGG AAACGCCTGG TATCTTTATA GTCCTGTCGG GTTTCGCCAC CTCTGACTTG AGGGTCGATT
     CCCAGCCTTG TCCTCTCGCG TGCTCCCTCG AAGGTCCCCC TTTGCGGACC ATAGAAATAT CAGGACAGCC CAAAGCGGTG GAGACTGAAC TCGCAGCTAA aluI                                                                tru9I
                                         pvuII                                                               mseI
      sfaNI                               nspBII                                        hinPI
                   nlaIV                                                                hhaI/cfoI asei/asnI/vspI
              acII                                                    bsrI    acII
6901 TTTGTGATGC TCGTCAGGGG GGCGGAGCCA ATGGAAAAAC GCCAGCTGGC ACGACAGGTT TCCCGACTGG AAAGCGGGCA GTGAGCCCAA CGCAATTAAT
     AAACACTACG AGCAGTCCCC CCGCCTCGGA TACCTTTTTG CGGTCGACCG TGCTGTCCAA AGGGCTGACC TTTGCGCCCGT CACTCGGGTT GCGTTAATTA
                                                                      ^deltal.PVU scrPI
                            mvaI
                            ecoRII                                              mspI
                            dsaV                                                hpaII
                       nlaIV bstNI                                                          acII
         mnlI         hglCI apyI[dcm+]                                                      bsrBI
         maeIII       banI  bsaJI
7001 GTGAGTTACC TCACTCATTA GGCACCCAG GCTTTACACT TTATGCTTCC GGCTCGTATG TTGTGTGTGA TTGTGACGCG ATAACAATTT CACACAGGAA
     CACTCAATGG AGTGAGTAAT CCGTGGGGTC CGAAATGTGA AATACGAAGG CCGAGCATAC AACACACACT AACACTCGCC TATTGTTAAA GTGTGTCCTT tru9I
                mseI
                aseI/asnI/vspI
         xmnI
     aluI  nlaIII   asp700
7101 ACAGCTATGA CCATGATTAC GAATTAA
     TGTCGATACT GGTACTAATG CTTAATT >length: 7127
```

FIG. 16V

METHOD FOR ENHANCING PROLIFERATION OR DIFFERENTIATION OF A CELL USING OB PROTEIN

CROSS REFERENCE

This application is a continuation-in-part of co-pending U.S. application Ser. No. 08/585,005 filed Jan. 8, 1996, which is now provisional application 60/064,855, filed Jan. 8, 1996, now abandoned which application is incorporated herein by reference and to which application priority is claimed under 35 USC §120.

BACKGROUND OF THE INVENTION

1. Field of the Invention

The present invention pertains generally to the WSX receptor. In particular, the invention relates to WSX ligands and uses therefor.

2. Description of Related Art

A. Hematopoiesis

The process of blood cell formation whereby red and white blood cells are replaced through the division of cells located in the bone marrow is called hematopoiesis. For a review of hematopoiesis see Dexter and Spooncer (*Ann. Rev. Cell Biol.* 3:423–441 (1987)).

There are many different types of blood cells which belong to distinct cell lineages. Along each lineage, there are cells at different stages of maturation. Mature blood cells are specialized for different functions. For example, erythrocytes are involved in $O_2$ and $CO_2$ transport; T and B lymphocytes are involved in cell and antibody mediated immune responses, respectively; platelets are required for blood clotting; and the granulocytes and macrophages act as general scavengers and accessory cells. Granulocytes can be further divided into basophils, eosinophils, neutrophils and mast cells.

Each of the various blood cell types arises from pluripotent or totipotent stem cells which are able to undergo self-renewal or give rise to progenitor cells or Colony Forming Units (CFU) that yield a more limited array of cell types. As stem cells progressively lose their ability to self-renew, they become increasingly lineage restricted. It has been shown that stem cells can develop into multipotent cells (called "CFC-Mix" by Dexter and Spooncer, supra). Some of the CFC-Mix cells can undergo renewal whereas others lead to lineage-restricted progenitors which eventually develop into mature myeloid cells (e.g., neutrophils, megakaryocytes, macrophages and basophils). Similarly, pluripotent stem cells are able to give rise to PreB and PreT lymphoid cell lineages which differentiate into mature B and T lymphocytes, respectively. Progenitors are defined by their progeny, e.g., granulocyte/macrophage colony-forming progenitor cells (GM-CFU) differentiate into neutrophils or macrophages; primitive erythroid burst-forming units (BFU-E) differentiate into erythroid colony-forming units (CFU-E) which give rise to mature erythrocytes. Similarly, the Meg-CFU, Eos-CFU and Bas-CFU progenitors are able to differentiate into megakaryocytes, eosinophils and basophils, respectively.

Hematopoietic growth factors (reviewed in D'Andrea, *NEJM* 330(12):839–846 (1994)) have been shown to enhance growth and/or differentiation of blood cells via activation of receptors present on the surface of blood progenitor cells of the bone marrow. While some of these growth factors stimulate proliferation of restricted lineages of blood cells, others enhance proliferation of multiple lineages of blood cells. For example, erythropoietin (EPO) supports the proliferation of erythroid cells, whereas interleukin-3 (IL-3) induces proliferation of erythroid and myeloid lineages and is therefore considered a multi-lineage factor.

In recent years, several hematopoietic growth factor receptors have been isolated. Due to their low abundance and their existence in both high-affinity and low-affinity forms, biochemical characterization of these receptors has been hampered.

Cytokine receptors frequently assemble into multi-subunit complexes. Sometimes, the α subunit of this complex is involved in binding the cognate growth factor and the β-subunit may contain an ability to transduce a signal to the cell. These receptors have been assigned to three subfamilies depending on the complexes formed. Subfamily 1 includes the receptors for erythropoietin (EPO), granutocyte colony-stimulating factor (G-CSF), interleukin-4 (IL-4), interleukin-7 (IL-7), growth hormone (GH) and prolactin (PRL). Ligand binding to receptors belonging to this subfamily is thought to result in homodimerization of the receptor. Subfamily 2 includes receptors for IL-3, granulocyte-macrophage colony-stimulating factor (GM-CSF), interleukin-5 (IL-5), interleukin-6 (IL-6), leukemia inhibitory factor (LIF), oncostatin M (OSM) and ciliary neurotrophic factor (CNTF). Subfamily 2 receptors are heterodimers having an α-subunit for ligand binding and β-subunit (either the shared β-subunit of the IL-3, GM-CSF and IL-5 receptors or the gp130 subunit of the IL-6, LIF, OSM and CNTF receptors) for signal transduction. Subfamily 3 contains only the interleukin-2 (IL-2) receptor. The β and γ subunits of the IL-2 receptor complex are cytokine-receptor polypeptides which associate with the α subunit of the unrelated Tac antigen.

B. Obesity

Obesity is the most common nutritional disorder which, according to recent epidemiologic studies, affects about one third of all Americans 20 years of age or older. Kuczmarski et al., *J. Am. Med. Assoc.* 272:205–11 (1994). Obesity is responsible for a variety of serious health problems, including cardiovascular disorders, type II diabetes, insulin-resistance, hypertension, hypertriglyceridemia, dyslipoproteinemia, and some forms of cancer. Pi-Sunyer, F., *Anns. Int. Med.* 119: 655–60 (1993); Colfitz, G., *Am. J. Clin. Nutr.* 55:503S–507S (1992). A single-gene mutation (the obesity or "ob" mutation) has been shown to result in obesity and type II diabetes in mice. Friedman, *Genomics* 11:1054–1062 (1991).

Zhang et al., *Nature* 372:425431 (1994) have recently reported the cloning and sequencing of the mouse ob gene and its human homologue, and suggested that the ob gene product, leptin or OB protein, may function as part of a signalling pathway from adipose tissue that acts to regulate the size of the body fat depot. Parabiosis experiments performed more than 20 years ago predicted that the genetically obese mouse containing two mutant copies of the ob gene (ob/ob mouse) does not produce a satiety factor which regulates its food intake, while the diabetic (db/db) mouse produces but does not respond to a satiety factor. Coleman and Hummal, *Am. J. Physiol.* 217:1298–1304 (1969); Coleman, *Diabetol* 9:294–98 (1973). Recent reports by three independent research teams have demonstrated that daily injections of recombinant OB protein inhibit food intake and reduce body weight and fat in grossly obese ob/ob mice but not in db/db mice (Pelleymounter et al., *Science* 269:540–43 (1995); Halaas et al., *Science* 269:543–46 (1995); Campfield et al., *Science* 269: 546–49 (1995)), suggesting that the OB protein is such a satiety factor as proposed in early cross-circulation studies.

Researchers suggest that at least one OB receptor is localized in the brain. The identification and expression cloning of a leptin receptor (OB-R) was reported by Tartaglia et al. *Cell* 83:1263–71 (1995). Various isoforms of a OB receptor are described by Cioffi et al. *Nature* 2:585–89 (1996). See, also, WO 96/08510.

The mouse db gene has recently been cloned (Lee et al. *Nature* 379:632 (1996) and Chen et al. *Cell* 84:491–495 (1996)). Previous data had suggested that the db gene encoded the receptor for the obese (ob) gene product, leptin (Coleman et al., *Diebetologia* 9:294–8 (1973) and Coleman et al., *Diebetologia* 14:141–8 (1978)). It has been very recently confirmed that the db/db mouse results from a truncated splice variant of the OB receptor which likely renders the receptor defective in signal transduction (Lee et al., *Nature* 379:632 (1996) and Chen et al., *Cell* 84: 491–495 (1996)).

SUMMARY OF THE INVENTION

In one aspect, the present invention pertains to the discovery herein that WSX ligands, such as obesity (OB) protein, play a role in hematopoiesis via signalling through the WSX receptor. The role of the WSX receptor-ligand signalling pathway appears to be at the level of the early hematopoietic precursor as is evident by the ability of OB protein to simulate myelopoiesis, erythropoiesis (e.g. splenic erythropoiesis) and most dramatically, lymphopoiesis. Accordingly, WSX ligands can be used to stimulate proliferation and/or differentiation and/or survival of hematopoietic progenitor cells either in vitro or in vivo (e.g. for treating hematopoietic diseases or disorders).

Thus, the invention provides a method for stimulating proliferation and/or differentiation of a cell which expresses the WSX receptor (especially the WSX receptor variant 13.2, which is demonstrated herein to have the capacity to transmit a proliferative signal) at its cell surface comprising the step of contacting the WSX receptor with an amount of WSX ligand which is effective for stimulating proliferation and/or OB protein differentiation of the cell. In prefered embodiments, the cell which is exposed to the WSX ligand is a hematopoeitic precursor, e.g. a CD34+ cell. The WSX ligand may be OB protein or an agonist antibody which binds to the WSX receptor. For in vivo use, the WSX ligand of choice may be a long half-life derivative of an OB protein, such as OB-immunoglobulin chimera and/or OB protein modified with a nonproteinaceous polymer, such as polyethylene glycol (PEG). The method contemplated herein may lead to an increase in the proliferation and/or differentiation of lymphoid, myeloid and/or erythroid blood cell lineages and encompasses both in vitro and in vivo methods. For in vitro uses, the cell possessing the WSX receptor may be present in cell culture. As to in vivo methods, the cell may be present in a mammal, especially a human (e.g. one who is suffering from decreased blood levels and who could benefit from an increase in various blood cells). Potential patients include those who have undergone chemo- or radiation therapy, or bone marrow transplantation therapy. Thus, the invention provides a method for repopulating blood cells (e.g. erythroid, myeloid and/or lymphoid blood cells) in a mammal comprising administering to the mammal a therapeutically effective amount of a WSX ligand.

Mammals which may benefit from an enhancement of lymphopoiesis include those predisposed to, or suffering from, any ony or more of the following exemplary conditions: lymphocytopenia; lymphorrhea; lymphostasis; immunodeficiency (e.g. HIV and AIDS); infections (including, for example, opportunistic infections and tuberculosis (TB)); lupus; and other disorders characterized by lymphocyte deficiency. An effective amount of the WSX ligand can be used in a method of immunopotentiation or to improve immune function in a mammal.

On the other hand, WSX receptor or WSX ligand antagonists (such as WSX receptor ECD or immunoadhesin, and WSX receptor or OB protein neutralizing antibodies) may be used in the treatment of those disorders wherein unacceptable lymphocyte levels are present in the mammal, particularly where this is caused by excessive activation of the WSX receptor. Examples of conditions in which administration of such an antagonist may be beneficial include: neoplastic disorders (such as Hodkin's disease; lymphosarcoma; lymphoblastoma; lymphocytic leukemia; and lymphoma) and lymphocytosis.

Diseases or disorders in which an increase in erythropoiesis may be beneficial include, but are not limited to: erythrocytopenia; erthrodegenerative disorders; erythroblastopenia; leukoerythroblastosis; erythroclasis; thalassemia; and anemia (e.g. hemolytic anemia, such as acquired, autoimmune, or microangiopathic hemolytic anemia; aplastic anemia; congenital anemia, e.g., congenital dyserythropoietic anemia, congenital hemolytic anemia or congenital hypoplastic anemia; dyshemopoietic anemia; Faconi's anemia; genetic anemia; hemorrhagic anemia; hyperchromic or hypochromic anemia; nutritional, hypoferric, or iron deficiency anemia; hypoplastic anemia; infectious anemia; lead anemia; local anemia; macrocytic or microcytic anemia; malignant or pernicious anemia; megaloblastic anemia; molecular anemia; normocytic anemia; physiologic anemia; traumatic or posthemorrhagic anemia; refractory anemia; radiation anemia; sickle cell anemia; splenic anemia; and toxic anemia).

Conversely, WSX receptor or WSX ligand antagonists may be used to treat those conditions in which excessive erythrocyte levels are present in a mammal, e.g. in neoplastic disorders such as erythroleukemia; erythroblastosis; and erythrocythemia or polycythemia).

An increase in myelopoiesis may be beneficial in any of the above-mentioned diseases or disorders as well as the following exemplary conditions: myelofibrosis; thrombocytopenia; hypoplasia; disseminated intravascular coagulation (DIC); immune (autoimmune) thrombocytopenic purpura (ITP); HIV induced ITP; myelodysplasia; thrombocytotic diseases and thrombocytosis.

Antagonists of the WSX receptor-WSX ligand interaction may also be used to treat myeloid cell-related conditions such as malignancies (e.g. myelosarcoma, myeloblastoma, myeloma, myeloleukemia and myelocytomatosis); myeloblastosis; myelocytosis; and myelosis.

The method may further involve the step of exposing hematopoeitic cells (whether they be in cell culture or in a mammal) to one or more other cytokines (e.g. lineage-specific cytokines) and this may lead to a synergistic enhancement of the proliferation and/or differentiation of the cells. Exemplary cytokines include thrombopoietin (TPO); erythropoietin (EPO); macrophage-colony stimulating factor (M-CSF); granulocyte-macrophage-CSF (GM-CSF); granulocyte-CSF (G-CSF); interleukin-1 (IL-1); IL-1α; IL-2; IL-3; IL-4; IL-5; IL-6; IL-7; IL-8; IL-9; IL-11; IL10; IL-12; leukemia inhibitory factor (LIF) or kit ligand (KL). In this embodiment, exposure to the cytokine may proceed, occur simultaneously with, or follow, exposure to the WSX ligand. Preferably, the WSX ligand and one or more further cytokines are administered simultaneously to the patient (where the method is an in vivo one) and, optionally, are combined to form a pharmaceutical composition.

For use in the above methods, the invention also provides an article of manufacture, comprising: a container; a label on the container; and a composition comprising an active agent within the container; wherein the composition is effective for enhancing proliferation and/or differentiation of cells comprising the WSX receptor in a mammal, the label on the container indicates that the composition can be used for enhancing proliferation and/or differentiation of those cells and the active agent in the composition is a WSX ligand. Optionally, the article of manufacture includes one or more futher containers which hold further cytokine(s) in a packaged combination with the container holding the WSX ligand.

In another embodiment, an effective amount of the WSX ligand may be used to improve engraftment in bone marrow transplantation or to stimulate mobilization of hematopoietic stem cells in a mammal prior to harvesting hematopoietic progenitors from the peripheral blood thereof.

According to a further aspect, the invention is concerned with the WSX cytokine receptor and a soluble form of the receptor which is the WSX receptor extracellular domain (ECD). The WSX receptor polypeptides are optionally conjugated with, or fused to, molecules which increase the serum half-lives thereof and can be formulated as pharmaceutical compositions comprising the polypeptide and a physiologically acceptable carrier.

In certain embodiments, the WSX receptor ECD may be used as an antagonist insofar as it may bind to WSX ligand and thereby reduce activation of endogenous WSX receptor. This may be useful in conditions characterized by excess levels of WSX ligand and/or excess WSX receptor activation in a mammal. WSX receptor ECD may, for example, be used to treat metabolic disorders (e.g., anorexia or steroid-induced truncalobesity), stem cell tumors and other tumors which express WSX receptor.

Pharmaceutical compositions of the WSX receptor ECD may further include a WSX ligand. Such dual compositions may be beneficial where it is therapeutically useful to prolong the half-life of WSX ligand and/or activate endogenous WSX receptor directly as a heterotrimeric complex.

The invention also relates to chimeric WSX receptor molecules, such as WSX receptor immunoadhesins (having long half-lives in the serum of a patient treated therewith) and epitope tagged WSX receptor. Immunoadhesins may be employed as WSX receptor antagonists in conditions or disorders in which neutralization of WSX receptor biological activity may be beneficial. Bispecific immunoadhesins (combining a WSX receptor ECD with a domain of another cytokine receptor) may form high affinity binding complexes for WSX ligand.

The invention further provides methods for identifying a molecule which binds to and/or activates the WSX receptor. This is useful for discovering molecules (such as peptides, antibodies, and small molecules) which are agonists or antagonists of the WSX receptor. Such methods generally involve exposing an immobilized WSX receptor to a molecule suspected of binding thereto and determining binding of the molecule to the immobilized WSX receptor and/or evaluating whether or not the molecule activates (or blocks activation of) the WSX receptor. In order to identify such WSX ligands, the WSX receptor may be expressed on the surface of a cell and used to screen libraries of synthetic compounds and naturally occurring compounds (e.g., endogenous sources of such naturally occurring compounds, such as serum). The WSX receptor can also be used as a diagnostic tool for measuring serum levels of endogenous WSX ligand.

In a further embodiment, a method for purifying a molecule which binds to the WSX receptor is provided. This can be used in the commercial production and purification of therapeutically active molecules which bind to this receptor. In the method, the molecule of interest (generally a composition comprising one or more contaminants) is adsorbed to immobilized WSX receptor (e.g., WSX receptor immunoadhesin immobilized on a protein A column). The contaminants, by virtue of their inability to bind to the WSX receptor, will generally flow through the column. Accordingly, it is then possible to recover the molecule of interest from the column by changing the elution conditions, such that the molecule no longer binds to the immobilized receptor.

In further embodiments, the invention provides antibodies that specifically bind to the WSX receptor. Preferred antibodies are monoclonal antibodies which are non-immunogenic in a human and bind to an epitope in the extracellular domain of the receptor. Preferred antibodies bind the WSX receptor with an affinity of at least about $10^6$ L/mole, more preferably $10^7$ L/mole.

Antibodies which bind to the WSX receptor may optionally be fused to a heterologous polypeptide and the antibody or fusion thereof may be used to isolate and purify WSX receptor from a source of the receptor.

In a further aspect, the invention provides a method for detecting the WSX receptor in vitro or in vivo comprising contacting the antibody with a sample suspected of containing the receptor and detecting if binding has occurred. Based on the observation herein that CD34+ cells possess WSX receptor, use of WSX antibodies for identification and/or enrichment of stem cell populations (in a similar manner to that in which CD34 antibodies are presently used) is envisaged.

For certain applications, it is desirable to have an agonist antibody which can be screened for as described herein. Such agonist antibodies are useful for activating the WSX receptor for in vitro uses whereby enhancement of proliferation and/or differentiation of a cell comprising the receptor is desired. Furthermore, these antibodies may be used to treat conditions in which an effective amount of WSX receptor activation leads to a therapeutic benefit in the mammal treated therewith. For example, the agonist antibody can be used to enhance survival, proliferation and/or differentiation of a cell comprising the WSX receptor. In particular, agonist antibodies and other WSX ligands may be used to stimulate proliferation of stem cells/progenitor cells either in vitro or in vivo. Other potential therapeutic applications include the use of agonist antibodies to treat metabolic disorders (such as obesity and diabetes) and to promote kidney, liver or lung growth and/or repair (e.g., in renal failure).

For therapeutic applications it is desirable to prepare a composition comprising the agonist antibody and a physiologically acceptable carrier. Optionally, such a composition may further comprise one or more cytokines.

In other embodiments, the antibody is a neutralizing antibody. Such molecules can be used to treat conditions characterized by unwanted or excessive activation of the WSX receptor.

In addition to the above, the invention provides isolated nucleic acid molecules, expression vectors and host cells encoding the WSX receptor which can be used in the recombinant production of WSX receptor as described herein. The isolated nucleic acid molecules and vectors are also useful for gene therapy applications to treat patients with WSX receptor defects and/or to increase responsiveness of cells to WSX ligand.

BRIEF DESCRIPTION OF THE DRAWINGS

FIGS. 1A–J together depict the double stranded nucleotide (SEQ ID NO:1) and deduced amino acid sequence (SEQ ID NO:2) encoding full length human WXS receptor variant 13.2. Nucleotides are numbered at the beginning of the sense strand. Amino acid residues are numbered at the beginning of the amino acid sequence. Restriction enzyme sites are depicted above the nucleotide sequence.

FIGS. 2A–D together depict an amino acid sequence alignment of full length human WSX receptor variants 6.4 (SEQ ID NO:3), 12.1 (SEQ ID NO:4) and 13.2, respectively. Homologous residues are boxed. WSX receptor variants 6.4, 12.1 and 13.2 are native sequence human WSX receptor variants which, without being bound to any one theory, appear to be generated by alternate splicing of WSX receptor mRNA. The putative signal peptide, transmembrane, Box 1, Box 2, and Box 3 domains are indicated. The extracellular and cytoplasmic domains are amino- and carboxy-terminal, respectively, to the transmembrane domain. The Box 1–3 domains shown correspond to the Box 1–3 motifs described in Baumann et al., *Mol. Cell. Biol.* 14(1):138–146 (1994).

FIGS. 3A–L together depict an alignment of the nucleotide sequences encoding human WXS receptor variants 6.4 (SEQ ID NO:5), 12.1 (SEQ ID NO:6) and 13.2, respectively.

FIGS. 4A–D depict an alignment of the full length human WSX receptor variant 13.2 amino acid sequence (top) with that of partial murine WSX receptor extracellular domain sequence (bottom) SEQ ID NO:7) obtained as described in Example 7. The putative murine signal peptide is marked with an arrow.

FIGS. 5A–M represent an alignment of the nucleotide sequences encoding human WSX receptor variant 13.2 (bottom) and partial murine WSX receptor extracellular domain (top) (SEQ ID NO:8), respectively.

FIG. 7 shows the human and murine oligonucleotides (SEQ ID NOS:9–38, respectively) used for the antisense experiment described in Example 8.

In FIG. 8, GH receptor-WSX receptor variant 12.1 or 13.2 chimeric proteins were expressed in Baf-3 cells as described in Example 5. These transfected cells and the parental Baf-3 line were stimulated with hGH and the incorporation of titrated thymidine determined.

In FIG. 9, Baf-3 cells were stably transfected with WSX receptor variant 13.2. Thymidine incorporation was then determined in these cell lines following stimulation with human OB protein.

In FIG. 10A, flASK cells were cultured in suspension culture containing serum with kit ligand (KL) or kit ligand and OB protein. Cell counts and cytospin analyses were performed 7 days later. In FIG. 10B, flASK cells were seeded into methylcellulose under either myeloid or lymphoid conditions as described in Example 10. Colony counts were performed 14 days later. For colonies produced under lymphoid conditions, FACS analysis demonstrated the vast majority of cells to be B220 positive. In FIG. 10C, flASK cells were seeded into methylcellulose containing kit ligand. To this base media, erythropoietin (EPO) or erythropoietin and OB protein were then added. The resultant colonies were counted 14 days later. FACS analysis demonstrated approximately 95% of these colonies to be TER 119 positive. All assays were performed in triplicate and confirmed in at least three independent experiments.

FIG. 12A shows cellular profiles determined using anti-B220, anti-CD43, and anti-TER119 antibodies. FIG. 12B shows cellular profiles of the spleens from the above groups.

FIGS. 16A–V together show the nucleotide sequence (SEQ ID NO:46) and the amino acid sequence (SEQ ID NO:47) of the human OB-immunoglobulin chimera in the plasmid described in Example 11.

DETAILED DESCRIPTION OF THE PREFERRED EMBODIMENTS

I. Definitions

Figure 6:
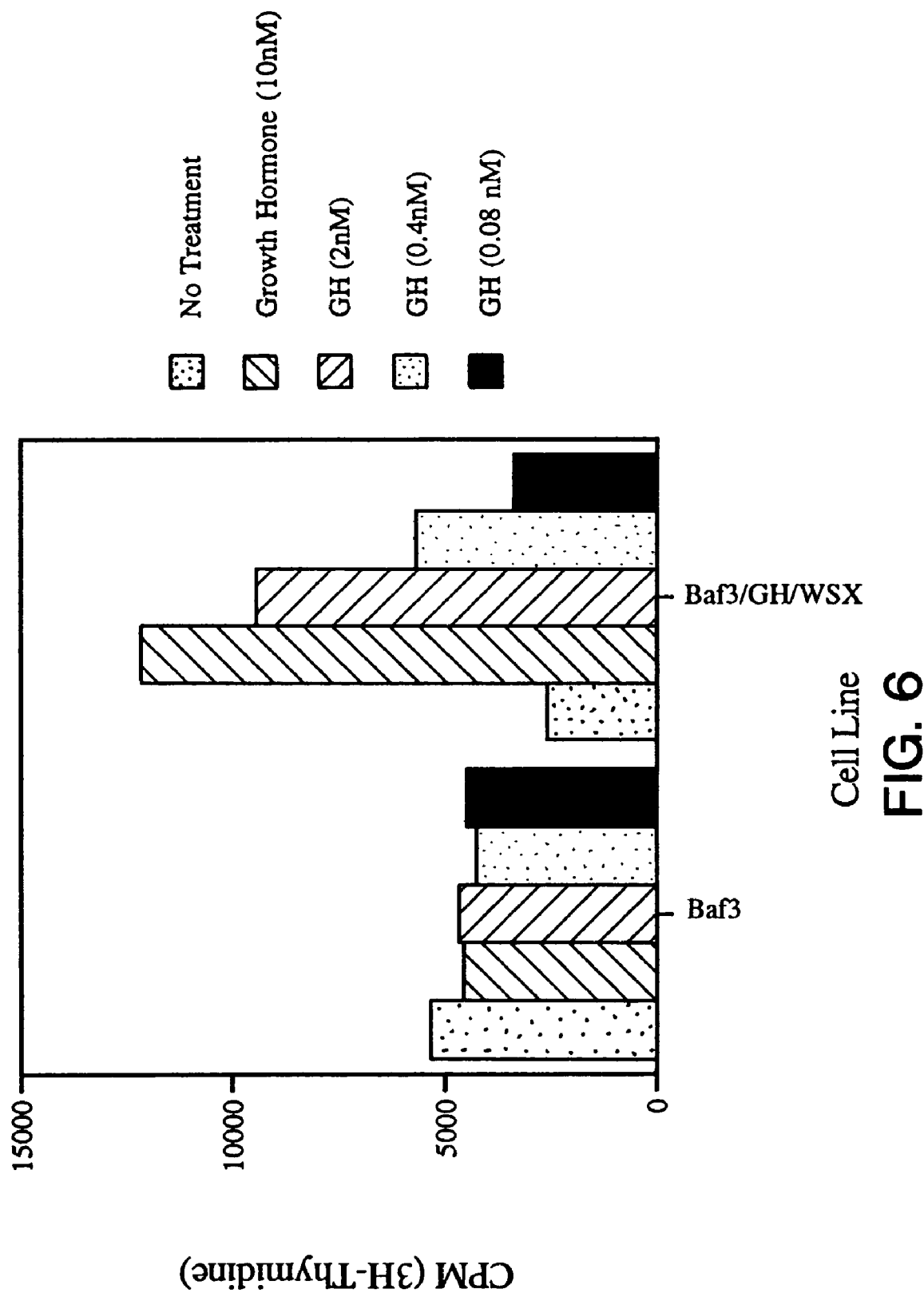
FIG. 6 is a bar graph depicting results of the thymidine incorporation assay described in Example 5. $^3$H-thymidine incorporation (counts per minute, CPM) in parental Baf3 cells or Baf3 cells electroporated with GH/WSX variant 13.2 chimera in the presence of varying concentrations of human growth hormone (GH) is shown.

In describing the present invention, the following terms will be employed, and are intended to be defined as indicated below.

The terms "WSX receptor" or "WSX receptor polypeptide" when used herein encompass native sequence WSX receptor; WSX receptor variants; WSX extracellular domain; and chimeric WSX receptor (each of which is defined herein). Optionally, the WSX receptor is not associated with native glycosylation. "Native glycosylation" refers to the carbohydrate moieties which are covalently attached to WSX receptor when it is produced in the mammalian cell from which it is derived in nature. Accordingly, human WSX receptor produced in a non-human cell is an example of a WSX receptor which is "not associated with native glycosylation". Sometimes, the WSX receptor is unglycosylated (e.g., as a result of being produced recombinantly in a prokaryote).

"WSX ligand" is a molecule which binds to and activates native sequence WSX receptor (especially WSX receptor variant 13.2). The ability of a molecule to bind to WSX receptor can be determined by the ability of a putative WSX ligand to bind to WSX receptor immunoadhesin (see Example 2) coated on an assay plate, for example. The thymidine incorporation assay provides a means for screening for WSX ligands which activate the WSX receptor. Exemplary WSX ligands include anti-WSX receptor agonist antibodies and OB protein (e.g., described in Zhang et al. *Nature* 372:425–431 (1994)).

The terms "OB protein" and "OB" are used interchangeably herein and refer to native sequence OB proteins (also known as "leptins") and their functional derivatives.

A "native sequence" polypeptide is one which has the same amino acid sequence as a polypeptide (e.g., WSX receptor or OB protein) derived from nature. Such native sequence polypeptides can be isolated from nature or can be produced by recombinant or synthetic means. Thus, a native sequence polypeptide can have the amino acid sequence of naturally occurring human polypeptide, murine polypeptide, or polypeptide from any other mammalian species.

The term "native sequence WSX receptor" specifically encompasses naturally-occurring truncated forms of the WSX receptor, naturally-occurring variant forms (e.g., alternatively spliced forms such as human WSX receptor variants 6.4, 12.1 and 13.2 described herein) and naturally-occurring allelic variants of the WSX receptor. The preferred native sequence WSX receptor is a mature native sequence human WSX receptor, such as human WSX receptor variant 6.4, human WSX receptor variant 12.1 or human WSX receptor variant 13.2 (each shown in FIGS. 2A–D). Most preferred is mature human WSX receptor variant 13.2.

The term "native sequence OB protein" includes those OB proteins from any animal species (e.g. human, murine, rabbit, cat, cow, sheep, chicken, porcine, equine, etc.) as occurring in nature. The definition specifically includes variants with or without a glutamine at amino acid position 49, using the amino acid numbering of Zhang et al., supra. The term "native sequence OB protein" includes the native proteins with or without the initiating N-terminal methionine (Met), and with or without the native signal sequence, either in monomeric or in dimeric form. The native sequence human and murine OB proteins known in the art are 167 amino acids long, contain two conserved cysteines, and have the features of a secreted protein. The protein is largely hydrophilic, and the predicted signal sequence cleavage site is at position 21, using the amino acid numbering of Zhang et al., supra. The overall sequence homology of the human and murine sequences is about 84%. The two proteins show a more extensive identity in the N-terminal region of the mature protein, with only four conservative and three non-conservative substitutions among the residues between the signal sequence cleavage site and the conserved Cys at position 117. The molecular weight of OB protein is about 16 kD in a monomeric form.

The "WSX receptor extracellular domain" (ECD) is a form of the WSX receptor which is essentially free of the transmembrane and cytoplasmic domains of WSX receptor, i.e., has less than 1% of such domains, preferably 0.5 to 0% of such domains, and more preferably 0.1 to 0% of such domains. Ordinarily, the WSX receptor ECD will have an amino acid sequence having at least about 95% amino acid sequence identity with the amino acid sequence of the ECD of WSX receptor indicated in FIGS. 2A–D for human WSX receptor variants 6.4, 12.1 and 13.2, preferably at least about 98%, more preferably at least about 99% amino acid sequence identity, and thus includes WSX receptor variants as defined below.

A "variant" polypeptide means a biologically active polypeptide as defined below having less than 100% sequence identity with a native sequence polypeptide (e.g., WSX receptor having the deduced amino acid sequence shown in FIGS. 1A–J for human WSX receptor variant 13.2). Such variants include polypeptides wherein one or more amino acid residues are added at the N- or C-terminus of, or within, the native sequence; from about one to thirty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active WSX receptor variant will have an amino acid sequence having at least about 90% amino acid sequence identity with human WSX receptor variant 13.2 shown in FIGS. 1A–J, preferably at least about 95%, more preferably at least about 99%. Ordinarily, a biologically active OB protein variant will have an amino acid sequence having at least about 90% amino acid sequence identity with a native sequence OB protein, preferably at least about 95%, more preferably at least about 99%.

A "chimeric" OB protein or WSX receptor is a polypeptide comprising OB protein or full-length WSX receptor or one or more domains thereof (e.g., the extracellular domain of the WSX receptor) fused or bonded to heterologous polypeptide. The chimeric WSX receptor will generally share at least one biological property in common with human WSX receptor variant 13.2. The chimeric OB protein will generally share at least one biological property in common with a native sequence OB protein. Examples of chimeric polypeptides include immunoadhesins and epitope tagged polyeptides.

The term "WSX immunoadhesin" is used interchangeably with the expression "WSX receptor-immunoglobulin chimera" and refers to a chimeric molecule that combines a portion of the WSX receptor (generally the extracellular domain thereof) with an immunoglobulin sequence. Likewise, an "OB protein immunoadhesin" or "OB-immunoglobulin chimera" refers to a chimeric molecule which combines OB protein (or a portion thereof) with an immunoglobulin sequence. The immunoglobulin sequence preferably, but not necessarily, is an immunoglobulin constant domain. The immunoglobulin moiety in the chimeras of the present invention may be obtained From IgG1, IgG2, IgG3 or IgG4 subtypes, IgA, IgE, IgD or IgM, but preferably IgG1 or IgG3.

The term "epitope tagged" when used herein refers to a chimeric polypeptide comprising WSX receptor or OB protein fused to a "tag polypeptide". The tag polypeptide has enough residues to provide an epitope against which an antibody thereagainst can be made, yet is short enough such that it does not interfere with biological activity of the WSX receptor or OB protein. The tag polypeptide preferably also is fairly unique so that the antibody thereagainst does not substantially cross-react with other epitopes. Suitable tag polypeptides generally have at least six amino acid residues and usually between about 8–50 amino acid residues (preferably between about 9–30 residues).

"Isolated" WSX receptor (or OB protein) means WSX receptor (or OB protein) that has been purified from a WSX receptor (or OB protein) source or has been prepared by recombinant or synthetic methods and is sufficiently free of other peptides or proteins (1) to obtain at least 15 and preferably 20 amino acid residues of the N-terminal or of an internal amino acid sequence by using a spinning cup sequenator or the best commercially available amino acid sequenator marketed or as modified by published methods as of the filing date of this application, or (2) to homogeneity by SDS-PAGE under non-reducing or reducing conditions using Coomassie blue or, preferably, silver stain. Homogeneity here means less than about 5% contamination with other source proteins.

"Essentially pure" protein means a composition comprising at least about 90% by weight of the protein, based on total weight of the composition, preferably at least about 95% by weight. "Essentially homogeneous" protein means a composition comprising at least about 99% by weight of protein, based on total weight of the composition.

"Biological property" when used in conjunction with either "WSX receptor" or "isolated WSX receptor" means having an effector or antigenic function or activity that is directly or indirectly caused or performed by native sequence WSX receptor (whether in its native or denatured conformation). Effector functions include ligand binding; and enhancement of survival, differentiation and/or proliferation of cells (especially proliferation of cells). However, effector functions do not include possession of an epitope or antigenic site that is capable of cross-reacting with antibodies raised against native sequence WSX receptor.

"Biological property" when used in conjunction with either "OB protein" or "isolated OB protein" means having an effector function that is directly or indirectly caused or performed by native sequence OB protein. Effector functions of native sequence OB protein include WSX receptor binding and activation; and enhancement of differentiation and/or proliferation of cells expressing this receptor (as determined in the thymidine incorporation assay, for example). A "biologically active" OB protein is one which possesses a biological property of native sequence OB protein.

A "functional derivative" of a native sequence OB protein is a compound having a qualitative biological property in common with a native sequence OB protein. "Functional derivatives" include, but are not limited to, fragments of native sequence OB proteins and derivatives of native sequence OB proteins and their fragments, provided that they have a biological activity in common with a corresponding native sequence OB protein. The term "derivative" encompasses both amino acid sequence variants of OB protein and covalent modifications thereof.

The phrase "long half-life" as used in connection with OB derivatives, concerns OB derivatives having a longer plasma half-life and/or slower clearance than a corresponding native sequence OB protein. The long half-life derivatives preferably will have a half-life at least about 1.5-times longer than a native OB protein; more preferably at least about 2-times longer than a native OB protein, more preferably at least about 3-time longer than a native OB protein. The native OB protein preferably is that of the individual to be treated.

An "antigenic function" means possession of an epitope or antigenic site that is capable of cross-reacting with antibodies raised against native sequence WSX receptor. The principal antigenic function of a WSX receptor is that it binds with an affinity of at least about $10^6$ L/mole to an antibody raised against native sequence WSX receptor. Ordinarily, the polypeptide binds with an affinity of at least about $10^7$ L/mole. The antibodies used to define "antigenic function" are rabbit polyclonal antibodies raised by formulating the WSX receptor in Freund's complete adjuvant, subcutaneously injecting the formulation, and boosting the immune response by intraperitoneal injection of the formulation until the titer of the anti-WSX receptor or antibody plateaus.

"Biologically active" when used in conjunction with either "WSX receptor" or "isolated WSX receptor" means a WSX receptor polypeptide that exhibits or shares an effector function of native sequence WSX receptor and that may (but need not) in addition possess an antigenic function. A principal effector function of the WSX receptor is its ability to induce proliferation of CD34+human umbilical cord blood cells in the colony assay described in Example 8.

"Antigenically active" WSX receptor is defined as a polypeptide that possesses an antigenic function of WSX receptor and that may (but need not) in addition possess an effector function.

"Percent amino acid sequence identity" is defined herein as the percentage of amino acid residues in the candidate sequence that are identical with the residues in the native sequence, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the candidate sequence shall be construed as affecting sequence identity or homology.

A "thymidine incorporation assay" can be used to screen for molecules which activate the WSX receptor. In order to perform this assay, IL-3 dependent Baf3 cells (Palacios et al., *Cell*, 41:727–734 (1985)) are stably transfected with full length native sequence WSX receptor as described in Example 4. The WSX receptor/Baf3 cells so generated are starved of IL-3 for, e.g., 24 hours in a humidified incubator at 37° C. in 5% $CO_2$ and air. Following IL-3 starvation, the cells are plated out in 96 well culture dishes with, or without, a test sample containing a potential agonist (such test samples are optionally diluted) and cultured for 24 hours in a cell culture incubator. 20 μl of serum free RPMI media containing 1 μCi of $^3H$ thymidine is added to each well for the last 6–8 hours. The cells are then harvested in 96 well filter plates and washed with water. The filters are then counted using a Packard Top Count Microplate Scintillation Counter, for example. Agonists are expected to induce a statistically significant increase (to a P value of 0.05) in $^3H$ uptake, relative to control. Preferred agonists leads to an increase in $^3H$ uptake which is at least two fold of that of the control.

An "isolated" WSX receptor nucleic acid molecule is a nucleic acid molecule that is identified and separated from at least one contaminant nucleic acid molecule with which it is ordinarily associated in the natural source of the WSX receptor nucleic acid. An isolated WSX receptor nucleic acid molecule is other than in the form or setting in which it is found in nature. Isolated WSX receptor nucleic acid molecules therefore are distinguished from the WSX receptor nucleic acid molecule as it exists in natural cells. However, an isolated WSX receptor nucleic acid molecule includes WSX receptor nucleic acid molecules contained in cells that ordinarily express WSX receptor where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

The term "antibody" is used in the broadest sense and specifically covers monoclonal antibodies, antibody compositions with polyepitopic specificity, bispecific antibodies, diabodies, and single-chain molecules, as well as antibody fragments (e.g., Fab, $F(ab')_2$, and Fv), so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256:495 (1975), or may be made by recombinant DNA methods (see, e.g., U.S. Pat. No. 4,816,567 (Cabilly et al.)). The "monoclonal antibodies" may also be isolated from phage antibody libraries using the techniques described in Clackson et al., Nature 352:624–628 (1991) and Marks et al., J. Mol. Biol. 222:581–597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly et al., supra; Morrison et al., Proc. Natl. Acad. Sci. USA, 81:6851–6855 (1984)).

"Humanized" forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature 321:522–525 (1986); Reichmann et al., Nature 332:323–329 (1988); and Presta, Curr. Op. Struct. Biol. 2:593–596 (1992). The humanized antibody includes a Primatized™ antibody wherein the antigen-binding region of the antibody is derived from an antibody produced by immunizing macaque monkeys with the antigen of interest.

"Non-immunogenic in a human" means that upon contacting the polypeptide of interest in a physiologically acceptable carrier and in a therapeutically effective amount with the appropriate tissue of a human, no state of sensitivity or resistance to the polypeptide of interest is demonstrable upon the second administration of the polypeptide of interest after an appropriate latent period (e.g., 8 to 14 days).

By "agonist antibody" is meant an antibody which is able to activate native sequence WSX receptor. WSX receptor activation can be determined using the thymidine incorporation assay described above.

A "neutralizing antibody" is one which is able to block or significantly reduce an effector function of native sequence WSX receptor or OB protein. For example, a neutralizing antibody may inhibit or reduce WSX receptor activation by a WSX ligand as determined in the thymidine incorporation assay.

An "antagonist" of the WSX receptor and/or OB protein is a molecule which prevents, or interferes with, binding and/or activation of the WSX receptor or OB protein. Such molecules can be screened for their ability to competitively inhibit WSX receptor activation by OB protein in the thymidine incorporation assay disclosed herein, for example. Examples of such molecules include: WSX receptor ECD; WSX receptor immunoadhesin; neutralizing antibodies against WSX receptor or OB protein; small molecule and peptide antagonists; and antisense nucleotides against the WSX receptor or ob gene.

The phrase "enhancing proliferation of a cell" encompasses the step of increasing the extent of growth and/or reproduction of the cell relative to an untreated cell either in vitro or in vivo. An increase in cell proliferation in cell culture can be detected by counting the number of cells before and after exposure to a molecule of interest. The extent of proliferation can be quantified via microscopic examination of the degree of confluency. Cell proliferation can also be quantified using the thymidine incorporation assay described herein.

By "enhancing differentiation of a cell" is meant the act of increasing the extent of the acquisition or possession of one or more characteristics or functions which differ from that of the original cell (i.e. cell specialization). This can be detected by screening for a change in the phenotype of the cell (e.g., identifying morphological changes in the cell).

A "hematopoietic progenitor cell" or "primitive hematopoietic cell" is one which is able to differentiate to form a more committed or mature blood cell type.

"Lymphoid blood cell lineages" are those hematopoietic precursor cells which are able to differentiate to form lymphocytes (B-cells or T-cells). Likewise, "lymphopoeisis" is the formation of lymphocytes.

"Erythroid blood cell lineages" are those hematopoietic precursor cells which are able to differentiate to form erythrocytes (red blood cells) and "erythropoeisis" is the formation of erythrocytes.

The phrase "myeloid blood cell lineages", for the purposes herein, encompasses all hematopoietic precursor cells, other than lymphoid and erythroid blood cell lineages as defined above, and "myelopoiesis" involves the formation of blood cells (other than lymphocytes and erythrocytes).

A "CD34+ cell population" is enriched for hematopoietic stem cells. A CD34+ cell population can be obtained from umbilical cord blood or bone marrow, for example. Human umbilical cord blood CD34+ cells can be selected for using immunomagnetic beads sold by Miltenyi (California), following the manufacturer's directions.

"Physiologically acceptable" carriers, excipients, or stabilizers are ones which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

As used herein, the term "salvage receptor binding epitope" refers to an epitope of the Fc region of an IgG molecule (e.g., IgG1, IgG2, IgG3, and IgG4) that is responsible for increasing the in vivo serum half-life of the IgG molecule. Exemplary salvage receptor binding epitope sequences include HQNLSDGK (SEQ ID NO:39); HQNISDGK (SEQ ID NO:40); HQSLGTQ (SEQ ID NO:41); VISSHLGQ (SEQ ID NO:42); and PKNSSMISNTP (SEQ ID NO:43).

The term "cytokine" is a generic term for proteins released by one cell population which act on another cell as intercellular mediators. Examples of such cytokines are lymphokines, monokines, and traditional polypeptide hormones. Included among the cytokines are OB protein; growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-$\alpha$ and -$\beta$; mullerian-inhibiting substance; mouse gonadotropin-associated peptide; inhibin; activin; vascular endothelial growth factor; integrin; thrombopoietin (TPO); nerve growth factors such as NGF-$\beta$; platelet-growth factor; transforming growth factors (TGFs) such as TGF-$\alpha$ and TGF-$\beta$; insulin-like growth factor-I and -II; erythropoietin (EPO); osteoinductive factors; interferons such as interferon-$\alpha$, -$\beta$, and -$\gamma$; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1$\alpha$, IL-2, IL-3, IL-4, IL-5, IL-6, IL-7, IL-8, IL-9, IL-11, IL-12; and other polypeptide factors including leukemia inhibitory factor (LIF) and kit ligand (KL). As used herein, the term cytokine includes proteins from natural sources or from recombinant cell culture and biologically active equivalents of the native sequence cytokines.

A "lineage-specific cytokine" is one which acts on relatively committed cells in the hematopoietic cascade and gives rise to an expansion in blood cells of a single lineage. Examples of such cytokines include EPO, TPO, and G-CSF.

"Treatment" refers to both therapeutic treatment and prophylactic or preventative measures. Those in need of treatment include those already with the disorder as well as those in which the disorder is to be prevented.

The term "obesity" is used to designate a condition of being overweight associated with excessive bodily fat. The desirable weight for a certain individual depends on a number of factors including sex, height, age, overall built, etc. The same factors will determine when an individual is considered obese. The determination of an optimum body weight for a given individual is well within the skill of an ordinary physician.

"Mammal" for purposes of treatment refers to any animal classified as a mammal, including humans, domestic and farm animals, and zoo, sports, or pet animals, such as dogs, horses, cats, cows, etc. Preferably, the mammal is human.

By "solid phase" is meant a non-aqueous matrix to which a reagent of interest (e.g., the WSX receptor or an antibody thereto) can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

II. Modes for Carrying Out the Invention

The present invention is based on the discovery of the WSX receptor. The experiments described herein demonstrate that this molecule is a cytokine receptor which appears to play a role in enhancing proliferation and/or differentiation of hematopoietic cells. In particular, this receptor has been found to be present in enriched human stem cell populations, thus indicating that WSX ligands, such as agonist antibodies, may be used to stimulate proliferation of hematopoietic stem cells/progenitor cells. Other uses for this receptor will be apparent from the following discussion.

A description follows as to how WSX receptor or OB proteins may be prepared.

A. Preparation of WSX Receptor or OB Protein

Techniques suitable for the production of WSX receptor or OB protein are well known in the art and include isolating WSX receptor or OB protein from an endogenous source of the polypeptide, peptide synthesis (using a peptide synthesizer) and recombinant techniques (or any combination of these techniques). The preferred technique for production of WSX receptor or OB protein is a recombinant technique to be described below.

Most of the discussion below pertains to recombinant production of WSX receptor or OB protein by culturing cells transformed with a vector containing WSX receptor or OB protein nucleic acid and recovering the polypeptide from the cell culture. It is further envisioned that the WSX receptor or OB protein of this invention may be produced by homologous recombination, as provided for in WO 91/06667, published 16 May 1991.

Briefly, this method involves transforming primary human cells containing a WSX receptor or OB protein-encoding gene with a construct (i.e., vector) comprising an amplifiable gene (such as dihydrofolate reductase (DHFR) or others discussed below) and at least one flanking region of a length of at least about 150 bp that is homologous with a DNA sequence at the locus of the coding region of the WSX receptor or OB protein gene to provide amplification of the WSX receptor or OB protein gene. The amplifiable gene must be at a site that does not interfere with expression of the WSX receptor or OB protein gene. The transformation is conducted such that the construct becomes homologously integrated into the genome of the primary cells to define an amplifiable region.

Primary cells comprising the construct are then selected for by means of the amplifiable gene or other marker present in the construct. The presence of the marker gene establishes the presence and integration of the construct into the host genome. No further selection of the primary cells need be made, since selection will be made in the second host. If desired, the occurrence of the homologous recombination event can be determined by employing PCR and either sequencing the resulting amplified DNA sequences or determining the appropriate length of the PCR fragment when DNA from correct homologous integrants is present and expanding only those cells containing such fragments. Also if desired, the selected cells may be amplified at this point by stressing the cells with the appropriate amplifying agent (such as methotrexate if the amplifiable gene is DHFR), so that multiple copies of the target gene are obtained. Preferably, however, the amplification step is not conducted until after the second transformation described below.

After the selection step, DNA portions of the genome, sufficiently large to include the entire amplifiable region, are isolated from the selected primary cells. Secondary mammalian expression host cells are then transformed with these genomic DNA portions and cloned, and clones are selected that contain the amplifiable region. The amplifiable region is then amplified by means of an amplifying agent if not already amplified in the primary cells. Finally, the secondary expression host cells now comprising multiple copies of the amplifiable region containing WSX receptor or OB protein are grown so as to express the gene and produce the protein.

1. Isolation of DNA Encoding WSX Receptor or OB Protein

The DNA encoding WSX receptor or OB protein may be obtained from any cDNA library prepared from tissue believed to possess the WSX receptor or OB protein mRNA and to express it at a detectable level. Accordingly, WSX receptor or OB protein DNA can be conveniently obtained from a cDNA library prepared from mammalian fetal liver. The WSX receptor or OB protein-encoding gene may also be obtained from a genomic library or by oligonucleotide synthesis.

Libraries are screened with probes (such as antibodies to the WSX receptor or OB protein, or oligonucleotides of about 20–80 bases) designed to identify the gene of interest or the protein encoded by it. Screening the cDNA or genomic library with the selected probe may be conducted using standard procedures as described in chapters 10–12 of Sambrook et al., *Molecular Cloning: A Laboratory Manual* (New York: Cold Spring Harbor Laboratory Press, 1989). An alternative means to isolate the gene encoding WSX receptor or OB protein is to use PCR methodology as described in section 14 of Sambrook et al., supra.

A preferred method of practicing this invention is to use carefully selected oligonucleotide sequences to screen cDNA libraries from various human tissues, preferably human fetal liver. The oligonucleotide sequences selected as probes should be of sufficient length and sufficiently unambiguous that false positives are minimized.

The oligonucleotide must be labeled such that it can be detected upon hybridization to DNA in the library being screened. The preferred method of labeling is to use $^{32}$P-labeled ATP with polynucleotide kinase, as is well known in the art, to radiolabel the oligonucleotide. However, other methods may be used to label the oligonucleotide, including, but not limited to, biotinylation or enzyme labeling.

Amino acid sequence variants of WSX receptor or OB protein are prepared by introducing appropriate nucleotide changes into the WSX receptor or OB protein DNA, or by synthesis of the desired WSX receptor or OB protein. Such variants represent insertions, substitutions, and/or specified deletions of, residues within or at one or both of the ends of the amino acid sequence of a naturally occurring human WSX receptor or OB protein, such as the WSX receptor variants shown in FIGS. 2A–D or the human OB protein of Zhang et al., supra. Preferably, these variants represent insertions and/or substitutions within or at one or both ends of the mature sequence, and/or insertions, substitutions and/or specified deletions within or at one or both of the ends of the signal sequence of the WSX receptor or OB protein. Any combination of insertion, substitution, and/or specified deletion is made to arrive at the final construct, provided that the final construct possesses the desired biological activity as defined herein. The amino acid changes also may alter post-translational processes of the WSX receptor or OB protein, such as changing the number or position of glycosylation sites, altering the membrane anchoring characteristics, and/or altering the intracellular location of the WSX receptor or OB protein by inserting, deleting, or otherwise affecting the leader sequence of the WSX receptor or OB protein.

Variations in the native sequence as described above can be made using any of the techniques and guidelines for conservative and non-conservative mutations set forth in U.S. Pat. No. 5,364,934. These include oligonucleotide-mediated (site-directed) mutagenesis, alanine scanning, and PCR mutagenesis. See also, for example, Table I therein and the discussion surrounding this table for guidance on selecting amino acids to change, add, or delete.

2. Insertion of Nucleic Acid into Replicable Vector

The nucleic acid (e.g., cDNA or genomic DNA) encoding the WSX receptor or OB protein is inserted into a replicable vector for further cloning (amplification of the DNA) or for expression. Many vectors are available. The vector components generally include, but are not limited to, one or more of the following: a signal sequence, an origin of replication, one or more marker genes, an enhancer element, a promoter, and a transcription termination sequence.

a. Signal Sequence Component

The WSX receptor or OB proteins of this invention may be produced recombinantly not only directly, but also as a fusion polypeptide with a heterologous polypeptide, which is preferably a signal sequence or other polypeptide having a specific cleavage site at the N-terminus of the mature protein or polypeptide. In general, the signal sequence may be a component of the vector, or it may be a part of the WSX receptor or OB protein DNA that is inserted into the vector. The heterologous signal sequence selected preferably is one that is recognized and processed (i.e., cleaved by a signal peptidase) by the host cell. For prokaryotic host cells that do not recognize and process the native WSX receptor or OB protein signal sequence, the signal sequence is substituted by a prokaryotic signal sequence selected, for example, from the group of the alkaline phosphatase, penicillinase, Ipp, or heat-stable enterotoxin II leaders. For yeast secretion the native signal sequence may be substituted by, e.g., the yeast invertase leader, a factor leader (including *Saccharomyces* and *Kluyveromyces* α-factor leaders, the latter described in U.S. Pat. No. 5,010,182 issued 23 Apr. 1991), or acid phosphatase leader, the *C. albicans* glucoamylase leader (EP 362,179 published 4 Apr. 1990), or the signal described in WO 90/13646 published 15 Nov. 1990. In mammalian cell expression the native signal sequence (e.g., the WSX receptor or OB protein presequence that normally directs secretion of WSX receptor or OB protein from human cells in vivo) is satisfactory, although other mammalian signal sequences may be suitable, such as signal sequences from other animal WSX receptors or OB proteins, and signal sequences from secreted polypeptides of the same or related species, as well as viral secretory leaders, for example, the herpes simplex gD signal.

The DNA for such precursor region is ligated in reading frame to DNA encoding the mature WSX receptor or OB protein.

b. Origin of Replication Component

Both expression and doning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e., they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using *Bacillus* species as hosts, for example, by including in the vector a DNA sequence that is complementary to a sequence found in *Bacillus* genomic DNA. Transfection of *Bacillus* with this vector results in homologous recombination with the genome and insertion of WSX receptor or OB protein DNA. However, the recovery of genomic DNA encoding WSX receptor or OB protein is more complex than that of an exogenously replicated vector because restriction enzyme digestion is required to excise the WSX receptor or OB protein DNA.

C. Selection Gene Component

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the WSX receptor or OB protein nucleic acid, such as DHFR or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes WSX receptor or OB protein. Amplification is the process by which genes in greater demand for the production of a protein critical for growth are reiterated in tandem within the chromosomes of successive generations of recombinant cells. Increased quantities of WSX receptor or OB protein are synthesized from the amplified DNA. Other examples of amplifiable genes include metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub et al., *Proc. Natl. Acad. Sci. USA* 77:4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding WSX receptor or OB protein. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060).

Alternatively, host cells (particularly wild-type hosts that contain endogenous DHFR) transformed or co-transformed with DNA sequences encoding WSX receptor or OB protein, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature* 282:39 (1979)). The trp1 gene provides a selection marker for a mutant strain of yeast lacking the ability to grow in tryptophan, for example, ATCC No. 44076 or PEP4-1. Jones, *Genetics* 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Bianchi et al., *Curr. Genet.* 12:185 (1987). More recently, an expression system for large-scale production of recombinant calf chymosin was reported for *K. lactis*. Van den Berg, *Bio/Technology* 8:135 (1990). Stable multicopy expression vectors for secretion of mature recombinant human serum albumin by industrial strains of *Kluyveromyces* have also been disclosed. Fleer et al., *Bio/Technology* 9:968–975 (1991).

d. Promoter Component

Expression and cloning vectors usually contain a promoter that is recognized by the host organism and is operably linked to the WSX receptor or OB protein nucleic acid. Promoters are untranslated sequences located upstream (5') to the start codon of a structural gene (generally within about 100 to 1000 bp) that control the transcription and translation of particular nucleic acid sequence, such as the WSX receptor or OB protein nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to WSX receptor or OB protein-encoding DNA by removing the promoter from the source DNA by restriction enzyme digestion and inserting the isolated promoter sequence into the vector. Both the native WSX receptor or OB protein promoter sequence and many heterologous promoters may be used to direct amplification and/or expression of the WSX receptor or OB protein DNA. However, heterologous promoters are preferred, as they generally permit greater transcription and higher yields of WSX receptor or OB protein as compared to the native WSX receptor or OB protein promoter.

Promoters suitable for use with prokaryotic hosts include the β-lactamase and lactose promoter systems (Chang et al., *Nature* 275:615 (1978); Goeddel et al., *Nature* 281:544 (1979)), alkaline phosphatase, a tryptophan (trp) promoter system (Goeddel, *Nucleic Acids Res.* 8:4057 (1980); EP 36,776), and hybrid promoters such as the tac promoter. deBoer et al., *Proc. Natl. Acad. Sci. USA* 80:21–25 (1983). However, other known bacterial promoters are suitable. Their nucleotide sequences have been published, thereby enabling a skilled worker operably to ligate them to DNA encoding WSX receptor or OB protein (Siebenlist et al., *Cell* 20:269 (1980)) using linkers or adaptors to supply any required restriction sites. Promoters for use in bacterial systems also will contain a Shine-Dalgarno (S.D.) sequence operably linked to the DNA encoding WSX receptor or OB protein.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase (Hitzeman et al., *J. Biol. Chem.* 255:2073 (1980)) or other glycolytic enzymes (Hess et al., *J. Adv. Enzyme Reg.* 7:149 (1968); Holland, Biochemistry 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

WSX receptor or OB protein transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, and from the promoter normally associated with the WSX receptor or OB protein sequence, provided such promoters are compatible with the host cell systems.

The early and late promoters of the SV40 virus are conveniently obtained as an SV40 restriction fragment that also contains the SV40 viral origin of replication. Fiers et al., *Nature* 273:113 (1978); Mulligan et al., *Science* 209:1422–1427 (1980); Pavlakis et al., *Proc. Natl. Acad. Sci. USA* 78:7398–7402 (1981). The immediate early promoter of the human cytomegalovirus is conveniently obtained as a HindIII E restriction fragment. Greenaway et al., *Gene* 18:355–360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature* 295:503–508 (1982) on expressing cDNA encoding immune interferon in monkey cells; Reyes et al., *Nature* 297:598–601 (1982) on expression of human β-interferon cDNA in mouse cells under the control of a thymidine kinase promoter from herpes simplex virus; Canaani et al., *Proc. Natl. Acad. Sci. USA* 79:5166–5170 (1982) on expression of the human interferon β1 gene in cultured mouse and rabbit cells; and Gorman et al., *Proc. Natl. Acad. Sci. USA* 79:6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

e. Enhancer Element Component

Transcription of a DNA encoding the WSX receptor or OB protein of this invention by higher eukaryotes is often increased by inserting an enhancer sequence into the vector. Enhancers are cis-acting elements of DNA, usually about from 10 to 300 bp, that act on a promoter to increase its transcription. Enhancers are relatively orientation and position independent, having been found 5' (Laimins et al., *Proc. Natl. Acad. Sci. USA* 78:993 (1981)) and 3' (Lusky et al., *Mol. Cell Bio.* 3:1108 (1983)) to the transcription unit, within an intron (Banerji et al., *Cell* 33:729 (1983)), as well as within the coding sequence itself. Osborne et al., *Mol. Cell Bio.* 4:1293 (1984). Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature* 297:17–18 (1982) on enhancing elements for activation of eukaryotic promoters. The enhancer may be spliced into the vector at a position 5' or 3' to the WSX receptor or OB protein-encoding sequence, but is preferably located at a site 5' from the promoter.

f. Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding WSX receptor or OB protein.

9. Construction and Analysis of Vectors

Construction of suitable vectors containing one or more of the above-listed components employs standard ligation techniques. Isolated plasmids or DNA fragments are cleaved, tailored, and re-ligated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.* 9:309 (1981) or by the method of Maxam et al., *Methods in Enzymology* 65:499 (1980).

h. Transient Expression Vectors

Particularly useful in the practice of this invention are expression vectors that provide for the transient expression in mammalian cells of DNA encoding WSX receptor or OB protein. In general, transient expression involves the use of an expression vector that is able to replicate efficiently in a host cell, such that the host cell accumulates many copies of the expression vector and, in turn, synthesizes high levels of a desired polypeptide encoded by the expression vector. Sambrook et al., supra, pp. 16.17–16.22. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of WSX receptor or OB protein that are biologically active WSX receptor or OB protein.

i. Suitable Exemplary Vertebrate Cell Vectors

Other methods, vectors, and host cells suitable for adaptation to the synthesis of WSX receptor or OB protein in recombinant vertebrate cell culture are described in Gething et al, *Nature* 293:620–625 (1981); Mantei et al, *Nature* 281:40–46 (1979); EP 117,060; and EP 117,058. A particularly useful plasmid for mammalian cell culture expression of WSX receptor or OB protein is pRK5 (EP 307,247) or pSVI6B. WO 91/08291 published 13 Jun. 1991.

3. Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting. Strain W3110 is a particularly preferred host or parent host because it is a common host strain for recombinant DNA product fermentations. Preferably, the host cell should secrete minimal amounts of proteolytic enzymes. For example, strain W3110 may be modified to effect a genetic mutation in the genes encoding proteins, with examples of such hosts including *E. coli* W3110 strain 27C7. The complete genotype of 27C7 is tonAΔ ptr3 phoAΔE15 Δ(argF-lac)169 ompTΔ degP41kan$^r$. Strain 27C7 was deposited on 30 Oct. 1991 in the American Type Culture Collection as ATCC No. 55,244. Alternatively, the strain of *E. coli* having mutant periplasmic protease disclosed in U.S. Pat. No. 4,946,783 issued 7 Aug. 1990 may be employed. Alternatively still, methods of cloning, e.g., PCR or other nucleic acid polymerase reactions, are suitable.

In addition to prokaryotes, eukaryotic microbes such as filamentous fungi or yeast are suitable cloning or expression hosts for WSX receptor or OB protein-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe* (Beach et al., *Nature*, 290:140 (1981); EP 139,383 published 2 May 1985); *Kluyveromyces* hosts (U.S. Pat. No. 4,943,529; Fleer et al., supra) such as, e.g., *K. lactis* (MW98-8C, CBS683, CBS4574), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., supra), *K. thermotolerans*, and *K. marxianus*; *yarrowia* (EP 402,226); *Pichia pastoris* (EP 183,070; Sreekrishna et al., *J. Basic Microbiol.* 28:265–278 (1988)); *Candida; Trichoderma reesia* (EP 244,234); *Neurospora crassa* (Case et al., *Proc. Natl. Acad. Sci. USA* 76:5259–5263 (1979)); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.* 112:284–289 (1983); Tilburn et al., *Gene* 26:205–221 (1983); Yelton et al., *Proc. Natl. Acad. Sci. USA* 81:1470–1474 (1984)) and *A. niger* Kelly et al., *EMBO J.* 4:475–479 (1985).

Suitable host cells for the expression of glycosylated WSX receptor or OB protein are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. See, e.g., Luckow et al., *Bio/Technology* 6:47–55 (1988); Miller et al., in *Genetic Engineering*, Setlow et al., eds., Vol. 8 (Plenum Publishing, 1986), pp. 277–279; and Maeda et al., *Nature* 315:592–594 (1985). A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the WSX receptor or OB protein-encoding DNA. During incubation of the plant cell culture with *A. tumefaciens*, the DNA encoding the WSX receptor or OB protein is transferred to the plant cell host such that it is transfected, and will, under appropriate conditions, express the WSX receptor or OB protein-encoding DNA. In addition, regulatory and signal sequences compatible with plant cells are available, such as the nopaline synthase promoter and polyadenylation signal sequences. Depicker et al., *J. Mol. Appl. Gen.* 1:561 (1982). In addition, DNA segments isolated from the upstream region of the T-DNA 780 gene are capable of activating or increasing transcription levels of plant-expressible genes in recombinant DNA-containing plant tissue. EP 321,196 published 21 Jun. 1989.

However, interest has been greatest in vertebrate cells, and propagation of vertebrate cells in culture (tissue culture) has become a routine procedure. See, e.g., Tissue Culture, Academic Press, Kruse and Patterson, editors (1973). Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243–251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44–68 (1982)); MRC 5 cells; FS4 cells; and a human hepatoma line (Hep G2).

Host cells are transfected and preferably transformed with the above-described expression or cloning vectors for WSX receptor or OB protein production and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene* 23:315 (1983) and WO 89/05859 published 29 Jun. 1989. In addition, plants may be transfected using ultrasound treatment as described in WO 91/00358 published 10 Jan. 1991.

For mammalian cells without such cell walls, the calcium phosphate precipitation method of Graham et al., *Virology* 52:456–457 (1978) is preferred. General aspects of mammalian cell host system transformations have been described in U.S. Pat. No. 4,399,216 issued 16 Aug. 1983. Transformations into yeast are typically carried out according to the method of Van Solingen et al., *J. Bact.* 130:946 (1977) and Hsiao et al., *Proc. Natl. Acad. Sci. USA* 76:3829 (1979). However, other methods for introducing DNA into cells, such as by nuclear microinjection, electroporation, bacterial protoplast fusion with intact cells, or polycations, e.g., polybrene, polyornithine, etc., may also be used. For various techniques for transforming mammalian cells, see Keown et al., *Methods in Enzymology* 185:527–537 (1990) and Mansour et al., *Nature* 336:348–352 (1988).

4. Culturing the Host Cells

Prokaryotic cells used to produce the WSX receptor or OB protein of this invention are cultured in suitable media as described generally in Sambrook et al., supra.

The mammalian host cells used to produce the WSX receptor or OB protein of this invention may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham et al. *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of mammalian cell cultures can be found in *Mammalian Cell Biotechnology: a Practical Approach*, M. Butler, ed. (IRL Press, 1991).

The host cells referred to in this disclosure encompass cells in culture as well as cells that are within a host animal.

5. Detecting Gene Amplification/Expression

Gene amplification and/or expression may be measured in a sample directly, for example, by conventional Southern blotting, Northern blotting to quantitate the transcription of mRNA (Thomas, *Proc. Natl. Acad. Sci. USA* 77:5201–5205 (1980)), dot blotting (DNA analysis), or in situ hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al., *Am. J. Clin. Path.* 75:734–738 (1980).

Antibodies useful for immunohistochemical staining and/or assay of sample fluids may be either monoclonal or polyclonal, and may be prepared as described herein.

6. Purification of WSX Receptor or OB Protein

WSX receptor (e.g., WSX receptor ECD) or OB protein preferably is recovered from the culture medium as a secreted polypeptide, although it also may be recovered from host cell lysates. If the WSX receptor is membrane-bound, it can be released from the membrane using a suitable detergent solution (e.g. Triton-X 100)

When WSX receptor or OB protein is produced in a recombinant cell other than one of human origin, the WSX receptor or OB protein is completely free of proteins or polypeptides of human origin. However, it is necessary to purify WSX receptor or OB protein from recombinant cell proteins or polypeptides to obtain preparations that are substantially homogeneous as to WSX receptor or OB protein. As a first step, the culture medium or lysate is centrifuged to remove particulate cell debris. WSX receptor or OB protein thereafter is purified from contaminant soluble proteins and polypeptides, with the following procedures being exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75™; and protein A Sepharose™ columns to remove contaminants such as IgG.

WSX receptor or OB protein variants in which residues have been deleted, inserted, or substituted are recovered in the same fashion as native sequence WSX receptor or OB protein, taking account of any substantial changes in properties occasioned by the variation. Immunoaffinity columns such as a rabbit polyclonal anti-WSX receptor or OB protein column can be employed to absorb the WSX receptor or OB protein variant by binding it to at least one remaining immune epitope.

A protease inhibitor such as phenyl methyl sulfonyl fluoride (PMSF) also may be useful to inhibit proteolytic degradation during purification, and antibiotics may be included to prevent the growth of adventitious contaminants.

7. Covalent Modifications

Covalent modifications of WSX receptor or OB protein are included within the scope of this invention. Both native sequence WSX receptor or OB protein and amino acid sequence variants of the WSX receptor or OB protein may be covalently modified. One type of covalent modification of the WSX receptor or OB protein is introduced into the molecule by reacting targeted amino acid residues of the WSX receptor or OB protein with an organic derivatizing agent that is capable of reacting with selected side chains or the N- or C-terminal residues of the WSX receptor or OB protein.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed under alkaline conditions because of the high $pK_a$ of the guanidine functional group. Furthermore, these reagents may react with the groups of lysine as well as with the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method being suitable.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking WSX receptor or OB protein to a water-insoluble support matrix or surface for use in the method for purifying anti-WSX receptor or OB protein antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-((p-azidophenyl)dithio)propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W.H. Freeman & Co., San Francisco, pp. 79–86 (1983)), acetylation of the N-terminal amine, and amidation of any C-terminal carboxyl group.

Another type of covalent modification of the WSX receptor or OB protein included within the scope of this invention comprises altering the native glycosylation pattern of the polypeptide. By altering is meant deleting one or more carbohydrate moieties found in native WSX receptor or OB protein, and/or adding one or more glycosylation sites that are not present in the native WSX receptor or OB protein.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxylamino acid, most commonly serine or threonine, although 5-hydroxyproline or 5-hydroxylysine may also be used.

Addition of glycosylation sites to the WSX receptor or OB protein is conveniently accomplished by altering the amino acid sequence such that it contains one or more of the above-described tripeptide sequences (for N-linked glycosylation sites). The alteration may also be made by the addition of, or substitution by, one or more serine or threonine residues to the native WSX receptor or OB protein sequence (for O-linked glycosylation sites). For ease, the WSX receptor or OB protein amino acid sequence is preferably altered through changes at the DNA level, particularly by mutating the DNA encoding the WSX receptor or OB protein at preselected bases such that codons are generated that will translate into the desired amino acids. The DNA mutation(s) may be made using methods described above and in U.S. Pat. No. 5,364,934, supra.

Another means of increasing the number of carbohydrate moieties on the WSX receptor or OB protein is by chemical or enzymatic coupling of glycosides to the polypeptide. These procedures are advantageous in that they do not require production of the polypeptide in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published 11 Sep. 1987, and in Aplin et al., *CRC Crit. Rev. Biochem.* 259–306 (1981).

Removal of carbohydrate moieties present on the WSX receptor or OB protein may be accomplished chemically or enzymatically. Chemical deglycosylation requires exposure of the polypeptide to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin, et al., *Arch. Biochem. Biophys.* 259:52 (1987) and by Edge et al., *Anal. Biochem.* 118:131 (1981). Enzymatic cleavage of carbohydrate moieties on polypeptides can be achieved by the use of a variety of endo- and exo-glycosidases as described by Thotakura et al., *Meth. Enzymol.* 138:350 (1987).

Glycosylation at potential glycosylation sites may be prevented by the use of the compound tunicamycin as described by Duskin et al., *J. Biol. Chem.* 257:3105 (1982). Tunicamycin blocks the formation of protein-N-glycoside linkages.

Another type of covalent modification of WSX receptor or OB protein comprises linking the WSX receptor or OB protein to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Since it is often difficult to predict in advance the characteristics of a variant WSX receptor or OB protein, it will be appreciated that some screening of the recovered variant will be needed to select the optimal variant. A change in the immunological character of the WSX receptor or OB protein molecule, such as affinity for a given antibody, is also able to be measured by a competitive-type immunoassay. The WSX receptor variant is assayed for changes in the ability of the protein to induce cell proliferation in the colony assay of Example 8. Other potential modifications of protein or polypeptide properties such as redox or thermal stability, hydrophobicity, susceptibility to proteolytic degradation, or the tendency to aggregate with carriers or into multimers are assayed by methods well known in the art.

8. Epitope-Tagged WSX Receptor or OB Protein

This invention encompasses chimeric polypeptides comprising WSX receptor or OB protein fused to a heterologous polypeptide. A chimeric WSX receptor or OB protein is one type of WSX receptor or OB protein variant as defined herein. In one preferred embodiment, the chimeric polypeptide comprises a fusion of the WSX receptor or OB protein with a tag polypeptide which provides an epitope to which an anti-tag antibody can selectively bind. The epitope tag is generally provided at the amino- or carboxyl-terminus of the WSX receptor or OB protein. Such epitope-tagged forms of the WSX receptor or OB protein are desirable as the presence thereof can be detected using a labeled antibody against the tag polypeptide. Also, provision of the epitope tag enables the WSX receptor or OB protein to be readily purified by affinity purification using the anti-tag antibody. Affinity purification techniques and diagnostic assays involving antibodies are described later herein.

Tag polypeptides and their respective antibodies are well known in the art. Examples include the flu HA tag polypeptide and its antibody 12CA5 (Field et al., *Mol. Cell. Biol.* 8:2159–2165 (1988)); the c-myc tag and the 8F9, 3C7, 6E10, G4, B7 and 9E10 antibodies thereto (Evan et al., *Molecular and Cellular Biology* 5:3610–3616 (1985)); and the Herpes Simplex virus glycoprotein D (gD) tag and its antibody. Paborsky et al., *Protein Engineering* 3(6):547–553 (1990). Other tag polypeptides have been disclosed. Examples include the Flag-peptide (Hopp et al., *BioTechnology* 6:1204–1210 (1988)); the KT3 epitope peptide (Martin et al., *Science* 255:192–194 (1992)); an α-tubulin epitope peptide (Skinner et al., *J. Biol. Chem.* 266:15163–15166 (1991)); and the T7 gene 10 protein peptide tag. Lutz-Freyermuth et al., *Proc. Natl. Acad. Sci. USA* 87:6393–6397 (1990). Once the tag polypeptide has been selected, an antibody thereto can be generated using the techniques disclosed herein.

The general methods suitable for the construction and production of epitope-tagged WSX receptor or OB protein are the same as those disclosed hereinabove. WSX receptor or OB protein-tag polypeptide fusions are most conveniently constructed by fusing the cDNA sequence encoding the WSX receptor or OB protein portion in-frame to the tag polypeptide DNA sequence and expressing the resultant DNA fusion construct in appropriate host cells. Ordinarily, when preparing the WSX receptor or OB protein-tag polypeptide chimeras of the present invention, nucleic acid encoding the WSX receptor or OB protein will be fused at its 3' end to nucleic acid encoding the N-terminus of the tag polypeptide, however 5' fusions are also possible.

Epitope-tagged WSX receptor or OB protein can be conveniently purified by affinity chromatography using the anti-tag antibody. The matrix to which the affinity antibody is attached is most often agarose, but other matrices are available (e.g. controlled pore glass or poly(styrenedivinyl) benzene). The epitope-tagged WSX receptor or OB protein can be eluted from the affinity column by varying the buffer pH or ionic strength or adding chaotropic agents, for example.

9. WSX Receptor or OB Protein Immunoadhesins

Chimeras constructed from a receptor sequence linked to an appropriate immunoglobulin constant domain sequence (immunoadhesins) are known in the art. Immunoadhesins reported in the literature include fusions of the T cell receptor* (Gascoigne et al, *Proc. Natl. Acad. Sci. USA* 84: 2936–2940 (1987)); CD4* (Capon et al., *Nature* 337: 525–531 (1989); Traunecker et al., *Nature* 339: 68–70 (1989); Zettmeissl et al., *DNA Cell Biol. USA* 9: 347–353 (1990); Byrn et al., *Nature* 344: 667–670 (1990)); L-selectin (homing receptor) ((Watson et al., *J. Cell. Biol.* 110:2221–2229 (1990); Watson et al, *Nature* 349: 164–167 (1991)); CD44* (Aruffo et al., *Cell* 61: 1303–1313 (1990)); CD28* and B7* (Linsley et al., *J. Exp. Med.* 173: 721–730 (1991)); CTLA-4* (Lisley et al., *J. Exp. Med.* 174: 561–569 (1991)); CD22* (Stamenkovic et al., *Cell* 66:1133–1144 (1991)); TNF receptor (Ashkenazi et al., *Proc. Natl. Acad. Sci. USA* 88: 10535–10539 (1991); Lesslauer et al., *Eur. J. Immunol.* 27: 2883–2886 (1991); Peppel et al, *J. Exp. Med.* 174:1483–1489 (1991)); NP receptors (Bennett et al, *J. Biol. Chem.* 266:23060–23067 (1991)); and IgE receptor α* (Ridgway et al, *J. Cell. Biol.* 115:abstr. 1448 (1991)), where the asterisk (*) indicates that the receptor is member of the immunoglobulin superfamily.

The simplest and most straightforward immunoadhesin design combines the binding region(s) of the "adhesin" protein with the hinge and Fc regions of an immunoglobulin heavy chain. Ordinarily, when preparing the WSX receptor or OB-immunoglobulin chimeras of the present invention, nucleic acid encoding OB protein or the extracellular domain of the WSX receptor will be fused C-terminally to nucleic acid encoding the N-terminus of an immunoglobulin constant domain sequence, however N-terminal fusions are also possible. For OB-immunoglobulin chimeras, an OB protein fragment which retains the ability to bind to the WSX receptor may be employed.

Typically, in such fusions the encoded chimeric polypeptide will retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain.

The precise site at which the fusion is made is not critical; particular sites are well known and may be selected in order to optimize the biological activity, secretion or binding characteristics of the WSX receptor or OB-immunoglobulin chimeras.

In some embodiments, the WSX receptor or OB-immunoglobulin chimeras are assembled as monomers, or hetero- or homo-multimers, and particularly as dimers or tetramers, essentially as illustrated in WO 91/08298.

In a preferred embodiment, the OB protein sequence or WSX receptor extracellular domain sequence is fused to the N-terminus of the C-terminal portion of an antibody (in particular the Fc domain), containing the effector functions of an immunoglobulin, e.g. immunoglobulin G1 (IgG1). It is possible to fuse the entire heavy chain constant region to the OB protein or WSX receptor extracellular domain sequence. However, more preferably, a sequence beginning in the hinge region just upstream of the papain cleavage site (which defines IgG Fc chemically; residue 216, taking the first residue of heavy chain constant region to be 114, or analogous sites of other immunoglobulins) is used in the fusion. In a particularly preferred embodiment, the OB protein or WSX receptor amino acid sequence is fused to the hinge region, CH2 and CH3, or the CH1, hinge, CH2 and CH3 domains of an IgG1, IgG2, or IgG3 heavy chain. The precise site at which the fusion is made is not critical, and the optimal site can be determined by routine experimentation.

In some embodiments, the WSX receptor or OB-immunoglobulin chimeras are assembled as multimers, and particularly as homo-dimers or -tetramers. Generally, these assembled immunoglobulins will have known unit structures. A basic four chain structural unit is the form in which IgG, IgD, and IgE exist. A four unit is repeated in the higher molecular weight immunoglobulins; IgM generally exists as a pentamer of basic four units held together by disulfide bonds. IgA globulin, and occasionally IgG globulin, may also exist in multimeric form in serum. In the case of multimer, each four unit may be the same or different.

Various exemplary assembled WSX receptor or OB-immunoglobulin chimeras within the scope herein are schematically diagrammed below:

(a) $AC_L$-$AC_L$;

(b) $AC_H$-($AC_H$, $AC_L$-$AC_H$, $AC_L$-$V_H C_H$, or $V_L C_L$-$AC_H$);

(c) $AC_L$-$AC_H$-($AC_L$-$AC_H$, $AC_L$-$V_H C_H$, $V_L C_L$-$AC_H$, or $V_L C_L$-$V_H C_H$);

(d) $AC_L$-$V_H C_H$-($AC_H$, or $AC_L$-$V_H C_H$, or $V_L C_L$-$AC_H$);

(e) $V_L C_L$-$AC_H$-($AC_L$-$V_H C_H$, or $V_L C_L$-$AC_H$); and (f) $(A-Y)_n$-$(V_L C_L$-$V_H C_H)_2$, wherein each A represents identical or different OB protein or WSX receptor amino acid sequences;

$V_L$ is an immunoglobulin light chain variable domain;

$V_H$ is an immunoglobulin heavy chain variable domain;

$C_L$ is an immunoglobulin light chain constant domain;

$C_H$ is an immunoglobulin heavy chain constant domain;

n is an integer greater than 1;

Y designates the residue of a covalent cross-linking agent.

In the interests of brevity, the foregoing structures only show key features; they do not indicate joining (J) or other domains of the immunoglobulins, nor are disulfide bonds shown. However, where such domains are required for binding activity, they shall be constructed as being present in the ordinary locations which they occupy in the immunoglobulin molecules.

Alternatively, the OB protein or WSX receptor extracellular domain sequence can be inserted between immunoglobulin heavy chain and light chain sequences such that an immunoglobulin comprising a chimeric heavy chain is obtained. In this embodiment, the OB protein or WSX receptor sequence is fused to the 3' end of an immunoglobulin heavy chain in each arm of an immunoglobulin, either between the hinge and the CH2 domain, or between the CH2 and CH3 domains. Similar constructs have been reported by Hoogenboom et al., *Mol. Immunol.*, 28:1027–1037 (1991).

Although the presence of an immunoglobulin light chain is not required in the immunoadhesins of the present invention, an immunoglobulin light chain might be present either covalently associated to an OB protein or WSX receptor-immunoglobulin heavy chain fusion polypeptide, or directly fused to the WSX receptor extracellular domain or OB protein. In the former case, DNA encoding an immunoglobulin light chain is typically coexpressed with the DNA encoding the OB protein or WSX receptor-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567 issued 28 Mar. 1989.

In a preferred embodiment, the immunoglobulin sequences used in the construction of the immunoadhesins of the present invention are from an IgG immunoglobulin heavy chain constant domain. For human immunoadhesins, the use of human IgG1 and IgG3 immunoglobulin sequences is preferred. A major advantage of using IgG1 is that IgG1 immunoadhesins can be purified efficiently on immobilized protein A. In contrast, purification of IgG3 requires protein G, a significantly less versatile medium. However, other structural and functional properties of immunoglobulins should be considered when choosing the Ig fusion partner for a particular immunoadhesin construction. For example, the IgG3 hinge is longer and more flexible, so it can accommodate larger adhesin domains that may not fold or function properly when fused to IgG1. Another consideration may be valency; IgG immunoadhesins are bivalent homodimers, whereas Ig subtypes like IgA and IgM may give rise to dimeric or pentameric structures, respectively, of the basic Ig homodimer unit. For immunoadhesins designed for in vivo application, the pharmacokinetic properties and the effector functions specified by the Fc region are important as well. Although IgG1, IgG2 and IgG4 all have in vivo half-lives of 21 days, their relative potencies at activating the complement system are different. IgG4 does not activate complement, and IgG2 is significantly weaker at complement activation than IgG1. Moreover, unlike IgG1, IgG2 does not bind to Fc receptors on mononuclear cells or neutrophils. While IgG3 is optimal for complement activation, its in vivo half-life is approximately one third of the other IgG isotypes. Another important consideration for immunoadhesins designed to be used as human therapeutics is the number of allotypic variants of the particular isotype. In general, IgG isotypes with fewer serologically-defined allotypes are preferred. For example, IgG1 has only four serologically-defined allotypic sites, two of which (G1m and 2) are located in the Fc region; and one of these sites G1 ml, is non-immunogenic. In contrast, there are 12 serologically-defined allotypes in IgG3, all of which are in the Fc region; only three of these sites (G3m5, 11 and 21) have one allotype which is nonimmunogenic. Thus, the potential immunogenicity of a γ3 immunoadhesin is greater than that of a γ1 immunoadhesin.

With respect to the parental immunoglobulin, a useful joining point is just upstream of the cysteines of the hinge that form the disulfide bonds between the two heavy chains. In a frequently used design, the codon for the C-terminal residue of the WSX receptor or OB protein part of the molecule is placed directly upstream of the codons for the sequence DKTHTCPPCP (SEQ ID NO:44) of the IgG1 hinge region.

The general methods suitable for the construction and expression of immunoadhesins are the same as those disclosed hereinabove with regard to WSX receptor and OB protein. Immunoadhesins are most conveniently constructed by fusing the cDNA sequence encoding the WSX receptor or OB protein portion in-frame to an Ig cDNA sequence. However, fusion to genomic Ig fragments can also be used (see, e.g., Gascoigne et al., *Proc. Natl. Acad. Sci. USA*, 84:2936–2940 (1987); Aruffo et al., *Cell* 61:1303–1313 (1990); Stamenkovic et al., *Cell* 66:1133–1144 (1991)). The latter type of fusion requires the presence of Ig regulatory sequences for expression. cDNAs encoding IgG heavy-chain constant regions can be isolated based on published sequence from cDNA libraries derived from spleen or peripheral blood lymphocytes, by hybridization or by polymerase chain reaction (PCR) techniques. The cDNAs encoding the WSX receptor or OB protein and Ig parts of the immunoadhesin are inserted in tandem into a plasmid vector that directs efficient expression in the chosen host cells. For expression in mammalian cells, pRK5-based vectors (Schall et al., *Cell* 61:361–370 (1990)) and CDM8-based vectors (Seed, *Nature* 329:840 (1989)) can be used. The exact junction can be created by removing the extra sequences between the designed junction codons using oligonucleotide-directed deletional mutagenesis (Zoller et al., *Nucleic Acids Res.* 10:6487 (1982); Capon et al., *Nature* 337:525–531 (1989)). Synthetic oligonucleotides can be used, in which each half is complementary to the sequence on either side of the desired junction; ideally, these are 36 to 48-mers. Alternatively, PCR techniques can be used to join the two parts of the molecule in-frame with an appropriate vector.

The choice of host cell line for the expression of the immunoadhesin depends mainly on the expression vector. Another consideration is the amount of protein that is required. Milligram quantities often can be produced by transient transfections. For example, the adenovirus EIA-transformed 293 human embryonic kidney cell line can be transfected transiently with pRK5-based vectors by a modification of the calcium phosphate method to allow efficient immunoadhesin expression. CDM8-based vectors can be used to transfect COS cells by the DEAE-dextran method (Aruffo et al., *Cell* 61:1303–1313 (1990); Zettmeissl et al., *DNA Cell Biol. US* 9:347–353 (1990)). If larger amounts of protein are desired, the immunoadhesin can be expressed after stable transfection of a host cell line. For example, a pRK5-based vector can be introduced into Chinese hamster ovary (CHO) cells in the presence of an additional plasmid encoding dihydrofolate reductase (DHFR) and conferring resistance to G418. Clones resistant to G418 can be selected in culture; these clones are grown in the presence of increasing levels of DHFR inhibitor methotrexate; clones are selected, in which the number of gene copies encoding the DHFR and immunoadhesin sequences is co-amplified. If the immunoadhesin contains a hydrophobic leader sequence at its N-terminus, it is likely to be processed and secreted by the transfected cells. The expression of immunoadhesins with more complex structures may require uniquely suited host cells; for example, components such as light chain or J chain may be provided by certain myeloma or hybridoma cell hosts (Gascoigne et al., 1987, supra, Martin et al., *J. Virol.* 67:3561–3568 (1993)).

Immunoadhesins can be conveniently purified by affinity chromatography. The suitability of protein A as an affinity ligand depends on the species and isotype of the immunoglobulin Fc domain that is used in the chimera. Protein A can be used to purify immunoadhesins that are based on human γ1, γ2, or γ4 heavy chains (Lindmark et al., *J. Immunol. Meth.* 62:1–13 (1983)). Protein G is recommended for all mouse isotypes and for human γ3 (Guss et al., *EMBO J.* 5:1567–1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. The conditions for binding an immunoadhesin to the protein A or G affinity column are dictated entirely by the characteristics of the Fc domain; that is, its species and isotype. Generally, when the proper ligand is chosen, efficient binding occurs directly from unconditioned culture fluid. One distinguishing feature of immunoadhesins is that, for human γ1 molecules, the binding capacity for protein A is somewhat diminished relative to an antibody of the same Fc type. Bound immunoadhesin can be efficiently eluted either at acidic pH (at or above 3.0), or in a neutral pH buffer containing a mildly chaotropic salt. This affinity chromatography step can result in an immunoadhesin preparation that is >95% pure.

Other methods known in the art can be used in place of, or in addition to, affinity chromatography on protein A or G to purify immunoadhesins. Immunoadhesins behave similarly to antibodies in thiophilic gel chromatography (Hutchens et al., *Anal. Biochem.* 159:217–226 (1986)) and immobilized metal chelate chromatography (Al-Mashikhi et al., *J. Dairy Sci.* 71:1756–1763 (1988)). In contrast to antibodies, however, their behavior on ion exchange columns is dictated not only by their isoelectric points, but also by a charge dipole that may exist in the molecules due to their chimeric nature.

If desired, the immunoadhesins can be made bispecific. Thus, the immunoadhesins of the present invention may combine a WSX receptor extracellular domain and a domain, such as the extracellular domain, of another cytokine receptor subunit. Exemplary cytokine receptors from which such bispecific immunoadhesin molecules can be made include TPO (or mpl ligand), EPO, G-CSF, IL-4, IL-7, GH, PRL, IL-3, GM-CSF, IL-5, IL-6, LIF, OSM, CNTF and IL-2 receptors. Alternatively, an OB protein domain may be combined with another cytokine, such as those exemplified herein, in the generation of a bispecific immunoadhesin. For bispecific molecules, trimeric molecules, composed of a chimeric antibody heavy chain in one arm and a chimeric antibody heavy chain-light chain pair in the other arm of their antibody-like structure are advantageous, due to ease of purification. In contrast to antibody-producing quadromas traditionally used for the production of bispecific immunoadhesins, which produce a mixture of ten tetramers, cells transfected with nucleic acid encoding the three chains of a trimeric immunoadhesin structure produce a mixture of only three molecules, and purification of the desired product from this mixture is correspondingly easier.

10. Long Half-Life Derivatives of OB Protein

Prefered OB protein functional derivatives for use in the methods of the present invention include OB-immunoglobulin chimeras (immunoadhesins) and other longer half-life molecules. Techniques for generating OB protein immunoadhesins have been described above. The prefered OB immunoadhesin is made according to the techniques described in Example 11 below.

Other derivatives of the OB proteins, which possess a longer half-life than the native molecules comprise the OB protein or an OB-immunoglobulin chimera covalently bonded to a nonproteinaceous polymer. The nonproteinaceous polymer ordinarily is a hydrophilic synthetic polymer, i.e., a polymer not otherwise found in nature. However, polymers which exist in nature and are produced by recombinant or in vitro methods are useful, as are polymers which are isolated from native sources. Hydrophilic polyvinyl polymers fall within the scope of this invention, e.g. polyvinylalcohol and polyvinylpyrrolidone. Particularly useful are polyalkylene ethers such as polyethylene glycol (PEG); polyelkylenes such as polyoxyethylene, polyoxypropylene, and block copolymers of polyoxyethylene and polyoxypropylene (Pluronics™); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextrane sulfate, dextran, dextrins, glycogen, or the polysaccharide subunit of acid mucopolysaccharides, e.g. hyaluronic acid; polymers of sugar alcohols such as polysorbitol and polymannitol; heparin or heparon. The polymer prior to cross-linking need not be, but preferably is, water soluble, but the final conjugate must be water soluble. In addition, the polymer should not be highly immunogenic in the conjugate form, nor should it possess viscosity that is incompatible with intravenous infusion or injection if it is intended to be administered by such routes.

Preferably the polymer contains only a single group which is reactive. This helps to avoid cross-linking of protein molecules. However, it is within the scope herein to optimize reaction conditions to reduce cross-linking, or to purify the reaction products through gel filtration or chromatographic sieves to recover substantially homogenous derivatives.

The molecular weight of the polymer may desirably range from about 100 to 500,000, and preferably is from about 1,000 to 20,000. The molecular weight chosen will depend upon the nature of the polymer and the degree of substitution. In general, the greater the hydrophilicity of the polymer and the greater the degree of substitution, the lower the molecular weight that can be employed. Optimal molecular weights will be determined by routine experimentation.

The polymer generally is covalently linked to the OB protein or to the OB-immunoglobulin chimera though a multifunctional crosslinking agent which reacts with the polymer and one or more amino acid or sugar residues of the OB protein or OB-immunoglobulin chimera to be linked. However, it is within the scope of the invention to directly crosslink the polymer by reacting a derivatized polymer with the hybrid, or via versa.

The covalent crosslinking site on the OB protein or OB-immunoglobulin chimera includes the N-terminal amino group and epsilon amino groups found on lysine residues, as well as other amino, imino, carboxyl, sulfhydryl, hydroxyl or other hydrophilic groups. The polymer may be covalently bonded directly to the hybrid without the use of a multifunctional (ordinarily bifunctional) crosslinking agent. Covalent binding to amino groups is accomplished by known chemistries based upon cyanuric chloride, carbonyl diimidazole, aldehyde reactive groups (PEG alkoxide plus diethyl acetal of bromoacetaldehyde; PEG plus DMSO and acetic anhydride, or PEG chloride plus the phenoxide of 4-hydroxybenzaldehyde, succinimidyl active esters, activated dithiocarbonate PEG, 2,4,5-trichlorophenylcloroformate or P-nitrophenylcloroformate activated PEG). Carboxyl groups are derivatized by coupling PEG-amine using carbodiimide.

Polymers are conjugated to oligosaccharide groups by oxidation using chemicals, e.g. metaperiodate, or enzymes, e.g. glucose or galactose oxidase (either of which produces the aldehyde derivative of the carbohydrate), followed by reaction with hydrazide or amino derivatized polymers, in the same fashion as is described by Heitzmann et al., *P.N.A.S.* 71:3537–41 (1974) or Bayer et al., *Methods in Enzymology* 62:310 (1979), for the labeling of oligosaccharides with biotin or avidin. Further, other chemical or enzymatic methods which have been used heretofore to link oligosaccharides are particularly advantageous because, in general, there are fewer substitutions than amino acid sites for derivatization, and the oligosaccharide products thus will be more homogenous. The oligosaccharide substituents also are optionally modified by enzyme digestion to remove sugars, e.g. by neuramimidase digestion, prior to polymer derivatization.

The polymer will bear a group which is directly reactive with an amino acid side chain, or the N- or C-terminus of the polypeptide linked, or which is reactive with the multifunctional cross-linking agent. In general, polymers bearing such reactive groups are known for the preparation of immobilized proteins. In order to use such chemistries here, one should employ a water soluble polymer otherwise derivatized in the same fashion as insoluble polymers heretofore employed for protein immobilization. Cyanogen bromide activation is a particularly useful procedure to employ in crosslinking polysaccharides.

"Water soluble" in reference to the starting polymer means that the polymer or its reactive intermediate used for conjugation is sufficiently water soluble to participate in a derivatization reaction.

"Water soluble" in reference to the polymer conjugate means that the conjugate is soluble in physiological fluids such as blood.

The degree of substitution with such a polymer will vary depending upon the number of reactive sites on the protein, whether all or a fragment of the protein is used, whether the protein is a fusion with a heterologous protein (e.g. an OB-immunoglobulin chimera), the molecular weight, hydrophilicity and other characteristics of the polymer, and the particular protein derivatization sites chosen. In general, the conjugate contains about from 1 to 10 polymer molecules, while any heterologous sequence may be substituted with an essentially unlimited number of polymer molecules so long as the desired activity is not significantly adversely affected. The optimal degree of cross-linking is easily determined by an experimental matrix in which the time, temperature and other reaction conditions are varied to change the degree of substitution, after which the ability of the conjugates to function in the desired fashion is determined.

The polymer, e.g. PEG, is cross-linked by a wide variety of methods known per se for the covalent modification of proteins with nonproteinaceous polymers such as PEG. Certain of these methods, however, are not preferred for the purposes herein. Cyanuronic chloride chemistry leads to many side reactions, including protein cross-linking. In addition, it may be particularly likely to lead to inactivation of proteins containing sulfhydryl groups. Carbonyl diimidazole chemistry (Beauchamp et al., *Anal Biochem.* 131: 25–33 (1983)) requires high pH (>8.5), which can inactivate proteins. Moreover, since the "activated PEG" intermediate can react with water, a very large molar excess of "activated PEG" over protein is required. The high concentrations of PEG required for the carbonyl diimidazole chemistry also led to problems in purification, as both gel filtration chromatography and hydrophilic interaction chromatography are adversely affected. In addition, the high concentrations of "activated PEG" may precipitate protein, a problem that per se has been noted previously (Davis, U.S. Pat. No. 4,179,337). On the other hand, aldehyde chemistry (Royer, U.S. Pat. No. 4,002,531) is more efficient since it requires only a 40-fold molar excess of PEG and a 1–2 hr incubation. However, the manganese dioxide suggested by Royer for preparation of the PEG aldehyde is problematic "because of the pronounced tendency of PEG to form complexes with metal-based oxidizing agents" (Harris et al., *J. Polym. Sci. Polym. Chem. Ed.* 22:341–52 (1984)). The use of a Moffatt oxidation, utilizing DMSO and acetic anhydride, obviates this problem. In addition, the sodium borohydride suggested by Royer must be used at high pH and has a significant tendency to reduce disulfide bonds. In contrast, sodium cyanoborohydride, which is effective at neutral pH and has very little tendency to reduce disulfide bonds is preferred.

Functionalized PEG polymers to modify the OB protein or OB-immunoglobulin chimeras of the present invention are available from Shearwater Polymers, Inc. (Huntsville, Ala.). Such commercially available PEG derivatives include, but are not limited to, amino-PEG, PEG amino acid esters, PEG-hydrazide, PEG-thiol, PEG-succinate, carboxymethylated PEG, PEG-propionic acid, PEG amino acids, PEG succinimidyl succinate, PEG succinimidyl propionate, succinimidyl ester of carboxymethylated PEG, succinimidyl carbonate of PEG, succinimidyl esters of amino acid PEGs, PEG-oxycarbonylimidazole, PEG-nitrophenyl carbonate, PEG tresylate, PEG-glycidyl ether, PEG-aldehyde, PEG vinylsulfone, PEG-maleimide, PEG-orthopyridyl-disulfide, heterofunctional PEGs, PEG vinyl derivatives, PEG silanes, and PEG phospholides. The reaction conditions for coupling these PEG derivatives will vary depending on the protein, the desired degree of PEGylation, and the PEG derivative utilized. Some factors involved in the choice of PEG derivatives include: the desired point of attachment (lysine or cysteine), hydrolytic stability and reactivity of the derivatives, stability, toxicity and antigenicity of the linkage, suitability for analysis, etc. Specific instructions for the use of any particular derivative are available from the manufacturer.

The long half-life conjugates of this invention are separated from the unreacted starting materials by gel filtration. Heterologous species of the conjugates are purified from one another in the same fashion. The polymer also may be water-insoluble, as a hydrophilic gel.

The conjugates may also be purified by ion-exchange chromatography. The chemistry of many of the electrophilically activated PEG's results in a reduction of amino group charge of the PEGylated product. Thus, high resolution ion exchange chromatography can be used to separate the free and conjugated proteins, and to resolve species with different levels of PEGylation. In fact, the resolution of different species (e.g. containing one or two PEG residues) is also possible due to the difference in the ionic properties of the unreacted amino acids.

B. Therapeutic Uses for the WSX Receptor

The WSX receptor and WSX receptor gene are believed to find therapeutic use for administration to a mammal in the treatment of diseases characterized by a decrease in hematopoietic cells. Examples of these diseases include: anemia (including macrocytic and aplastic anemia); thrombocytopenia; hypoplasia; disseminated intravascular coagulation (DIC); myelodysplasia; immune (autoimmune) thrombocytopenic purpura (ITP); and HIV induced ITP. Additionally, these WSX receptor molecules may be useful in treating myeloproliferative thrombocytotic diseases as well as thrombocytosis from inflammatory conditions and in iron deficiency. WSX receptor polypeptide and WSX receptor gene which lead to an increase in hematopoietic cell proliferation may also be used to enhance repopulation of mature blood cell lineages in cells having undergone chemo- or radiation therapy or bone marrow transplantation therapy. Generally, the WSX receptor molecules are expected to lead to an enhancement of the proliferation and/or differentiation (but especially proliferation) of primitive hematopoietic cells.

Other potential therapeutic applications for WSX receptor and WSX receptor gene include the treatment of obesity and diabetes and for promoting kidney, liver and lung growth and/or repair (e.g. in renal failure).

The WSX receptor may be administered alone or in combination with cytokines (such as OB protein), growth factors or antibodies in the above-identified clinical situations. This may facilitate an effective lowering of the dose of WSX receptor. Suitable dosages for such additional molecules will be discussed below.

Administration of WSX receptor to a mammal having depressed levels of endogenous WSX receptor or a defective WSX receptor gene is contemplated, preferably in the situation where such depressed levels lead to a pathological disorder, or where there is lack of activation of the WSX receptor. In these embodiments where the full length WSX receptor is to be administered to the patient, it is contemplated that the gene encoding the receptor may be administered to the patient via gene therapy technology.

In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA*, 83:4143–4146 (1986)). The oligonucleotides can be modified to enhance their uptake, e.g., by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11:205–210 (1993)). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., *J. Biol. Chem.* 262:4429–4432 (1987); and Wagner et al., *Proc. Natl. Acad. Sci. USA* 87:3410–3414 (1990). For review of the currently known gene marking and gene therapy protocols see Anderson et al., *Science* 256:808–813 (1992).

The invention also provides antagonists of WSX receptor activation (e.g. WSX receptor ECD, WSX receptor immunoadhesins and WSX receptor antisense nucleic acid; neutralizing antibodies and uses thereof are discussed in section E below). Administration of WSX receptor antagonist to a mammal having increased or excessive levels of endogenous WSX receptor activation is contemplated, preferably in the situation where such levels of WSX receptor activation lead to a pathological disorder.

In one embodiment, WSX receptor antagonist molecules may be used to bind endogenous ligand in the body, thereby causing desensitized WSX receptors to become responsive to WSX ligand, especially when the levels of WSX ligand in the serum exceed normal physiological levels. Also, it may be beneficial to bind endogenous WSX ligand which is activating undesired cellular responses (such as proliferation of tumor cells). Potential therapeutic applications for WSX antagonists include for example, treatment of metabolic disorders (e.g., anorexia and steroid-induced truncalobesity), stem cell tumors and other tumors which express WSX receptor.

Pharmaceutical compositions of the WSX receptor ECD may further include a WSX ligand. Such dual compositions may be beneficial where it is therapeutically useful to prolong half-life of WSX ligand, and/or activate endogenous WSX receptor directly as a heterotrimeric complex.

Therapeutic formulations of WSX receptor are prepared for storage by mixing WSX receptor having the desired degree of purity with optional physiologically acceptable carriers, excipients, or stabilizers (*Remington's Pharmaceutical Sciences,* 16th edition, Osol, A., Ed., (1980)), in the form of lyophilized cake or aqueous solutions. Acceptable carriers, excipients, or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or non-ionic surfactants such as Tween, Pluronics™ or polyethylene glycol (PEG).

The WSX receptor also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles, and nanocapsules), or in macroemulsions. Such techniques are disclosed in *Remington's Pharmaceutical Sciences,* supra.

WSX receptor to be used for in vivo administration must be sterile. This is readily accomplished by filtration through sterile filtration membranes, prior to or following lyophilization and reconstitution. WSX receptor ordinarily will be stored in lyophilized form or in solution.

Therapeutic WSX receptor compositions generally are placed into a container having a sterile access port, for example, an intravenous solution bag or vial having a stopper pierceable by a hypodermic injection needle.

The route of WSX receptor administration is in accord with known methods, e.g., those routes set forth above for specific indications, as well as the general routes of injection or infusion by intravenous, intraperitoneal, intracerebral, intramuscular, intraocular, intraarterial, or intralesional means, or sustained release systems as noted below. WSX receptor is administered continuously by infusion or by bolus injection. Generally, where the disorder permits, one should formulate and dose the WSX receptor for site-specific delivery.

Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al., *J. Biomed. Mater Res.* 15:167–277 (1981) and Langer, *Chem. Tech.* 12:98–105 (1982) or poly(vinylalcohol)), polylactides (U.S. Pat. No. 3,773,919, EP 58,481), copolymers of L-glutamic acid and γ ethyl-L-glutamate (Sidman et al., *Biopolymers* 22:547–556 (1983)), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release WSX receptor compositions also include liposomally entrapped WSX receptor. Liposomes containing WSX receptor are prepared by methods known per se: DE 3,218,121; Epstein et al., *Proc. Natl. Acad. Sci. USA* 82:3688–3692 (1985); Hwang et al., *Proc. Natl. Acad. Sci. USA* 77:4030–4034 (1980); EP 52,322; EP 36,676; EP 88,046; EP 143,949; EP 142,641; Japanese patent application 83–118008; U.S. Pat. Nos. 4,485,045 and 4,544,545;

and EP 102,324. Ordinarily the liposomes are of the small (about 200–800 Angstroms) unilamellar type in which the lipid content is greater than about 30 mol. % cholesterol, the selected proportion being adjusted for the optimal WSX receptor therapy.

When applied topically, the WSX receptor is suitably combined with other ingredients, such as carriers and/or adjuvants. There are no limitations on the nature of such other ingredients, except that they must be physiologically acceptable and efficacious for their intended administration, and cannot degrade the activity of the active ingredients of the composition. Examples of suitable vehicles include ointments, creams, gels, or suspensions, with or without purified collagen. The compositions also may be impregnated into transdermal patches, plasters, and bandages, preferably in liquid or semi-liquid form.

For obtaining a gel formulation, the WSX receptor formulated in a liquid composition may be mixed with an effective amount of a water-soluble polysaccharide or synthetic polymer such as PEG to form a gel of the proper viscosity to be applied topically. The polysaccharide that may be used includes, for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, nontoxic, simple to prepare, and not too runny or viscous, and will not destabilize the WSX receptor held within it.

Preferably the polysaccharide is an etherified cellulose derivative, more preferably one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. Most preferred herein is methylcellulose.

The polyethylene glycol useful for gelling is typically a mixture of low and high molecular weight PEGs to obtain the proper viscosity. For example, a mixture of a PEG of molecular weight 400–600 with one of molecular weight 1500 would be effective for this purpose when mixed in the proper ratio to obtain a paste.

The term "water soluble" as applied to the polysaccharides and PEGs is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K, or Cs salts.

If methylcellulose is employed in the gel, preferably it comprises about 2–5%, more preferably about 3%, of the gel and the WSX receptor is present in an amount of about 300–1000 mg per ml of gel.

An effective amount of WSX receptor to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. Typically, the clinician will administer the WSX receptor until a dosage is reached that achieves the desired effect. A typical daily dosage for systemic treatment might range from about 1 μg/kg to up to 10 mg/kg or more, depending on the factors mentioned above. As an alternative general proposition, the WSX receptor is formulated and delivered to the target site or tissue at a dosage capable of establishing in the tissue a WSX receptor level greater than about 0.1 ng/cc up to a maximum dose that is efficacious but not unduly toxic. This intra-tissue concentration should be maintained if possible by continuous infusion, sustained release, topical application, or injection at empirically determined frequencies. The progress of this therapy is easily monitored by conventional assays.

C. Non-Therapeutic Uses for the WSX Receptor

WSX receptor nucleic acid is useful for the preparation of WSX receptor polypeptide by recombinant techniques exemplified herein which can then be used for production of anti-WSX receptor antibodies having various utilities described below.

The WSX receptor (polypeptide or nucleic acid) can be used to induce proliferation and/or differentiation of cells in vitro. In particular, it is contemplated that this molecule may be used to induce proliferation of stem cell/progenitor cell populations (e.g. CD34+ cell populations obtained as described in Example 8 below). These cells which are to be grown ex vivo may simultaneously be exposed to other known growth factors or cytokines, such as those described herein. This results in proliferation and/or differentiation of the cells having the WSX receptor.

In yet another aspect of the invention, the WSX receptor may be used for affinity purification of WSX ligand. Briefly, this technique involves: (a) contacting a source of WSX ligand with an immobilized WSX receptor under conditions whereby the WSX ligand to be purified is selectively adsorbed onto the immobilized receptor; (b) washing the immobilized WSX receptor and its support to remove non-adsorbed material; and (c) eluting the WSX ligand molecules from the immobilized WSX receptor to which they are adsorbed with an elution buffer. In a particularly preferred embodiment of affinity purification, WSX receptor is covalently attaching to an inert and porous matrix (e.g., agarose reacted with cyanogen bromide). Especially preferred is a WSX receptor immunoadhesin immobilized on a protein A column. A solution containing WSX ligand is then passed through the chromatographic material. The WSX ligand adsorbs to the column and is subsequently released by changing the elution conditions (e.g. by changing pH or ionic strength).

The WSX receptor may be used for competitive screening of potential agonists or antagonists for binding to the WSX receptor. Such agonists or antagonists may constitute potential therapeutics for treating conditions characterized by insufficient or excessive WSX receptor activation, respectively.

The preferred technique for identifying molecules which bind to the WSX receptor utilizes a chimeric receptor (e.g., epitope tagged WSX receptor or WSX receptor immunoadhesin) attached to a solid phase, such as the well of an assay plate. Binding of molecules which are optionally labelled (e.g., radiolabelled) to the immobilized receptor can be evaluated.

To identify WSX receptor agonists or antagonists, the thymidine incorporation assay can be used. For screening for antagonists, the WSX receptor can be exposed to a WSX ligand followed by the putative antagonist, or the WSX ligand and antagonist can be added to the WSX receptor simultaneously, and the ability of the antagonist to block receptor activation can be evaluated.

The WSX receptor polypeptides are also useful as molecular weight markers. To use a WSX receptor polypeptide as a molecular weight marker, gel filtration chromatography or SDS-PAGE, for example, will be used to separate protein(s) for which it is desired to determine their molecular weight(s) in substantially the normal way. The WSX receptor and other molecular weight markers will be used as standards to provide a range of molecular weights. For example, phosphorylase b (mw=97,400), bovine serum albumin (mw=68,000), ovalbumin (mw=46,000), WSX receptor (mw=44,800), trypsin inhibitor (mw=20,100), and lysozyme (mw=14,400) can be used as mw markers. The other molecular weight markers mentioned here can be purchased commercially from Amersham Corporation, Arlington Heights, Ill. The molecular weight markers are generally labeled to facilitate detection thereof. For example, the markers may be biotinylated and following separation can be incubated with streptavidin-horseradish peroxidase so that the various markers can be detected by light detection.

The purified WSX receptor, and the nucleic acid encoding it, may also be sold as reagents for mechanism studies of WSX receptor and its ligands, to study the role of the WSX receptor and WSX ligand in normal growth and development, as well as abnormal growth and development, e.g., in malignancies.

WSX receptor variants are useful as standards or controls in assays for the WSX receptor for example ELISA, RIA, or RRA, provided that they are recognized by the analytical system employed, e.g., an anti-WSX receptor antibody.

D. WSX Receptor Antibody Preparation

1. Polyclonal Antibodies

Polyclonal antibodies are generally raised in animals by multiple subcutaneous (sc) or intraperitoneal (ip) injections of the relevant antigen and an adjuvant. In that the preferred epitope is in the ECD of the WSX receptor, it is desirable to use WSX receptor ECD or a molecule comprising the ECD (e.g., WSX receptor immunoadhesin) as the antigen for generation of polyclonal and monoclonal antibodies. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining 1 mg or 1 µg of the peptide or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

2. Monoclonal Antibodies

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., *Nature* 256:495 (1975), or may be made by recombinant DNA methods (Cabilly et al., supra).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59–103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies (Kozbor, *J. Immunol.* 133:3001 (1984); Brodeur et al., *Monoclonal Antibody Production Techniques and Applications*, pp. 51–63 (Marcel Dekker, Inc., New York, 1987)).

Culture medium in which hybridoma cells are growing is assayed for production of monodonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.* 107:220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., *Curr. Opinion in Immunol.* 5:256–262 (1993) and Plückthun, *Immunol. Revs.* 130:151–188 (1992).

In a further embodiment, antibodies or antibody fragments can be isolated from antibody phage libraries generated using the techniques described in McCafferty et al., *Nature* 348:552–554 (1990). Clackson et al., *Nature* 352: 624–628 (1991) and Marks et al., *J. Mol. Biol.* 222:581–597 (1991) describe the isolation of murine and human antibodies, respectively, using phage libraries. Subsequent publications describe the production of high affinity (nM range) human antibodies by chain shuffling (Mark et al., *Bio/Technology* 10:779–783 (1992)), as well as combinatorial infection and in vivo recombination as a strategy for constructing very large phage libraries (Waterhouse et al., *Nuc. Acids. Res.* 21:2265–2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (Cabilly et al., supra; Morrison, et al., *Proc. Nat. Acad. Sci. USA* 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

3. Humanized and Human Antibodies

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature* 321:522–525 (1986); Riechmann et al., *Nature* 332:323–327 (1988); Verhoeyen et al., *Science* 239:1534–1536 (1988)), by substituting rodent CDRs or CDR sequences for the corresponding sequences of a human antibody. Accordingly, such "humanized" antibodies are chimeric antibodies (Cabilly et al., supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.* 151:2296 (1993); Chothia et al., *J. Mol. Biol.* 196:901 (1987)). Another method uses a particular framework derived from the consensus sequence of all human antibodies of a particular subgroup of light or heavy chains. The same framework may be used for several different humanized antibodies (Carter et al., *Proc. Natl. Acad. Sci. USA* 89:4285 (1992); Presta et al., *J. Immunol.* 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA* 90:2551 (1993); Jakobovits et al., *Nature* 362:255–258 (1993); Bruggermann et al., *Year in Immuno.* 7:33 (1993). Human antibodies can also be produced in phage-display libraries (Hoogenboom et al., *J. Mol. Biol.* 227:381 (1991); Marks et al., *J. Mol. Biol.* 222:581 (1991)).

4. Bispecific Antibodies

Bispecific antibodies (BsAbs) are antibodies that have binding specificities for at least two different antigens.

BsAbs can be used as tumor targeting or imaging agents and can be used to target enzymes or toxins to a cell possessing the WSX receptor. Such antibodies can be derived from full length antibodies or antibody fragments (e.g. F(ab')$_2$ bispecific antibodies). In accordance with the present invention, the BsAb may possess one arm which binds the WSX receptor and another arm which binds to a cytokine or another cytokine receptor (or a subunit thereof) such as the receptors for TPO, EPO, G-CSF, IL-4, IL-7, GH, PRL; the α or β subunits of the IL-3, GM-CSF, IL-5, IL-6, LIF, OSM and CNTF receptors; or the α, β or γ subunits of the IL-2 receptor complex. For example, the BsAb may bind both WSX receptor and gp130.

Methods for making bispecific antibodies are known in the art. Traditional production of full length bispecific antibodies is based on the coexpression of two immunoglobulin heavy chain-light chain pairs, where the two chains have different specificities (Millstein et al., *Nature* 305:537–539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, published 13 May 1993, and in Traunecker et al., *EMBO J.* 10:3655–3659 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published Mar. 3, 1994. For further details of generating bispecific antibodies see, for example, Suresh et al., *Methods in Enzymology* 121:210 (1986).

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. The following techniques can also be used for the production of bivalent antibody fragments which are not necessarily bispecific. According to these techniques, Fab'-SH fragments can be recovered from *E. coli* which can be chemically coupled to form bivalent antibodies. Shalaby et al., *J. Exp. Med.* 175:217–225 (1992) describe the production of a fully humanized BsAb F(ab')$_2$ molecule. Each Fab' fragment was separately secreted from *E. coli* and subjected to directed chemical coupling in vitro to form the BsAb. The BsAb thus formed was able to bind to cells overexpressing the HER2 receptor and normal human T cells, as well as trigger the lytic activity of human cytotoxic lymphocytes against human breast tumor targets. See also Rodrigues et al., *Int. J. Cancers* (Suppl.) 7:45–50 (1992).

Various techniques for making and isolating bivalent antibody fragments directly from recombinant cell culture have also been described. For example, bivalent heterodimers have been produced using leucine zippers. Kostelny et al., *J. Immunol.* 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., *Proc. Natl. Acad. Sci. USA* 90:6444–6448 (1993) has provided an alternative mechanism for making BsAb fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making BsAb fragments by the use of single-chain Fv (sFv) dimers has also been reported. See Gruber et al., *J. Immunol.* 152:5368 (1994).

E. Therapeutic Uses for WSX Receptor Ligands and Antibodies

The WSX ligands (e.g. OB protein and anti-WSX receptor agonist antibodies) of the present invention are useful, in one embodiment, for weight reduction, and specifically, in the treatment of obesity and other disorders associated with the abnormal expression or function of the OB gene, other metabolic disorders such as diabetes and bulimia, for reducing excessive levels of insulin in human patients (e.g. to restore or improve the insulin-sensitivity of such patients).

In addition, the WSX ligands can be used for the treatment of kidney ailments, hypertension, and lung dysfunctions, such as emphysema.

In a further embodiment, the WSX ligands (such as agonist WSX receptor antibodies) of the present invention can be used to enhance repopulation of mature blood cell lineages in mammals having undergone chemo- or radiation therapy or bone marrow transplantation therapy. Generally, the ligands will act via an enhancement of the proliferation and/or differentiation (but especially proliferation) of primitive hematopoietic cells. The ligands may similarly be useful for treating diseases characterized by a decrease in blood cells. Examples of these diseases include: anemia (including macrocytic and aplastic anemia); thrombocytopenia; hypoplasia; immune (autoimmune) thrombocytopenic purpura (ITP); and HIV induced ITP. Also, the ligands may be used to treat a patient having suffered a hemorrhage. WSX ligands may also be used to treat metabolic disorders such as obesity and diabetes mellitus, or to promote kidney, liver or lung growth and/or repair (e.g., in renal failure).

The WSX receptor ligands and antibodies may be administered alone or in concert with one or more cytokines. Furthermore, as an alternative to adminstration of the WSX ligand protein, gene therapy techniques (discussed in the section above entitled "Therapeutic Uses for the WSX Receptor") are also contemplated herein.

Potential therapeutic applications for WSX receptor neutralizing antibodies include the treatment of metabolic disorders (such as cachexia, anorexia and bulimia), stem cell tumors and other tumors at sites of WSX receptor expression, especially those tumors characterized by overexpression of WSX receptor.

For therapeutic applications, the WSX receptor ligands and antibodies of the invention are administered to a mammal, preferably a human, in a physiologically acceptable dosage form, including those that may be administered to a human intravenously as a bolus or by continuous infusion over a period of time, by intramuscular, intraperitoneal, intra-cerobrospinal, subcutaneous, intra-articular, intrasynovial, intrathecal, oral, topical, or inhalation routes. The WSX receptor ligands and antibodies also are suitably administered by intratumoral, peritumoral, intralesional, or perilesional routes or to the lymph, to exert local as well as systemic therapeutic effects.

Such dosage forms encompass physiologically acceptable carriers that are inherently non-toxic and non-therapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and PEG. Carriers for topical or gel-based forms of WSX receptor antibodies include polysaccharides such as sodium carboxymethylcellulose or methylcellulose, polyvinylpyrrolidone, polyacrylates, polyoxyethylene-polyoxypropylene-block polymers, PEG, and wood wax alcohols. For all administrations, conventional depot forms are suitably used. Such forms include, for example, microcapsules, nano-capsules, liposomes, plasters, inhalation forms, nose sprays, sublingual tablets, and sustained-release preparations. The WSX receptor ligand or antibody will typically be formulated in such vehicles at a concentration of about 0.1 mg/ml to 100 mg/ml.

Suitable examples of sustained-release preparations include semipermeable matrices of solid hydrophobic polymers containing the WSX receptor ligand or antibody, which matrices are in the form of shaped articles, e.g. films, or microcapsules. Examples of sustained-release matrices include polyesters, hydrogels (for example, poly(2-hydroxyethyl-methacrylate) as described by Langer et al., supra and Langer, supra, or poly(vinylalcohol), polylactides (U.S. Pat. No. 3,773,919), copolymers of L-glutamic acid and γ ethyl-L-glutamate (Sidman et al., supra), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated WSX receptor antibodies remain in the body for a long time, they may denature or aggregate as a result of exposure to moisture at 370C, resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release WSX receptor ligand or antibody compositions also include liposomally entrapped antibodies. Liposomes containing the WSX receptor ligand or antibody are prepared by methods known in the art, such as described in Epstein et al, *Proc. Natl. Acad. Sci. USA* 82:3688 (1985); Hwang et al., *Proc. Natl. Acad. Sci. USA* 77:4030 (1980); and U.S. Pat. Nos. 4,485,045 and 4,544,545. Ordinarily, the liposomes are the small (about 200–800 Angstroms) unilamelar type in which the lipid content is greater than about 30 mol. % cholesterol, the selected proportion being adjusted for the optimal WSX receptor ligand or antibody therapy. Liposomes with enhanced circulation time are disclosed in U.S. Pat. No. 5,013,556.

For the prevention or treatment of disease, the appropriate dosage of WSX receptor ligand or antibody will depend on the type of disease to be treated, as defined above, the severity and course of the disease, whether the antibodies are administered for preventive or therapeutic purposes, previous therapy, the patient's clinical history and response to the WSX receptor ligand or antibody, and the discretion of the attending physician. The WSX receptor ligand or antibody is suitably administered to the patient at one time or over a series of treatments.

Depending on the type and severity of the disease, about 1 μg/kg to 15 mg/kg of WSX receptor ligand or antibody is an initial candidate dosage for administration to the patient, whether, for example, by one or more separate administrations, or by continuous infusion. A typical daily dosage might range from about 1 μg/kg to 100 μg/kg (e.g. 1–50 μg/kg) or more, depending on the factors mentioned above. For example, the dose may be the same as that for other cytokines such as G-CSF, GM-CSF and EPO. For repeated administrations over several days or longer, depending on the condition, the treatment is sustained until a desired suppression of disease symptoms occurs. However, other dosage regimens may be useful. The progress of this therapy is easily monitored by conventional techniques and assays.

When one or more cytokines are co-administered with the WSX receptor ligand, lesser doses of the WSX ligand may be employed. Suitable doses of a cytokine are from about 1 μg/kg to about 15 mg/kg of cytokine. A typical daily dosage of the cytokine might range from about 1 μg/kg to 100 μg/kg (e.g. 1–50 μg/kg) or more. For example, the dose may be the same as that for other cytokines such as G-CSF, GM-CSF and EPO. The cytokine(s) may be administered prior to, simultaneously with, or following administration of the WSX ligand. The cytokine(s) and WSX ligand may be combined to form a pharmaceutically composition for simultaneous administration to the mammal. In certain embodiments, the amounts of WSX ligand and cytokine are such that a synergistic repopulation of blood cells (or synergistic increase in proliferation and/or differentiation of hematopoietic cells) occurs in the mammal upon administration of the WSX ligand and cytokine thereto. In other words, the coordinated action of the two or more agents (i.e. the WSX ligand and cytokine(s)) with respect to repopulation of blood cells (or proliferation/differentiation of hematopoietic cells) is greater than the sum of the individual effects of these molecules.

F. Articles of Manufacture

In another embodiment of the invention, an article of manufacture containing materials useful for the treatment of the conditions described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the WSX ligand. The label on, or associated with, the container indicates that the composition is used for treating the condition of choice. The article of manufacture may further comprise a second container holding a cytokine for co-administration with the WSX ligand. Further container(s) may be provided with the article of manufacture which may hold, for example, a pharmaceutically-acceptable buffer, such as phosphate-buffered saline, Ringer's solution or dextrose solution. The article of manufacture may further include other materials desirable from a commercial and user standpoint, including other buffers, diluents, filters, needles, syringes, and package inserts with instructions for use.

G. Non-Therapeutic Uses for WSX Receptor Ligands and Antibodies

WSX receptor ligands and antibodies may be used for detection of and/or enrichment of hematopoietic stem cell/progenitor cell populations in a similar manner to that in which CD34 antibodies are presently used. For stem cell enrichment, the WSX receptor antibodies may be utilized in the techniques known in the art such as immune panning, flow cytometry or immunomagnetic beads.

In accordance with one in vitro application of the WSX ligands, cells comprising the WSX receptor are provided and placed in a cell culture medium. Examples of such WSX-receptor-containing cells include hematopoietic progenitor cells, such as CD34+ cells.

Suitable tissue culture media are well known to persons skilled in the art and include, but are not limited to, Minimal Essential Medium (MEM), RPMI-1640, and Dulbecco's Modified Eagle's Medium (DMEM). These tissue culture medias are commercially available from Sigma Chemical Company (St. Louis, Mo.) and GIBCO (Grand Island, N.Y.). The cells are then cultured in the cell culture medium under conditions sufficient for the cells to remain viable and grow in the presence of an effective amount of WSX ligand and, optionally, further cytokines and growth factors. The cells can be cultured in a variety of ways, including culturing in a clot, agar, or liquid culture.

The cells are cultured at a physiologically acceptable temperature such as 37° C., for example, in the presence of an effective amount of WSX ligand. The amount of WSX ligand may vary, but preferably is in the range of about 10 ng/ml to about 1 mg/ml. The WSX ligand can of course be added to the culture at a dose determined empirically by those in the art without undue experimentation. The concentration of WSX ligand in the culture will depend on various factors, such as the conditions under which the cells and WSX ligand are cultured. The specific temperature and duration of incubation, as well as other culture conditions, can be varied depending on such factors as, e.g., the concentration of the WSX ligand, and the type of cells and medium.

It is contemplated that using WSX ligand to enhance cell proliferation and/or differentiation in vitro will be useful in a variety of ways. For instance, hematopoietic cells cultured in vitro in the presence of WSX ligand can be infused into a mammal suffering from reduced levels of the cells. Also, the cultured hematopoietic cells may be used for gene transfer for gene therapy applications. Stable in vitro cultures can be also used for isolating cell-specific factors and for expression of endogenous or recombinantly introduced proteins in the cell. WSX ligand may also be used to enhance cell survival, proliferation and/or differentiation of cells which support the growth and/or differentiation of other cells in cell culture.

The WSX receptor antibodies of the invention are also useful as affinity purification agents. In this process, the antibodies against WSX receptor are immobilized on a suitable support, such a Sephadex resin or filter paper, using methods well known in the art. The immobilized antibody then is contacted with a sample containing the WSX receptor to be purified, and thereafter the support is washed with a suitable solvent that will remove substantially all the material in the sample except the WSX receptor, which is bound to the immobilized antibody. Finally, the support is washed with another suitable solvent, such as glycine buffer, pH 5.0, that will release the WSX receptor from the antibody.

WSX receptor antibodies may also be useful in diagnostic assays for WSX receptor, e.g., detecting its expression in specific cells, tissues, or serum. For diagnostic applications, antibodies typically will be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$; a fluorescent or chemiluminescent compound, such as fluorescein isothiocyanate, rhodamine, or luciferin; radioactive isotopic labels, such as, e.g., $^{125}I$, $^{32}P$, $^{14}C$, or $^3H$; or an enzyme, such as alkaline phosphatase, beta-galactosidase, or horseradish peroxidase.

Any method known in the art for separately conjugating the polypeptide variant to the detectable moiety may be employed, including those methods described by Hunter et al., *Nature* 144:945 (1962); David et al., *Biochemistry* 13:1014 (1974); Pain et al., *J. Immunol. Meth* 40:219 (1981); and Nygren, *J. Histochem. and Cytochem.* 30:407 (1982).

The antibodies of the present invention may be employed in any known assay method, such as competitive binding assays, direct and indirect sandwich assays, and immunoprecipitation assays. Zola, *Monoclonal Antibodies: A Manual of Techniques*, pp. 147–158 (CRC Press, Inc., 1987).

Competitive binding assays rely on the ability of a labeled standard to compete with the test sample analyte for binding with a limited amount of antibody. The amount of WSX receptor in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

III. Experimental

Below are examples of specific embodiments for carrying out the present invention. The examples are offered for illustrative purposes only, and are not intended to limit the scope of the present invention in any way.

The disclosures of all publications, patents and patent applications cited herein, whether supra or infra, are hereby incorporated by reference in their entirety.

EXAMPLE 1

Cloning of Human WSX Receptor

An oligonucleotide probe designated WSX.6 #1 was synthesized based upon the T73849 EST sequence. The WSX.6 #1 probe was a 51mer having the following sequence: 5' GTCAGTCTCCCAGTTCCAGACTTGTGT-GCAGTCTATGCTGTTCAGGTGCGC-3' (SEQ ID NO:45).

The radiolabeled WSX.6 #1 probe was used to probe $1.2 \times 10^6$ clones from a random and oligo dT primed λgt10 fetal liver library (Clontech, Palo Alto, Calif.). Following hybridization at 42° C. overnight, the filters were washed at 50° C. in 0.5×SSC and 0.1% NaDodSO$_4$ (SDS). From the initial screen, 10 clones were selected and upon subsequent screening 5 individual plaque pure clones were isolated. Of these 5 individual clones, four clones designated 1, 5, 6 and 9 were subcloned into pBSSK (Stratagene) following EcoRI digestion. Sequence analysis revealed clone and clone 9 contained the putative initiation methionine and signal peptide. Clone 6 (designated 6.4) contained the most 3' end sequence and subsequently was used for further screening.

To obtain the full length gene, clone 6.4 (fragment Nsi-Hind III) was radiolabeled and used to screen $1.2 \times 10^6$ clones from a λgt10 library constructed from a hepatoma Hep3B cell line. This screen resulted in 24 positive clones. Following PCR analysis of the clones using λgt10 primers (F and R), the four longest clones 12.1, 13.2, 22.3, and 24.3 were isolated. These clones were subcloned into pBSSK⁻ using the EcoRI site, and following examination by restriction enzyme digest, clones 12.1 and 13.2 were submitted for sequencing. DNA sequencing was performed with the Taq dye deoxynucleotide terminator cycle sequencing kit on an automated Applied Biosystems DNA sequencer.

The assembled contiguous sequence from all the isolated clones encoded a consensus amino terminus for the newly identified polypeptide designated the WSX receptor. However, sequence analysis revealed that at least three naturally occurring variants of the WSX receptor exist which have different cytoplasmic regions. These variants appear to be differentially spliced at the lysine residue at position 891. Clone 6.4 stops 5 amino acids after Lys 891. Clone 12.1 is different from 13.2 and 6.4 following Lys 891 and encodes a putative box 2 region which is distinct from that encoded by clone 13.2. Clone 13.2 contains a potential box 1 region and following Lys 891 encodes putative box 2 and box 3 motifs. See, Baumann et al., *Mol. Cell. Biol.* 14(1):138–146 (1994).

The full length WSX gene based on the clone 13.2 cytoplasmic region putatively encodes an 1165 amino acid transmembrane protein. The 841 amino acid extracellular domain (ECD) contains two WSXWS domains. The ECD is followed by a 24 amino acid transmembrane domain and a 300 amino acid cytoplasmic region.

EXAMPLE 2

WSX Receptor Immunoadhesin

Using polymerase chain amplification, a WSX receptor immunoadhesin was created by engineering an in-frame fusion of the WSX receptor gene extracellular domain (WSX.ECD) with human CH2CH3(Fc)IgG (Bennett et al., *J. Biol. Chem.* 266(34):23060–23067 (1991)) at the C terminus of the ECD and cloned into pBSSK⁻ (Stratagene). For expression, the WSX-Fc was excised with ClaI and BstEII and ligated into the pRK5.HuIF.grbhlgG Genenase I vector (Beck et al., *Molecular Immunology* 31(17):1335–1344 (1994)), to create the plasmid pRK5.WSX-IgG Genenase I. This plasmid was transiently transfected into 293 cells using standard calcium phosphate transfection techniques. The transfected cells were cultured at 37° C. in 5% CO$_2$ in DMEM F12 50:50 supplemented with 10% FBS, 100 mM HEPES (pH 7.2) and 1 mM glutamine. The WSX receptor immunoadhesin was purified using a ProSepA™ protein A column.

EXAMPLE 3

Antibody Production

In order to raise antibodies against the WSX receptor, the WSX receptor immunoadhesin of Example 2 was used to inoculate rabbits to raise polyclonal antibodies and mice to raise monoclonal antibodies using conventional technology.

EXAMPLE 4

Generation of a Cell Line Expressing WSX Receptor

The nucleic acid encoding full length WSX receptor variant 13.2 was inserted in the pRKtkNeo plasmid (Holmes et al., *Science* 253:1278–1280(1991)). 100 μgs of the pRK-tkNeo. WSX plasmid thus generated was linearized, ethanol precipitated and resuspended in 100 μL of RPMI 1640. $7 \times 10^6$ Baf3 cells ($5 \times 10^5$/ml) were suspended in 900 μL of RPMI and added to the linearized plasmid. Following electroporation at 325V, 1180 μF using a BRL electroporation apparatus, the cells were plated into 15 mls of RPMI 1640 containing 5% WEHI3B conditioned media and 15% serum. 48 hours later cells were selected in 2 mg/ml G418.

To obtain the Baf3/WSX cell line expressing WSX receptor variant 13.2, the G418 selected clones were analyzed by FACS using the rabbit polyclonal antisera raised against the WSX-Fc chimeric protein as described above. The highest expressing clone (designated E6) was sorted by FACS to maintain a population with a high level of WSX receptor expression.

EXAMPLE 5

Role of WSX Receptor in Cellular Proliferation

Figure 8:
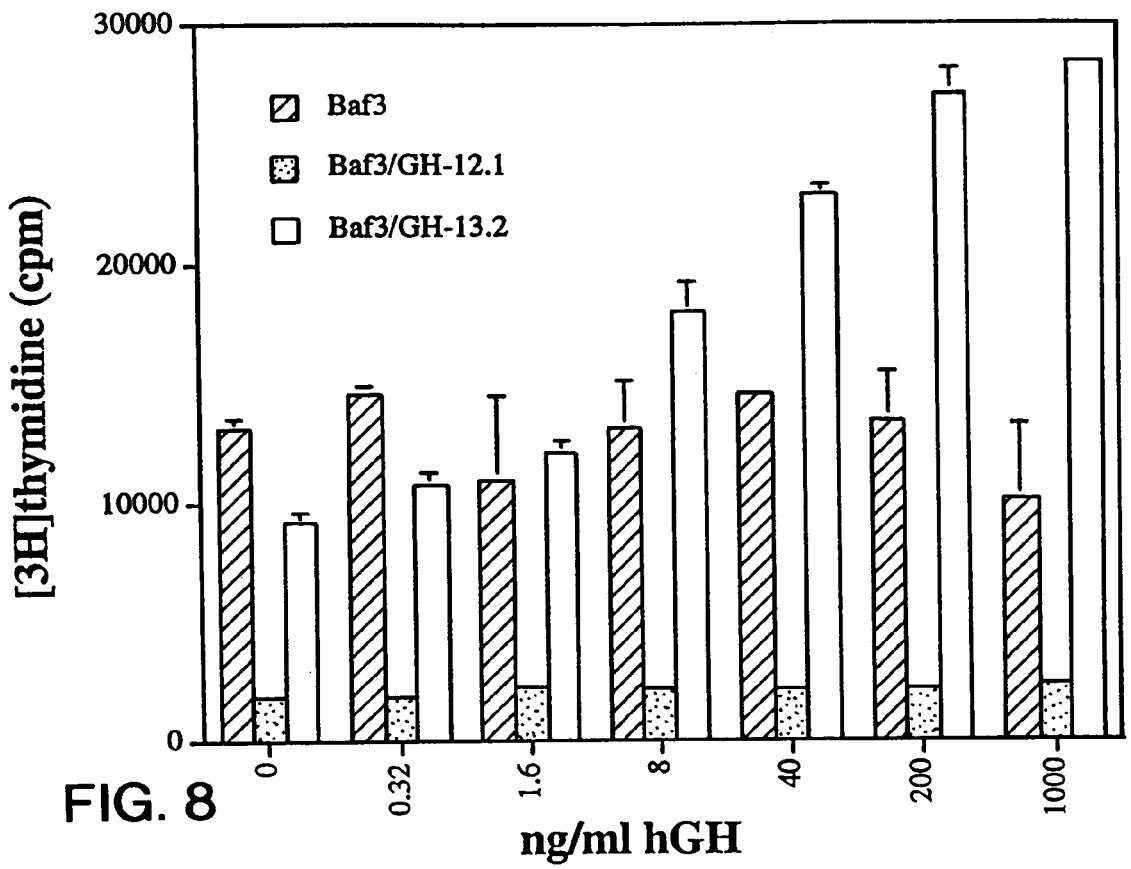
FIGS. 8 and 9 show thymidine incorporation assays in Baf-3 cells. For these assays, cells were deprived of IL-3 for 16–18 hours (in RPMI 1640 supplemented with 10% fetal calf serum (FCS)). Cells were washed in serum free RPMI 1640 and plated at 50,000 cells per well in 0.2 mls of serum free RPMI 1640 supplemented with the indicated concentration of human GH or human OB protein. Cells were stimulated for 24 hours and thymidine incorporation was determined as described (Zeigler et al. *Blood* 84:2422–2430 (1994)). Assays were performed in triplicate and the results were confirmed in three independent experiments.

The proliferative potentials of WSX receptor variants 13.2 and 12.1 were tested by constructing human growth hormone receptor-WSX receptor (GH-WSX) fusions encoding chimeric proteins consisting of the GH receptor extracellular and transmembrane domains and the WSX receptor variant 13.2 or 12.1 intracellular domains. These chimeric gene fusions were transfected into the IL-3 dependent cell line Baf3. The ability of the GH-WSX transfected Baf3 cells to respond to exogenous growth hormone (GH) was tested in a thymidine incorporation assay. As can be seen in FIGS. 6 and 8, the GH-WSX receptor variant 13.2 chimera was capable of increasing thymidine uptake in the transfected Baf3 cells, thus indicating the proliferative potential of the WSX receptor variant 13.2. However, WSX receptor variant 12.1 was unable to transmit a proliferative signal in this experiment (FIG. 8).

Materials and Methods

Recombinant PCR was used to generate the chimeric receptors containing the extracellular and transmembrane domains of the hGH receptor and the cytoplasmic domain of either WSX receptor variant 12.1 or variant 13.2. In short, the cytoplasmic domain of either variant 12.1 or 13.2 beginning with Arg at amino acid 866 and extending down to amino acid 958 or amino acid 1165 respectively, was fused in frame, by sequential PCR, to the hGH receptor extracellular and transmembrane domain beginning with Met at amino acid 18 and extending down to Arg at amino acid 274. The GH-WSX chimera was constructed by first using PCR to generate the extracellular and transmembrane domain of the human GH receptor. The 3' end primer used for this PCR contained 20 nucleotides at the 5' end of the primer corresponding to the first 20 nucleotides of the WSX cytoplasmic domain. The 3' end of the chimera was generated using PCR where the 5' end primer contained the last 19 nucleotides of the human GH receptor transmembrane domain. To generate the full length chimera, the 5' end of the human GH receptor product was combined with the 3' end WSX receptor cytoplasmic PCR product and subsequently amplified to create a fusion of the two products.

This chimeric fusion was digested with ClaI and XbaI and ligated to pRKtkNeo (Holmes et al., *Science* 253:1278–1280 (1991)) to create the chimeric expression vector. The IL-3 dependent cell line Baf3 was then electroporated with this hGH/WSX chimeric expression vector.

Briefly, 100 μg of the pRKtkNeo/GH.WSX plasmid was linearized, ethanol precipitated and resuspended in 100 μL of RPMI 1640. $7 \times 10^6$ Baf3 cells ($5 \times 10^5$/ml) were suspended in 900 μL of RPMI and added to the linearized plasmid. Following electroporation at 325V, 1180 μF using a BRL electroporation apparatus, the cells were plated into 15 mls of RPMI 1640 containing 5% wehi conditioned media and 15% serum. 48 hours later, cells were selected in 2 mg/ml G418.

To obtain the Baf3/GH.WSX cell lines, the G418 selected cells were FACS sorted using an anti-human GH Mab (3B7) at 1 μg/ml. The top 10% expressing cells were selected and expanded.

EXAMPLE 6

Expression Analysis of the WSX Receptor

The expression profile of the WSX receptor was initially examined by Northern analysis. Northern blots of human fetal or adult tissue mRNA were obtained from Clontech (Palo Alto, Calif.). A transcript of approximately 6 kb was detected in human fetal lung, liver and kidney. In the adult, low level expression was detected in a variety of tissues including liver, placenta, lung skeletal muscle, kidney, ovary, prostate and small intestine.

PCR analysis of human cord blood identified transcripts in $CD34^+$ subfraction. By PCR analysis, all three variants of the WSX receptor were present in $CD34^+$ cells. The $CD34^-$ subfraction appeared negative by this same PCR analysis.

By PCR analysis, both the 6.4 variant and 13.2 variant were evident in the $AA4^+$ $Sca^+$ $Kit^+$ (fIASK) cell population isolated from the mid-gestation fetal liver as described in Zeigler et al., *Blood* 84:2422–2430 (1994). No clones containing the 12.1 variant cytoplasmic tail have been isolated from murine tissues.

Human B cells isolated from peripheral blood using anti-CD19/20 antibodies were also positive for short form (6.4 variant) and long form (13.2 variant) receptor mRNA expression.

The WSX receptor appears to be expressed on both progenitor and more mature hematopoietic cells.

EXAMPLE 7

Cloning of Murine WSX Receptor

The human WSX receptor was used as a probe to isolate murine WSX receptor. The pRKtkNeo WSX plasmid of Example 4 was digested using Ssp1. This Ssp1 fragment (1624 bps) was isolated, and radiolabelled, and used to screen a murine liver λg10 library (Clontech). This resulted in 4 positive clones which were isolated and sequenced after sub-cloning into pBSSK via EcoR1 digestion. The resultant clones, designated 1, 2, 3, 4 showed homology to the extracellular domain of the human WSX receptor; the contiguous sequences resulting from these clones extended from the initiation methionine to tryptophan at position 783. The overall similarity of human WSX receptor and murine WSX receptor is 73% over this region of the respective extracellular domains (see FIGS. 4A–D).

EXAMPLE 8

The Role of WSX Receptor in Hematopoietic Cell Proliferation

The presence of the WSX receptor in the enriched human stem cell population $CD34^+$ from cord blood is indicative of a potential role for this receptor in stem cell/progenitor cell proliferation.

The proliferation of $CD34^+$ human blood cells in methylcellulose media (Stem Cell Technologies) was determined in the presence or absence of WSX receptor antisense oligonucleotides. These experiments were also repeated in the murine hematopoietic system using $AA4^+$ $Sca^+$ $Kit^+$ stem cells from the murine fetal liver. In both instances, the antisense oligonucleotides statistically significantly inhibited colony formation from the hematopoietic progenitor cells. See Table 1 below. The anti-proliferative effects were most pronounced using the −20 antisense and the +85 antisense oligonucleotide constructs. This inhibition was not lineage specific to any particular myeloid lineage that resulted from the progenitor expansion. The principal effect of the antisense oligonucleotides was a reduction of overall colony numbers. The size of the individual colonies was also reduced.

Antisense oligonucleotide experiments using both human and murine stem cells demonstrated an inhibition of myeloid colony formation. Although, the reduction in myelopoiesis observed in these assays could be prevented by the additional inclusion of G-CSF and GM-CSF in the culture medium. These data serve to illustrate the redundancy of cytokine action in the myelopoietic compartment.

TABLE 1

| EXPERIMENT | OLIGO | AVG. COLONY # | % INHIBITION |
|---|---|---|---|
| Human Cord Blood (KL) | (−20) AS | 32 | |
| | (−20) S | 100 | 70 |
| | (−20) SCR | 114 | |
| | (+85) AS | 80 | |
| | (+85) S | 123 | 38 |
| | (+85) SCR | 138 | |
| | Control | 158 | |
| Human Cord Blood (IL-3, IL-6, KL) | (−20) AS | 78 | |
| | (−20) S | 188 | 54 |
| | (−20) SCR | 151 | |
| | (+85) AS | 167 | |
| | (+85) S | 195 | 18 |
| | (+85) SCR | 213 | |
| | Control | 266 | |
| Human Cord Blood (KL) | (−20) AS | 42 | |
| | (−20) S | 146 | 69 |
| | (−20) SCR | 121 | |
| | (+85) AS | 123 | |
| | (+85) S | 162 | 23 |
| | (+85) SCR | 156 | |
| | Control | 145 | |
| Murine Fetal Liver (KL) | (+84) AS | 33 | |
| | (+84) S | 86 | 54 |
| | (+84) SCR | 57 | |
| | (−20) AS | 27 | |
| | (−20) S | 126 | 71 |
| | (−20) SCR | 60 | |
| | (−99) AS | 109 | |
| | (−99) S | 93 | 0 |
| | (−99) SCR | 109 | |
| | Control | 121 | |
| Murine Fetal Liver (KL) | (−23) AS | 51 | |
| | (−213) S | 60 | 10 |
| | (−213) SCR | 53 | |
| | (+211) AS | 58 | |
| | (+211) S | 54 | 3 |
| | (+211) SCR | 66 | |
| | Control | 59 | |

Materials and Methods

Human stem cells: Human umbilical cord blood was collected in PBS/Heparin (1000 μ/ml). The mononuclear fraction was separated using a dextran gradient and any remaining red blood cells lysed in 20 mM $NH_4$ Cl. $CD34^+$ cells were isolated using $CD34^+$ immunomagnetic beads (Miltenyi, CA). These isolated $CD34^+$ cells were found to be 90–97% $CD34^+$ by FACS analysis.

Murine stem cells: Midgestation fetal liver were harvested and positively selected for the $AA4^-$ antigen by immune panning. The $AA4^-$ positive fraction was then further enriched for stem cell content by FACS isolation of the $AA4^+$ $Sca^+$ $Kit^+$ fraction.

Antisense experiments: Oligodeoxynucleotides were synthesized against regions of the human or murine WSX receptors. For each oligonucleotide chosen, antisense (AS), sense (S) and scrambled (SCR) versions were synthesized (see FIG. 7). + or − indicates position relative the initiation methionine of the WSX receptor. $CD34^+$ or $AA4^+$ $Sca^+$ $Kit^+$ cells were incubated at a concentration of $10^3$/ml in 50:50 DMEM/F12 media supplemented with 10% FBS, L-glutamine, and GIBCO™ lipid concentrate containing either sense, antisense or scrambled oligonucleotides at a concentration of 70 μg/ml. After 16 hours, a second aliquot of the respective oligonucleotide was added (35 μg/ml) and the cells incubated for a further 6 hours.

Colony assays: 5000 cells from each of the above conditions were aliquoted into 5 ml of methylcellulose (Stem Cell Technologies) containing kit ligand (KL) (25 ng/ml), interleukin-3 (IL-3) (25 ng/ml) and interleukin-6 (IL-6) (50 ng/ml). The methylcellulose cultures were then incubated at 37° C. for 14 days and the resultant colonies counted and phenotyped. All assays were performed in triplicate.

EXAMPLE 9

WSX Receptor Variant 13.2 is a Receptor for OB Protein

Figure 9:
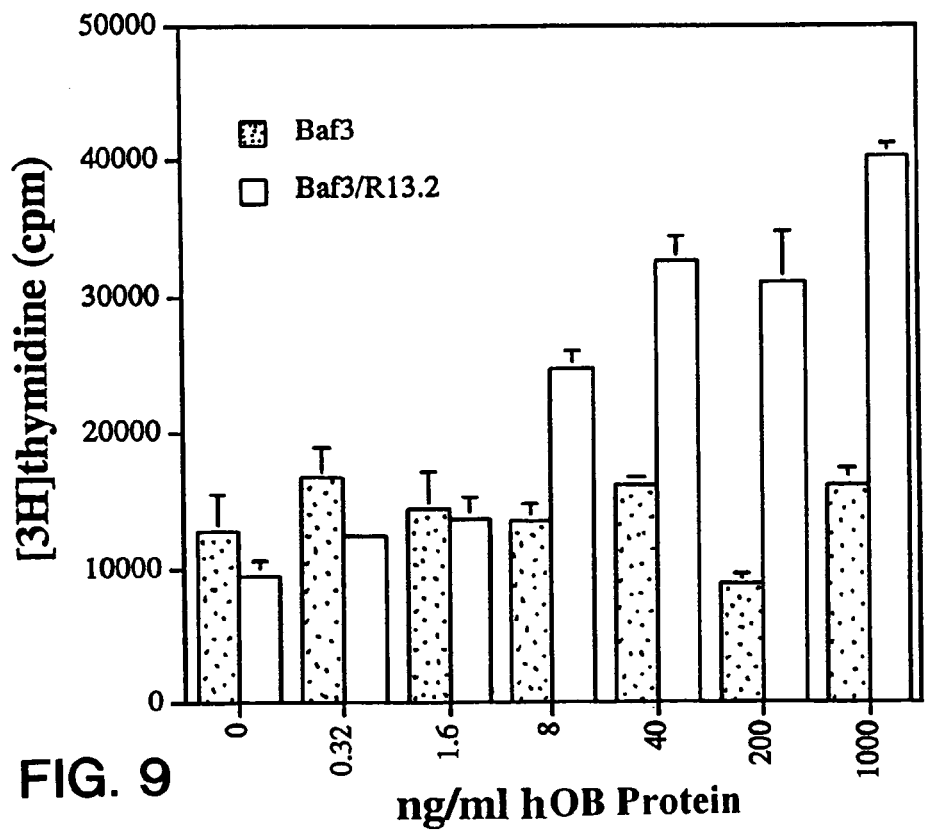

The WSX receptor variant 13.2 has essentially the same amino acid sequence as the recently cloned leptin (OB) receptor. See Tartaglia et al., *Cell* 83:1263–1271 (1995). OB protein was able to stimulate thymidine incorporation in Baf3 cells transfected with WSX receptor variant 13.2 as described in Example 4 (See FIG. 9).

OB protein expression in hematopoietic cells was studied. Oligonucleotide primers designed specifically against the OB protein illustrated the presence of this ligand in fetal liver and fetal brain as well as in two fetal liver stromal cell lines, designated 10-6 and 7-4. Both of these immortalized stromal cell lines have been demonstrated to support both myeloid and lymphoid proliferation of stem cell populations (Zeigler et al., *Blood* 84:2422–2430 (1994)).

EXAMPLE 10

Role of OB Protein in Hematopoiesis

To examine the hematopoietic activity of OB protein, a variety of in vitro assays were performed.

Murine fetal liver flASK stem cells were isolated from the midgestational fetal liver as described in Zeigler et al., *Blood* 84:2422–2430 (1994) and studied in stem cell suspension culture or methylcellulose assays.

For the stem cell suspension cultures, twenty thousand of the flASK cells were seeded in individual wells in a 12 well format in DMEM 4.5/F12 media supplemented with 10% heat inactivated fetal calf serum (Hyclone, Logan, Utah) and L-glutamine. Growth factors were added at the following concentrations: kit ligand (KL) at 25 ng/mL, interleukin-3 (IL-3) at 25 ng/mL, interleukin-6 (IL-6) at 50 ng/mL, G-CSF at 100 ng/mL, GM-CSF at 100 ng/mL, EPO at 2 U/mL, interleukin-7 (IL-7) at 100 ng/mL (all growth factors from R and D Systems, Minneapolis, Minn.). OB protein was added at 100 ng/mL unless indicated otherwise. Recombinant OB protein was produced as described in Levin et al., *Proc. Natl. Acad. Sci.* (USA) 93:1726–1730 (1996).

Figure 10A:
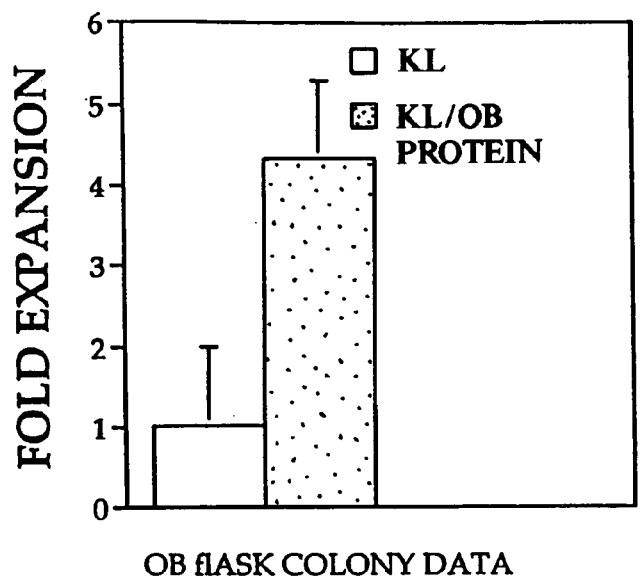
In FIGS. 10A–C, murine fetal liver AA4$^+$ Sca$^+$ kit$^+$ (flASK) stem cells were cultured in suspension culture or methylcellulose.

In keeping with its ability to transduce a proliferative signal in Baf3 cells (see previous Example), OB protein dramatically stimulated the expansion of flASK cells grown in suspension culture in the presence of kit ligand (FIG. 10A). The addition of OB protein alone to these suspension cultures was unable to effect survival of the hematopoietic stem cells (HSCs). When a variety of hematopoietic growth factors in suspension culture assays were tested, the main synergy of OB protein appeared to be with KL, GM-CSF and IL-3 (Table 2). No preferential expansion of any particular lineage was observed from cytospin analysis of the resultant cultures.

TABLE 2

| Factor | KL | KL + OB protein | OB protein |
|---|---|---|---|
| N/A | 128+/−9 | 192+/−13 | — |
| G-CSF | 131+/−3 | 177+/−8 | 30+/−5 |
| GM-CSF | 148+/−4 | 165+/−6 | 134+/−10 |
| IL-3 | 189+/−7 | 187+/−4 | 144+/− |
| IL-6 | 112+/−4 | 198+/−5 | 32+/−3 |
| EPO | 121+/−3 | 177+/−8 | 30+/−6 |
| IL-3 & IL-6 | 112+/−12 | 198+/−7 | 32+/−7 | flASK stem cells were isolated. Twenty thousand cells were plated in suspension culture with the relevant growth factor combination. Cells were harvested and counted after 7 days. Cell numbers are presented ×10$^3$. Assays were performed in triplicate and repeated in two independent experiments.

Methylcellulose assays were performed as previously described (Zeiger et al., supra). Briefly, methylcellulose colony assays were performed using "complete" methylcellulose or pre-B methylcellulose medium (Stem Cell Technologies, Vancouver, British Columbia, Canada) with the addition of 25 ng/mL KL (R and D Systems, Minneapolis, Minn.). Cytospin analyses of the resultant colonies were performed as previously described in Zeigler et al.

Figure 10B:
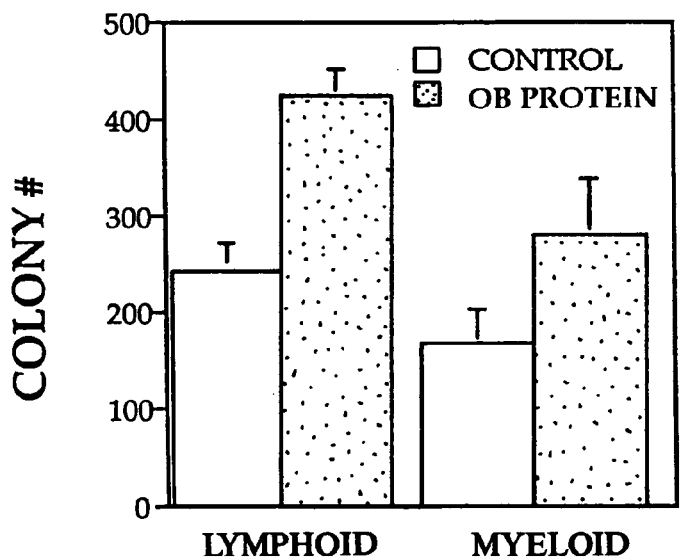
Figure 10C:
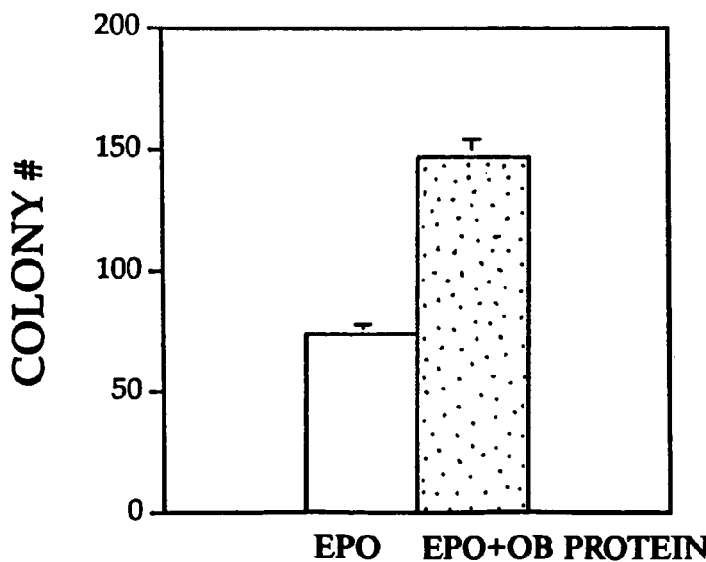

When these methylcellulose assays were employed, OB protein augmented myeloid colony formation and dramatically increased lymphoid and erythroid colony formation (FIGS. 10B and 10C) which demonstrates that OB protein can act on very early cells of the hematopoietic lineage. Importantly, the hematopoietic activity of OB protein was not confined to fetal liver stem cells, the murine bone marrow stem cell population; Lin$^{lo}$Sca$^+$ also proliferated in response to OB protein (KL: 5 fold expansion, KL and OB protein: 10 fold expansion).

Further hematopoietic analysis of the role of the WSX receptor was carried out by examining hematopoietic defects in the db/db mouse.

Figure 11:
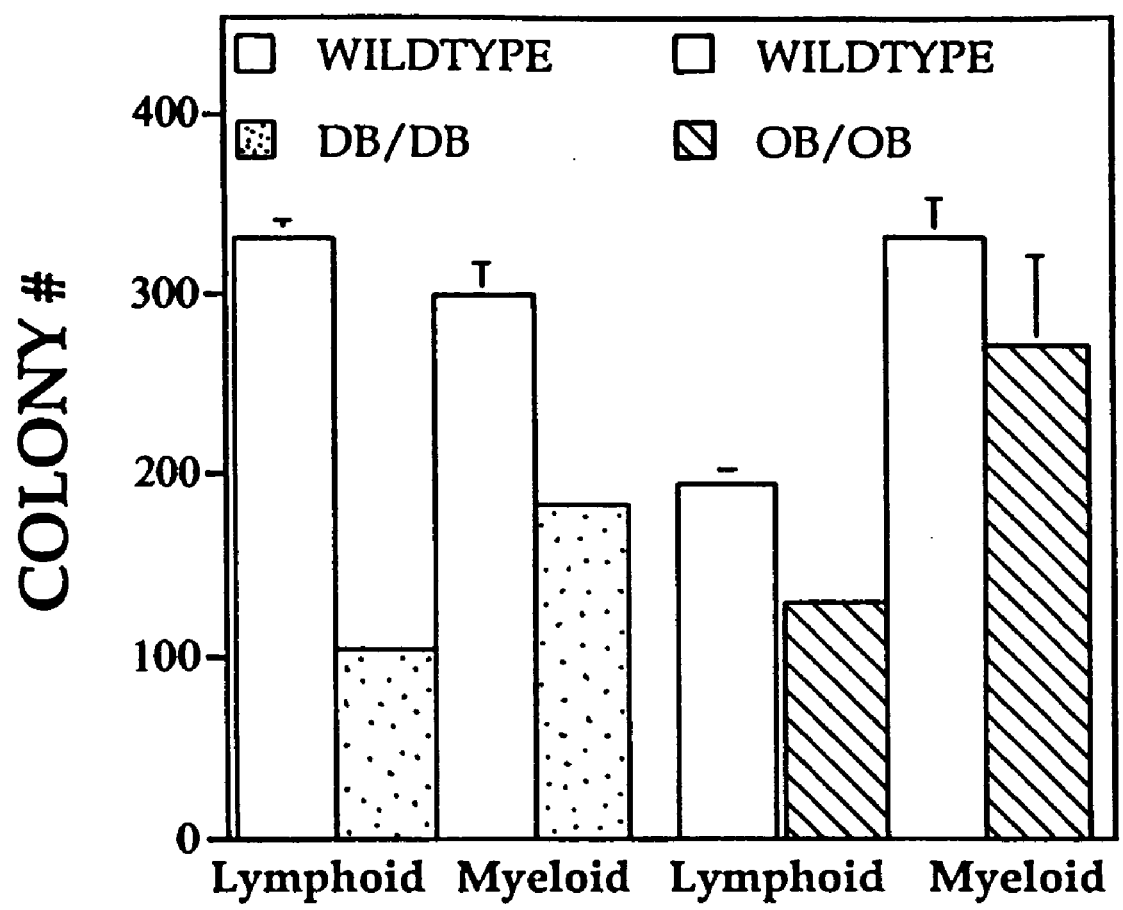
FIG. 11 illustrates methylcellulose assays to determine the colony forming potential of db/db, ob/ob and the corresponding wild-type marrow. 100,000 bone marrow cells were seeded into methylcellulose and the resultant colonies counted after 14 days. Assays were performed using both myeloid and lymphoid conditions. Assays were performed in triplicate and the experiments were repeated a minimum of 3 times.

These defects were assessed by measuring the proliferative potential of db/db homozygous mutant marrow. Under conditions favoring either myeloid (Humphries et al., *Proc. Natl. Acad. Sci.* (USA) 78:3629–3633 (1981)) or lymphoid (McNiece et al., *J. Immunol.* 146:3785–90 (1991)) expansion, the colony forming potential of the db/db marrow was significantly reduced when compared to the wild-type control marrow (FIG. 11). This was particularly evident when the comparison was made under pre-B methylcellulose conditions where KL and IL-7 are used to drive lymphopoiesis (McNiece et al., supra). Corresponding analysis of the complementary mouse mutation ob/ob, which is deficient in the production of OB protein (Zhang et al., *Nature* 372:425–431 (1994)), also indicated that the lymphoproliferative capacity is compromised in the absence of a functional OB protein signalling pathway (FIG. 11). However, this reduction was less than the reduction observed using db/db marrow.

Figure 12A:
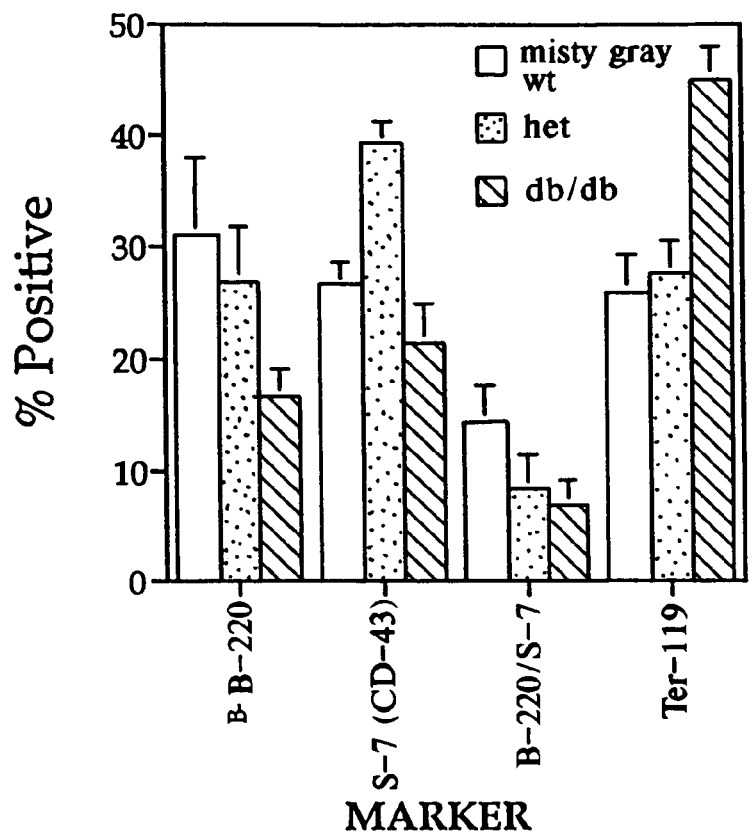
FIGS. 12A–B show bone marrow cellular profiles in wild-type misty gray homozygotes, misty gray/db heterozygotes, and homozygote db/db mice. Overall cellularity in the db/db marrow was unchanged compared to controls.

Analysis of the cellular profile of the db/db and wild-type marrow revealed significant differences between the two. Overall cellularity of the db/db marrow was unchanged. However, when various B cell populations in the db/db marrow were examined, both decreased levels of B220$^+$ and B220$^+$/CD43$^+$ cells were found. B220$^+$ cells represent all B cell lineages while CD43 is considered to be expressed preferentially on the earliest cells of the B cell hierarchy (Hardy et al., *J. Exp. Med.* 173:1213–25 (1991)). No differences were observed between the CD4/CD8 staining profiles of the two groups. The TER119 (a red cell lineage marker) population was increased in the db/db marrow (FIG. 12A).

Figure 12B:
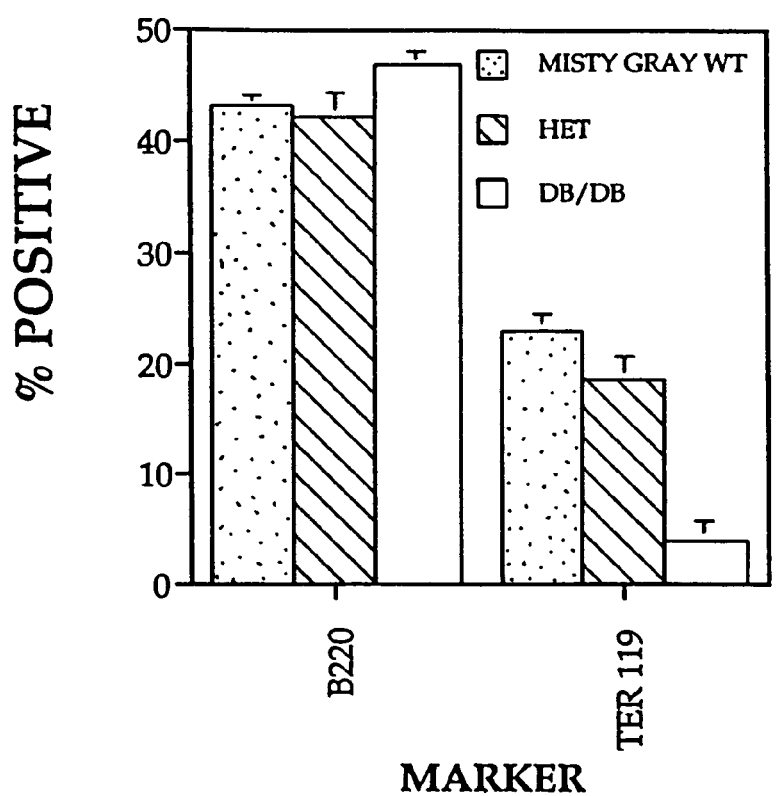

Comparison of the spleens from the two groups revealed a significant decrease in both tissue weight and cellularity of the db/db mice compared to the homozygote misty gray controls (0.063±0.009 g vs. 0.037±0.006 g and 1.10×10 ±1× 10$^4$ vs. 4.3×10$^6$±10$^3$ cells>p0.05). This decreased cellularity in the db spleen was reflected in a marked reduction in TER119 staining (FIG. 12B). This result appears to confirm the synergy demonstrated between OB protein and EPO and points to a role for OB protein in the regulation of erythropoiesis.

Examination of the hematopoietic compartment of the db/db mouse in vivo demonstrated a significant reduction in peripheral blood lymphocytes when compared to heterozygote or wild-type controls. Db/db mice fail to regulate blood glucose levels and become diabetic at approximately 6–8 weeks of age; therefore, peripheral blood counts as the animals matured were followed.

Figure 13A:
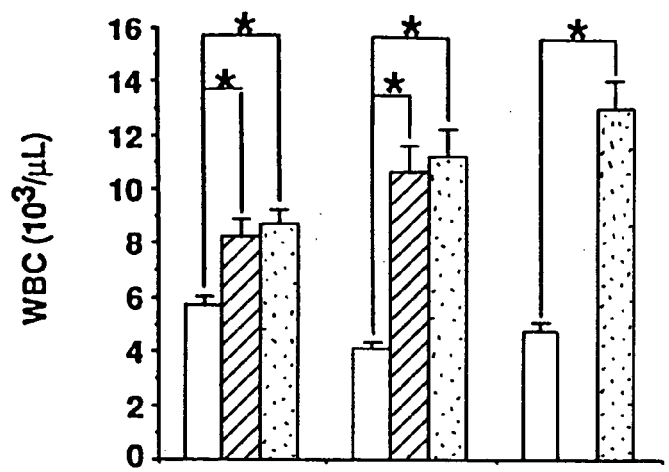
FIGS. 13A–C are an analysis of peripheral blood in db/db homozygotes, db/db misty gray heterozygotes and misty gray homozygotes. 40 microliters of peripheral blood was taken via orbital bleed and analyzed on a Serrono Baker system 9018. All areas described by the boxes represent the mean±one standard deviation of the two parameters.
Figure 13B:
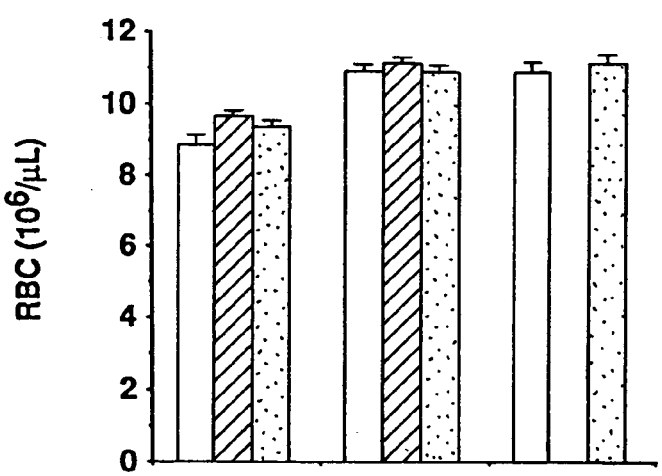
Figure 13C:
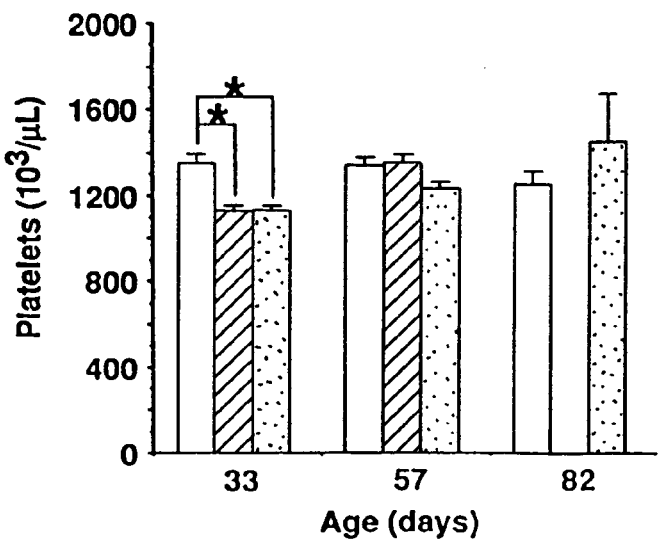

For procurement of blood samples, prior to the experiment and at time points throughout the study, 40 µL of blood was taken from the orbital sinus and immediately diluted into 10 mL of diluent to prevent clotting. The complete blood count from each blood sample was measured on a Serrono Baker system 9018 blood analyzer within 60 min. of collection. Only half the animals in each dose group were bled on any given day, thus, each animal was bled on alternate time points. Blood glucose levels were measured in orbital sinus blood samples using One Touch glucose meters and test strips (Johnson and Johnson). The results of this experiment are shown in FIGS. 13A–C.

This analysis demonstrated that peripheral blood lymphocytes are significantly reduced at all time points compared to control animals and that the peripheral lymphocyte population of the db/db mouse does not change significantly with age. FACS analysis revealed that the decreased lymphocyte population represented a decrease in both B220$^+$ cells and CD4/CD8 cells. Both erythrocyte and platelets are at wild-type levels throughout all time periods examined. The peripheral blood lymphocyte levels in ob/ob homozygous mutant mice were unchanged from wild-type controls.

Figure 14:
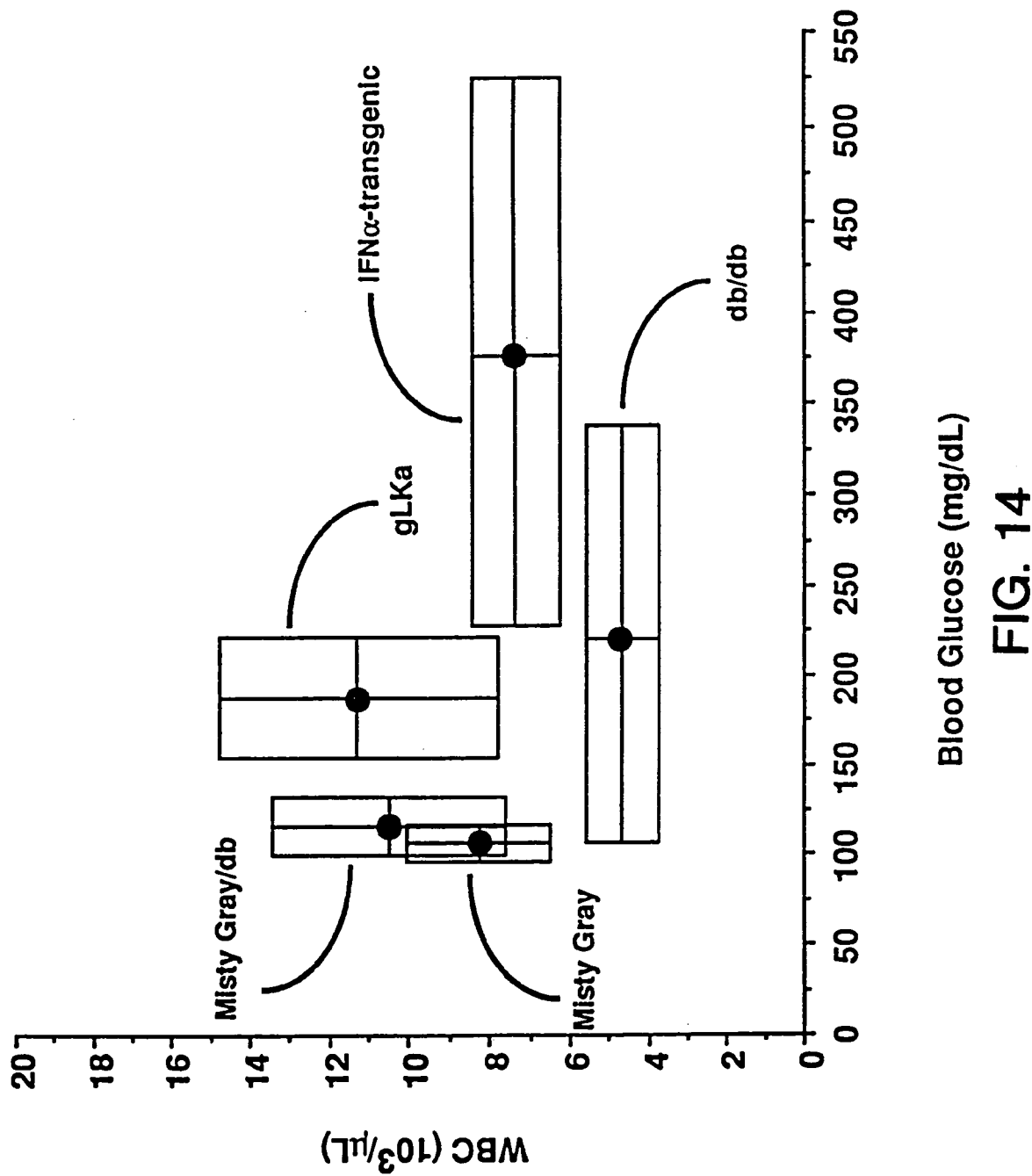
FIG. 14 is a comparison of peripheral lymphocyte counts and blood glucose level. Five groups of animals, misty-gray, misty-gray/db, db/db, interferon α-transgenic, and glucokinase transgenic heterozygote mice (gLKa) were sampled via retro-orbital bleed. Blood glucose levels in these mice were determined. All areas described by the boxes represent the mean±standard deviation of the two parameters.
Figure 15A:
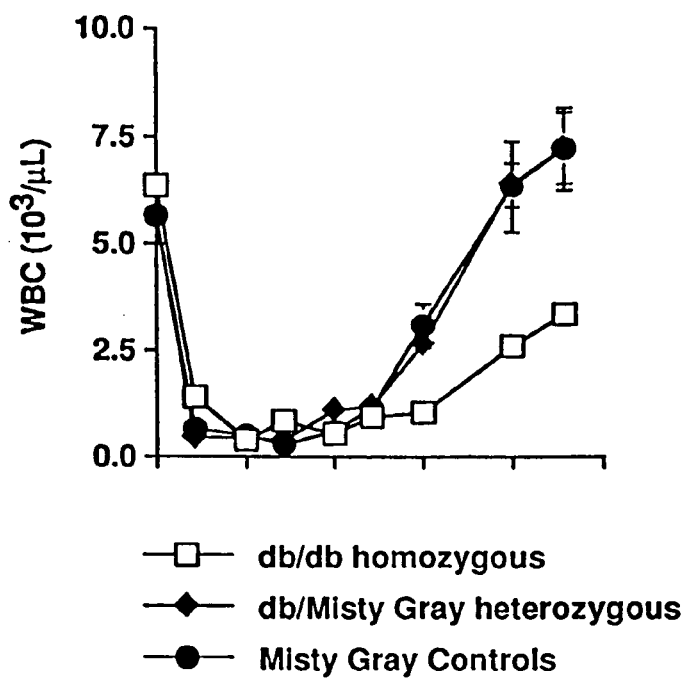
In FIGS. 15A–C, misty gray homozygotes, db/misty gray heterozygotes, and homozygous db/db mice were subjected to sub-lethal irradiation and the recovery kinetics of the peripheral blood was determined via retro-orbital bleeds.
Figure 15B:
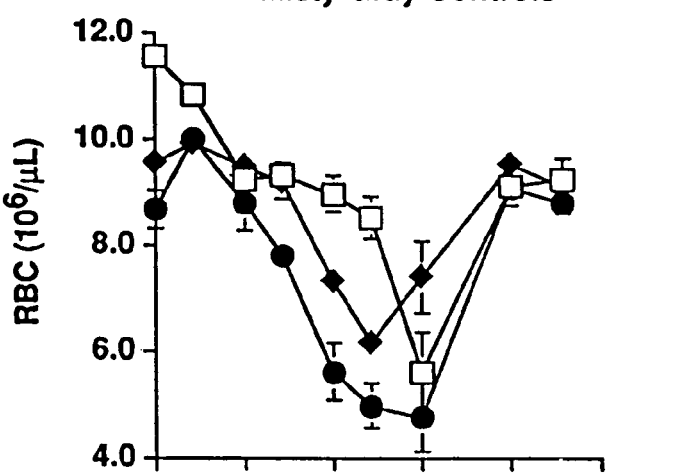
Figure 15C:
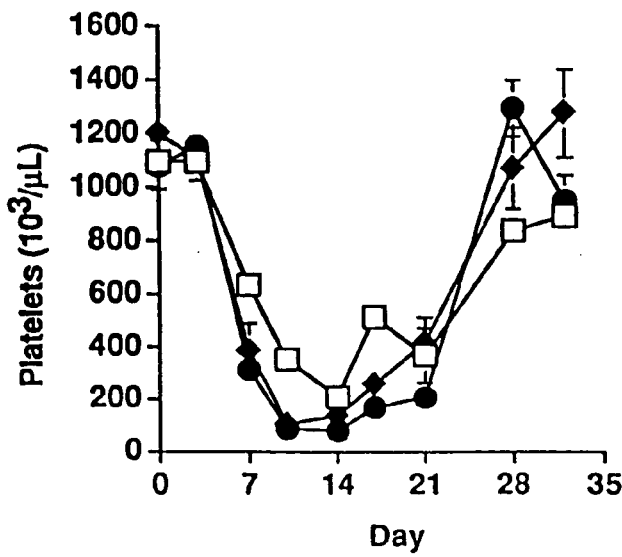

Hematopoietic analysis of the db/db mouse can be complicated by the onset of diabetes. Therefore, the impact of high glucose levels on lymphopoiesis was examined by comparing the peripheral blood profiles and blood glucose levels in two other diabetic models, the glucokinase knockout heterozygote mouse (Grupe et al., *Cell* 83:69–78 (1995)) and the IFN-α transgenic mouse (Stewart et al., *Science* 260:1942–6 (1993)). Comparison of peripheral lymphocytes and blood glucose in db/db mice, their appropriate controls and the high glucose models illustrated no relationship between blood-glucose and lymphocyte counts (FIG. 14). These results suggest therefore that the lymphoid defects observed in the db/db mouse are directly attributed to the hematopoietic function of the OB protein signalling pathway.

To test the capacity of the db/db hematopoietic compartment to respond to challenge, the db/db mice and controls were subjected to sub-lethal irradiation C57BLKS/J db/db, C57BLKS/Jm$^+$/db, and C57BLKS/J$^+$m/$^+$m mice were subjected to sub-lethal whole body irradiation (750 cGy, 190 cGy/min) as a single dose from a $^{137}$Cs source. Ten animals were used per experimental group. The kinetics of hematopoietic recovery were then followed by monitoring the peripheral blood during the recovery phase. This experiment illustrated the inability of the db/db hematopoietic system to fully recover the lymphopoietic compartment of the peripheral blood 35 days post-irradiation. Platelet levels in these mice followed the same recovery kinetics as controls, however the reduction in erythrocytes lagged behind controls by 7–10 days. This finding may reflect the increased TER 119 population found in the marrow of the db/db mice (FIG. 12A).

Materials and Methods

Bone marrow, spleens and peripheral blood was harvested from the diabetic mouse strains: C57BLKS/J db/db (mutant), C57BLKS/J m+/db (lean heterozygote control littermate), C57BLKS/J+m/+m (lean homozygote misty gray coat control littermate) and the obese mouse strains: C57BL/6J-ob/ob (mutant) and the C57BL/6J-ob/+ (lean littermate control). All strains from the Jackson Laboratory, Bar Harbor, Me. A minimum of five animals were used per experimental group. Femurs were flushed with Hank's balanced salt solution (HBSS) plus 2% FCS and a single cell suspension was made of the bone marrow cells. Spleens were harvested and the splenic capsule was ruptured and filtered through a nylon mesh. Peripheral blood was collected through the retro-orbital sinus in phosphate buffered saline (PBS) with 10 U/mL heparin and 1 mmol EDTA and processed as previously described. The bone marrow, splenocytes and peripheral blood were then stained with the monoclonal antibodies against the following antigens: B220/CD45R (Pan B cell) FITC antimouse, TER-119/erythroid cell R-PE antimouse, CD4 (L3T4), FITC antimouse, CDB (Ly 3.2), FITC antimouse, and sIgM (Igh-6b), FITC antimouse (All monoclonals from Pharmigen, San Diego, Calif.). The appropriate isotype controls were included in each experiment. For methylcellulose assays, the bone marrow from five animals per group was pooled and 100,000 cell aliquots from each group used for each assay point.

EXAMPLE 11

Expression of OB-Immunoadhesin

Using protein engineering techniques, the human OB protein was expressed as a fusion with the hinge, CH2 and CH3 domains of IgG1. DNA constructs encoding the chimera of the human OB protein and IgG1 Fc domains were made with the Fc region clones of human IgG1. Human OB cDNA was obtained by PCR from human fat cell dscDNA (Clontech Buick-Clone cDNA product). The source of the IgG1 cDNA was the plasmid pBSSK-CH2CH3. The chimera contained the coding sequence of the full length OB protein (amino acids 1–167 in FIG. 16) and human IgG1 sequences beginning at aspartic acid 216 (taking amino acid 114 as the first residue of the heavy chain constant region (Kabat et al., *Sequences of Proteins of Immunological Interest* 4th ed. (1987)), which is the first residue of the IgG1 hinge after the cysteine residue involved in heavy-light chain bonding, and ending with residues 441 to include the CH2 and CH3 Fc domains of IgG1. There was an insert of codons for three amino acids (GlyValThr) between the OB protein and IgG1 coding sequences. If necessary, this short linker sequence can easily be deleted, for example by site directed deletion mutagenesis, to create an exact junction between the coding sequences of the OB protein and the IgG1 hinge region. The coding sequence of the OB-IgG1 immunoadhesin was subcloned into the pRK5-based vector pRK5tk-neo which contains a neomycine selectable marker, for transient expression in 293 cells using the calcium phosphate technique (Suva et al., *Science* 237:893–896 (1987)). 293 cells were cultured in HAM's: Low Glucose DMEM medium (50:50), containing 10% FBS and 2 mM L-Gln. For purification of OB-IgG1 chimeras, cells were changed to serum free production medium PS24 the day after transfection and media collected after three days. The culture media was filtered.

The filtered 293 cell supernatant (400 ml) containing recombinant human OB-IgG1 was made 1 mM in phenylmethylsulfonyl fluoride and 2 μg/ml in aprotinin. This material was loaded at 4° C. onto a 1×4.5 cm Protein A agarose column (Pierce catalog # 20365) equilibrated in 100 mM HEPES pH 8. The flow rate was 75 ml/h. Once the sample was loaded, the column was washed with equilibration buffer until the $A_{280}$ reached baseline. The OB-IgG1 protein was eluted with 3.5 M $MgCl_2$+2% glycerol (unbuffered) at a flow rate of 15 ml/h. The eluate was collected with occasional mixing into 10 ml of 100 mM HEPES pH 8 to reduce the $MgCl_2$ concentration by approximately one-half and to raise the pH. The eluted protein was then dialyzed into phosphate buffered saline, concentrated, sterile filtered and stored either at 4° C. or frozen at −70° C. The OB-IgG1 immunoadhesin prepared by this method is estimated by SDS-PAGE to be greater than 90% pure.

EXAMPLE 12

Preparation of PEG-OB

The PEG derivatives of the human OB protein were prepared by reaction of hOB protein purified by reverse phase chromatography with a succinimidyl derivative of PEG propionic acid (SPA-PEG) having a nominal molecular weight of 10 kD, which had been obtained from Shearwater Polymers, Inc. (Huntsville, Ala.). After purification of the hOB protein by reverse phase chromatography, an approximately 1–2 mg/ml solution of the protein in 0.1% trifluoroacetic acid and approximately 40% acetonitrile, was diluted with ⅓ to ½ volume of 0.2 M borate buffer and the pH adjusted to 8.5 with NaOH. SPA-PEG was added to the reaction mixture to make 1:1 and 1:2 molar ratios of protein to SPA-PEG and the mixture was allowed to incubate at room temperature for one hour. After reaction and purification by gel electrophoresis or ion exchange chromatography, the samples were extensively dialyzed against phosphate-buffered saline and sterilized by filtration through a 0.22 micron filter. Samples were stored at 40C. Under these conditions, the PEG-hOB resulting from the 1:1 molar ratio protein to SPA-PEG reaction consisted primarily of molecules with one 10 kD PEG attached with minor amounts of the 2 PEG-containing species. The PEG-hOB from the 1:2 molar reaction consisted of approximately equal amounts of 2 and 3 PEGs attached to hOB, as determined by SDS gel electrophoresis. In both reactions, small amounts of unreacted protein were also detected. This unreacted protein can be efficiently removed by the gel filtration or ion exchange steps as needed. The PEG derivatives of the human OB protein can also be prepared essentially following the aldehyde chemistry described in EP 372,752 published Jun. 13, 1990.

SEQUENCE LISTING (1) GENERAL INFORMATION:

(iii) NUMBER OF SEQUENCES: 47

(2) INFORMATION FOR SEQ ID NO:1:

(i) SEQUENCE CHARACTERISTICS:
       (A) LENGTH: 4102 base pairs
       (B) TYPE: Nucleic Acid
       (C) STRANDEDNESS: Double
       (D) TOPOLOGY: Linear (xi) SEQUENCE DESCRIPTION: SEQ ID NO:1:

```
GAATTCTCGA GTCGACGGCG GGCGTTAAAG CTCTCGTGGC ATTATCCTTC          50

AGTGGGGCTA TTGGACTGAC TTTTCTTATG CTGGGATGTG CCTTAGAGGA         100

TTATGGGTGT ACTTCTCTGA AGTAAGATGA TTTGTCAAAA ATTCTGTGTG         150

GTTTTGTTAC ATTGGGAATT TATTTATGTG ATAACTGCGT TTAACTTGTC         200

ATATCCAATT ACTCCTTGGA GATTTAAGTT GTCTTGCATG CCACCAAATT         250

CAACCTATGA CTACTTCCTT TTGCCTGCTG GACTCTCAAA GAATACTTCA         300

AATTCGAATG GACATTATGA GACAGCTGTT GAACCTAAGT TTAATTCAAG         350

TGGTACTCAC TTTTCTAACT TATCCAAAAC AACTTTCCAC TGTTGCTTTC         400

GGAGTGAGCA AGATAGAAAC TGCTCCTTAT GTGCAGACAA CATTGAAGGA         450

AAGACATTTG TTTCAACAGT AAATTCTTTA GTTTTTCAAC AAATAGATGC         500

AAACTGGAAC ATACAGTGCT GGCTAAAAGG AGACTTAAAA TTATTCATCT         550

GTTATGTGGA GTCATTATTT AAGAATCTAT TCAGGAATTA TAACTATAAG         600

GTCCATCTTT TATATGTTCT GCCTGAAGTG TTAGAAGATT CACCTCTGGT         650

TCCCCAAAAA GGCAGTTTTC AGATGGTTCA CTGCAATTGC AGTGTTCATG         700

AATGTTGTGA ATGTCTTGTG CCTGTGCCAA CAGCCAAACT CAACGACACT         750

CTCCTTATGT GTTTGAAAAT CACATCTGGT GGAGTAATTT TCCAGTCACC         800

TCTAATGTCA GTTCAGCCCA TAAATATGGT GAAGCCTGAT CCACCATTAG         850

GTTTGCATAT GGAAATCACA GATGATGGTA ATTTAAAGAT TTCTTGGTCC         900

AGCCCACCAT TGGTACCATT TCCACTTCAA TATCAAGTGA AATATTCAGA         950

GAATTCTACA ACAGTTATCA GAGAAGCTGA CAAGATTGTC TCAGCTACAT        1000

CCCTGCTAGT AGACAGTATA CTTCCTGGGT CTTCGTATGA GGTTCAGGTG        1050

AGGGGCAAGA GACTGGATGG CCCAGGAATC TGGAGTGACT GGAGTACTCC        1100

TCGTGTCTTT ACCACACAAG ATGTCATATA CTTTCCACCT AAAATTCTGA        1150

CAAGTGTTGG GTCTAATGTT TCTTTTCACT GCATCTATAA GAAGGAAAAC        1200

AAGATTGTTC CCTCAAAAGA GATTGTTTGG TGGATGAATT AGCTGAGAA         1250

AATTCCTCAA AGCCAGTATG ATGTTGTGAG TGATCATGTT AGCAAAGTTA        1300

CTTTTTTCAA TCTGAATGAA ACCAAACCTC GAGGAAAGTT TACCTATGAT        1350

GCAGTGTACT GCTGCAATGA ACATGAATGC CATCATCGCT ATGCTGAATT        1400

ATATGTGATT GATGTCAATA TCAATATCTC ATGTGAAACT GATGGGTACT        1450

TAACTAAAAT GACTTGCAGA TGGTCAACCA GTACAATCCA GTCACTTGCG        1500

GAAAGCACTT TGCAATTGAG GTATCATAGG AGCAGCCTTT ACTGTTCTGA        1550
```

```
TATTCCATCT ATTCATCCCA TATCTGAGCC CAAAGATTGC TATTTGCAGA      1600

GTGATGGTTT TTATGAATGC ATTTTCCAGC CAATCTTCCT ATTATCTGGC      1650

TACACAATGT GGATTAGGAT CAATCACTCT CTAGGTTCAC TTGACTCTCC      1700

ACCAACATGT GTCCTTCCTG ATTCTGTGGT GAAGCCACTG CCTCCATCCA      1750

GTGTGAAAGC AGAAATTACT ATAAACATTG GATTATTGAA AATATCTTGG      1800

GAAAAGCCAG TCTTTCCAGA GAATAACCTT CAATTCCAGA TTCGCTATGG      1850

TTTAAGTGGA AAAGAAGTAC AATGGAAGAT GTATGAGGTT TATGATGCAA      1900

AATCAAAATC TGTCAGTCTC CCAGTTCCAG ACTTGTGTGC AGTCTATGCT      1950

GTTCAGGTGC GCTGTAAGAG GCTAGATGGA CTGGGATATT GGAGTAATTG      2000

GAGCAATCCA GCCTACACAG TTGTCATGGA TATAAAAGTT CCTATGAGAG      2050

GACCTGAATT TTGGAGAATA ATTAATGGAG ATACTATGAA AAAGGAGAAA      2100

AATGTCACTT TACTTTGGAA GCCCCTGATG AAAAATGACT CATTGTGCAG      2150

TGTTCAGAGA TATGTGATAA ACCATCATAC TTCCTGCAAT GGAACATGGT      2200

CAGAAGATGT GGGAAATCAC ACGAAATTCA CTTTCCTGTG GACAGAGCAA      2250

GCACATACTG TTACGGTTCT GGCCATCAAT TCAATTGGTG CTTCTGTTGC      2300

AAATTTTAAT TTAACCTTTT CATGGCCTAT GAGCAAAGTA AATATCGTGC      2350

AGTCACTCAG TGCTTATCCT TTAAACAGCA GTTGTGTGAT TGTTTCCTGG      2400

ATACTATCAC CCAGTGATTA CAAGCTAATG TATTTTATTA TTGAGTGGAA      2450

AAATCTTAAT GAAGATGGTG AAATAAAATG GCTTAGAATC TCTTCATCTG      2500

TTAAGAAGTA TTATATCCAT GATCATTTTA TCCCCATTGA GAAGTACCAG      2550

TTCAGTCTTT ACCCAATATT TATGGAAGGA GTGGGAAAAC CAAAGATAAT      2600

TAATAGTTTC ACTCAAGATG ATATTGAAAA ACACCAGAGT GATGCAGGTT      2650

TATATGTAAT TGTGCCAGTA ATTATTTCCT CTTCCATCTT ATTGCTTGGA      2700

ACATTATTAA TATCACACCA AAGAATGAAA AAGCTATTTT GGGAAGATGT      2750

TCCGAACCCC AAGAATTGTT CCTGGGCACA AGGACTTAAT TTTCAGAAGC      2800

CAGAAACGTT TGAGCATCTT TTTATCAAGC ATACAGCATC AGTGACATGT      2850

GGTCCTCTTC TTTTGGAGCC TGAAACAATT TCAGAAGATA TCAGTGTTGA      2900

TACATCATGG AAAAATAAAG ATGAGATGAT GCCAACAACT GTGGTCTCTC      2950

TACTTTCAAC AACAGATCTT GAAAAGGGTT CTGTTTGTAT TAGTGACCAG      3000

TTCAACAGTG TTAACTTCTC TGAGGCTGAG GGTACTGAGG TAACCTATGA      3050

GGACGAAAGC CAGAGACAAC CCTTTGTTAA ATACGCCACG CTGATCAGCA      3100

ACTCTAAACC AAGTGAAACT GGTGAAGAAC AAGGGCTTAT AAATAGTTCA      3150

GTCACCAAGT GCTTCTCTAG CAAAAATTCT CCGTTGAAGG ATTCTTTCTC      3200

TAATAGCTCA TGGGAGATAG AGGCCCAGGC ATTTTTTATA TTATCAGATC      3250

AGCATCCCAA CATAATTTCA CCACACCTCA CATTCTCAGA AGGATTGGAT      3300

GAACTTTTGA AATTGGAGGG AAATTTCCCT GAAGAAAATA ATGATAAAAA      3350

GTCTATCTAT TATTTAGGGG TCACCTCAAT CAAAAAGAGA GAGAGTGGTG      3400

TGCTTTTGAC TGACAAGTCA AGGGTATCGT GCCCATTCCC AGCCCCCTGT      3450

TTATTCACGG ACATCAGAGT TCTCCAGGAC AGTTGCTCAC ACTTTGTAGA      3500
```

-continued

| | |
|---|---|
| AAATAATATC AACTTAGGAA CTTCTAGTAA GAAGACTTTT GCATCTTACA | 3550 |
| TGCCTCAATT CCAAACTTGT TCTACTCAGA CTCATAAGAT CATGGAAAAC | 3600 |
| AAGATGTGTG ACCTAACTGT GTAATTTCAC TGAAGAAACC TTCAGATTTG | 3650 |
| TGTTATAATG GGTAATATAA AGTGTAATAG ATTATAGTTG TGGGTGGGAG | 3700 |
| AGAGAAAAGA AACCAGAGTC AAATTTGAAA ATAATTGTTC CAAATGAATG | 3750 |
| TTGTCTGTTT GTTCTCTCTT AGTAACATAG ACAAAAAATT TGAGAAAGCC | 3800 |
| TTCATAAGCC TACCAATGTA GACACGCTCT TCTATTTTAT TCCCAAGCTC | 3850 |
| TAGTGGGAAG GTCCCTTGTT TCCAGCTAGA AATAAGCCCA ACAGACACCA | 3900 |
| TCTTTTGTGA GATGTAATTG TTTTTTCAGA GGGCGTGTTG TTTTACCTCA | 3950 |
| AGTTTTTGTT TTGTACCAAC ACACACACAC ACACACATTC TTAACACATG | 4000 |
| TCCTTGTGTG TTTTGAGAGT ATATTATGTA TTTATATTTT GTGCTATCAG | 4050 |
| ACTGTAGGAT TTGAAGTAGG ACTTTCCTAA ATGTTTAAGA TAAACAGAAT | 4100 |
| TC | 4102 |

(2) INFORMATION FOR SEQ ID NO:2:

(i) SEQUENCE CHARACTERISTICS:
        (A) LENGTH: 1165 amino acids
        (B) TYPE: Amino Acid
        (D) TOPOLOGY: Linear (xi) SEQUENCE DESCRIPTION: SEQ ID NO:2:

```
Met Ile Cys Gln Lys Phe Cys Val Val Leu Leu His Trp Glu Phe
 1               5                  10                  15

Ile Tyr Val Ile Thr Ala Phe Asn Leu Ser Tyr Pro Ile Thr Pro
                20                  25                  30

Trp Arg Phe Lys Leu Ser Cys Met Pro Pro Asn Ser Thr Tyr Asp
                35                  40                  45

Tyr Phe Leu Leu Pro Ala Gly Leu Ser Lys Asn Thr Ser Asn Ser
                50                  55                  60

Asn Gly His Tyr Glu Thr Ala Val Glu Pro Lys Phe Asn Ser Ser
                65                  70                  75

Gly Thr His Phe Ser Asn Leu Ser Lys Thr Thr Phe His Cys Cys
                80                  85                  90

Phe Arg Ser Glu Gln Asp Arg Asn Cys Ser Leu Cys Ala Asp Asn
                95                 100                 105

Ile Glu Gly Lys Thr Phe Val Ser Thr Val Asn Ser Leu Val Phe
               110                 115                 120

Gln Gln Ile Asp Ala Asn Trp Asn Ile Gln Cys Trp Leu Lys Gly
               125                 130                 135

Asp Leu Lys Leu Phe Ile Cys Tyr Val Glu Ser Leu Phe Lys Asn
               140                 145                 150

Leu Phe Arg Asn Tyr Asn Tyr Lys Val His Leu Leu Tyr Val Leu
               155                 160                 165

Pro Glu Val Leu Glu Asp Ser Pro Leu Val Pro Gln Lys Gly Ser
               170                 175                 180

Phe Gln Met Val His Cys Asn Cys Ser Val His Glu Cys Cys Glu
               185                 190                 195

Cys Leu Val Pro Val Pro Thr Ala Lys Leu Asn Asp Thr Leu Leu
               200                 205                 210

Met Cys Leu Lys Ile Thr Ser Gly Gly Val Ile Phe Gln Ser Pro
```

-continued

```
                        215                 220                 225
Leu Met Ser Val Gln Pro Ile Asn Met Val Lys Pro Asp Pro Pro
                230                 235                 240
Leu Gly Leu His Met Glu Ile Thr Asp Asp Gly Asn Leu Lys Ile
                245                 250                 255
Ser Trp Ser Ser Pro Pro Leu Val Pro Phe Pro Leu Gln Tyr Gln
                260                 265                 270
Val Lys Tyr Ser Glu Asn Ser Thr Thr Val Ile Arg Glu Ala Asp
                275                 280                 285
Lys Ile Val Ser Ala Thr Ser Leu Leu Val Asp Ser Ile Leu Pro
                290                 295                 300
Gly Ser Ser Tyr Glu Val Gln Val Arg Gly Lys Arg Leu Asp Gly
                305                 310                 315
Pro Gly Ile Trp Ser Asp Trp Ser Thr Pro Arg Val Phe Thr Thr
                320                 325                 330
Gln Asp Val Ile Tyr Phe Pro Pro Lys Ile Leu Thr Ser Val Gly
                335                 340                 345
Ser Asn Val Ser Phe His Cys Ile Tyr Lys Lys Glu Asn Lys Ile
                350                 355                 360
Val Pro Ser Lys Glu Ile Val Trp Trp Met Asn Leu Ala Glu Lys
                365                 370                 375
Ile Pro Gln Ser Gln Tyr Asp Val Val Ser Asp His Val Ser Lys
                380                 385                 390
Val Thr Phe Phe Asn Leu Asn Glu Thr Lys Pro Arg Gly Lys Phe
                395                 400                 405
Thr Tyr Asp Ala Val Tyr Cys Cys Asn Glu His Glu Cys His His
                410                 415                 420
Arg Tyr Ala Glu Leu Tyr Val Ile Asp Val Asn Ile Asn Ile Ser
                425                 430                 435
Cys Glu Thr Asp Gly Tyr Leu Thr Lys Met Thr Cys Arg Trp Ser
                440                 445                 450
Thr Ser Thr Ile Gln Ser Leu Ala Glu Ser Thr Leu Gln Leu Arg
                455                 460                 465
Tyr His Arg Ser Ser Leu Tyr Cys Ser Asp Ile Pro Ser Ile His
                470                 475                 480
Pro Ile Ser Glu Pro Lys Asp Cys Tyr Leu Gln Ser Asp Gly Phe
                485                 490                 495
Tyr Glu Cys Ile Phe Gln Pro Ile Phe Leu Leu Ser Gly Tyr Thr
                500                 505                 510
Met Trp Ile Arg Ile Asn His Ser Leu Gly Ser Leu Asp Ser Pro
                515                 520                 525
Pro Thr Cys Val Leu Pro Asp Ser Val Val Lys Pro Leu Pro Pro
                530                 535                 540
Ser Ser Val Lys Ala Glu Ile Thr Ile Asn Ile Gly Leu Leu Lys
                545                 550                 555
Ile Ser Trp Glu Lys Pro Val Phe Pro Glu Asn Asn Leu Gln Phe
                560                 565                 570
Gln Ile Arg Tyr Gly Leu Ser Gly Lys Glu Val Gln Trp Lys Met
                575                 580                 585
Tyr Glu Val Tyr Asp Ala Lys Ser Lys Ser Val Ser Leu Pro Val
                590                 595                 600
Pro Asp Leu Cys Ala Val Tyr Ala Val Gln Val Arg Cys Lys Arg
                605                 610                 615
```

-continued

```
Leu Asp Gly Leu Gly Tyr Trp Ser Asn Trp Ser Asn Pro Ala Tyr
            620                 625                 630

Thr Val Val Met Asp Ile Lys Val Pro Met Arg Gly Pro Glu Phe
            635                 640                 645

Trp Arg Ile Ile Asn Gly Asp Thr Met Lys Lys Glu Lys Asn Val
            650                 655                 660

Thr Leu Leu Trp Lys Pro Leu Met Lys Asn Asp Ser Leu Cys Ser
            665                 670                 675

Val Gln Arg Tyr Val Ile Asn His His Thr Ser Cys Asn Gly Thr
            680                 685                 690

Trp Ser Glu Asp Val Gly Asn His Thr Lys Phe Thr Phe Leu Trp
            695                 700                 705

Thr Glu Gln Ala His Thr Val Thr Val Leu Ala Ile Asn Ser Ile
            710                 715                 720

Gly Ala Ser Val Ala Asn Phe Asn Leu Thr Phe Ser Trp Pro Met
            725                 730                 735

Ser Lys Val Asn Ile Val Gln Ser Leu Ser Ala Tyr Pro Leu Asn
            740                 745                 750

Ser Ser Cys Val Ile Val Ser Trp Ile Leu Ser Pro Ser Asp Tyr
            755                 760                 765

Lys Leu Met Tyr Phe Ile Ile Glu Trp Lys Asn Leu Asn Glu Asp
            770                 775                 780

Gly Glu Ile Lys Trp Leu Arg Ile Ser Ser Ser Val Lys Lys Tyr
            785                 790                 795

Tyr Ile His Asp His Phe Ile Pro Ile Glu Lys Tyr Gln Phe Ser
            800                 805                 810

Leu Tyr Pro Ile Phe Met Glu Gly Val Gly Lys Pro Lys Ile Ile
            815                 820                 825

Asn Ser Phe Thr Gln Asp Asp Ile Glu Lys His Gln Ser Asp Ala
            830                 835                 840

Gly Leu Tyr Val Ile Val Pro Val Ile Ile Ser Ser Ser Ile Leu
            845                 850                 855

Leu Leu Gly Thr Leu Leu Ile Ser His Gln Arg Met Lys Lys Leu
            860                 865                 870

Phe Trp Glu Asp Val Pro Asn Pro Lys Asn Cys Ser Trp Ala Gln
            875                 880                 885

Gly Leu Asn Phe Gln Lys Pro Glu Thr Phe Glu His Leu Phe Ile
            890                 895                 900

Lys His Thr Ala Ser Val Thr Cys Gly Pro Leu Leu Leu Glu Pro
            905                 910                 915

Glu Thr Ile Ser Glu Asp Ile Ser Val Asp Thr Ser Trp Lys Asn
            920                 925                 930

Lys Asp Glu Met Met Pro Thr Thr Val Val Ser Leu Leu Ser Thr
            935                 940                 945

Thr Asp Leu Glu Lys Gly Ser Val Cys Ile Ser Asp Gln Phe Asn
            950                 955                 960

Ser Val Asn Phe Ser Glu Ala Glu Gly Thr Glu Val Thr Tyr Glu
            965                 970                 975

Asp Glu Ser Gln Arg Gln Pro Phe Val Lys Tyr Ala Thr Leu Ile
            980                 985                 990

Ser Asn Ser Lys Pro Ser Glu Thr Gly Glu Glu Gln Gly Leu Ile
            995                 1000                1005
```

```
Asn Ser Ser Val Thr Lys Cys Phe Ser Ser Lys Asn Ser Pro Leu
            1010                1015                1020

Lys Asp Ser Phe Ser Asn Ser Ser Trp Glu Ile Glu Ala Gln Ala
            1025                1030                1035

Phe Phe Ile Leu Ser Asp Gln His Pro Asn Ile Ile Ser Pro His
            1040                1045                1050

Leu Thr Phe Ser Glu Gly Leu Asp Glu Leu Leu Lys Leu Glu Gly
            1055                1060                1065

Asn Phe Pro Glu Glu Asn Asn Asp Lys Lys Ser Ile Tyr Tyr Leu
            1070                1075                1080

Gly Val Thr Ser Ile Lys Lys Arg Glu Ser Gly Val Leu Leu Thr
            1085                1090                1095

Asp Lys Ser Arg Val Ser Cys Pro Phe Pro Ala Pro Cys Leu Phe
            1100                1105                1110

Thr Asp Ile Arg Val Leu Gln Asp Ser Cys Ser His Phe Val Glu
            1115                1120                1125

Asn Asn Ile Asn Leu Gly Thr Ser Ser Lys Lys Thr Phe Ala Ser
            1130                1135                1140

Tyr Met Pro Gln Phe Gln Thr Cys Ser Thr Gln Thr His Lys Ile
            1145                1150                1155

Met Glu Asn Lys Met Cys Asp Leu Thr Val
            1160                1165

(2) INFORMATION FOR SEQ ID NO:3:

(i) SEQUENCE CHARACTERISTICS:
        (A) LENGTH: 896 amino acids
        (B) TYPE: Amino Acid
        (D) TOPOLOGY: Linear (xi) SEQUENCE DESCRIPTION: SEQ ID NO:3:

Met Ile Cys Gln Lys Phe Cys Val Val Leu Leu His Trp Glu Phe
 1               5                  10                  15

Ile Tyr Val Ile Thr Ala Phe Asn Leu Ser Tyr Pro Ile Thr Pro
            20                  25                  30

Trp Arg Phe Lys Leu Ser Cys Met Pro Pro Asn Ser Thr Tyr Asp
            35                  40                  45

Tyr Phe Leu Leu Pro Ala Gly Leu Ser Lys Asn Thr Ser Asn Ser
            50                  55                  60

Asn Gly His Tyr Glu Thr Ala Val Glu Pro Lys Phe Asn Ser Ser
            65                  70                  75

Gly Thr His Phe Ser Asn Leu Ser Lys Thr Thr Phe His Cys Cys
            80                  85                  90

Phe Arg Ser Glu Gln Asp Arg Asn Cys Ser Leu Cys Ala Asp Asn
            95                  100                 105

Ile Glu Gly Lys Thr Phe Val Ser Thr Val Asn Ser Leu Val Phe
            110                 115                 120

Gln Gln Ile Asp Ala Asn Trp Asn Ile Gln Cys Trp Leu Lys Gly
            125                 130                 135

Asp Leu Lys Leu Phe Ile Cys Tyr Val Glu Ser Leu Phe Lys Asn
            140                 145                 150

Leu Phe Arg Asn Tyr Asn Tyr Lys Val His Leu Leu Tyr Val Leu
            155                 160                 165

Pro Glu Val Leu Glu Asp Ser Pro Leu Val Pro Gln Lys Gly Ser
            170                 175                 180
```

```
Phe Gln Met Val His Cys Asn Cys Ser Val His Glu Cys Cys Glu
            185                 190                 195

Cys Leu Val Pro Val Pro Thr Ala Lys Leu Asn Asp Thr Leu Leu
            200                 205                 210

Met Cys Leu Lys Ile Thr Ser Gly Gly Val Ile Phe Gln Ser Pro
            215                 220                 225

Leu Met Ser Val Gln Pro Ile Asn Met Val Lys Pro Asp Pro Pro
            230                 235                 240

Leu Gly Leu His Met Glu Ile Thr Asp Asp Gly Asn Leu Lys Ile
            245                 250                 255

Ser Trp Ser Ser Pro Leu Val Pro Phe Pro Leu Gln Tyr Gln
            260                 265                 270

Val Lys Tyr Ser Glu Asn Ser Thr Thr Val Ile Arg Glu Ala Asp
            275                 280                 285

Lys Ile Val Ser Ala Thr Ser Leu Leu Val Asp Ser Ile Leu Pro
            290                 295                 300

Gly Ser Ser Tyr Glu Val Gln Val Arg Gly Lys Arg Leu Asp Gly
            305                 310                 315

Pro Gly Ile Trp Ser Asp Trp Ser Thr Pro Arg Val Phe Thr Thr
            320                 325                 330

Gln Asp Val Ile Tyr Phe Pro Pro Lys Ile Leu Thr Ser Val Gly
            335                 340                 345

Ser Asn Val Ser Phe His Cys Ile Tyr Lys Lys Glu Asn Lys Ile
            350                 355                 360

Val Pro Ser Lys Glu Ile Val Trp Trp Met Asn Leu Ala Glu Lys
            365                 370                 375

Ile Pro Gln Ser Gln Tyr Asp Val Val Ser Asp His Val Ser Lys
            380                 385                 390

Val Thr Phe Phe Asn Leu Asn Glu Thr Lys Pro Arg Gly Lys Phe
            395                 400                 405

Thr Tyr Asp Ala Val Tyr Cys Cys Asn Glu His Glu Cys His His
            410                 415                 420

Arg Tyr Ala Glu Leu Tyr Val Ile Asp Val Asn Ile Asn Ile Ser
            425                 430                 435

Cys Glu Thr Asp Gly Tyr Leu Thr Lys Met Thr Cys Arg Trp Ser
            440                 445                 450

Thr Ser Thr Ile Gln Ser Leu Ala Glu Ser Thr Leu Gln Leu Arg
            455                 460                 465

Tyr His Arg Ser Ser Leu Tyr Cys Ser Asp Ile Pro Ser Ile His
            470                 475                 480

Pro Ile Ser Glu Pro Lys Asp Cys Tyr Leu Gln Ser Asp Gly Phe
            485                 490                 495

Tyr Glu Cys Ile Phe Gln Pro Ile Phe Leu Leu Ser Gly Tyr Thr
            500                 505                 510

Met Trp Ile Arg Ile Asn His Ser Leu Gly Ser Leu Asp Ser Pro
            515                 520                 525

Pro Thr Cys Val Leu Pro Asp Ser Val Val Lys Pro Leu Pro Pro
            530                 535                 540

Ser Ser Val Lys Ala Glu Ile Thr Ile Asn Ile Gly Leu Leu Lys
            545                 550                 555

Ile Ser Trp Glu Lys Pro Val Phe Pro Glu Asn Asn Leu Gln Phe
            560                 565                 570

Gln Ile Arg Tyr Gly Leu Ser Gly Lys Glu Val Gln Trp Lys Met
```

-continued

```
                575                 580                 585
Tyr Glu Val Tyr Asp Ala Lys Ser Lys Ser Val Ser Leu Pro Val
            590                 595                 600
Pro Asp Leu Cys Ala Val Tyr Ala Val Gln Val Arg Cys Lys Arg
            605                 610                 615
Leu Asp Gly Leu Gly Tyr Trp Ser Asn Trp Ser Asn Pro Ala Tyr
            620                 625                 630
Thr Val Val Met Asp Ile Lys Val Pro Met Arg Gly Pro Glu Phe
            635                 640                 645
Trp Arg Ile Ile Asn Gly Asp Thr Met Lys Glu Lys Asn Val
            650                 655                 660
Thr Leu Leu Trp Lys Pro Leu Met Lys Asn Asp Ser Leu Cys Ser
            665                 670                 675
Val Gln Arg Tyr Val Ile Asn His His Thr Ser Cys Asn Gly Thr
            680                 685                 690
Trp Ser Glu Asp Val Gly Asn His Thr Lys Phe Thr Phe Leu Trp
            695                 700                 705
Thr Glu Gln Ala His Thr Val Thr Val Leu Ala Ile Asn Ser Ile
            710                 715                 720
Gly Ala Ser Val Ala Asn Phe Asn Leu Thr Phe Ser Trp Pro Met
            725                 730                 735
Ser Lys Val Asn Ile Val Gln Ser Leu Ser Ala Tyr Pro Leu Asn
            740                 745                 750
Ser Ser Cys Val Ile Val Ser Trp Ile Leu Ser Pro Ser Asp Tyr
            755                 760                 765
Lys Leu Met Tyr Phe Ile Ile Glu Trp Lys Asn Leu Asn Glu Asp
            770                 775                 780
Gly Glu Ile Lys Trp Leu Arg Ile Ser Ser Val Lys Lys Tyr
            785                 790                 795
Tyr Ile His Asp His Phe Ile Pro Ile Glu Lys Tyr Gln Phe Ser
            800                 805                 810
Leu Tyr Pro Ile Phe Met Glu Gly Val Gly Lys Pro Lys Ile Ile
            815                 820                 825
Asn Ser Phe Thr Gln Asp Asp Ile Glu Lys His Gln Ser Asp Ala
            830                 835                 840
Gly Leu Tyr Val Ile Val Pro Val Ile Ser Ser Ser Ile Leu
            845                 850                 855
Leu Leu Gly Thr Leu Leu Ile Ser His Gln Arg Met Lys Lys Leu
            860                 865                 870
Phe Trp Glu Asp Val Pro Asn Pro Lys Asn Cys Ser Trp Ala Gln
            875                 880                 885
Gly Leu Asn Phe Gln Lys Arg Thr Asp Ile Leu
            890                 895 896
```

(2) INFORMATION FOR SEQ ID NO:4:

(i) SEQUENCE CHARACTERISTICS:
        (A) LENGTH: 923 amino acids
        (B) TYPE: Amino Acid
        (D) TOPOLOGY: Linear (xi) SEQUENCE DESCRIPTION: SEQ ID NO:4:

```
Met Ile Cys Gln Lys Phe Cys Val Val Leu Leu His Trp Glu Phe
 1               5                  10                  15
Ile Tyr Val Ile Thr Ala Phe Asn Leu Ser Tyr Pro Ile Thr Pro
```

-continued

```
                20                  25                  30
Trp Arg Phe Lys Leu Ser Cys Met Pro Pro Asn Ser Thr Tyr Asp
                35                  40                  45
Tyr Phe Leu Leu Pro Ala Gly Leu Ser Lys Asn Thr Ser Asn Ser
                50                  55                  60
Asn Gly His Tyr Glu Thr Ala Val Glu Pro Lys Phe Asn Ser Ser
                65                  70                  75
Gly Thr His Phe Ser Asn Leu Ser Lys Thr Thr Phe His Cys Cys
                80                  85                  90
Phe Arg Ser Glu Gln Asp Arg Asn Cys Ser Leu Cys Ala Asp Asn
                95                  100                 105
Ile Glu Gly Lys Thr Phe Val Ser Thr Val Asn Ser Leu Val Phe
                110                 115                 120
Gln Gln Ile Asp Ala Asn Trp Asn Ile Gln Cys Trp Leu Lys Gly
                125                 130                 135
Asp Leu Lys Leu Phe Ile Cys Tyr Val Glu Ser Leu Phe Lys Asn
                140                 145                 150
Leu Phe Arg Asn Tyr Asn Tyr Lys Val His Leu Leu Tyr Val Leu
                155                 160                 165
Pro Glu Val Leu Glu Asp Ser Pro Leu Val Pro Gln Lys Gly Ser
                170                 175                 180
Phe Gln Met Val His Cys Asn Cys Ser Val His Glu Cys Cys Glu
                185                 190                 195
Cys Leu Val Pro Val Pro Thr Ala Lys Leu Asn Asp Thr Leu Leu
                200                 205                 210
Met Cys Leu Lys Ile Thr Ser Gly Gly Val Ile Phe Gln Ser Pro
                215                 220                 225
Leu Met Ser Val Gln Pro Ile Asn Met Val Lys Pro Asp Pro Pro
                230                 235                 240
Leu Gly Leu His Met Glu Ile Thr Asp Asp Gly Asn Leu Lys Ile
                245                 250                 255
Ser Trp Ser Ser Pro Pro Leu Val Pro Phe Pro Leu Gln Tyr Gln
                260                 265                 270
Val Lys Tyr Ser Glu Asn Ser Thr Thr Val Ile Arg Glu Ala Asp
                275                 280                 285
Lys Ile Val Ser Ala Thr Ser Leu Leu Val Asp Ser Ile Leu Pro
                290                 295                 300
Gly Ser Ser Tyr Glu Val Gln Val Arg Gly Lys Arg Leu Asp Gly
                305                 310                 315
Pro Gly Ile Trp Ser Asp Trp Ser Thr Pro Arg Val Phe Thr Thr
                320                 325                 330
Gln Asp Val Ile Tyr Phe Pro Pro Lys Ile Leu Thr Ser Val Gly
                335                 340                 345
Ser Asn Val Ser Phe His Cys Ile Tyr Lys Lys Glu Asn Lys Ile
                350                 355                 360
Val Pro Ser Lys Glu Ile Val Trp Trp Met Asn Leu Ala Glu Lys
                365                 370                 375
Ile Pro Gln Ser Gln Tyr Asp Val Val Ser Asp His Val Ser Lys
                380                 385                 390
Val Thr Phe Phe Asn Leu Asn Glu Thr Lys Pro Arg Gly Lys Phe
                395                 400                 405
Thr Tyr Asp Ala Val Tyr Cys Cys Asn Glu His Glu Cys His His
                410                 415                 420
```

-continued

```
Arg Tyr Ala Glu Leu Tyr Val Ile Asp Val Asn Ile Asn Ile Ser
            425                 430                 435

Cys Glu Thr Asp Gly Tyr Leu Thr Lys Met Thr Cys Arg Trp Ser
            440                 445                 450

Thr Ser Thr Ile Gln Ser Leu Ala Glu Ser Thr Leu Gln Leu Arg
            455                 460                 465

Tyr His Arg Ser Ser Leu Tyr Cys Ser Asp Ile Pro Ser Ile His
            470                 475                 480

Pro Ile Ser Glu Pro Lys Asp Cys Tyr Leu Gln Ser Asp Gly Phe
            485                 490                 495

Tyr Glu Cys Ile Phe Gln Pro Ile Phe Leu Leu Ser Gly Tyr Thr
            500                 505                 510

Met Trp Ile Arg Ile Asn His Ser Leu Gly Ser Leu Asp Ser Pro
            515                 520                 525

Pro Thr Cys Val Leu Pro Asp Ser Val Val Lys Pro Leu Pro Pro
            530                 535                 540

Ser Ser Val Lys Ala Glu Ile Thr Ile Asn Ile Gly Leu Leu Lys
            545                 550                 555

Ile Ser Trp Glu Lys Pro Val Phe Pro Glu Asn Asn Leu Gln Phe
            560                 565                 570

Gln Ile Arg Tyr Gly Leu Ser Gly Lys Glu Val Gln Trp Lys Met
            575                 580                 585

Tyr Glu Val Tyr Asp Ala Lys Ser Lys Ser Val Ser Leu Pro Val
            590                 595                 600

Pro Asp Leu Cys Ala Val Tyr Ala Val Gln Val Arg Cys Lys Arg
            605                 610                 615

Leu Asp Gly Leu Gly Tyr Trp Ser Asn Trp Ser Asn Pro Ala Tyr
            620                 625                 630

Thr Val Val Met Asp Ile Lys Val Pro Met Arg Gly Pro Glu Phe
            635                 640                 645

Trp Arg Ile Ile Asn Gly Asp Thr Met Lys Lys Glu Lys Asn Val
            650                 655                 660

Thr Leu Leu Trp Lys Pro Leu Met Lys Asn Asp Ser Leu Cys Ser
            665                 670                 675

Val Gln Arg Tyr Val Ile Asn His His Thr Ser Cys Asn Gly Thr
            680                 685                 690

Trp Ser Glu Asp Val Gly Asn His Thr Lys Phe Thr Phe Leu Trp
            695                 700                 705

Thr Glu Gln Ala His Thr Val Thr Val Leu Ala Ile Asn Ser Ile
            710                 715                 720

Gly Ala Ser Val Ala Asn Phe Asn Leu Thr Phe Ser Trp Pro Met
            725                 730                 735

Ser Lys Val Asn Ile Val Gln Ser Leu Ser Ala Tyr Pro Leu Asn
            740                 745                 750

Ser Ser Cys Val Ile Val Ser Trp Ile Leu Ser Pro Ser Asp Tyr
            755                 760                 765

Lys Leu Met Tyr Phe Ile Ile Glu Trp Lys Asn Leu Asn Glu Asp
            770                 775                 780

Gly Glu Ile Lys Trp Leu Arg Ile Ser Ser Ser Val Lys Lys Tyr
            785                 790                 795

Tyr Ile His Asp His Phe Ile Pro Ile Glu Lys Tyr Gln Phe Ser
            800                 805                 810
```

-continued

```
Leu Tyr Pro Ile Phe Met Glu Gly Val Gly Lys Pro Lys Ile Ile
            815                 820                 825

Asn Ser Phe Thr Gln Asp Asp Ile Glu Lys His Gln Ser Asp Ala
            830                 835                 840

Gly Leu Tyr Val Ile Val Pro Val Ile Ile Ser Ser Ser Ile Leu
            845                 850                 855

Leu Leu Gly Thr Leu Leu Ile Ser His Gln Arg Met Lys Lys Leu
            860                 865                 870

Phe Trp Glu Asp Val Pro Asn Pro Lys Asn Cys Ser Trp Ala Gln
            875                 880                 885

Gly Leu Asn Phe Gln Lys Met Phe Arg Thr Pro Arg Ile Val Pro
            890                 895                 900

Gly His Lys Asp Leu Ile Phe Arg Arg Cys Leu Lys Ala Ala Cys
            905                 910                 915

Ser Leu Arg Val Ile Thr Thr Pro
            920         923
```

(2) INFORMATION FOR SEQ ID NO:5:

(i) SEQUENCE CHARACTERISTICS:
        (A) LENGTH: 3004 base pairs
        (B) TYPE: Nucleic Acid
        (C) STRANDEDNESS: Single
        (D) TOPOLOGY: Linear (xi) SEQUENCE DESCRIPTION: SEQ ID NO:5:

```
GAATTCCGGG TTAAAGCTCT CGTGGCATTA TCCTTCAGTG GGCTATTGG           50

ACTGACTTTT CTTATGCTGG GATGTGCCTT AGAGGATTAT GGATTTGCCA          100

GTTCACCCTG ACCATCTTGA AAATAAGTTA TCTCTGATCT CTGTCTGTAT          150

GTTACTTCTC TCCCCTCACC AATGGAGAAC AAATGTGGGC AAAGTGTACT          200

TCTCTGAAGT AAGATGATTT GTCAAAAATT CTGTGTGGTT TTGTTACATT          250

GGGAATTTAT TTATGTGATA ACTGCGTTTA ACTTGTCATA TCCAATTACT          300

CCTTGGAGAT TTAAGTTGTC TTGCATGCCA CCAAATTCAA CCTATGACTA          350

CTTCCTTTTG CCTGCTGGAC TCTCAAAGAA TACTTCAAAT TCGAATGGAC          400

ATTATGAGAC AGCTGTTGAA CCTAAGTTTA ATTCAAGTGG TACTCACTTT          450

TCTAACTTAT CCAAAACAAC TTTCCACTGT TGCTTTCGGA GTGAGCAAGA          500

TAGAAACTGC TCCTTATGTG CAGACAACAT TGAAGGAAAG ACATTTGTTT          550

CNACAGTAAA TTCTTTAGTT TTTCAACAAA TAGATGCAAA CTGGAACATA          600

CAGTGCTGGC TAAAAGGAGA CTTAAAATTA TTCATCTGTT ATGTGGAGTC          650

ATTATTTAAG AATCTATTCA GGAATTATAA CTATAAGGTC CATCTTTTAT          700

ATGTTCTGCC TGAAGTGTTA AAGATTCAC CTCTGGTTCC CCAAAAAGGC           750

AGTTTTCAGA TGGTTCACTG CAATTGCAGT GTTCATGAAT GTTGTGAATG          800

TCTTGTGCCT GTGCCAACAG CCAAACTCAA CGACACTCTC CTTATGTGTT          850

TGAAAATCAC ATCTGGTGGA GTAATTTTCC AGTCACCTCT AATGTCAGTT          900

CAGCCCATAA ATATGGTGAA GCCTGATCCA CCATTAGGTT TGCATATGGA          950

AATCACAGAT GATGGTAATT TAAAGATTTC TTGGTCCAGC CCACCATTGG         1000

TACCATTTCC ACTTCAATAT CAAGTGAAAT ATTCAGAGAA TTCTACAACA         1050

GTTATCAGAG AAGCTGACAA GATTGTCTCA GCTACATCCC TGCTAGTAGA         1100
```

```
CAGTATACTT CCTGGGTCTT CGTATGAGGT TCAGGTGAGG GGCAAGAGAC        1150

TGGATGGCCC AGGAATCTGG AGTGACTGGA GTACTCCTCG TGTCTTTACC        1200

ACACAAGATG TCATATACTT CCACCTAAA ATTCTGACAA GTGTTGGGTC         1250

TAATGTTTCT TTTCACTGCA TCTATAAGAA GGAAAACAAG ATTGTTCCCT        1300

CAAAAGAGAT TGTTTGGTGG ATGAATTTAG CTGAGAAAAT TCCTCAAAGC        1350

CAGTATGATG TTGTGAGTGA TCATGTTAGC AAAGTTACTT TTTTCAATCT        1400

GAATGAAACC AAACCTCGAG GAAAGTTTAC CTATGATGCA GTGTACTGCT        1450

GCAATGAACA TGAATGCCAT CATCGCTATG CTGAATTATA TGTGATTGAT        1500

GTCAATATCA ATATCTCATG TGAAACTGAT GGGTACTTAA CTAAAATGAC        1550

TTGCAGATGG TCAACCAGTA CAATCCAGTC ACTTGCGGAA AGCACTTTGC        1600

AATTGAGGTA TCATAGGAGC AGCCTTTACT GTTCTGATAT TCCATCTATT        1650

CATCCCATAT CTGAGCCCAA AGATTGCTAT TTGCAGAGTG ATGGTTTTTA        1700

TGAATGCATT TTCCAGCCAA TCTTCCTATT ATCTGGCTAC ACAATGTGGA        1750

TTAGGATCAA TCACTCTCTA GGTTCACTTG ACTCTCCACC AACATGTGTC        1800

CTTCCTGATT CTGTGGTGAA GCCACTGCCT CCATCCAGTG TGAAAGCAGA        1850

AATTACTATA AACATTGGAT TATTGAAAAT ATCTTGGGAA AAGCCAGTCT        1900

TTCCAGAGAA TAACCTTCAA TTCCAGATTC GCTATGGTTT AAGTGGAAAA        1950

GAAGTACAAT GGAAGATGTA TGAGGTTTAT GATGCAAAAT CAAAATCTGT        2000

CAGTCTCCCA GTTCCAGACT TGTGTGCAGT CTATGCTGTT CAGGTGCGCT        2050

GTAAGAGGCT AGATGGACTG GGATATTGGA GTAATTGGAG CAATCCAGCC        2100

TACACAGTTG TCATGGATAT AAAAGTTCCT ATGAGAGGAC CTGAATTTTG        2150

GAGAATAATT AATGGAGATA CTATGAAAAA GGAGAAAAAT GTCACTTTAC        2200

TTTGGAAGCC CCTGATGAAA AATGACTCAT TGTGCAGTGT TCAGAGATAT        2250

GTGATAAACC ATCATACTTC CTGCAATGGA ACATGGTCAG AAGATGTGGG        2300

AAATCACACG AAATTCACTT TCCTGTGGAC AGAGCAAGCA CATACTGTTA        2350

CGGTTCTGGC CATCAATTCA ATTGGTGCTT CTGTTGCAAA TTTTAATTTA        2400

ACCTTTTCAT GGCCTATGAG CAAAGTAAAT ATCGTGCAGT CACTCAGTGC        2450

TTATCCTTTA AACAGCAGTT GTGTGATTGT TTCCTGGATA CTATCACCCA        2500

GTGATTACAA GCTAATGTAT TTTATTATTG AGTGGAAAAA TCTTAATGAA        2550

GATGGTGAAA TAAAATGGCT TAGAATCTCT TCATCTGTTA AGAAGTATTA        2600

TATCCATGAT CATTTTATCC CCATTGAGAA GTACCAGTTC AGTCTTTACC        2650

CAATATTTAT GGAAGGAGTG GGAAAACCAA AGATAATTAA TAGTTTCACT        2700

CAAGATGATA TTGAAAAACA CCAGAGTGAT GCAGGTTTAT ATGTAATTGT        2750

GCCAGTAATT ATTTCCTCTT CCATCTTATT GCTTGGAACA TTATTAATAT        2800

CACACCAAAG AATGAAAAAG CTATTTTGGG AAGATGTTCC GAACCCCAAG        2850

AATTGTTCCT GGGCACAAGG ACTTAATTTT CAGAAGAGAA CGGACATTCT        2900

TTGAAGTCTA ATCATGATCA CTACAGATGA ACCCAATGTG CCAACTTCCC        2950

AACAGTCTAT AGAGTATTAG AAGATTTTA CATTTTGAAG AAGGGCCGGA        3000

ATTC                                                          3004
```

-continued (2) INFORMATION FOR SEQ ID NO:6:

(i) SEQUENCE CHARACTERISTICS:
        (A) LENGTH: 3102 base pairs
        (B) TYPE: Nucleic Acid
        (C) STRANDEDNESS: Single
        (D) TOPOLOGY: Linear (xi) SEQUENCE DESCRIPTION: SEQ ID NO:6:

```
GAATTCTCGA GTCGACGGCG GGCGTTAAAG CTCTCGTGGC ATTATCCTTC         50

AGTGGGGCTA TTGGACTGAC TTTTCTTATG CTGGGATGTG CCTTAGAGGA        100

TTATGGGTGT ACTTCTCTGA AGTAAGATGA TTTGTCAAAA ATTCTGTGTG        150

GTTTTGTTAC ATTGGGAATT TATTTATGTG ATAACTGCGT TTAACTTGTC        200

ATATCCAATT ACTCCTTGGA GATTTAAGTT GTCTTGCATG CCACCAAATT        250

CAACCTATGA CTACTTCCTT TTGCCTGCTG GACTCTCAAA GAATACTTCA        300

AATTCGAATG GACATTATGA GACAGCTGTT GAACCTAAGT TTAATTCAAG        350

TGGTACTCAC TTTTCTAACT TATCCAAAAC AACTTTCCAC TGTTGCTTTC        400

GGAGTGAGCA AGATAGAAAC TGCTCCTTAT GTGCAGACAA CATTGAAGGA        450

AAGACATTTG TTTCAACAGT AAATTCTTTA GTTTTTCAAC AAATAGATGC        500

AAACTGGAAC ATACAGTGCT GGCTAAAAGG AGACTTAAAA TTATTCATCT        550

GTTATGTGGA GTCATTATTT AAGAATCTAT TCAGGAATTA TAACTATAAG        600

GTCCATCTTT TATATGTTCT GCCTGAAGTG TTAGAAGATT CACCTCTGGT        650

TCCCCAAAAA GGCAGTTTTC AGATGGTTCA CTGCAATTGC AGTGTTCATG        700

AATGTTGTGA ATGTCTTGTG CCTGTGCCAA CAGCCAAACT CAACGACACT        750

CTCCTTATGT GTTTGAAAAT CACATCTGGT GGAGTAATTT TCCAGTCACC        800

TCTAATGTCA GTTCAGCCCA TAAATATGGT GAAGCCTGAT CCACCATTAG        850

GTTTGCATAT GGAAATCACA GATGATGGTA ATTTAAAGAT TTCTTGGTCC        900

AGCCCACCAT TGGTACCATT TCCACTTCAA TATCAAGTGA AATATTCAGA        950

GAATTCTACA ACAGTTATCA GAGAAGCTGA CAAGATTGTC TCAGCTACAT       1000

CCCTGCTAGT AGACAGTATA CTTCCTGGGT CTTCGTATGA GGTTCAGGTG       1050

AGGGGCAAGA GACTGGATGG CCCAGGAATC TGGAGTGACT GGAGTACTCC       1100

TCGTGTCTTT ACCACACAAG ATGTCATATA CTTTCCACCT AAAATTCTGA       1150

CAAGTGTTGG GTCTAATGTT TCTTTTCACT GCATCTATAA GAAGGAAAAC       1200

AAGATTGTTC CCTCAAAAGA GATTGTTTGG TGGATGAATT TAGCTGAGAA       1250

AATTCCTCAA AGCCAGTATG ATGTTGTGAG TGATCATGTT AGCAAAGTTA       1300

CTTTTTTCAA TCTGAATGAA ACCAAACCTC GAGGAAAGTT TACCTATGAT       1350

GCAGTGTACT GCTGCAATGA ACATGAATGC CATCATCGCT ATGCTGAATT       1400

ATATGTGATT GATGTCAATA TCAATATCTC ATGTGAAACT GATGGGTACT       1450

TAACTAAAAT GACTTGCAGA TGGTCAACCA GTACAATCCA GTCACTTGCG       1500

GAAAGCACTT TGCAATTGAG GTATCATAGG AGCAGCCTTT ACTGTTCTGA       1550

TATTCCATCT ATTCATCCCA TATCTGAGCC AAAGATTGC TATTTGCAGA        1600

GTGATGGTTT TTATGAATGC ATTTTCCAGC CAATCTTCCT ATTATCTGGC       1650

TACACAATGT GGATTAGGAT CAATCACTCT CTAGGTTCAC TTGACTCTCC       1700

ACCAACATGT GTCCTTCCTG ATTCTGTGGT GAAGCCACTG CCTCCATCCA       1750
```

-continued

```
GTGTGAAAGC AGAAATTACT ATAAACATTG GATTATTGAA AATATCTTGG          1800

GAAAAGCCAG TCTTTCCAGA GAATAACCTT CAATTCCAGA TTCGCTATGG          1850

TTTAAGTGGA AAAGAAGTAC AATGGAAGAT GTATGAGGTT TATGATGCAA          1900

AATCAAAATC TGTCAGTCTC CCAGTTCCAG ACTTGTGTGC AGTCTATGCT          1950

GTTCAGGTGC GCTGTAAGAG GCTAGATGGA CTGGGATATT GGAGTAATTG          2000

GAGCAATCCA GCCTACACAG TTGTCATGGA TATAAAAGTT CCTATGAGAG          2050

GACCTGAATT TTGGAGAATA ATTAATGGAG ATACTATGAA AAAGGAGAAA          2100

AATGTCACTT TACTTTGGAA GCCCCTGATG AAAAATGACT CATTGTGCAG          2150

TGTTCAGAGA TATGTGATAA ACCATCATAC TTCCTGCAAT GGAACATGGT          2200

CAGAAGATGT GGGAAATCAC ACGAAATTCA CTTTCCTGTG ACAGAGCAA           2250

GCACATACTG TTACGGTTCT GGCCATCAAT TCAATTGGTG CTTCTGTTGC          2300

AAATTTTAAT TTAACCTTTT CATGGCCTAT GAGCAAAGTA AATATCGTGC          2350

AGTCACTCAG TGCTTATCCT TTAAACAGCA GTTGTGTGAT TGTTTCCTGG          2400

ATACTATCAC CCAGTGATTA CAAGCTAATG TATTTTATTA TTGAGTGGAA          2450

AAATCTTAAT GAAGATGGTG AAATAAAATG GCTTAGAATC TCTTCATCTG          2500

TTAAGAAGTA TTATATCCAT GATCATTTTA TCCCCATTGA GAAGTACCAG          2550

TTCAGTCTTT ACCCAATATT TATGGAAGGA GTGGGAAAAC CAAAGATAAT          2600

TAATAGTTTC ACTCAAGATG ATATTGAAAA ACACCAGAGT GATGCAGGTT          2650

TATATGTAAT TGTGCCAGTA ATTATTTCCT CTTCCATCTT ATTGCTTGGA          2700

ACATTATTAA TATCACACCA AAGAATGAAA AAGCTATTTT GGGAAGATGT          2750

TCCGAACCCC AAGAATTGTT CCTGGGCACA AGGACTTAAT TTTCAGAAGA          2800

TGTTCCGAAC CCAAGAATT GTTCCTGGGC ACAAGGACTT AATTTTCAGA          2850

AGATGCTTGA AGGCAGCATG TTCGTTAAGA GTCATCACCA CTCCCTAATC          2900

TCAAGTACCC AGGGACACAA ACACTGCGGA AGGCCACAGG GTCCTCTGCA          2950

TAGGAAAACC AGAGACCTTT GTTCACTTGT TTATCTGCTG ACCCTCCCTC          3000

CACTATTGTC CTATGACCCT GCCAAATCCC CCTCTGTGAG AAACACCCAA          3050

GAATGATCAA TAAAAAAAAA AAAAAAAAA AAAAAGTCG ACTCGAGAAT            3100

TC                                                             3102
```

(2) INFORMATION FOR SEQ ID NO:7:

(i) SEQUENCE CHARACTERISTICS:
        (A) LENGTH: 783 amino acids
        (B) TYPE: Amino Acid
        (D) TOPOLOGY: Linear (xi) SEQUENCE DESCRIPTION: SEQ ID NO:7:

```
Met Met Cys Gln Lys Phe Tyr Val Val Leu Leu His Trp Glu Phe
 1               5                  10                  15

Leu Tyr Val Ile Ala Ala Leu Asn Leu Ala Tyr Pro Ile Ser Pro
                20                  25                  30

Trp Lys Phe Lys Leu Phe Cys Gly Pro Pro Asn Thr Thr Asp Asp
                35                  40                  45

Ser Phe Leu Ser Pro Ala Gly Ala Pro Asn Asn Ala Ser Ala Leu
                50                  55                  60
```

-continued

```
Lys Gly Ala Ser Glu Ala Ile Val Glu Ala Lys Phe Asn Ser Ser
            65                  70                  75
Gly Ile Tyr Val Pro Glu Leu Ser Lys Thr Val Phe His Cys Cys
            80                  85                  90
Phe Gly Asn Glu Gln Gly Gln Asn Cys Ser Ala Leu Thr Asp Asn
            95                 100                 105
Thr Glu Gly Lys Thr Leu Ala Ser Val Val Lys Ala Ser Val Phe
           110                 115                 120
Arg Gln Leu Gly Val Asn Trp Asp Ile Glu Cys Trp Met Lys Gly
           125                 130                 135
Asp Leu Thr Leu Phe Ile Cys His Met Glu Pro Leu Pro Lys Asn
           140                 145                 150
Pro Phe Lys Asn Tyr Asp Ser Lys Val His Leu Leu Tyr Asp Leu
           155                 160                 165
Pro Glu Val Ile Asp Asp Ser Pro Leu Pro Leu Lys Asp Ser
           170                 175                 180
Phe Gln Thr Val Gln Cys Asn Cys Ser Leu Arg Gly Cys Glu Cys
           185                 190                 195
His Val Pro Val Pro Arg Ala Lys Leu Asn Tyr Ala Leu Leu Met
           200                 205                 210
Tyr Leu Glu Ile Thr Ser Ala Gly Val Ser Phe Gln Ser Pro Leu
           215                 220                 225
Met Ser Leu Gln Pro Met Leu Val Val Lys Pro Asp Pro Pro Leu
           230                 235                 240
Gly Leu His Met Glu Val Thr Asp Asp Gly Asn Leu Lys Ile Ser
           245                 250                 255
Trp Asp Ser Gln Thr Met Ala Pro Phe Pro Leu Gln Tyr Gln Val
           260                 265                 270
Lys Tyr Leu Glu Asn Ser Thr Ile Val Arg Glu Ala Ala Glu Ile
           275                 280                 285
Val Ser Ala Thr Ser Leu Leu Val Asp Ser Val Leu Pro Gly Ser
           290                 295                 300
Ser Tyr Glu Val Gln Val Arg Ser Lys Arg Leu Asp Gly Ser Gly
           305                 310                 315
Val Trp Ser Asp Trp Ser Ser Pro Gln Val Phe Thr Thr Gln Asp
           320                 325                 330
Val Val Tyr Phe Pro Pro Lys Ile Leu Thr Ser Val Gly Ser Asn
           335                 340                 345
Ala Ser Phe His Cys Ile Tyr Lys Asn Glu Asn Gln Ile Val Ser
           350                 355                 360
Ser Lys Gln Ile Val Trp Trp Arg Asn Leu Ala Glu Lys Ile Pro
           365                 370                 375
Glu Ile Gln Tyr Ser Ile Val Ser Asp Arg Val Ser Lys Val Thr
           380                 385                 390
Phe Ser Asn Leu Lys Ala Thr Arg Pro Arg Gly Lys Phe Thr Tyr
           395                 400                 405
Asp Ala Val Tyr Cys Cys Asn Glu Gln Ala Cys His His Arg Tyr
           410                 415                 420
Ala Glu Leu Tyr Val Ile Asp Val Asn Ile Asn Ile Ser Cys Glu
           425                 430                 435
Thr Asp Gly Tyr Leu Thr Lys Met Thr Cys Arg Trp Ser Pro Ser
           440                 445                 450
Thr Ile Gln Ser Leu Val Gly Ser Thr Val Gln Leu Arg Tyr His
```

```
                          455                 460                 465
Arg Cys Ser Leu Tyr Cys Pro Asp Ser Pro Ser Ile His Pro Thr
                470                 475                 480

Ser Glu Pro Lys Thr Ala Ser Tyr Arg Glu Thr Ala Phe Met Asn
                485                 490                 495

Val Phe Ser Ser Gln Ser Phe Tyr Tyr Leu Ala Ile Gln Cys Gly
                500                 505                 510

Phe Arg Ile Asn His Ser Leu Gly Ser Leu Asp Ser Pro Pro Thr
                515                 520                 525

Cys Val Leu Pro Asp Ser Val Val Lys Pro Leu Pro Pro Ser Asn
                530                 535                 540

Val Lys Ala Glu Ile Thr Val Asn Thr Gly Leu Leu Lys Val Ser
                545                 550                 555

Trp Glu Lys Pro Val Phe Pro Glu Asn Asn Leu Gln Phe Gln Ile
                560                 565                 570

Arg Tyr Gly Leu Ser Gly Lys Glu Ile Gln Trp Lys Thr His Glu
                575                 580                 585

Val Phe Asp Ala Lys Ser Lys Ser Ala Ser Leu Leu Val Ser Asp
                590                 595                 600

Leu Cys Ala Val Tyr Val Val Gln Val Arg Cys Arg Arg Leu Asp
                605                 610                 615

Gly Leu Gly Tyr Trp Ser Asn Trp Ser Ser Pro Ala Tyr Thr Leu
                620                 625                 630

Val Met Asp Val Lys Val Pro Met Arg Gly Pro Glu Phe Trp Arg
                635                 640                 645

Lys Met Asp Gly Asp Val Thr Lys Lys Glu Arg Asn Val Thr Leu
                650                 655                 660

Leu Trp Lys Pro Leu Thr Lys Asn Asp Ser Leu Cys Ser Val Arg
                665                 670                 675

Arg Tyr Val Val Lys His Arg Thr Ala His Asn Gly Thr Trp Ser
                680                 685                 690

Glu Asp Val Gly Asn Arg Thr Asn Leu Thr Phe Leu Trp Thr Glu
                695                 700                 705

Pro Ala His Thr Val Thr Val Leu Ala Val Asn Ser Leu Gly Ala
                710                 715                 720

Ser Leu Val Asn Phe Asn Leu Thr Phe Ser Trp Pro Met Ser Lys
                725                 730                 735

Val Ser Ala Val Glu Ser Leu Ser Ala Tyr Pro Leu Ser Ser Ser
                740                 745                 750

Cys Val Ile Leu Ser Trp Thr Leu Ser Pro Asp Asp Tyr Ser Leu
                755                 760                 765

Leu Tyr Leu Val Ile Glu Trp Lys Ile Leu Asn Glu Asp Asp Gly
                770                 775                 780

Met Lys Trp
        783

(2) INFORMATION FOR SEQ ID NO:8:

(i) SEQUENCE CHARACTERISTICS:
        (A) LENGTH: 2868 base pairs
        (B) TYPE: Nucleic Acid
        (C) STRANDEDNESS: Single
        (D) TOPOLOGY: Linear (xi) SEQUENCE DESCRIPTION: SEQ ID NO:8:
```

-continued

| | | | | |
|---|---|---|---|---|
| GGGCCCCCCC | TCGAAGTCGA | CGGTATCGAT | AAGCTTGATA | TCGAATTCCG | 50 |
| GCCGGGACAC | AGGTGGGACA | CTCTTTTAGT | CCTCAATCCC | TGGCGCGAGG | 100 |
| CCACCCAAGG | CAACGCAGGA | CGCAGGGCGT | TTGGGGACCA | GGCAGCAGAC | 150 |
| TGGGGCGGTA | CCTGCGGAGA | GCCACGCAAC | TTCTCCAGGC | CTCTGACTAC | 200 |
| TTTGGAAACT | GCCCGGGGCT | GCGACATCAA | CCCCTTAAGT | CCCGGAGGCG | 250 |
| GAAAGAGGGT | GGGTTGGTTT | GAAAGACACA | AGGAAGAAAA | ATGTGCTGTG | 300 |
| GGGCGGGTTA | AGTTTCCCAC | CCTCTTCCCC | CTTCCCGAGC | AAATTAGAAA | 350 |
| CAAAACAAAT | AGAAAAGCCA | GCCCTCCGGC | CAACCAAAGC | CCCAAGCGGA | 400 |
| GCCCCAAGCG | GAGCCCCAGC | CGGAGCACTC | CTTTAAAAGG | ATTTGCAGCG | 450 |
| GTGAGGAAAA | AACCAGACCC | GACCGAGGAA | TCGTTCTGCA | AATCCAGGTG | 500 |
| TACACCTCTG | AAGAAAGATG | ATGTGTCAGA | AATTCTATGT | GGTTTTGTTA | 550 |
| CACTGGGAAT | TTCTTTATGT | GATAGCTGCA | CTTAACCTGG | CATATCCAAT | 600 |
| CTCTCCCTGG | AAATTTAAGT | TGTTTTGTGG | ACCACCGAAC | ACAACCGATG | 650 |
| ACTCCTTTCT | CTCACCTGCT | GGAGCCCCAA | ACAATGCCTC | GGCTTTGAAG | 700 |
| GGGGCTTCTG | AAGCAATTGT | TGAAGCTAAA | TTTAATTCAA | GTGGTATCTA | 750 |
| CGTTCCTGAG | TTATCCAAAA | CAGTCTTCCA | CTGTTGCTTT | GGGAATGAGC | 800 |
| AAGGTCAAAA | CTGCTCTGCA | CTCACAGACA | ACACTGAAGG | GAAGACACTG | 850 |
| GCTTCAGTAG | TGAAGGCTTC | AGTTTTTCGC | CAGCTAGGTG | TAAACTGGGA | 900 |
| CATAGAGTGC | TGGATGAAAG | GGGACTTGAC | ATTATTCATC | TGTCATATGG | 950 |
| AGCCATTACC | TAAGAACCCC | TTCAAGAATT | ATGACTCTAA | GGTCCATCTT | 1000 |
| TTATATGATC | TGCCTGAAGT | CATAGATGAT | TCGCCTCTGC | CCCCACTGAA | 1050 |
| AGACAGCTTT | CAGACTGTCC | AATGCAACTG | CAGTCTTCGG | GGATGTGAAT | 1100 |
| GTCATGTGCC | AGTACCCAGA | GCCAAACTCA | ACTACGCTCT | TCTGATGTAT | 1150 |
| TTGAAATCA | CATCTGCCGG | TGTGAGTTTT | CAGTCACCTC | TGATGTCACT | 1200 |
| GCAGCCCATG | CTTGTTGTGA | AACCCGATCC | ACCCTTAGGT | TTGCATATGG | 1250 |
| AAGTCACAGA | TGATGGTAAT | TTAAAGATTT | CTTGGGACAG | CCAAACAATG | 1300 |
| GCACCATTTC | CGCTTCAATA | TCAGGTGAAA | TATTTAGAGA | ATTCTACAAT | 1350 |
| TGTAAGAGAG | GCTGCTGAAA | TTGTCTCAGC | TACATCTCTG | CTGGTAGACA | 1400 |
| GTGTGCTTCC | TGGATCTTCA | TATGAGGTCC | AGGTGAGGAG | CAAGAGACTG | 1450 |
| GATGGTTCAG | GAGTCTGGAG | TGACTGGAGT | TCACCTCAAG | TCTTTACCAC | 1500 |
| ACAAGATGTT | GTGTATTTTC | CACCCAAAAT | TCTGACTAGT | GTTGGATCGA | 1550 |
| ATGCTTCCTT | TCATTGCATC | TACAAAAACG | AAAACCAGAT | TGTCTCCTCA | 1600 |
| AAACAGATAG | TTTGGTGGAG | GAATCTAGCT | GAGAAAATCC | CTGAGATACA | 1650 |
| GTACAGCATT | GTGAGTGACC | GAGTTAGCAA | AGTTACCTTC | TCCAACCTGA | 1700 |
| AAGCCACCAG | ACCTCGAGGG | AAGTTTACCT | ATGACGCAGT | GTACTGCTGC | 1750 |
| AATGAGCAGG | CGTGCCATCA | CCGCTATGCT | GAATTATACG | TGATCGATGT | 1800 |
| CAATATCAAT | ATATCATGTG | AAACTGACGG | GTACTTAACT | AAAATGACTT | 1850 |
| GCAGATGGTC | ACCCAGCACA | ATCCAATCAC | TAGTGGGAAG | CACTGTGCAG | 1900 |
| CTGAGGTATC | ACAGGTGCAG | CCTGTATTGT | CCTGATAGTC | CATCTATTCA | 1950 |
| TCCTACGTCT | GAGCCCAAAA | CTGCGTCTTA | CAGAGAGACG | GCTTTTATGA | 2000 |

-continued

| | |
|---|---|
| ATGTGTTTTC CAGCCAATCT TTCTATTATC TGGCTATACA ATGTGGATTC | 2050 |
| AGGATCAACC ATTCTTTAGG TTCACTTGAC TCGCCACCAA CGTGTGTCCT | 2100 |
| TCCTGACTCC GTAGTAAAAC CACTACCTCC ATCTAACGTA AAAGCAGAGA | 2150 |
| TTACTGTAAA CACTGGATTA TTGAAAGTAT CTTGGGAAAA GCCAGTCTTT | 2200 |
| CCGGAGAATA ACCTTCAATT CCAGATTCGA TATGGCTTAA GTGGAAAAGA | 2250 |
| AATACAATGG AAGACACATG AGGTATTCGA TGCAAAGTCA AAGTCTGCCA | 2300 |
| GCCTGCTGGT GTCAGACCTC TGTGCAGTCT ATGTGGTCCA GGTTCGCTGC | 2350 |
| CGGCGGTTGG ATGGACTAGG ATATTGGAGT AATTGGAGCA GTCCAGCCTA | 2400 |
| TACGCTTGTC ATGGATGTAA AAGTTCCTAT GAGAGGGCCT GAATTTTGGA | 2450 |
| GAAAAATGGA TGGGGACGTT ACTAAAAAGG AGAGAAATGT CACCTTGCTT | 2500 |
| TGGAAGCCCC TGACGAAAAA TGACTCACTG TGTAGTGTGA GGAGGTACGT | 2550 |
| GGTGAAGCAT CGTACTGCCC ACAATGGGAC GTGGTCAGAA GATGTGGGAA | 2600 |
| ATCGGACCAA TCTCACTTTC CTGTGGACAG AACCAGCGCA CACTGTTACA | 2650 |
| GTTCTGGCTG TCAATTCCCT CGGCGCTTCC CTTGTGAATT TTAACCTTAC | 2700 |
| CTTCTCATGG CCCATGAGTA AAGTGAGTGC TGTGGAGTCA CTCAGTGCTT | 2750 |
| ATCCCCTGAG CAGCAGCTGT GTCATCCTTT CCTGGACACT GTCACCTGAT | 2800 |
| GATTATAGTC TGTTATATCT GGTTATTGAA TGGAAGATCC TTAATGAAGA | 2850 |
| TGATGGAATG AAGTGGCT | 2868 |

(2) INFORMATION FOR SEQ ID NO:9:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:9:

| | |
|---|---|
| GGGTTAAGTT TCCCACCC | 18 |

(2) INFORMATION FOR SEQ ID NO:10:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:10:

| | |
|---|---|
| GGGTGGGAAA CTTAACCC | 18 |

(2) INFORMATION FOR SEQ ID NO:11:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:11:

| | |
|---|---|
| AGGATACAGT GGGATCCC | 18 |

(2) INFORMATION FOR SEQ ID NO:12:

(i) SEQUENCE CHARACTERISTICS:
            (A) LENGTH: 18 base pairs
            (B) TYPE: Nucleic Acid
            (C) STRANDEDNESS: Single
            (D) TOPOLOGY: Linear (xi) SEQUENCE DESCRIPTION: SEQ ID NO:12:

GCCCGAGCAC TCCTTTAA                                                        18

(2) INFORMATION FOR SEQ ID NO:13:

(i) SEQUENCE CHARACTERISTICS:
            (A) LENGTH: 18 base pairs
            (B) TYPE: Nucleic Acid
            (C) STRANDEDNESS: Single
            (D) TOPOLOGY: Linear (xi) SEQUENCE DESCRIPTION: SEQ ID NO:13:

TTAAAGGAGT GCTCCCGC                                                        18

(2) INFORMATION FOR SEQ ID NO:14:

(i) SEQUENCE CHARACTERISTICS:
            (A) LENGTH: 18 base pairs
            (B) TYPE: Nucleic Acid
            (C) STRANDEDNESS: Single
            (D) TOPOLOGY: Linear (xi) SEQUENCE DESCRIPTION: SEQ ID NO:14:

GAGCGGCCCT GTTAGATA                                                        18

(2) INFORMATION FOR SEQ ID NO:15:

(i) SEQUENCE CHARACTERISTICS:
            (A) LENGTH: 18 base pairs
            (B) TYPE: Nucleic Acid
            (C) STRANDEDNESS: Single
            (D) TOPOLOGY: Linear (xi) SEQUENCE DESCRIPTION: SEQ ID NO:15:

GTATACACCT CTGAAGAA                                                        18

(2) INFORMATION FOR SEQ ID NO:16:

(i) SEQUENCE CHARACTERISTICS:
            (A) LENGTH: 18 base pairs
            (B) TYPE: Nucleic Acid
            (C) STRANDEDNESS: Single
            (D) TOPOLOGY: Linear (xi) SEQUENCE DESCRIPTION: SEQ ID NO:16:

TTCTTCAGAG GTGTACAC                                                        18

(2) INFORMATION FOR SEQ ID NO:17:

(i) SEQUENCE CHARACTERISTICS:
            (A) LENGTH: 18 base pairs
            (B) TYPE: Nucleic Acid
            (C) STRANDEDNESS: Single
            (D) TOPOLOGY: Linear (xi) SEQUENCE DESCRIPTION: SEQ ID NO:17:

ATGCGAGGCT ACTTCTAT                                                        18

(2) INFORMATION FOR SEQ ID NO:18:

(i) SEQUENCE CHARACTERISTICS:

(A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:18:

CTCTCCCTGG AAATTTAA                                                         18

(2) INFORMATION FOR SEQ ID NO:19:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:19:

TTAAATTTCC AGGGAGAG                                                         18

(2) INFORMATION FOR SEQ ID NO:20:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:20:

ATTTGAAGGA GTTAAGCC                                                         18

(2) INFORMATION FOR SEQ ID NO:21:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:21:

AATTTAATTC AAGTGGTA                                                         18

(2) INFORMATION FOR SEQ ID NO:22:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:22:

TACCAGTTGA ATTAAATT                                                         18

(2) INFORMATION FOR SEQ ID NO:23:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:23:

GTATCACTTC ATAATATA                                                         18

(2) INFORMATION FOR SEQ ID NO:24:

(i) SEQUENCE CHARACTERISTICS:
        (A) LENGTH: 18 base pairs

```
        (B) TYPE: Nucleic Acid
        (C) STRANDEDNESS: Single
        (D) TOPOLOGY: Linear (xi) SEQUENCE DESCRIPTION: SEQ ID NO:24:

GATGGTCAGG GTGAACTG                                                        18

(2) INFORMATION FOR SEQ ID NO:25:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:25:

CAGTTCACCC TGACCATC                                                        18

(2) INFORMATION FOR SEQ ID NO:26:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:26:

GAGGCGAATG TGCGGATT                                                        18

(2) INFORMATION FOR SEQ ID NO:27:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:27:

CTTAAATCTC CAAGGAGT                                                        18

(2) INFORMATION FOR SEQ ID NO:28:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:28:

ACTCCTTGGA GATTTAAG                                                        18

(2) INFORMATION FOR SEQ ID NO:29:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:29:

AAGTCTTAAG CCAGACTT                                                        18

(2) INFORMATION FOR SEQ ID NO:30:

(i) SEQUENCE CHARACTERISTICS:
        (A) LENGTH: 18 base pairs
        (B) TYPE: Nucleic Acid
```

```
            (C) STRANDEDNESS: Single
            (D) TOPOLOGY: Linear (xi) SEQUENCE DESCRIPTION: SEQ ID NO:30:

TCTAAGGCAC ATCCCAGC                                              18

(2) INFORMATION FOR SEQ ID NO:31:

(i) SEQUENCE CHARACTERISTICS:
            (A) LENGTH: 18 base pairs
            (B) TYPE: Nucleic Acid
            (C) STRANDEDNESS: Single
            (D) TOPOLOGY: Linear (xi) SEQUENCE DESCRIPTION: SEQ ID NO:31:

GCTGGGATGT GCCTTAGA                                              18

(2) INFORMATION FOR SEQ ID NO:32:

(i) SEQUENCE CHARACTERISTICS:
            (A) LENGTH: 18 base pairs
            (B) TYPE: Nucleic Acid
            (C) STRANDEDNESS: Single
            (D) TOPOLOGY: Linear (xi) SEQUENCE DESCRIPTION: SEQ ID NO:32:

CGCAATGAAT TGACCCCC                                              18

(2) INFORMATION FOR SEQ ID NO:33:

(i) SEQUENCE CHARACTERISTICS:
            (A) LENGTH: 18 base pairs
            (B) TYPE: Nucleic Acid
            (C) STRANDEDNESS: Single
            (D) TOPOLOGY: Linear (xi) SEQUENCE DESCRIPTION: SEQ ID NO:33:

TACTTCAGAG AAGTACAC                                              18

(2) INFORMATION FOR SEQ ID NO:34:

(i) SEQUENCE CHARACTERISTICS:
            (A) LENGTH: 18 base pairs
            (B) TYPE: Nucleic Acid
            (C) STRANDEDNESS: Single
            (D) TOPOLOGY: Linear (xi) SEQUENCE DESCRIPTION: SEQ ID NO:34:

GTGTACTTCT CTGAAGTA                                              18

(2) INFORMATION FOR SEQ ID NO:35:

(i) SEQUENCE CHARACTERISTICS:
            (A) LENGTH: 18 base pairs
            (B) TYPE: Nucleic Acid
            (C) STRANDEDNESS: Single
            (D) TOPOLOGY: Linear (xi) SEQUENCE DESCRIPTION: SEQ ID NO:35:

GAATCACGGT AACTATCA                                              18

(2) INFORMATION FOR SEQ ID NO:36:

(i) SEQUENCE CHARACTERISTICS:
            (A) LENGTH: 18 base pairs
            (B) TYPE: Nucleic Acid
            (C) STRANDEDNESS: Single
```

```
        (D) TOPOLOGY: Linear (xi) SEQUENCE DESCRIPTION: SEQ ID NO:36:

CAGCTGTCTC ATAATGTC                                                18

(2) INFORMATION FOR SEQ ID NO:37:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:37:

GACATTATGA GACAGCTG                                                18

(2) INFORMATION FOR SEQ ID NO:38:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:38:

TTCGTCAAGC CATCTGAT                                                18

(2) INFORMATION FOR SEQ ID NO:39:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO:39:

His Gln Asn Leu Ser Asp Gly Lys
 1               5           8

(2) INFORMATION FOR SEQ ID NO:40:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO:40:

His Gln Asn Ile Ser Asp Gly Lys
 1               5           8

(2) INFORMATION FOR SEQ ID NO:41:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO:41:

His Gln Ser Leu Gly Thr Gln
 1               5       7

(2) INFORMATION FOR SEQ ID NO:42:

(i) SEQUENCE CHARACTERISTICS:
        (A) LENGTH: 8 amino acids
        (B) TYPE: Amino Acid
        (D) TOPOLOGY: Linear
```

(xi) SEQUENCE DESCRIPTION: SEQ ID NO:42:

Val Ile Ser Ser His Leu Gly Gln
 1               5           8

(2) INFORMATION FOR SEQ ID NO:43:

(i) SEQUENCE CHARACTERISTICS:
        (A) LENGTH: 11 amino acids
        (B) TYPE: Amino Acid
        (D) TOPOLOGY: Linear (xi) SEQUENCE DESCRIPTION: SEQ ID NO:43:

Pro Lys Asn Ser Ser Met Ile Ser Asn Thr Pro
 1               5                  10  11

(2) INFORMATION FOR SEQ ID NO:44:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO:44:

Asp Lys Thr His Thr Cys Pro Pro Cys Pro
 1               5                  10

(2) INFORMATION FOR SEQ ID NO:45:

(i) SEQUENCE CHARACTERISTICS:
        (A) LENGTH: 51 base pairs
        (B) TYPE: Nucleic Acid
        (C) STRANDEDNESS: Single
        (D) TOPOLOGY: Linear (xi) SEQUENCE DESCRIPTION: SEQ ID NO:45:

| | | |
|---|---|---|
| GTCAGTCTCC CAGTTCCAGA CTTGTGTGCA GTCTATGCTG TTCAGGTGCG | | 50 |
| C | | 51 |

(2) INFORMATION FOR SEQ ID NO:46:

(i) SEQUENCE CHARACTERISTICS:
        (A) LENGTH: 7127 base pairs
        (B) TYPE: Nucleic Acid
        (C) STRANDEDNESS: Double
        (D) TOPOLOGY: Linear (xi) SEQUENCE DESCRIPTION: SEQ ID NO:46:

| | |
|---|---|
| TTCGAGCTCG CCCGACATTG ATTATTGACT AGTTATTAAT AGTAATCAAT | 50 |
| TACGGGGTCA TTAGTTCATA GCCCATATAT GGAGTTCCGC GTTACATAAC | 100 |
| TTACGGTAAA TGGCCCGCCT GGCTGACCGC CCAACGACCC CCGCCCATTG | 150 |
| ACGTCAATAA TGACGTATGT TCCCATAGTA ACGCCAATAG GGACTTTCCA | 200 |
| TTGACGTCAA TGGGTGGAGT ATTTACGGTA AACTGCCCAC TTGGCAGTAC | 250 |
| ATCAAGTGTA TCATATGCCA AGTACGCCCC CTATTGACGT CAATGACGGT | 300 |
| AAATGGCCCG CCTGGCATTA TGCCCAGTAC ATGACCTTAT GGGACTTTCC | 350 |
| TACTTGGCAG TACATCTACG TATTAGTCAT CGCTATTACC ATGGTGATGC | 400 |
| GGTTTTGGCA GTACATCAAT GGGCGTGGAT AGCGGTTTGA CTCACGGGGA | 450 |
| TTTCCAAGTC TCCACCCCAT TGACGTCAAT GGGAGTTTGT TTTGGCACCA | 500 |
| AAATCAACGG GACTTTCCAA AATGTCGTAA CAACTCCGCC CCATTGACGC | 550 |

| | |
|---|---|
| AAATGGGCGG TAGGCGTGTA CGGTGGGAGG TCTATATAAG CAGAGCTCGT | 600 |
| TTAGTGAACC GTCAGATCGC CTGGAGACGC CATCCACGCT GTTTTGACCT | 650 |
| CCATAGAAGA CACCGGGACC GATCCAGCCT CCGCGGCCGG GAACGGTGCA | 700 |
| TTGGAACGCG GATTCCCCGT GCCAAGAGTG ACGTAAGTAC CGCCTATAGA | 750 |
| GTCTATAGGC CCACCCCCTT GGCTTCGTTA GAACGCGGCT ACAATTAATA | 800 |
| CATAACCTTA TGTATCATAC ACATACGATT TAGGTGACAC TATAGAATAA | 850 |
| CATCCACTTT GCCTTTCTCT CCACAGGTGT CCACTCCCAG GTCCAACTGC | 900 |
| ACCTCGGTTC TATCGATATG CATTGGGGAA CCCTGTGCGG ATTCTTGTGG | 950 |
| CTTTGGCCCT ATCTTTTCTA TGTCCAAGCT GTGCCCATCC AAAAAGTCCA | 1000 |
| AGATGACACC AAAACCCTCA TCAAGACAAT TGTCACCAGG ATCAATGACA | 1050 |
| TTTCACACAC GCAGTCAGTC TCCTCCAAAC AGAAAGTCAC CGGTTTGGAC | 1100 |
| TTCATTCCTG GGCTCCACCC CATCCTGACC TTATCCAAGA TGGACCAGAC | 1150 |
| ACTGGCAGTC TACCAACAGA TCCTCACCAG TATGCCTTCC AGAAACGTGA | 1200 |
| TCCAAATATC CAACGACCTG GAGAACCTCC GGGATCTTCT TCACGTGCTG | 1250 |
| GCCTTCTCTA AGAGCTGCCA CTTGCCCTGG GCCAGTGGCC TGGAGACCTT | 1300 |
| GGACAGCCTG GGGGGTGTCC TGGAAGCTTC AGGCTACTCC ACAGAGGTGG | 1350 |
| TGGCCCTGAG CAGGCTGCAG GGGTCTCTGC AGGACATGCT GTGGCAGCTG | 1400 |
| GACCTCAGCC CTGGGTGCGG GGTCACCGAC AAAACTCACA CATGCCCACC | 1450 |
| GTGCCCAGCA CCTGAACTCC TGGGGGGACC GTCAGTCTTC CTCTTCCCCC | 1500 |
| CAAAACCCAA GGACACCCTC ATGATCTCCC GGACCCCTGA GGTCACATGC | 1550 |
| GTGGTGGTGG ACGTGAGCCA CGAAGACCCT GAGGTCAAGT TCAACTGGTA | 1600 |
| CGTGGACGGC GTGGAGGTGC ATAATGCCAA GACAAAGCCG CGGGAGGAGC | 1650 |
| AGTACAACAG CACGTACCGT GTGGTCAGCG TCCTCACCGT CCTGCACCAG | 1700 |
| GACTGGCTGA ATGGCAAGGA GTACAAGTGC AAGGTCTCCA ACAAAGCCCT | 1750 |
| CCCAGCCCCC ATCGAGAAAA CCATCTCCAA AGCCAAAGGG CAGCCCCGAG | 1800 |
| AACCACAGGT GTACACCCTG CCCCCATCCC GGGAAGAGAT GACCAAGAAC | 1850 |
| CAGGTCAGCC TGACCTGCCT GGTCAAAGGC TTCTATCCCA GCGACATCGC | 1900 |
| CGTGGAGTGG GAGAGCAATG GGCAGCCGGA GAACAACTAC AAGACCACGC | 1950 |
| CTCCCGTGCT GGACTCCGAC GGCTCCTTCT TCCTCTACAG CAAGCTCACC | 2000 |
| GTGGACAAGA GCAGGTGGCA GCAGGGGAAC GTCTTCTCAT GCTCCGTGAT | 2050 |
| GCATGAGGCT CTGCACAACC ACTACACGCA GAAGAGCCTC TCCCTGTCTC | 2100 |
| CGGGTAAATG AGTGCGACGG CCCTAGAGTC GACCTGCAGA AGCTTCTAGA | 2150 |
| GTCGACCTGC AGAAGCTTGG CCGCCATGGC CCAACTTGTT TATTGCAGCT | 2200 |
| TATAATGGTT ACAAATAAAG CAATAGCATC ACAAATTTCA CAAATAAAGC | 2250 |
| ATTTTTTTCA CTGCATTCTA GTTGTGGTTT GTCCAAACTC ATCAATGTAT | 2300 |
| CTTATCATGT CTGGATCGAT CGGGAATTAA TTCGGCGCAG CACCATGGCC | 2350 |
| TGAAATAACC TCTGAAAGAG GAACTTGGTT AGGTACCTTC TGAGGCGGAA | 2400 |
| AGAACCAGCT GTGGAATGTG TGTCAGTTAG GGTGTGGAAA GTCCCCAGGC | 2450 |
| TCCCCAGCAG GCAGAAGTAT GCAAAGCATG CATCTCAATT AGTCAGCAAC | 2500 |
| CAGGTGTGGA AAGTCCCCAG GCTCCCCAGC AGGCAGAAGT ATGCAAAGCA | 2550 |

```
TGCATCTCAA TTAGTCAGCA ACCATAGTCC CGCCCCTAAC TCCGCCCATC        2600

CCGCCCCTAA CTCCGCCCAG TTCCGCCCAT TCTCCGCCCC ATGGCTGACT        2650

AATTTTTTTT ATTTATGCAG AGGCCGAGGC CGCCTCGGCC TCTGAGCTAT        2700

TCCAGAAGTA GTGAGGAGGC TTTTTTGGAG GCCTAGGCTT TTGCAAAAAG        2750

CTGTTAATTC GAACACGCAG ATGCAGTCGG GGCGGCGCGG TCCCAGGTCC        2800

ACTTCGCATA TTAAGGTGAC GCGTGTGGCC TCGAACACCG AGCGACCCTG        2850

CAGCGACCCG CTTAACAGCG TCAACAGCGT GCCGCAGATC TGATCAAGAG        2900

ACAGGATGAG GATCGTTTCG CATGATTGAA CAAGATGGAT TGCACGCAGG        2950

TTCTCCGGCC GCTTGGGTGG AGAGGCTATT CGGCTATGAC TGGGCACAAC        3000

AGACAATCGG CTGCTCTGAT GCCGCCGTGT TCCGGCTGTC AGCGCAGGGG        3050

CGCCCGGTTC TTTTTGTCAA GACCGACCTG TCCGGTGCCC TGAATGAACT        3100

GCAGGACGAG GCAGCGCGGC TATCGTGGCT GGCCACGACG GGCGTTCCTT        3150

GCGCAGCTGT GCTCGACGTT GTCACTGAAG CGGGAAGGGA CTGGCTGCTA        3200

TTGGGCGAAG TGCCGGGGCA GGATCTCCTG TCATCTCACC TTGCTCCTGC        3250

CGAGAAAGTA TCCATCATGG CTGATGCAAT GCGGCGGCTG CATACGCTTG        3300

ATCCGGCTAC CTGCCCATTC GACCACCAAG CGAAACATCG CATCGAGCGA        3350

GCACGTACTC GGATGGAAGC CGGTCTTGTC GATCAGGATG ATCTGGACGA        3400

AGAGCATCAG GGGCTCGCGC CAGCCGAACT GTTCGCCAGG CTCAAGGCGC        3450

GCATGCCCGA CGGCGAGGAT CTCGTCGTGA CCCATGGCGA TGCCTGCTTG        3500

CCGAATATCA TGGTGGAAAA TGGCCGCTTT TCTGGATTCA TCGACTGTGG        3550

CCGGCTGGGT GTGGCGGACC GCTATCAGGA CATAGCGTTG GCTACCCGTG        3600

ATATTGCTGA AGAGCTTGGC GGCGAATGGG CTGACCGCTT CCTCGTGCTT        3650

TACGGTATCG CCGCTCCCGA TTCGCAGCGC ATCGCCTTCT ATCGCCTTCT        3700

TGACGAGTTC TTCTGAGCGG GACTCTGGGG TTCGAAATGA CCGACCAAGC        3750

GACGCCCAAC CTGCCATCAC GAGATTTCGA TTCCACCGCC GCCTTCTATG        3800

AAAGGTTGGG CTTCGGAATC GTTTTCCGGG ACGCCGGCTG GATGATCCTC        3850

CAGCGCGGGG ATCTCATGCT GGAGTTCTTC GCCCACCCCG GGAGATGGGG        3900

GAGGCTAACT GAAACACGGA AGGAGACAAT ACCGGAAGGA ACCCGCGCTA        3950

TGACGGCAAT AAAAAGACAG AATAAAACGC ACGGGTGTTG GGTCGTTTGT        4000

TCATAAACGC GGGGTTCGGT CCCAGGGCTG GCACTCTGTC GATACCCCAC        4050

CGAGACCCCA TTGGGGCCAA TACGCCCGCG TTTCTTCCTT TTCCCCACCC        4100

CAACCCCCAA GTTCGGGTGA AGGCCCAGGG CTCGCAGCCA ACGTCGGGGC        4150

GGCAAGCCCG CCATAGCCAC GGGCCCCGTG GGTTAGGGAC GGGGTCCCCC        4200

ATGGGGAATG GTTTATGGTT CGTGGGGGTT ATTCTTTTGG GCGTTGCGTG        4250

GGGTCAGGTC CACGACTGGA CTGAGCAGAC AGACCCATGG TTTTTGGATG        4300

GCCTGGGCAT GGACCGCATG TACTGGCGCG ACACGAACAC CGGGCGTCTG        4350

TGGCTGCCAA ACACCCCCGA CCCCCAAAAA CCACCGCGCG GATTTCTGGC        4400

GCCGCCGGAC GAACTAAACC TGACTACGGC ATCTCTGCCC CTTCTTCGCT        4450

GGTACGAGGA GCGCTTTTGT TTTGTATTGG TCACCACGGC CGAGTTTCCG        4500
```

```
CGGGACCCCG GCCAGGGCAC CTGTCCTACG AGTTGCATGA TAAAGAAGAC      4550

AGTCATAAGT GCGGCGACGA TAGTCATGCC CCGCGCCCAC CGGAAGGAGC      4600

TGACTGGGTT GAAGGCTCTC AAGGGCATCG GTCGAGCGGC CGCATCAAAG      4650

CAACCATAGT ACGCGCCCTG TAGCGGCGCA TTAAGCGCGG CGGGTGTGGT      4700

GGTTACGCGC AGCGTGACCG CTACACTTGC CAGCGCCCTA GCGCCCGCTC      4750

CTTTCGCTTT CTTCCCTTCC TTTCTCGCCA CGTTCGCCGG CTTTCCCCGT      4800

CAAGCTCTAA ATCGGGGGCT CCCTTTAGGG TTCCGATTTA GTGCTTTACG      4850

GCACCTCGAC CCCAAAAAAC TTGATTTGGG TGATGGTTCA CGTAGTGGGC      4900

CATCGCCCTG ATAGACGGTT TTTCGCCCTT TGACGTTGGA GTCCACGTTC      4950

TTTAATAGTG GACTCTTGTT CCAAACTGGA ACAACACTCA ACCCTATCTC      5000

GGGCTATTCT TTTGATTTAT AAGGGATTTT GCCGATTTCG GCCTATTGGT      5050

TAAAAAATGA GCTGATTTAA CAAAAATTTA ACGCGAATTT TAACAAAATA      5100

TTAACGTTTA CAATTTTATG GTGCAGGCCT CGTGATACGC CTATTTTTAT      5150

AGGTTAATGT CATGATAATA ATGGTTTCTT AGACGTCAGG TGGCACTTTT      5200

CGGGGAAATG TGCGCGGAAC CCCTATTTGT TTATTTTTCT AAATACATTC      5250

AAATATGTAT CCGCTCATGA GACAATAACC CTGATAAATG CTTCAATAAT      5300

ATTGAAAAAG GAAGAGTATG AGTATTCAAC ATTTCCGTGT CGCCCTTATT      5350

CCCTTTTTTG CGGCATTTTG CCTTCCTGTT TTTGCTCACC CAGAAACGCT      5400

GGTGAAAGTA AAAGATGCTG AAGATCAGTT GGGTGCACGA GTGGGTTACA      5450

TCGAACTGGA TCTCAACAGC GGTAAGATCC TTGAGAGTTT TCGCCCCGAA      5500

GAACGTTTTC CAATGATGAG CACTTTTAAA GTTCTGCTAT GTGGCGCGGT      5550

ATTATCCCGT GATGACGCCG GGCAAGAGCA ACTCGGTCGC CGCATACACT      5600

ATTCTCAGAA TGACTTGGTT GAGTACTCAC CAGTCACAGA AAAGCATCTT      5650

ACGGATGGCA TGACAGTAAG AGAATTATGC AGTGCTGCCA TAACCATGAG      5700

TGATAACACT GCGGCCAACT TACTTCTGAC AACGATCGGA GGACCGAAGG      5750

AGCTAACCGC TTTTTTGCAC AACATGGGGG ATCATGTAAC TCGCCTTGAT      5800

CGTTGGGAAC CGGAGCTGAA TGAAGCCATA CCAAACGACG AGCGTGACAC      5850

CACGATGCCA GCAGCAATGG CAACAACGTT GCGCAAACTA TTAACTGGCG      5900

AACTACTTAC TCTAGCTTCC CGGCAACAAT TAATAGACTG GATGGAGGCG      5950

GATAAAGTTG CAGGACCACT TCTGCGCTCG GCCCTTCCGG CTGGCTGGTT      6000

TATTGCTGAT AAATCTGGAG CCGGTGAGCG TGGGTCTCGC GGTATCATTG      6050

CAGCACTGGG GCCAGATGGT AAGCCCTCCC GTATCGTAGT TATCTACACG      6100

ACGGGGAGTC AGGCAACTAT GGATGAACGA AATAGACAGA TCGCTGAGAT      6150

AGGTGCCTCA CTGATTAAGC ATTGGTAACT GTCAGACCAA GTTTACTCAT      6200

ATATACTTTA GATTGATTTA AAACTTCATT TTTAATTTAA AAGGATCTAG      6250

GTGAAGATCC TTTTTGATAA TCTCATGACC AAAATCCCTT AACGTGAGTT      6300

TTCGTTCCAC TGAGCGTCAG ACCCCGTAGA AAAGATCAAA GGATCTTCTT      6350

GAGATCCTTT TTTTCTGCGC GTAATCTGCT GCTTGCAAAC AAAAAAACCA      6400

CCGCTACCAG CGGTGGTTTG TTTGCCGGAT CAAGAGCTAC CAACTCTTTT      6450

TCCGAAGGTA ACTGGCTTCA GCAGAGCGCA GATACCAAAT ACTGTCCTTC      6500
```

```
                                                   -continued

TAGTGTAGCC GTAGTTAGGC CACCACTTCA AGAACTCTGT AGCACCGCCT       6550

ACATACCTCG CTCTGCTAAT CCTGTTACCA GTGGCTGCTG CCAGTGGCGA       6600

TAAGTCGTGT CTTACCGGGT TGGACTCAAG ACGATAGTTA CCGGATAAGG       6650

CGCAGCGGTC GGGCTGAACG GGGGGTTCGT GCACACAGCC CAGCTTGGAG       6700

CGAACGACCT ACACCGAACT GAGATACCTA CAGCGTGAGC ATTGAGAAAG       6750

CGCCACGCTT CCCGAAGGGA GAAAGGCGGA CAGGTATCCG GTAAGCGGCA       6800

GGGTCGGAAC AGGAGAGCGC ACGAGGGAGC TTCCAGGGGG AAACGCCTGG       6850

TATCTTTATA GTCCTGTCGG GTTTCGCCAC CTCTGACTTG AGCGTCGATT       6900

TTTGTGATGC TCGTCAGGGG GGCGGAGCCT ATGGAAAAAC GCCAGCTGGC       6950

ACGACAGGTT TCCCGACTGG AAAGCGGGCA GTGAGCGCAA CGCAATTAAT       7000

GTGAGTTACC TCACTCATTA GGCACCCCAG GCTTTACACT TTATGCTTCC       7050

GGCTCGTATG TTGTGTGGAA TTGTGAGCGG ATAACAATTT CACACAGGAA       7100

ACAGCTATGA CCATGATTAC GAATTAA                                7127
```

(2) INFORMATION FOR SEQ ID NO:47:

(i) SEQUENCE CHARACTERISTICS:
        (A) LENGTH: 397 amino acids
        (B) TYPE: Amino Acid
        (D) TOPOLOGY: Linear (xi) SEQUENCE DESCRIPTION: SEQ ID NO:47:

```
Met His Trp Gly Thr Leu Cys Gly Phe Leu Trp Leu Trp Pro Tyr
 1               5                  10                  15

Leu Phe Tyr Val Gln Ala Val Pro Ile Gln Lys Val Gln Asp Asp
                20                  25                  30

Thr Lys Thr Leu Ile Lys Thr Ile Val Thr Arg Ile Asn Asp Ile
                35                  40                  45

Ser His Thr Gln Ser Val Ser Ser Lys Gln Lys Val Thr Gly Leu
                50                  55                  60

Asp Phe Ile Pro Gly Leu His Pro Ile Leu Thr Leu Ser Lys Met
                65                  70                  75

Asp Gln Thr Leu Ala Val Tyr Gln Gln Ile Leu Thr Ser Met Pro
                80                  85                  90

Ser Arg Asn Val Ile Gln Ile Ser Asn Asp Leu Glu Asn Leu Arg
                95                 100                 105

Asp Leu Leu His Val Leu Ala Phe Ser Lys Ser Cys His Leu Pro
               110                 115                 120

Trp Ala Ser Gly Leu Glu Thr Leu Asp Ser Leu Gly Gly Val Leu
               125                 130                 135

Glu Ala Ser Gly Tyr Ser Thr Glu Val Val Ala Leu Ser Arg Leu
               140                 145                 150

Gln Gly Ser Leu Gln Asp Met Leu Trp Gln Leu Asp Leu Ser Pro
               155                 160                 165

Gly Cys Gly Val Thr Asp Lys Thr His Thr Cys Pro Pro Cys Pro
               170                 175                 180

Ala Pro Glu Leu Leu Gly Gly Pro Ser Val Phe Leu Phe Pro Pro
               185                 190                 195

Lys Pro Lys Asp Thr Leu Met Ile Ser Arg Thr Pro Glu Val Thr
               200                 205                 210
```

-continued

```
Cys Val Val Val Asp Val Ser His Glu Asp Pro Glu Val Lys Phe
            215             220             225

Asn Trp Tyr Val Asp Gly Val Glu Val His Asn Ala Lys Thr Lys
            230             235             240

Pro Arg Glu Glu Gln Tyr Asn Ser Thr Tyr Arg Val Val Ser Val
            245             250             255

Leu Thr Val Leu His Gln Asp Trp Leu Asn Gly Lys Glu Tyr Lys
            260             265             270

Cys Lys Val Ser Asn Lys Ala Leu Pro Ala Pro Ile Glu Lys Thr
            275             280             285

Ile Ser Lys Ala Lys Gly Gln Pro Arg Glu Pro Gln Val Tyr Thr
            290             295             300

Leu Pro Pro Ser Arg Glu Glu Met Thr Lys Asn Gln Val Ser Leu
            305             310             315

Thr Cys Leu Val Lys Gly Phe Tyr Pro Ser Asp Ile Ala Val Glu
            320             325             330

Trp Glu Ser Asn Gly Gln Pro Glu Asn Asn Tyr Lys Thr Thr Pro
            335             340             345

Pro Val Leu Asp Ser Asp Gly Ser Phe Phe Leu Tyr Ser Lys Leu
            350             355             360

Thr Val Asp Lys Ser Arg Trp Gln Gln Gly Asn Val Phe Ser Cys
            365             370             375

Ser Val Met His Glu Ala Leu His Asn His Tyr Thr Gln Lys Ser
            380             385             390

Leu Ser Leu Ser Pro Gly Lys
            395     397
```

What is claimed is:

1. A method for enhancing proliferation or differentiation of a cell of the hematopoietic lineage comprising an OB receptor having a WSX motif, comprising administering to the cell to an amount of OB protein which is effective for enhancing proliferation or differentiation of the cell with the proviso that a further cytokine is not concurrently administered to the cell.

2. The method of claim 1 wherein the OB receptor is the OB receptor variant 13.2.

3. The method of claim 1 wherein the cell is a hematopoietic progenitor cell.

4. The method of claim 3 wherein the cell is a CD34+ cell.

5. The method of claim 1 which enhances proliferation of the cell.

6. The method of claim 1 which enhances differentiation of the cell.

7. The method of claim 1 wherein the OB protein is human OB protein.

8. The method of claim 1 wherein the OB protein is a long half-life derivative of an OB protein.

9. The method of claim 8 wherein the derivative is an OB-immunoglobulin chimera.

10. The method of claim 8 wherein the derivative is modified with a nonproteinaceous polymer.

11. The method of claim 10 wherein the nonproteinaceous polymer is polyethylene glycol (PEG).

12. The method of claim 1 which enhances proliferation or differentiation of lymphoid blood cell lineages.

13. The method of claim 1 which enhances proliferation or differentiation of myeloid blood cell lineages.

14. The method of claim 1 which enhances proliferation or differentiation of erythroid blood cell lineages.

15. The method of claim 1 further comprising exposing the cell to thrombopoietin (TPO).

16. The method of claim 1 wherein the cell is in cell culture.

17. The method of claim 1 wherein the cell is present in a mammal.

18. The method of claim 17 wherein the mammal is a human.

19. A method for repopulating blood cells in a mammal comprising administering to the mammal a therapeutically effective amount of OB protein with the proviso that a further cytokine is not concurrently administered to the mammal to repopulate blood cells.

20. The method of claim 19 further comprising administering thrombopoietin (TPO) to the mammal.

21. The method of claim 20 wherein the mammal has decreased blood cell levels caused by chemotherapy, radiation therapy, or bone marrow transplantation therapy.

22. The method of claim 19 wherein the blood cells are erythroid cells.

23. The method of claim 19 wherein the blood cells are myeloid cells.

24. The method of claim 19 wherein the blood cells are lymphoid cells.

25. The method of claim 19 comprising administering a further cytokine to the mammal.

26. The method of claim 25, wherein the cytokine is selected from the group consisting of EPO, KL, GM-CSF, IL-3, and combinations thereof.

27. The method of claim 25, wherein the cytokine is selected from the group consisting of lymphokine, monokine, polypeptide hormone, growth hormone, human growth hormone, N-methionyl human growth hormone, bovine growth hormone, parathyroid hormone, thyroxine, insulin, proinsulin, relaxin, prorelaxin, glycoprotein hormone, follicle stimulating hormone (FSH), thyroid stimulating hormone (TSH), luteinizing hormone (LH), hepatic growth factor, fibroblast growth factor, prolactin, placental lactogen, tumor necrosis factor-α, tumor necrosis factor-β, mullerian-inhibiting substance, mouse gonadotropin-associated peptide, inhibin, activin, vascular endothelial growth factor, integrin, thrombopoietin (TPO), nerve growth factor, NGF-β, platelet-growth factor, transforming growth factor (TGF), TGF-α, TGF-β, insulin-like growth factor-I insulin-like growth factor-II, erythropoietin (EPO), osteoinductive factor, interferon, interferon-α, interferon-β, interferon-γ, colony stimulating factor, (CSF), macrophage-CSF (M-CSF), granulocyte-macrophage-CSF (GM-CSF), granulocyte-CSF (G-CSF), interleukin (IL), IL-1, IL-1α, IL-2, IL-3, IL-4, IL-5, IL-6, IL-7, IL-8, IL-9, IL-11, IL-12, leukemia inhibitory factor (LIF), kit ligand (KL), and combinations thereof.

28. The method of claim 1 or claim 19, wherein a sequence of said OB protein shares at least 84% sequence homology with a mouse OB protein sequence.

29. The method of claim 1 or claim 19, wherein a sequence of said OB protein is at least 90% identical to a mouse OB protein sequence.

30. The method of claim 1 or claim 19, wherein a sequence of said OB protein is at least 95% identical to a mouse OB protein sequence.

31. The method of claim 1 or claim 19, wherein a sequence of said OB protein is at least 99% identical to a mouse OB protein sequence.

32. The method of claim 1 or claim 19, wherein a sequence of said OB protein shares at least 84% sequence homology with a human OB protein sequence.

33. The method of claim 1 or claim 19, wherein a sequence of said OB protein is at least 90% identical to a human OB protein sequence.

34. The method of claim 1 or claim 19, wherein a sequence of said OB protein is at least 95% identical to a human OB protein sequence.

35. The method of claim 1 or claim 19, wherein a sequence of said OB protein is at least 99% identical to a human OB protein sequence.

36. The method of claim 1 or claim 19, wherein said OB protein is encoded by a nucleic acid sequence that hybridizes to a mouse nucleic acid sequence, wherein said mouse nucleic acid sequence encodes a mouse OB protein.

37. The method of claim 1 or claim 19, wherein said OB protein is encoded by a nucleic acid sequence that hybridizes to a human nucleic acid sequence, wherein said human nucleic acid sequence encodes a human OB protein, and wherein said hybridization occurs under moderately stringent conditions.

* * * * *

UNITED STATES PATENT AND TRADEMARK OFFICE
CERTIFICATE OF CORRECTION

| | |
|---|---|
| PATENT NO. | : 7,074,397 B1 |
| APPLICATION NO. | : 08/667197 |
| DATED | : July 11, 2006 |
| INVENTOR(S) | : Matthews |

It is certified that error appears in the above-identified patent and that said Letters Patent is hereby corrected as shown below:

On the first page, Col. 2 Item [56] (U.S. Patent Documents), line 12, please delete "Campfiled et al." and insert --Campfield et al.-- therefor.

On the first page, Col. 2 Item [56] (Other Publications), line 43, please delete "Migliarcia et al." and insert --Migliaccio et al.-- therefor.

On page 2, Col. 1 Item [56] (Foreign Patent Documents), line 11, after "WO 97/48419 12/1997" please insert --A61K 48/00--.

On page 2, Col. 1 Item [56] (Foreign Patent Documents), line 12, after "WO 97/48806 12/1997" please insert --C12N 15/16--.

On page 2, Col. 1 Item [56] (Foreign Patent Documents), line 14, after "07/1998" please insert --C12N 15/62--.

On page 2, Col. 1 Item [56] (Other Publications), line 18, please delete "TM" and insert --TM.-- therefor.

On page 2, Col. 2 Item [56] (Other Publications), line 7, after "for" please insert --a--.

On page 2, Col. 2 Item [56] (Other Publications), line 9, after "Mutagenesis" please delete "." and insert --,-- therefor.

On page 2, Col. 2 Item [56] (Other Publications), line 13, please delete "Funct. . Genet." and insert --Funct., Genet.--, therefor.

On page 2, Col. 2 Item [56] (Other Publications), line 15, please delete "anti-p1185$^{HER2}$" and insert --anti-p185$^{HER2}$-- therefor.

UNITED STATES PATENT AND TRADEMARK OFFICE
CERTIFICATE OF CORRECTION

PATENT NO.      : 7,074,397 B1
APPLICATION NO. : 08/667197
DATED           : July 11, 2006
INVENTOR(S)     : Matthews It is certified that error appears in the above-identified patent and that said Letters Patent is hereby corrected as shown below:

On page 2, Col. 2 Item [56] (Other Publications), line 22, after "role" insert --of--.

On page 3, Col. 1 Item [56] (Other Publications), line 15, after "leptin" please insert --receptor--.

On page 3, Col. 1 Item [56] (Other Publications), line 27, please delete "Role" and insert --role-- therefor.

On page 3, Col. 1 Item [56] (Other Publications), line 46, please delete "Introduction" and insert --Induction-- therefor.

On page 3, Col. 1 Item [56] (Other Publications), line 54, please delete "Lodegment" and insert --Lodgement-- therefor.

On page 3, Col. 2 Item [56] (Other Publications), line 9, after "Blood" please insert --84--.

On page 3, Col. 2 Item [56] (Other Publications), line 13, please delete "(1492)." and insert --(1992).-- therefor.

On page 3, Col. 2 Item [56] (Other Publications), line 39, please delete "Treaty" and insert --Treat-- therefor.

On Sheet 6 of 74, line 19 (FIG. 1F), please delete "apyl [dcm+" and insert --apyl [dcm+]-- therefor.

On Drawing Sheet 37 of 74, lines 4-5 (FIG. 5G), please delete " 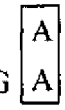 " and insert --  -- therefor.

UNITED STATES PATENT AND TRADEMARK OFFICE
CERTIFICATE OF CORRECTION

| | |
|---|---|
| PATENT NO. | : 7,074,397 B1 |
| APPLICATION NO. | : 08/667197 |
| DATED | : July 11, 2006 |
| INVENTOR(S) | : Matthews |

It is certified that error appears in the above-identified patent and that said Letters Patent is hereby corrected as shown below:

On Drawing Sheet 69 of 74, line 28 (FIG. 16Q), please delete "haeIII/paI" and insert --haeIII/paII-- therefor.

In Col. 2, line 18, please delete "granutocyte" and insert --granulocyte-- therefore.

In Col. 2, line 34, please delete "α subunit" and insert --α-subunit-- therefor.

In Col. 7, line 18, please delete "13.2," and insert --13.2 (SEQ ID NO:2),-- therefor.

In Col. 7, line 29-31, please delete "FIGS. 3A-L together depict an alignment of the nucleotide sequences encoding human WXS receptor variants 6.4 (SEQ ID NO:5), 12.1 (SEQ ID NO:6) and 13.2, respectively." and insert the same on line 29 as a separate paragraph.

In Col. 7, line 31, please delete "13.2," and insert --13.2 (SEQ ID NO:1),-- therefor.

In Col. 7, line 33, after "(top)" please insert --(SEQ ID NO:2)--.

In Col. 7, line 41 (approx.), after "(bottom)" please insert --(SEQ ID NO:1)--.

In Col. 10, line 61, please delete "From" and insert --from-- therefor.

In Col. 19, line 42, please delete "a factor" and insert --α-factor-- therefor.

In Col. 19, line 61, please delete "doning" and insert --cloning-- therefor.

In Col. 23, line 62, please delete "9." and insert --g.-- therefor.

In Col. 24, line 34 (approx.), please delete "et al," and insert --et al.,-- therefor.

UNITED STATES PATENT AND TRADEMARK OFFICE
CERTIFICATE OF CORRECTION

PATENT NO. : 7,074,397 B1
APPLICATION NO. : 08/667197
DATED : July 11, 2006
INVENTOR(S) : Matthews It is certified that error appears in the above-identified patent and that said Letters Patent is hereby corrected as shown below:

In Col. 24, line 34 (approx.), please delete "et al," and insert --et al.,-- therefor.

In Col. 25, line 30 (approx.), please delete "niger" and insert --niger.-- therefor.

In Col. 32, line 25, please delete "et al," and insert --et al.,-- therefor.

In Col. 32, line 31, please delete "et al," and insert --et al.,-- therefor.

In Col. 32, line 38, please delete "et al," and insert --et al.,-- therefor.

In Col. 32, line 39, please delete "et al," and insert --et al.,-- therefor.

In Col. 38, line 25, please delete "neuramimidase" and insert --neuraminidase-- therefor.

In Col. 42, line 35, please delete "Mater" and insert --Mater.-- therefor.

In Col. 46, line 50, please delete "monodonal" and insert --monoclonal-- therefor.

In Col. 52, line 7, please delete "370C," and insert --37°C.,-- therefor.

In Col. 52, line 21, please delete "et al," and insert --et al.,-- therefor.

In Col. 55, line 41 (approx.), please delete "clone" and insert --clone 5-- therefor.

In Col. 59, line 43 (approx.), after "Murine Fetal Liver (KL)" please delete "(-23) AS" and insert --(-213) AS-- therefor.

In Col. 63, line 36, please delete "CDB" and insert --CD8-- therefor.

UNITED STATES PATENT AND TRADEMARK OFFICE
CERTIFICATE OF CORRECTION

PATENT NO.       : 7,074,397 B1
APPLICATION NO. : 08/667197
DATED            : July 11, 2006
INVENTOR(S)      : Matthews It is certified that error appears in the above-identified patent and that said Letters Patent is hereby corrected as shown below:

In Col. 64, line 54, please delete "40C." and insert --4°C.-- therefor.

Signed and Sealed this

Twenty-fourth Day of March, 2009

JOHN DOLL
*Acting Director of the United States Patent and Trademark Office*

UNITED STATES PATENT AND TRADEMARK OFFICE
CERTIFICATE OF CORRECTION

PATENT NO.       : 7,074,397 B1
APPLICATION NO. : 08/667197
DATED            : July 11, 2006
INVENTOR(S)      : Matthews It is certified that error appears in the above-identified patent and that said Letters Patent is hereby corrected as shown below:

In the Claims, please delete the entire claim set and replace it with the following claim set:

Claim 1 Col. 121 Line 37-44
--1. A method for enhancing proliferation or differentiation of a cell of the hematopoietic lineage comprising an OB receptor having a WSX motif, comprising administering to the cell to an amount of OB protein which is effective for enhancing proliferation or differentiation of the cell with the proviso that a further cytokine is not concurrently administered to the cell.--

Claim 2 Col. 121 Line 44
--2. The method of claim 1 wherein the OB receptor is the OB receptor variant 13.2.--

Claim 3 Col. 121 Line 46-47
--3. The method of claim 1 wherein the cell is a hematopoietic progenitor cell.--

Claim 4 Col. 121 Line 48
--4. The method of claim 3 wherein the cell is a CD34+ cell.--

Claim 5 Col. 121 Line 49-50
--5. The method of claim 1 which enhances proliferation of the cell.--

Claim 6 Col. 121 Line 51-52
--6. The method of claim 1 which enhances differentiation of the cell.--

Claim 7 Col. 121 Line 54-55
--7. The method of claim 1 wherein the OB protein is human OB protein.--

Claim 8 Col. 121 Line 56-57
--8. The method of claim 1 wherein the OB protein is a long half-life derivative of an OB protein.--

Claim 9 Col. 121 Line 58-59
--9. The method of claim 8 wherein the derivative is an OB-immunoglobulin chimera.--

Claim 10 Col. 121 Line 60-61
--10. The method of claim 8 wherein the derivative is modified with a nonproteinaceous polymer.--

Claim 11 Col. 121 Line 62-63
--11. The method of claim 10 wherein the nonproteinaceous polymer is polyethylene glycol (PEG).--

Claim 12 Col. 121 Line 64-65
--12. The method of claim 1 which enhances proliferation or differentiation of lymphoid blood cell lineages.--

Claim 13 Col. 121 Line 66-67
--13. The method of claim 1 which enhances proliferation or differentiation of myeloid blood cell lineages.--

Claim 14 Col. 122 Line 36-37
--14. The method of claim 1 which enhances proliferation or differentiation of erythroid blood cell lineages.--

Claim 15 Col. 122 Line 38
--15. The method of claim 1 further comprising exposing the cell to thrombopoietin (TPO).--

Claim 16 Col. 122 Line 39
--16. The method of claim 1 wherein the cell is in cell culture.--

Claim 17 Col. 122 Line 40
--17. The method of claim 1 wherein the cell is present in a mammal.--

Claim 18 Col. 122 Line 44
--18. The method of claim 17 wherein the mammal is a human.--

Claim 19 Col. 122 Line 47-51
19. A method for repopulating blood cells in a mammal comprising administering to the mammal a therapeutically effective amount of OB protein, with the proviso that a further cytokine is not concurrently administered to the mammal to repopulate blood cells when the OB protein is administered to the mammal.--

Claim 20 Col. 122 Line 52-53
--20. The method of claim 19 further comprising administering thrombopoietin (TPO) to the mammal.--

Claim 21 Col. 122 Line 54-56
--21. The method of claim 20 wherein the mammal has decreased blood cell levels caused by chemotherapy, radiation therapy, or bone marrow transplantation therapy.--

Claim 22 Col. 122 Line 57
--22. The method of claim 19 wherein the blood cells are erythroid cells.--

Claim 23 Col. 122 Line 59
--23. The method of claim 19 wherein the blood cells are myeloid cells.--

Claim 24 Col. 122 Line 65
--24. The method of claim 19 wherein the blood cells are lymphoid cells.--

Signed and Sealed this

Twenty-third Day of March, 2010

David J. Kappos
*Director of the United States Patent and Trademark Office*